(12) United States Patent
Bicknell et al.

(10) Patent No.: US 7,740,830 B2
(45) Date of Patent: Jun. 22, 2010

(54) IMAGING, DIAGNOSIS AND TREATMENT OF DISEASE

(75) Inventors: Roy Bicknell, Oxford (GB); Lukasz Huminiecki, Cambridge (GB)

(73) Assignee: Cancer Research Technology Limited, London (GB)

( * ) Notice: Subject to any disclaimer, the term of this patent is extended or adjusted under 35 U.S.C. 154(b) by 173 days.

(21) Appl. No.: 11/824,445

(22) Filed: Jun. 29, 2007

(65) Prior Publication Data

US 2008/0219924 A1    Sep. 11, 2008

Related U.S. Application Data

(63) Continuation of application No. 11/429,627, filed on May 4, 2006, now Pat. No. 7,582,440, which is a continuation of application No. 10/416,090, filed as application No. PCT/GB01/04906 on Nov. 6, 2001, now Pat. No. 7,498,034.

(60) Provisional application No. 60/245,566, filed on Nov. 6, 2000, provisional application No. 60/273,662, filed on Mar. 7, 2001.

(51) Int. Cl.
*G01N 33/53* (2006.01)
*A61K 49/00* (2006.01)

(52) U.S. Cl. .................... 424/9.1; 424/9.5; 424/9.6; 424/9.3; 424/1.49; 435/4; 435/7.21

(58) Field of Classification Search .................. None
See application file for complete search history.

(56) References Cited

U.S. PATENT DOCUMENTS

| | | | |
|---|---|---|---|
| 6,069,007 | A | 5/2000 | Rossi et al. |
| 6,225,118 | B1 | 5/2001 | Grant et al. |
| 7,163,797 | B2 | 1/2007 | Ruben et al. |
| 7,498,034 | B2 | 3/2009 | Bicknell et al. |
| 2003/0072736 | A1 | 4/2003 | Baker et al. |
| 2004/0071711 | A1 | 4/2004 | Bicknell et al. |
| 2006/0099143 | A1 | 5/2006 | Bicknell et al. |
| 2006/0263369 | A1 | 11/2006 | Bicknell et al. |
| 2007/0025913 | A1 | 2/2007 | Bicknell et al. |
| 2008/0019963 | A1 | 1/2008 | Bicknell et al. |
| 2008/0145359 | A1 | 6/2008 | Bicknell et al. |
| 2008/0166295 | A1 | 7/2008 | Bicknell et al. |

FOREIGN PATENT DOCUMENTS

| | | |
|---|---|---|
| EP | 0 682 113 A2 | 11/1995 |
| EP | 1 074 617 A2 | 7/2000 |
| WO | WO 99/06423 A1 | 2/1999 |
| WO | WO 99/11293 A1 | 3/1999 |
| WO | WO 99/46281 A2 | 9/1999 |
| WO | WO 99/53051 A2 | 10/1999 |
| WO | WO 00/53756 A2 | 9/2000 |
| WO | WO 01/23523 A2 | 4/2001 |

OTHER PUBLICATIONS

Tockman et al, Cancer Research vol. 52 p. 2711s (1992).*
Skolnick et al. (Trends in Biotech., 18(1):34-39, 2000).*
Amalfitano, A and Parks, R.J. Separating fact from fiction: assessing the potential of modified adenovirus vectors for use in human gene therapy. Curr Gene Ther. May 2002;2(2):111-33. Review.
Bechard, D. et al., Characterization of the secreted form of endothelial-cell-specific molecule 1 by specific monoclonal antibodies. J Vasc Res. Sep.-Oct. 2000;37(5):417-25.
Bortoluzzi, S. et al., The human adult skeletal muscle transcriptional profile reconstructed by a novel computational approach. Genome Res. Mar. 2000;10(3):344-9.
Brose, K. et al., Slit proteins bind Robo receptors and have an evolutionarily conserved role in repulsive axon guidance. Cell. Mar. 19, 1999;96(6):795-806.
Chen, H. et al., Characterization of gene expression in resting and activated mast cells. J Exp Med. Nov. 2, 1998;188(9):1657-68. Erratum in: J Exp Med Dec. 21, 1998;188(12):2387.
Clark, D.E. et al., Localization of VEGF and expression of its receptors flt and KDR in human placenta throughout pregnancy. Hum Reprod. May 1996;11(5):1090-8.
Cole, K.A. et al., The genetics of cancer—a 3D model. Nat Genet. Jan. 1999;21(1 Suppl):38-41. Review.
Compton, J., Nucleic acid sequence-based amplification. Nature. Mar. 7, 1991;350(6313):91-2.
Cserzö, M. et al., Prediction of transmembrane alpha-helices in prokaryotic membrane proteins: the dense alignment surface method. Protein Eng. Jun. 1997;10(6):673-6.
Cwirla, S.E. et al., Peptides on phage: a vast library of peptides for identifying ligands. Proc Natl Acad Sci U S A. Aug. 1990;87(16):6378-82.
Dillon, N. and Sabbattini, P. Functional gene expression domains: defining the functional unit of eukaryotic gene regulation. Bioessays. Jul. 2000;22(7):657-65. Review.
Dorai, T. et al., Development of a hammerhead ribozyme against BCL-2. II. Ribozyme treatment sensitizes hormone-resistant prostate cancer cells to apoptotic agents. Anticancer Res. Sep.-Oct. 1997;17(5A):3307-12.
Felbor, U. et al., Genomic organization and chromosomal localization of the interphotoreceptor matrix proteoglycan-1 (IMPG1) gene: a candidate for 6q-linked retinopathies. Cytogenet Cell Genet. 1998;81(1):12-7.
Fong, G.H. et al., Role of the Flt-1 receptor tyrosine kinase in regulating the assembly of vascular endothelium. Nature. Jul. 6, 1995;376(6535):66-70.

(Continued)

*Primary Examiner*—Sheela J Huff
(74) *Attorney, Agent, or Firm*—Wolf, Greenfield & Sacks, P.C.

(57) ABSTRACT

The present invention relates to endothelial cell-specific genes and encoded polypeptides and materials and uses thereof in the imaging, diagnosis and treatment of conditions involving the vascular endothelium.

17 Claims, 56 Drawing Sheets

OTHER PUBLICATIONS

Figure 1:
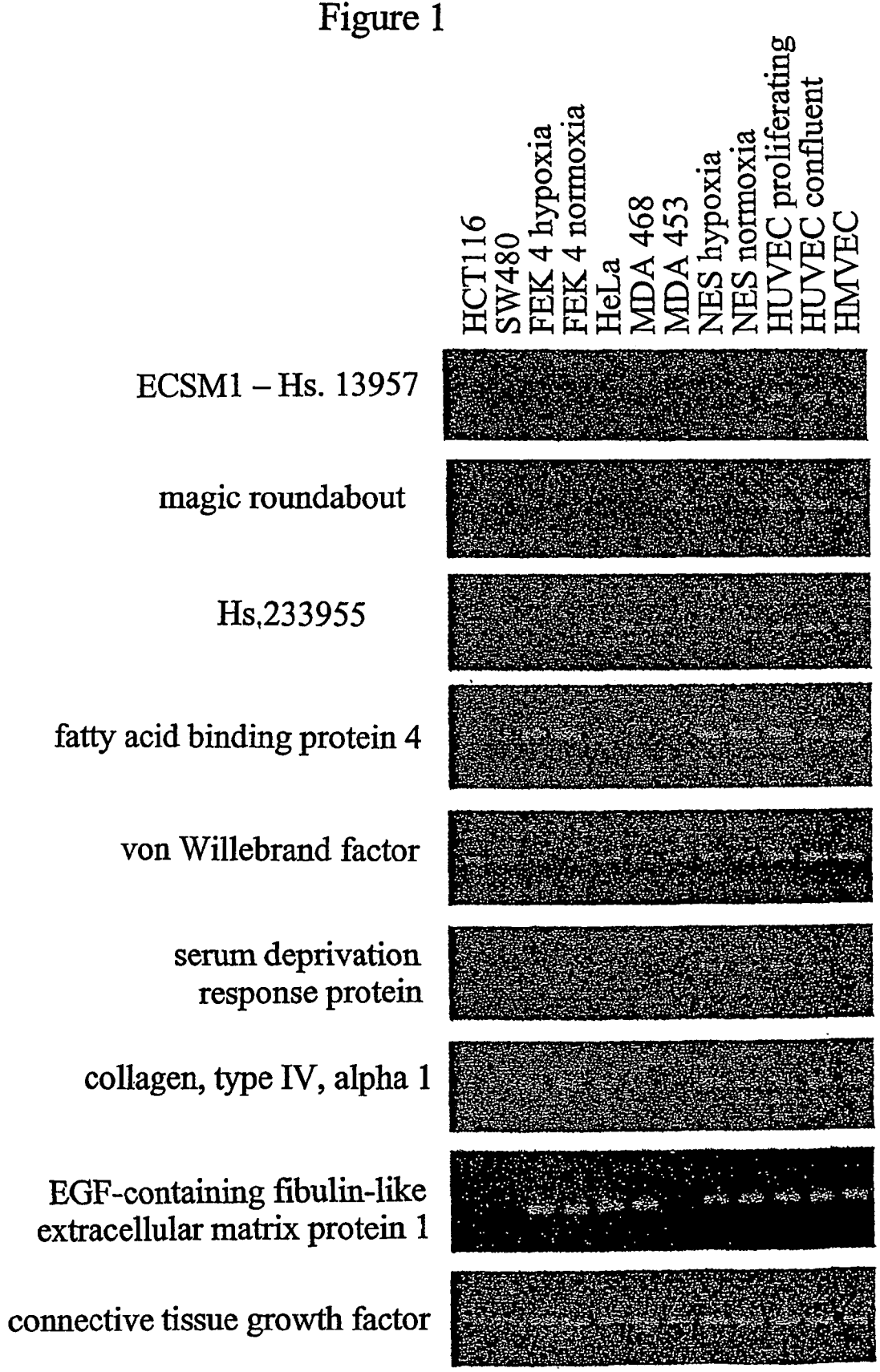

Gerhold, D. and Caskey, C.T. It's the genes! EST access to human genome content. Bioessays. Dec. 1996;18(12):973-81. Review.

Ginsburg, D. et al., Human von Willebrand factor (vWF): isolation of complementary DNA (cDNA) clones and chromosomal localization. Science. Jun. 21, 1985;228(4706):1401-6.

Hayward, C.P. et al., An autosomal dominant, qualitative platelet disorder associated with multimerin deficiency, abnormalities in platelet factor V, thrombospondin, von Willebrand factor, and fibrinogen and an epinephrine aggregation defect. Blood. Jun. 15, 1996;87(12):4967-78.

Hayward, C.P. et al; Multimerin is found in the alpha-granules of resting platelets and is synthesized by a megakaryocytic cell line. J Clin Invest. Jun. 1993;91(6):2630-9.

Hayward, C.P. et al., Studies of multimerin in human endothelial cells. Blood. Feb. 15, 1998;91(4):1304-17.

von Heijne, G., Membrane protein structure prediction. Hydrophobicity analysis and the positive-inside rule. J Mol Biol. May 20, 1992;225(2):487-94.

Höckel, M. and Vaupel, P. Tumor hypoxia: definitions and current clinical, biologic, and molecular aspects. J Natl Cancer Inst. Feb. 21, 2001;93(4):266-76. Review.

Huminiecki, L. et al., Magic roundabout is a new member of the roundabout receptor family that is endothelial specific and expressed at sites of active angiogenesis. Genomics. Apr. 2002;79(4):547-52.

Huminiecki, L., In Silico cloning of novel endothelial specific genes: Their role in Angiogenesis. Angiogenesis. 2001; 7:220-221.

Huminiecki, L. and Bicknell, R. In silico cloning of novel endothelial-specific genes. Genome Res. Nov. 2000;10(11):1796-806.

Itoh, K. et al., Expression profile of active genes in granulocytes. Blood. Aug. 15, 1998;92(4):1432-41.

Kidd, T. et al., Roundabout controls axon crossing of the CNS midline and defines a novel subfamily of evolutionarily conserved guidance receptors. Cell. Jan. 23, 1998;92(2):205-15.

Lassalle, P. et al., ESM-1 is a novel human endothelial cell-specific molecule expressed in lung and regulated by cytokines. J Biol Chem. Aug. 23, 1996;271(34):20458-64.

Li, H.S. et al., Vertebrate slit, a secreted ligand for the transmembrane protein roundabout, is a repellent for olfactory bulb axons. Cell. Mar. 19, 1999;96(6):807-18.

Matthews, W. et al., A receptor tyrosine kinase cDNA isolated from a population of enriched primitive hematopoietic cells and exhibiting close genetic linkage to c-kit. Proc Natl Acad Sci U S A. Oct. 15, 1991;88(20):9026-30.

Maxwell, P.H. et al., The tumour suppressor protein VHL targets hypoxia-inducible factors for oxygen-dependent proteolysis. Nature. May 20, 1999;399(6733):271-5.

Nichols, W.L. et al., Identification of human megakaryocyte coagulation factor V. Blood. Jun. 1985;65(6):1396-406.

Nielsen, H. et al., Identification of prokaryotic and eukaryotic signal peptides and prediction of their cleavage sites. Protein Eng. Jan. 1997;10(1):1-6.

Obermair, A. et al., Vascular endothelial growth factor and its receptors in male fertility. Fertil Steril. Aug. 1999;72(2):269-75.

Partanen, J. et al., A novel endothelial cell surface receptor tyrosine kinase with extracellular epidermal growth factor homology domains. Mol Cell Biol. Apr. 1992;12(4):1698-707.

Petrenko, O. et al., The molecular characterization of the fetal stem cell marker AA4. Immunity. Jun. 1999;10(6):691-700.

Sato, T.N. et al., Tie-1 and tie-2 define another class of putative receptor tyrosine kinase genes expressed in early embryonic vascular system. Proc Natl Acad Sci U S A. Oct. 15, 1993;90(20):9355-8. Erratum in: Proc Natl Acad Sci U S A Dec. 15, 1993;90(24):12056.

Sato, T.N. et al., Distinct roles of the receptor tyrosine kinases Tie-1 and Tie-2 in blood vessel formation. Nature. Jul. 6, 1995;376(6535):70-4.

Schuler, G.D., Pieces of the puzzle: expressed sequence tags and the catalog of human genes. J Mol Med. Oct. 1997;75(10):694-8. Review.

Shalaby, F. et al., Failure of blood-island formation and vasculogenesis in Flk-1-deficient mice. Nature. Jul. 6, 1995;376(6535):62-6.

Shibuya, M. et al., Nucleotide sequence and expression of a novel human receptor-type tyrosine kinase gene (flt) closely related to the fms family. Oncogene. Apr. 1990;5(4):519-24.

Skolnick, J. and Fetrow, J.S. From genes to protein structure and function: novel applications of computational approaches in the genomic era. Trends Biotechnol. Jan. 2000;18(1):34-9. Review.

Soker, S. et al., Neuropilin-1 is expressed by endothelial and tumor cells as an isoform-specific receptor for vascular endothelial growth factor. Cell. Mar. 20, 1998;92(6):735-45.

Sporn, L.A. et al., Biosynthesis of von Willebrand protein by human megakaryocytes. J Clin Invest. Sep. 1985;76(3):1102-6.

Strausberg, R.L. et al., New opportunities for uncovering the molecular basis of cancer. Nat Genet. Apr. 1997;15 Spec No. 415-6.

Suda, T. et al., Hematopoiesis and angiogenesis. Int J Hematol. Feb. 2000;71(2):99-107. Review.

Stein, C.A. and Cheng, Y.C. Antisense oligonucleotides as therapeutic agents—is the bullet really magical? Science. Aug. 20, 1993;261(5124):1004-12. Review.

Tamura, N. et al., cDNA cloning and gene expression of human type Ialpha cGMP-dependent protein kinase. Hypertension. Mar. 1996;27(3 Pt 2):552-7.

Vasmatzis, G. et al., Discovery of three genes specifically expressed in human prostate by expressed sequence tag database analysis. Proc Natl Acad Sci U S A. Jan. 6, 1998;95(1):300-4.

Velculescu, V.E. et al., Serial analysis of gene expression. Science. Oct. 20, 1995;270(5235):484-7.

Verma, I.M. and Somia, N. Gene therapy—promises, problems and prospects. Nature. Sep. 18, 1997;389(6648):239-42.

Vikkula, M. et al., Vascular dysmorphogenesis caused by an activating mutation in the receptor tyrosine kinase TIE2. Cell. Dec. 27, 1996;87(7):1181-90.

Welle, S. et al., Inventory of high-abundance mRNAs in skeletal muscle of normal men. Genome Res. May 1999;9(5):506-13.

Ziegler, B.L. et al., KDR receptor: a key marker defining hematopoietic stem cells. Science. Sep. 3, 1999;285(5433):1553-8.

GenBank Accession No. Q9NWJ8; Tanigami (Feb. 2000).

GenBank Accession No. AK025195; Sugano et al. (Aug. 2000).

GenBank Accession No. BB536291; Arakawa et al. (Jun. 2000).

GenBank Accession No. AC011562; Birren et al. (Oct. 1999).

GenBank Accession No. AK000805; Sugano et al. (Feb. 2000).

GENBANK Submission; NIH/NCBI; Accession No. AAL31867; Huminiecki. (PRI Nov. 15, 2001).

GENBANK Submission; NIH/NCBI; Accession No. AF361473; Huminiecki. (PRI Nov. 15, 2001).

[No Author] Recombinant Mouse EphA2/Fc Chimera. R &D Systems, Catalog No. 639-A2. Lot No. BCB08. Mar. 31, 2005.

Aaronson et al., Toward the development of a gene index to the human genome: an assessment of the nature of high-throughput EST sequence data. Genome Res. Sep. 1996;6(9):829-45.

Abbas et al., "Antibodies and Antigens" Cellular and Molecular Immunology, $2^{nd}$ edition 1994;41-43.

Adams et al., Initial assessment of human gene diversity and expression patterns based upon 83 million nucleotides of cDNA sequence. Nature. Sep. 28, 1995;377(6547 Suppl):3-174.

Adams et al., Roles of ephrinB ligands and EphB receptors in cardiovascular development: demarcation of arterial/venous domains, vascular morphogenesis, and sprouting angiogenesis. Genes Dev. Feb. 1, 1999;13(3):295-306.

Aiello et al., Suppression of retinal neovascularization in vivo by inhibition of vascular endothelial growth factor (VEGF) using soluble VEGF-receptor chimeric proteins. Proc Natl Acad Sci U S A. Nov. 7, 1995;92(23):10457-61.

AngioKit Protocol, Catalogue No. ZHA-1000, by TCS CellWorks Ltd, Buckingham MK18 2LR, UK.

Asano et al., Inhibition of tumor growth and metastasis by an immunoneutralizing monoclonal antibody to human vascular endothelial growth factor/vascular permeability factor121. Cancer Res. Nov. 15, 1995;55(22):5296-301.

Auerbach et al., Angiogenesis assays: problems and pitfalls. Cancer Metastasis Rev. 2000;19(1-2):167-72. Review.

Banerji et al., LYVE-1, a new homologue of the CD44 glycoprotein, is a lymph-specific receptor for hyaluronan. J Cell Biol. Feb. 22, 1999;144(4):789-801.

Bashaw et al., Chimeric axon guidance receptors: the cytoplasmic domains of slit and netrin receptors specify attraction versus repulsion. Cell. Jun. 25, 1999;97(7):917-26.

Bashaw et al., Repulsive axon guidance: Abelson and Enabled play opposing roles downstream of the roundabout receptor. Cell. Jun. 23, 2000;101(7):703-15.

Bates et al., Identification and analysis of a novel member of the ubiquitin family expressed in dendritic cells and mature B cells. Eur J Immunol. Oct. 1997;27(10):2471-7.

BD BioCoat TM Angiogenesis System—Endothelial Cell Migration; available as Catalog No. 354143 from BD Biosciences, Bedford, MA (2002).

Bernstein et al., Characterization of a human fovea cDNA library and regional differential gene expression in the human retina. Genomics. Mar. 15, 1996;32(3):301-8.

Bohlen et al., Chapter 24: Vascular Endothelial Growth Factor Receptor: Antibodies for Anti-Angiogenesis Therapy. Tumor Angiogenesis: Basic Mechanisms and Cancer Therapy. Dieter Marmé and Norbert Fusenig, eds. Published by Springer, 2007: 425-452. ISBN 354033176X, 9783540331766.

Boyle et al., DNA immunization: induction of higher avidity antibody and effect of route on T cell cytotoxicity. Proc Natl Acad Sci U S A. Dec. 23, 1997;94(26):14626-31.

Carmeliet et al., Angiogenesis in cancer and other diseases. Nature. Sep. 14, 2000;407(6801):249-57.

Casset et al., A peptide mimetic of an anti-CD4 monoclonal antibody by rational design. Biochem Biophys Res Commun Jul. 18, 2003;307(1):198-205.

Chatterjee et al., Idiotypic antibody immunotherapy of cancer. Cancer Immunol Immunother. Feb. 1994;38(2):75-82.

Cross et al., FGF and VEGF function in angiogenesis: signalling pathways, biological responses and therapeutic inhibition. Trends Pharmacol Sci. Apr. 2001;22(4):201-7.

Dermer, Another anniversary for the war on cancer. Biotechnology. 1994;12:320.

Dobrzanski et al., Antiangiogenic and antitumor efficacy of EphA2 receptor antagonist. Cancer Res. Feb. 1, 2004;64(3):910-9.

Freshney et al., Culture of Animal Cells. A Manual of Basic Technique. Alan R. Liss, Inc. 1983; New York: 3-4.

Gariano et al., Retinal angiogenesis in development and disease. Nature. Dec. 15, 2005;438(7070):960-6.

Goetze et al., Leptin induces endothelial cell migration through Akt, which is inhibited by PPARgamma-ligands. Hypertension. Nov. 2002;40(5):748-54.

Gura et al., Systems for identifying new drugs are often faulty. Science. Nov. 7, 1997;278(5340):1041-2.

Hagedorn et al., A short peptide domain of platelet factor 4 blocks angiogenic key events induced by FGF-2. FASEB J. Mar. 2001;15(3):550-2. Epub Jan. 5, 2001.

Holm et al., Functional mapping and single chain construction of the anti-cytokeratin 8 monoclonal antibody TS1. Mol Immunol. Feb. 2007;44(6):1075-84. Epub Sep. 20, 2006.

Hori et al., Differential effects of angiostatic steroids and dexamethasone on angiogenesis and cytokine levels in rat sponge implants. Br J Pharmacol. Aug. 1996;118(7):1584-91.

Hortsch, The L1 family of neural cell adhesion molecules: old proteins performing new tricks. Neuron. Oct. 1996;17(4):587-93.

Jain et al., Tumor angiogenesis and accessibility: role of vascular endothelial growth factor. Semin Oncol. Dec. 2002;29(6 Suppl 16):3-9.

Jain, Barriers to drug delivery in solid tumors. Sci Am. Jul. 1994;271(1):58-65.

Kettleborough et al., Humanization of a mouse monoclonal antibody by CDR-grafting: the importance of framework residues on loop conformation. Protein Eng. Oct. 1991;4(7):773-83.

Khurana et al., Role of angiogenesis in cardiovascular disease: a critical appraisal. Circulation. Sep. 20, 2005;112(12):1813-24.

Kuwano et al., Angiogenesis factors. Intern Med. Jul. 2001;40(7):565-72.

Landis et al., The measurement of observer agreement for categorical data. Biometrics. Mar. 1977;33(1):159-74.

Legg et al., Slits and Roundabouts in cancer, tumour angiogenesis and endothelial cell migration. Angiogenesis. 2008;11(1):13-21. Epub Feb. 9, 2008. Review.

Maier et al., In vitro inhibition of endothelial cell growth by the antiangiogenic drug AGM-1470 (TNP-470) and the anti-endoglin antibody TEC-11. Anticancer Drugs. Mar. 1997;8(3):238-44.

Miller et al., Synthesis and antitumor activity of boronated dipeptides containing aromatic amino acids. Anticancer Res. Sep.-Oct. 1997;17(5A):3299-306.

Min et al., Capsaicin inhibits in vitro and in vivo angiogenesis. Cancer Res. Jan. 15, 2004;64(2):64451.

Park et al., Robo4 is a vascular-specific receptor that inhibits endothelial migration. Dev Biol. Sep. 1, 2003;261(1):251-67.

Rudikoff et al., Single amino acid substitution altering antigen-binding specificity. Proc Natl Acad Sci U S A. Mar. 1982;79(6):1979-83.

Ruggeri et al., CEP-7055: a novel, orally active pan inhibitor of vascular endothelial growth factor receptor tyrosine kinases with potent antiangiogenic activity and antitumor efficacy in preclinical models. Cancer Res. Sep. 15, 2003;63(18):5978-91.

Rupnick et al., Adipose tissue mass can be regulated through the vasculature. Proc Natl Acad Sci U S A. Aug 6, 2002;99(16):10730-5. Epub Jul. 29, 2002.

Seaver et al., Monoclonal antibodies in industry: more difficult than originally thought. Genetic Engineering News. Aug. 1994;14(14):10 and 21.

Sierra-Honigmann et al., Biological action of leptin as an angiogenic factor. Science. Sep. 11, 1998;281(5383):1683-6.

Smith, Angiogenesis, vascular endothelial growth factor and the endometrium. Hum Reprod Update. Sep.-Oct. 1998;4(5):509-19.

Staton et al., Current methods for assaying angiogenesis in vitro and in vivo. Int J Exp Pathol. Oct. 2004;85(5):233-48. Review.

Sun et al., Blocking angiogenesis and tumorigenesis with GFA-116, a synthetic molecule that inhibits binding of vascular endothelial growth factor to its receptor. Cancer Res. May 15, 2004;64(10):3586-92.

Trachsel et al., Antibodies for angiogenesis inhibition, vascular targeting and endothelial cell transcytosis. Adv Drug Deliv Rev. Aug. 7, 2006;58(5-6):735-54. Epub May 20, 2006.

Trikha et al., CNTO 95, a fully human monoclonal antibody that inhibits alphav integrins, has antitumor and antiangiogenic activity in vivo. Int J Cancer. Jun. 20, 2004;110(3):326-35.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Van Der Schaft et al., The designer anti-angiogenic peptide anginex targets tumor endothelial cells and inhibits tumor growth in animal models. FASEB J. Dec. 2002;16(14):1991-3. Epub Oct. 18, 2002.

Verhoeyen et al., Reshaping human antibodies: grafting an antilysozyme activity. Science. Mar. 25, 1998;239(4847):1534-6.

West et al., Chapter 11: Three-Dimensional in Vitro Angiogenesis in the Rat Aortic Ring Model. Methods in Molecular Biology, Angiogenesis Protocols. S. Martin and C. Murray, eds. $2^{nd}$ Ed: 467:189-210. Humana Press, 2009.

Fuchs et al., Species specificity of anti-acetylcholine receptor antibodies elicited by synthetic peptides. Biochemistry. Jul. 28, 1987;26(15):4611-4616.

Oshima et al., Generation of species-specific antihemoglobin antibodies by immunization with synthetic peptides of human hemoglobin. Protein Chem. Dec. 1989;8(6):767-778.

Rankin et al., Regulation of left-right patterning in mice by growth/differentiation factor-1. Nat Genet. Mar. 2000;24(3):262-265.

Sipos et al., Cloning and sequencing of the genes coding for the 10- and 60-kDa heat shock proteins from Pseudomonas aeruginosa and mapping of a species-specific epitope. Infect Immun. Sep. 1991;59(9):3219-3226.

* cited by examiner

Figure 2 (page 1 of 2)

```
    TGTCTGCTTATGCGGTGGCTCGCTGCTCAGAACAGGATGGCAGAGATGAGCACCACCATC
  1 ------+---------+---------+---------+---------+---------+  60
    AAAAACTCAAGGACCAGTGCTGTGGGTCCAGTCATCTGTTTCATGGAATTCACCAGTCTG
 61 ------+---------+---------+---------+---------+---------+ 120

GTATCTTCAAAATCCAGAAGGATGATGGCAGAGATGGCAGGAAGAGGAAGAGGGTAATCTG
121 ------+---------+---------+---------+---------+---------+ 180
                              M  A  G  R  R  K  R  V  I  W

GAAGAGTTTCCGGACCTACTCTGCTGTGTGATTAAACAACCACCAGGAAATTTTGATGA
181 ------+---------+---------+---------+---------+---------+ 240
     K  S  F  R  T  Y  S  A  A  V  I  K  Q  P  P  G  N  F  D  D

CACTGTTCTCCTGAGCTCCCTCCCTTTCCTCGGGGAAGAAAAGCATTGAAACTACAAAAAT
241 ------+---------+---------+---------+---------+---------+ 300
     T  V  L  L  S  S  L  S  S  G  K  K  S  I  E  T  T  K  I

AAAGTGTATTGGCTGGAGTGAGGTCTCAGTGTCTGCTTATGCGGTGGCTCGCTGCTCAG
301 ------+---------+---------+---------+---------+---------+ 360
     K  C  Y  L  A  G  V  R  S  H  V  C  L  C  G  G  S  L  L  R

AACAGGGAACCATTGGAGATACTCATTACTCTTTGAAGGCTTACAGTGGAATGGAATTCAA
361 ------+---------+---------+---------+---------+---------+ 420
     T  G  N  H  W  R  Y  S  L  L  F  E  G  L  Q  W  N  E  F  K

ATACGACTTATTTGAGGAATTGAAGTTGACTTTATGGAGCTGATAAGAATCTTCTTGGAG
421 ------+---------+---------+---------+---------+---------+ 480
     Y  D  L  F  E  E  L  K  L  T  L  W  S  *

AAAAAAGACTGGTACTTCTGAATTAACCAAAATCACAGTATTCTGAAGATGATTCTACA
481 ------+---------+---------+---------+---------+---------+ 540
```

Figure 2 (page 2 of 2)

```
541  AAGCCTGCTGTTTCTACAAAGGCTGCTGATGATTCTACAAAGCCTGCTGTAGTGTTGCT  600
601  GTGGCCTCTGCTTAAAAAGTAGAAAACACATTGATGCAGCATGTTCACCCCAACCTCCC  660
661  TGCCTAAAGGCCTCAGGGGCCCCTCCTTGGGAAGAGGGAAGGGCGCCGTGAGGATTGGTA  720
721  AAGAGCCCGAATTAGGGGGGATGGGAGTGGTGGGAGAATAAGGGGACACCTTCCATCCT  780
781  TGGGATGCTCACCCTGCCCAAATTGACCTTCCTGATGAAAGGCCAGCTCCCAGAAATGTG  840
841  CCCTACAGTTACCTACTTTCACCCTAAACCCTGCCCTTAGTCAAATCCTTTCTTTTTT  900
901  AAGCAATCAACTTCAATTCCTTGTATAACCCCAGTATAAAAGGGCTTTTATACCATTCT  960
961  ATCCTATTGCATGTAAGCCTTGGGTTTGGGAGGTAACAGTGTGGGATTCCCCCATTTCAT  1020
1021 TTCCCTGCCACCCAAACATGCCTGTTTTTTTTTAAGCAATATTAAATGTTTGTACTTCAG  1080
1081 AAAAAAAAAAAAAAAAAAAA  1100
```

Figure 4 (page 1 of 3)

```
    AACTGGTTGCGACACTGCGGTGTTGCACTCTGGCTGCTGCTTCTGGGCACCGCTGTGTGT
  1 ---------+---------+---------+---------+---------+---------+ 60
      N  W  L  R  H  C  G  V  A  L  W  L  L  L  L  G  T  A  V  C  -

ATCCACCGCCGTCGCCGAGCTAGGGTGCTTCTGGGCCCAGGTCTGTACAGATATACCAGT
 61 ---------+---------+---------+---------+---------+---------+ 120
      I  H  R  R  R  R  A  R  V  L  L  G  P  G  L  Y  R  Y  T  S  -

GAGGATGCCATCCTAAAACACAGGATGGATCACAGTGACTCCCAGTGGTTGGCAGACACT
121 ---------+---------+---------+---------+---------+---------+ 180
      E  D  A  I  L  K  H  R  M  D  H  S  D  S  Q  W  L  A  D  T  -

TGGCGTTCCACCTCTGGCTCTCGGGACCTGAGCAGCAGCAGCAGCCTCAGCAGTCGGCTG
181 ---------+---------+---------+---------+---------+---------+ 240
      W  R  S  T  S  G  S  R  D  L  S  S  S  S  S  L  S  S  R  L  -

GGGGCGGATGCCCGGGACCCACTAGACTGTCGTCGCTCCTTGCTCTCCTGGGACTCCCGA
241 ---------+---------+---------+---------+---------+---------+ 300
      G  A  D  A  R  D  P  L  D  C  R  R  S  L  L  S  W  D  S  R  -

AGCCCCGGCGTGCCCCTGCTTCCAGACACCAGCACTTTTTATGGCTCCCTCATCGCTGAG
301 ---------+---------+---------+---------+---------+---------+ 360
      S  P  G  V  P  L  L  P  D  T  S  T  F  Y  G  S  L  I  A  E  -

CTGCCCTCCAGTACCCCAGCCAGGCCAAGTCCCCAGGTCCCAGCTGTCAGGCGCCTCCCA
361 ---------+---------+---------+---------+---------+---------+ 420
      L  P  S  S  T  P  A  R  P  S  P  Q  V  P  A  V  R  R  L  P  -

CCCCAGCTGGCCCAGCTCTCCAGCCCCTGTTCCAGCTCAGACAGCCTCTGCAGCCGCAGG
421 ---------+---------+---------+---------+---------+---------+ 480
      P  Q  L  A  Q  L  S  S  P  C  S  S  S  D  S  L  C  S  R  R  -

GGACTCTCTTCTCCCCGCTTGTCTCTGGCCCCTGCAGAGGCTTGGAAGGCCAAAAAGAAG
481 ---------+---------+---------+---------+---------+---------+ 540
      G  L  S  S  P  R  L  S  L  A  P  A  E  A  W  K  A  K  K  K  -

CAGGAGCTGCAGCATGCCAACAGTTCCCCACTGCTCCGGGGCAGCCACTCCTTGGAGCTC
541 ---------+---------+---------+---------+---------+---------+ 600
      Q  E  L  Q  H  A  N  S  S  P  L  L  R  G  S  H  S  L  E  L  -

CGGGCCTGTGAGTTAGGAAATAGAGGTTCCAAGAACCTTTCCCAAAGCCCAGGGGCTGTG
601 ---------+---------+---------+---------+---------+---------+ 660
      R  A  C  E  L  G  N  R  G  S  K  N  L  S  Q  S  P  G  A  V  -
```

Figure 4 (page 2 of 3)

```
        CCCCAAGCTCTGGTTGCCTGGCGGGCCCTGGGACCGAAACTCCTCAGCTCCTCAAATGAG
  661   ---------+---------+---------+---------+---------+---------+  720
         P  Q  A  L  V  A  W  R  A  L  G  P  K  L  L  S  S  S  N  E   -

CTGGTTACTCGTCATCTCCCTCCAGCACCCCTCTTTCCTCATGAAACTCCCCCAACTCAG
  721   ---------+---------+---------+---------+---------+---------+  780
         L  V  T  R  H  L  P  P  A  P  L  F  P  H  E  T  P  P  T  Q   -

AGTCAACAGACCCAGCCTCCGGTGGCACCACAGGCTCCCTCCTCCATCCTGCTGCCAGCA
  781   ---------+---------+---------+---------+---------+---------+  840
         S  Q  Q  T  Q  P  P  V  A  P  Q  A  P  S  S  I  L  L  P  A   -

GCCCCCATCCCCATCCTTAGCCCCTGCAGTCCCCCTAGCCCCCAGGCCTCTTCCCTCTCT
  841   ---------+---------+---------+---------+---------+---------+  900
         A  P  I  P  I  L  S  P  C  S  P  P  S  P  Q  A  S  S  L  S   -

GGCCCCAGCCCAGCTTCCAGTCGCCTGTCCAGCTCCTCACTGTCATCCCTGGGGGAGGAT
  901   ---------+---------+---------+---------+---------+---------+  960
         G  P  S  P  A  S  S  R  L  S  S  S  S  L  S  S  L  G  E  D   -

CAAGACAGCGTGCTGACCCCTGAGGAGGTAGCCCTGTGCTTGGAACTCAGTGAGGGTGAG
  961   ---------+---------+---------+---------+---------+---------+ 1020
         Q  D  S  V  L  T  P  E  E  V  A  L  C  L  E  L  S  E  G  E   -

GAGACTCCCAGGAACAGCGTCTCTCCCATGCCAAGGGCTCCTTCACCCCCCACCACCTAT
 1021   ---------+---------+---------+---------+---------+---------+ 1080
         E  T  P  R  N  S  V  S  P  M  P  R  A  P  S  P  P  T  T  Y   -

GGGTACATCAGCGTCCCAACAGCCTCAGAGTTCACGGACATGGGCAGGACTGGAGGAGGG
 1081   ---------+---------+---------+---------+---------+---------+ 1140
         G  Y  I  S  V  P  T  A  S  E  F  T  D  M  G  R  T  G  G  G   -

GTGGGGCCCAAGGGGGGAGTCTTGCTGTGCCCACCTCGGCCCTGCCTCACCCCCACCCCC
 1141   ---------+---------+---------+---------+---------+---------+ 1200
         V  G  P  K  G  G  V  L  L  C  P  P  R  P  C  L  T  P  T  P   -

AGCGAGGGCTCCTTAGCCAATGGTTGGGGCTCAGCCTCTGAGGACAATGCCGCCAGCGCC
 1201   ---------+---------+---------+---------+---------+---------+ 1260
         S  E  G  S  L  A  N  G  W  G  S  A  S  E  D  N  A  A  S  A   -

AGAGCCAGCCTTGTCAGCTCCTCCGATGGCTCCTTCCTCGCTGATGCTCACTTTGCCCGG
 1261   ---------+---------+---------+---------+---------+---------+ 1320
         R  A  S  L  V  S  S  S  D  G  S  F  L  A  D  A  H  F  A  R   -
```

Figure 4 (page 3 of 3)

```
     GCCCTGGCAGTGGCTGTGGATAGCTTTGGTTTCGGTCTAGAGCCCAGGGAGGCAGACTGC
1321 ---------+---------+---------+---------+---------+---------+ 1380
      A  L  A  V  A  V  D  S  F  G  F  G  L  E  P  R  E  A  D  C   -

GTCTTCATAGGTATGTGAGGTCTCCCCATCTTACTCCTCACTCATGCCCCTTGCCTTTCT
1381 ---------+---------+---------+---------+---------+---------+ 1440
      V  F  I  G  M  *                                              -

AACAACTGTTATCATGTCATCATTGTTAAAAAAAAAAAAAAAAAAAAAAAAAAAAAAA
1441 ---------+---------+---------+---------+---------+------ 1496
```

Figure 5 (page 1 of 3)

ECSM4 Length: 2076

```
   1 AGGGGACTCT CTTCTCCCCG CTTGTCTCTG GCCCCTGCAG AGGCTTGGAA
  51 GGCCAAAAAG AAAGCAGGAG CTGCAGCATG CCAACAGTTC CCCACTGCTC
 101 CGGGGCAGCC ACTCCTTAGA GCTCCGGGCC TGTGAGTTAG GAAATAGAGG
 151 TTCCAAGAAC CTTTCCCAAA GCCCAGGAGC TGTGCCCCAA GCTCTGGTTG
 201 CCTGGCGGGC CCTGGGACCG AAACTCCTCA GCTCCTCAAA TGAGCTGGTT
 251 ACTCGTCATC TCCCTCCAGC ACCCTCTTT CCTCATGAAA CTCCCCCAAC
 301 TCAGAGTCAA CAGACCCAGC CTCCGGTGGC ACCACAGGCT CCCTCCTCCA
 351 TCCTGCTGCC AGCAGCCCCC ATCCCCATCC TTAGCCCCTG CAGTCCCCCT
 401 AGCCCCCAGG CCTCTTCCCT CTCTGGCCCC AGCCCAGCTT CCAGTCGCCT
 451 GTCCAGCTCC TCACTGTCAT CCCTGGGGGA GGATCAAGAC AGCGTGCTGA
 501 CCCCTGAGGA GGTAGCCCTG TGCTTGGAAC TCAGTGAGGG TGAGGAGACT
 551 CCCAGGAACA GCGTCTCTCC CATGCCAAGG GTTCCTTCAC CCCCCACCAC
 601 CTATGGGTAC ATCAGCGTCC CAACAGCCTC AGAGTTCACG GACATGGGCA
 651 GGACTGGAGG AGGGGTGGGG CCCAAGGGGG GAGTCTTGCT GTGCCCACCT
 701 CGGCCCTGCC TCACCCCCAC CCCCAGCGAG GGCTCCTTAG CCAATGGTTG
 751 GGGCTCAGCC TCTGAGGACA ATGCCGCCAG CGCCAGAGCC AGCCTTGTCA
 801 GCTCCTCCGA TGGCTCCTTC CTCGCTGATG CTCACTTTGC CCGGGCCCTG
 851 GCAGTGGCTG TGGATAGCTT TGGTTTCGGT CTAGAGCCCA GGGAGGCAGA
 901 CTGCGTCTTC ATAGATGCCT CATCACCTCC CTCCCACGG GATTGAGATC
 951 TTCCTGACCC CCAACCTCTC CCTGCCCCTG TGGGAAGTGG AGGCCAGACT
1001 GGTTGGAAGA CAATGGAAGG TCAGCCACAC CCAGCGGCTG GGAAGGGGGA
1051 TGCCTCCCTG GCCCCTGAC TCTCAGATCT CTTCCCAGAG AAGTCAGCTC
1101 CACTGTCGTA TGCCCAAGGG TGGGTGCTTC TCCTGTAGAT TACTCCTGAA
1151 CCGTGTCCCT GAGACTTCCC AGACGGGAAT CAGAACCACT TCTCCTGTCC
1201 ACCCACAAGA CCTGGGCTGT GGTGTGTGGG TCTTGGCCTG TGTTTCTCTG
1251 CAGCTGGGGT CCACCTTCCC AAGCCTCCAG AGAGTTCTCC CTCCACGATT
1301 GTGAAAACAA ATGAAAACAA AATTAGAGCA AAGCTGTACC TGGGAGCCCT
```

Figure 5 (page 2 of 3)

```
1351  CAGGGAGCAA AACATCATCT CCACCTGACT CCTAGCCACT GCTTTCTCCT
1401  CTGTGCCATC CACTCCCACC ACCCAGGTTG TTTTTGGCCT GAAGGAGCAA
1451  GCCCTGCCTG CTGGCTTTTC CCCCCAACCA TTTGGGATTC ACAGGGAAGT
1501  GGGAGGGAGC CCAGAGGGTG GCCTTTTGTG GGAGGGACAG CAGTGGCTGC
1551  TGGGGAGAG GGCTGTGGAG GAAGGAGCTT CTCGGAGCCC CCTCTCAGCC
1601  TTACCTGGGC CCCTCCTCTA GAGAAGAGCT CAACTCTCTC CCAACCCTCA
1651  CCAATGGAAA GAAAATAATT ATGAATGCCG ACTGAGGCAC TGAGGCCCCT
1701  ACCTCATGCC CAAAACAAAG GGGTTCAAGG CTGGGTCTAG CGAGGATGCT
1751  TGAAGGAAGG GAGGTATGGA GCCCGTAGGT CAAAAGCACC CATCCTCGTA
1801  CTGTTGTCAC TATGAGCTTA AGAAATTTGA TACCATAAAA TGGTAAAGAC
1851  TTGAGTTCTG TGAGATCATT CCCCGGAGCA CCATTTTTAG GGGAGCACCT
1901  GGAGAGATGG CAAGAATTTC CTGAGTTAGG CAGGGATCAG GCATTCATTG
1951  ACACTCAGGG AGTGTCACAC ATTTCTGTTC TGCAATTAAA GGGAGAATGA
2001  GGTTCATCCA CCAAATTTTA AGCAGAATAT AGGAAGGGCA GGGGTGGGGA
2051  GTTTCAGGGT CTGCTGGTCC TGGGCA
```

Figure 5 (page 3 of 3)

START: 2    STOP: 948

Translation:

Length: 315

```
  1  GDSLLPACLW PLQRLGRPKR KQELQHANSS PLLRGSHSLE LRACELGNRG

51  SKNLSQSPGA VPQALVAWRA LGPKLLSSSN ELVTRHLPPA PLFPHETPPT

101  QSQQTQPPVA PQAPSSILLP AAPIPILSPC SPPSPQASSL SGPSPASSRL

151  SSSSLSSLGE DQDSVLTPEE VALCLELSEG EETPRNSVSP MPRVPSPPTT

201  YGYISVPTAS EFTDMGRTGG GVGPKGGVLL CPPRPCLTPT PSEGSLANGW

251  GSASEDNAAS ARASLVSSSD GSFLADAHFA RALAVAVDSF GFGLEPREAD

301  CVFIDASSPP SPRD*
```

Figure 6 (page 1 of 2)

```
Gap Weight:      50      Average Match: 10.000
    Length Weight:    3    Average Mismatch:  0.000

Quality:   9397            Length:   2553
             Ratio:  6.281              Gaps:      1
Percent Similarity: 92.738   Percent Identity: 92.738

Match display thresholds for the alignment(s):
                  | = IDENTITY
                  : = 5
                  . = 1 magic.seq x hs.111518.rev September 13, 2000 14:21  ..
```

```
451 TCCAGCTCAGACAGCCTCTGCAGCCGCAGGGGACTCTCTTCTCCCCGCTT 500
                                |||||||||||||||||||||||
  1 .........................AGGGGACTCTCTTCTCCCCGCTT 23

501 GTCTCTGGCCCCTGCAGAGGCTTGGAAGGCCAAAAAG.AAGCAGGAGCTG 549
    ||||||||||||||||||||||||||||||||||||| |||||||||||
 24 GTCTCTGGCCCCTGCAGAGGCTTGGAAGGCCAAAAAGAAAGCAGGAGCTG 73

550 CAGCATGCCAACAGTTCCCCACTGCTCCGGGGCAGCCACTCCTTGGAGCT 599
    |||||||||||||||||||||||||||||||||||||||||||| ||||
 74 CAGCATGCCAACAGTTCCCCACTGCTCCGGGGCAGCCACTCCTTAGAGCT 123

600 CCGGGCCTGTGAGTTAGGAAATAGAGGTTCCAAGAACCTTTCCCAAAGCC 649
    ||||||||||||||||||||||||||||||||||||||||||||||||||
124 CCGGGCCTGTGAGTTAGGAAATAGAGGTTCCAAGAACCTTTCCCAAAGCC 173

650 CAGGGGCTGTGCCCCAAGCTCTGGTTGCCTGGCGGGCCCTGGGACCGAAA 699
    ||||  |||||||||||||||||||||||||||||||||||||||||||
174 CAGGAGCTGTGCCCCAAGCTCTGGTTGCCTGGCGGGCCCTGGGACCGAAA 223

700 CTCCTCAGCTCCTCAAATGAGCTGGTTACTCGTCATCTCCCTCCAGCACC 749
    |||||||||||||||||||||||||||||||||||||||||||||||||
224 CTCCTCAGCTCCTCAAATGAGCTGGTTACTCGTCATCTCCCTCCAGCACC 273

750 CCTCTTTCCTCATGAAACTCCCCCAACTCAGAGTCAACAGACCCAGCCTC 799
    ||||||||||||||||||||||||||||||||||||||||||||||||||
274 CCTCTTTCCTCATGAAACTCCCCCAACTCAGAGTCAACAGACCCAGCCTC 323

800 CGGTGGCACCACAGGCTCCCTCCTCCATCCTGCTGCCAGCAGCCCCCATC 849
    ||||||||||||||||||||||||||||||||||||||||||||||||||
324 CGGTGGCACCACAGGCTCCCTCCTCCATCCTGCTGCCAGCAGCCCCCATC 373

850 CCCATCCTTAGCCCCTGCAGTCCCCCTAGCCCCCAGGCCTCTTCCCTCTC 899
    ||||||||||||||||||||||||||||||||||||||||||||||||||
374 CCCATCCTTAGCCCCTGCAGTCCCCCTAGCCCCCAGGCCTCTTCCCTCTC 423
```

Figure 6 (page 2 of 2)

```
 900 TGGCCCCAGCCCAGCTTCCAGTCGCCTGTCCAGCTCCTCACTGTCATCCC  949
     ||||||||||||||||||||||||||||||||||||||||||||||||||
 424 TGGCCCCAGCCCAGCTTCCAGTCGCCTGTCCAGCTCCTCACTGTCATCCC  473

950 TGGGGGAGGATCAAGACAGCGTGCTGACCCCTGAGGAGGTAGCCCTGTGC  999
     ||||||||||||||||||||||||||||||||||||||||||||||||||
 474 TGGGGGAGGATCAAGACAGCGTGCTGACCCCTGAGGAGGTAGCCCTGTGC  523

1000 TTGGAACTCAGTGAGGGTGAGGAGACTCCCAGGAACAGCGTCTCTCCCAT 1049
     ||||||||||||||||||||||||||||||||||||||||||||||||||
 524 TTGGAACTCAGTGAGGGTGAGGAGACTCCCAGGAACAGCGTCTCTCCCAT  573

1050 GCCAAGGGCTCCTTCACCCCCACCACCTATGGGTACATCAGCGTCCCAA  1099
     ||||||||| ||||||||||||||||||||||||||||||||||||||||
 574 GCCAAGGGTTCCTTCACCCCCACCACCTATGGGTACATCAGCGTCCCAA   623

1100 CAGCCTCAGAGTTCACGGACATGGGCAGGACTGGAGGAGGGGTGGGGCCC 1149
     ||||||||||||||||||||||||||||||||||||||||||||||||||
 624 CAGCCTCAGAGTTCACGGACATGGGCAGGACTGGAGGAGGGGTGGGGCCC  673

1150 AAGGGGGGAGTCTTGCTGTGCCCACCTCGGCCCTGCCTCACCCCCACCCC 1199
     ||||||||||||||||||||||||||||||||||||||||||||||||||
 674 AAGGGGGGAGTCTTGCTGTGCCCACCTCGGCCCTGCCTCACCCCCACCCC  723

1200 CAGCGAGGGCTCCTTAGCCAATGGTTGGGGCTCAGCCTCTGAGGACAATG 1249
     ||||||||||||||||||||||||||||||||||||||||||||||||||
 724 CAGCGAGGGCTCCTTAGCCAATGGTTGGGGCTCAGCCTCTGAGGACAATG  773

1250 CCGCCAGCGCCAGAGCCAGCCTTGTCAGCTCCTCCGATGGCTCCTTCCTC 1299
     ||||||||||||||||||||||||||||||||||||||||||||||||||
 774 CCGCCAGCGCCAGAGCCAGCCTTGTCAGCTCCTCCGATGGCTCCTTCCTC  823

1300 GCTGATGCTCACTTTGCCCGGGCCCTGGCAGTGGCTGTGGATAGCTTTGG 1349
     ||||||||||||||||||||||||||||||||||||||||||||||||||
 824 GCTGATGCTCACTTTGCCCGGGCCCTGGCAGTGGCTGTGGATAGCTTTGG  873

1350 TTTCGGTCTAGAGCCCAGGGAGGCAGACTGCGTCTTCATAGGTATGTGAG 1399
     |||||||||||||||||||||||||||||||||||||||||| |   | |
 874 TTTCGGTCTAGAGCCCAGGGAGGCAGACTGCGTCTTCATAGATGCCTCAT  923

1400 GTCTCCCCATCTTACTCCTCACTCATGCCCCTTGCCTTTCTAACAACTGT 1449
       | ||| |  ||       ||  |||  ||                | |
 924 CACCTCCCTCCCCACGGGATTGAGATCTTCCTGACCCCCAACCTCTCCCT  973

1450 TATCATGTCATCATTGTTAAAAAAAAAAAAAAAAAAAAAAAAAAAAAA... 1496
      | |||   |  ||      ||     |      || ||||    ||
 974 GCCCCTGTGGGAAGTGGAGGCCAGACTGGTTGGAAGACAATGGAAGGTCA 1023
```

Figure 7 (page 1 of 2)

Mouse magic roundabout contig sequence:

Length: 1271

```
  1  GGGTCTTTAC AGTTTTATAG AATTAAGTTC CTTAAGCTCA GAGTGGGGGT
 51  AGAAATGAGA ATAGGGAATT GGTTCCCTGT CTTCCTGCGT CCTTATCCTT
101  TCAGTCTCCT CCAATGATTT CACTTTGAAG GATTGAATGT GAGGCTGTAT
151  AGGGGCCAGT GCATCCAGAA CGTTTCTCCA TAAGTTTCCT TGGATGGTTG
201  TGAATGGGGA AAGGGTTGAG TTGGTGTTGT AAGGGAGGAG TCCAAGTTAA
251  TATTAGAGGG GTCTTCCACA GGTCCACCAA CAGAGGCCCT CACCAAAAAA
301  CATTTCTGTC CTTCCTGAAG ACCTGGTTGG CTTCCCTTCT TTCCATGATC
351  CACTTAGGCG GGAGCTCCGG AGCCAGGCTT ACTTAGGCCA AAGGTTCTGG
401  TTGTGGAGAG TCTGCTGTCC TGAAGATGCT GTCTTGTTCT CAGTGGGAAT
451  CCAAGACTCC CGTGATCATA TTTTGGTTTG CTTTCATTTA TTTTAACAAT
501  CCCAATGACA GAGCTCTCCA GAAGCCTAGT GACAGTGGAC TTCTATTACA
551  GAGAAGCATA GGCCAAGACC TCCACATGTG AGAAAGCCAG GGGACAGACA
601  GGAGAGTGGT CTGGGTGCTC TTCTGGCCTT CTCAGGGACA ATTCAGGAGG
651  AATCACACAG CCTTGGGCAC AGCACCAGTT AGCCAACTTC GCTGGGAAGA
```

Figure 7 (page 2 of 2)

```
701  GGCCCTAGAA TCAGGAGGCC AGGGAGGCAG CCCCCTCCCC AGCCTCTGGG
751  TGTGGCTGAT CTCAGCATCT TCCAACCAGT CTGGCCTCCA CTCCCACAAA
801  GGCAGAGAGA AGCTTCGGGT CAGGGAGAGA TCACCCCGAG GGGAGGGAGG
851  TGATGAGGCA TCAGTGAAGA CACAGTCAGC TTCCCTGGGA TCCAGACTGA
901  GGCCAAAGCT ATCCACAGCC ACTGCCAGGG CACGAGCAAA GTGAGTATCA
951  GCGAGGAAGG AGCCATCAGA AGAGCTAACC AGGCTGGCCC TGGCGCTGGG
1001 GACATTGTCC TCAGAAGCTG AGCCCCAACC ATTGGCCAGG GAGCCCTCGC
1051 TGGGTGTAGG GGTGGGGCAG GGCCGAGGTG GATACAGTAA GTTCCCAACC
1101 TCAGACCCCA CGCCCCCGCC AGCTCTGCCC ATGTCTGCCA GTCCTGAGCA
1151 GGTTGGTATG CTGATATAGC CATAGGTTGT TGGCGGGGAA GGAGCTCTTG
1201 GCATAGGAGA TACACTGTTC GTGGGTGTCT CCTCCCCATC ACTGAGCTCC
1251 AGACACAGGG CTACCTCCTC G
```

Mousemagic (mouse ECSM4) amino acid sequence

EEVALCLELSDGEETPTNSVSPMPRAPSPPTTYGYISIPTCSGLADMGRAGGGVGSEVGNLL
YPPRPCPTPTPSEGSLANGWGSASEDNVPSARASLVSSSDGSFLADTHEFARALAVAVDSFGL
SLDPREADCVFTDASSPPSPRGDLSLTRSFSLPLWEWRPDWLEDAEISHTQRLGRGLPPWPP
DSRASSQRSWLTGAVPKAV

Figure 8 (page 1 of 2)

```
P1;T30805 - dutt1 protein - mouse
N;Alternate names: transmembrane receptor protein Robo1 homolog SCORES    z-score: 292.0 E(): 3.3e-09
>>PIR2:T30805                                              (1612 aa)
Z-score: 292.0 expect(): 3.3e-09
Smith-Waterman score: 318;    28.0% identity in 472 aa overlap
(8-409:936-1383)

10        20        30
magic.pep                         MDHSDSQWLADTWRSTSGSRD------LSSSSSLSS
                                  ||||| ::::::       ::::: :|
T30805      PTVTYQRGGEAVSSGGRPGLLNISEPATQPWLADTWPNTGNNHNDCSINCCTAGNGNSDS
                  910       920       930       940       950       960

40        50        60        70
magic.pep   RLGADARDPLDCRRSLLSW-DSRSPGVPLLPDTSTFYGSL------IAEL-----PSSTPA
             :  ::|  |   |:::||| |: || |:::|:: :|||       |::|     |:
T30805      NLTTYSR-PADCIANYNNQLDNKQTNL-MLPE-STVYGDVDLSNKINEMKTFNSPNLKDG
                970       980       990      1000      1010      1020

80        90       100       110       120       130
magic.pep   R----PSPQ-VPAVRRLPPQLAQLSSPCSSSDSLCSRRGLSSP----RLSLAPAE--AWKAK
             :   :|:  |:|::  :::|:|| ::|: :|::: : |:::     :|: |||   |  :
T30805      RFVNPSGQPTPYATTQLIQ-ANLSNNMNNGAGDSSEKHWKPPGQQKPEVAPIQYNIMEQN
                1030      1040      1050      1060      1070      1080

140              150       160       170
magic.pep   KKQELQHANSS---PLLR-------GSHSLELRACEL-GNRGSKNLSQSPGAVPQALV
            :|::| |:|::   ||::        ::: |:  |:: |:: :  :|:| |   |:|
T30805      KLNKDYRANDTIPPTIPYNQSYDQNTGGSYNSSDRGSSTSGSQGHKKGARTPKAPKQGGM
                1090      1100      1110      1120      1130      1140
```

Figure 8 (page 2 of 2)

```
magic.pep   180        190        200        210        220        230
            AWRALGPKLLSSSNELVTRHLPPAPLFPHETPPTQSQQTQPPVAPQAPSSILLPAAPIPI
                                       ||       | ||    ::  :   |||
T30805      NWADL------------LPPPP---AHPPPHSNSEEYNMSVDESYDQEMPCPVPPAPM
            1150       1160       1170       1180 magic.pep   240        250        260        270        280
            LSPCSP---------PSPQASSLSGPSPASSRLSSSLSSLGEDQDSVLTPEEVALCLE-
            ::|         |:    :  |    |       ||       |||   ||:|||
T30805      YLQQDELQEEEDERGPTPPVRG-AASSPAAVSYSHQSTATLTPSPQEELQPM-LQDCPED
            1190       1200       1210       1220       1230       1240 magic.pep   290        300        310        320        330        340
            LSEGEETP----RNSVSPM--PRAPSPPTTYGYISVPTASEF-TDMGRTGGGVGPKGGVLL
            |::  :      ||:  |     | ||| || | |         |
            LGHMPHPPDRRRQPVSPPPPPPRPISPPHTYGYISGPLVSDMDTDAPEEEEDEADMEVAKM
            1250       1260       1270       1280       1290       1300 magic.pep   350        360        370        380
            CPPRPCL-------TPTPS-----EGSLANGWGSASE-DNAASARASLVSSSDGSFLAD
            ||                      |:  :         |           ::|:|:|
T30805      QTRLLLRGLEQTPASSVGDLESSVTGSMINGWGSASEEDNISSGRSS-VSSSDGSFFTD
            1310       1320       1330       1340       1350       1360 magic.pep   390        400        410
            AHFARALAVAVDSFGFGLEPREADCVFIGM
            |||||        :::
            ADFAQAVAAAEYAGLKVARRQMQDAAGRRHFHASQCPRPTSPVSTDSNMSAVVIQKARP
            1370       1380       1390       1400       1410       1420
```

Figure 9 (page 1 of 2)

```
T30805 - dutt1 protein - mouse
N;Alternate names: transmembrane receptor protein Robo1 homolog
C;Species: Mus musculus (house mouse)
C;Date: 22-Oct-1999 #sequence_revision 22-Oct-1999 #text_change 22-Oct-1999
C;Accession: T30805
R;Wu, M.C.; Lowe, N.; Fordham, R.; Rabbitts, P. . . . .

SCORES    z-score: 299.4 E(): 1.3e-09
>>PIR2:T30805                                                      (1612aa)
 Z-score: 299.4 expect() : 1.3e-09
Smith-Waterman score: 263;   35.9% identity in 198 aa overlap
(11-186:1251-1445)

10        20        30        40
mousemagic.p         EEVALCLELSDGEETPTNSVSPMPRABPPTTYGYISIPT
                                     ::  |:  |   |||  |||||||||||
T30805      TATLTPSPQEELQPMLQDCPEDLGHMPHPPDRRRQPV-SPPPPPRPSPPHTYGYISGPL
              1230      1240      1250      1260      1270

50        60          70                 80
mousemagic.p CSGL-ADMGRAG-GGVGSEVGN------LLYPPRPCPTPTPSE-----GSLANGWGSAS
                |:|:  ::  ::||:::    ||  :  |:::  :::         ||:  |||||||
T30805      VSDMDTDAPEEEEDEADMEVAKMQTRRLLLRGLEQTPASSVGDLESSVGSMINGWGSAS
              1280      1290      1300      1310      1320      1330
```

Figure 9 (page 2 of 2)

```
                    90        100       110       120       130       140
mousemagic.p  E-DNVPSARASLVSSSDGSFLADTHFARALAVAVDSFGLSLDPRE----ADCVFTDASSP
              |  |::|::|  ||||||||||  ||:|:|  ||:||:::|  ||:  |:  |  |:
T30805        EEDNISSGRSS-VSSSSDGSFFTDADFAQAVAAAEYAGLKVARRQMDAAGRRHFHASQC
              1340      1350      1360      1370      1380      1390

150       160       170       180       190
mousemagic.p  PSPRGDLSLTTRSFS-LPLWEWRPDWLEDAEISHTQRLGRG--LPPWPPDSRASSQRSWLT
              |  |  :||  :  |  ||    :  :||  :  |||  :|  |||  ||||  |||  |
T30805        PRPTSPVSTDSNMSAVVIQKARPAKKQKHQPGHLRREAYADDLPP-PPVPPPAIKSPTVQ
              1400      1410      1420      1430      1440      1450

200
mousemagic.p  GAVPKAV

T30805        SKAQLEVRPVMVPKLASIEARTDRSSDRKGGSYKGREALDGRQVTDLRTNPSDPREAQEQ
              1460      1470      1480      1490      1500      1510
```

Figure 10

Gap Weight:        8      Average Match:    2.912
    Length Weight:     2      Average Mismatch: -2.003

Quality:    597           Length:      135
                Ratio:  4.422            Gaps:        0
Percent Similarity: 87.407   Percent Identity: 85.185

Match display thresholds for the alignment(s):
                | = IDENTITY
                : = 2
                . = 1 mousemagic.pep x magic.pep September 12, 2000 18:05  ..

```
  1 EEVALCLELSDGEETPTNSVSPMPRAPSPPTTYGYISIPTCSGLADMGRA 50
    ||||||||||:||||| |||||||||||||||||||:|| |    ||||
280 EEVALCLELSEGEETPRNSVSPMPRAPSPPTTYGYISVPTASEFTDMGRT 329

51 GGGVGSEVGNLLYPPRPCPTPTPSEGSLANGWGSASEDNVPSARASLVSS 100
    |||| . | || ||||| ||||||||||||||||||||| |||||||||
330 GGGVGPKGGVLLCPPRPCLTPTPSEGSLANGWGSASEDNAASARASLVSS 379

101 SDGSFLADTH FARALAVAVDSFGLSLDPREADCVF 135
    |||||||| |||||||||||||  |:|||||||||
380 SDGSFLADAH FARALAVAVDSFGFGLEPREADCVF 414
```

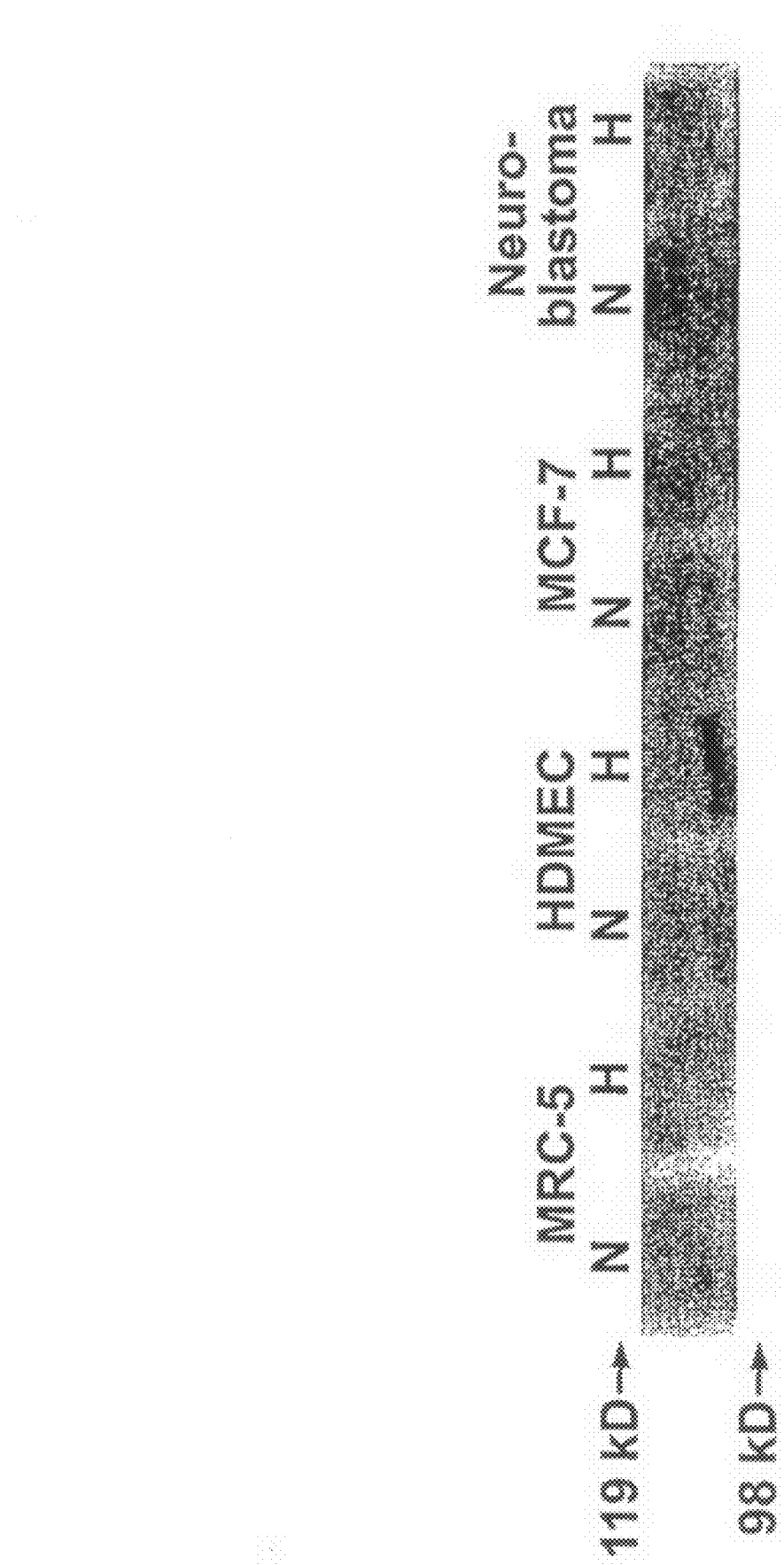

Figure 12 (page 1 of 4)

```
       GCGGCCGCGAATTCGGCACGAGCAGCAGGACAAAGTGCTCGGGACAAGGACATAGGGCTG
  1    ----------+---------+---------+---------+---------+---------+   60

AGAGTAGCCATGGGCTCTGGAGGAGACAGCCTCCTGGGGGGCAGGGGTTCCCTGCCTCTG
 61    ----------+---------+---------+---------+---------+---------+   120
                  M  G  S  G  G  D  S  L  L  G  G  R  G  S  L  P  L
       CTGCTCCTGCTCATCATGGGAGGCATGGCTCAGGACTCCCCGCCCCAGATCCTAGTCCAC
121    ----------+---------+---------+---------+---------+---------+   180
        L  L  L  L  I  M  G  G  M  A  Q  D  S  P  P  Q  I  L  V  H
       CCCCAGGACCAGCTGTTCCAGGGCCCTGGCCCTGCCAGGATGAGCTGCCAAGCCTCAGGC
181    ----------+---------+---------+---------+---------+---------+   240
        P  Q  D  Q  L  F  Q  G  P  G  P  A  R  M  S  C  Q  A  S  G
       CAGCCACCTCCCACCATCCGCTGGTTGCTGAATGGGCAGCCCCTGAGCATGGTGCCCCCA
241    ----------+---------+---------+---------+---------+---------+   300
        Q  P  P  P  T  I  R  W  L  L  N  G  Q  P  L  S  M  V  P  P
       GACCCACACCACCTCCTGCCTGATGGGACCCTTCTGCTGCTACAGCCCCCTGCCCGGGGA
301    ----------+---------+---------+---------+---------+---------+   360
        D  P  H  H  L  L  P  D  G  T  L  L  L  L  Q  P  P  A  R  G
       CATGCCCACGATGGCCAGGCCCTGTCCACAGACCTGGGTGTCTACACATGTGAGGCCAGC
361    ----------+---------+---------+---------+---------+---------+   420
        H  A  H  D  G  Q  A  L  S  T  D  L  G  V  Y  T  C  E  A  S
       AACCGGCTTGGCACGGCAGTCAGCAGAGGCGCTCGGCTGTCTGTGGCTGTCCTCCGGGAG
421    ----------+---------+---------+---------+---------+---------+   480
        N  R  L  G  T  A  V  S  R  G  A  R  L  S  V  A  V  L  R  E
       GATTTCCAGATCCAGCCTCGGGACATGGTGGCTGTGGTGGGTGAGCAGTTTACTCTGGAA
481    ----------+---------+---------+---------+---------+---------+   540
        D  F  Q  I  Q  P  R  D  M  V  A  V  V  G  E  Q  F  T  L  E
       TGTGGGCCGCCCTGGGGCCACCCAGAGCCCACAGTCTCATGGTGGAAAGATGGGAAACCC
541    ----------+---------+---------+---------+---------+---------+   600
        C  G  P  P  W  G  H  P  E  P  T  V  S  W  W  K  D  G  K  P
       CTGGCCCTCCAGCCCGGAAGGCACACAGTGTCCGGGGGGTCCCTGCTGATGGCAAGAGCA
601    ----------+---------+---------+---------+---------+---------+   660
        L  A  L  Q  P  G  R  H  T  V  S  G  G  S  L  L  M  A  R  A
       GAGAAGAGTGACGAAGGGACCTACATGTGTGTGGCCACCAACAGCGCAGGACATAGGGAG
661    ----------+---------+---------+---------+---------+---------+   720
        E  K  S  D  E  G  T  Y  M  C  V  A  T  N  S  A  G  H  R  E
       AGCCGCGCAGCCCGGGTTTCCATCCAGGAGCCCCAGGACTACACGGAGCCTGTGGAGCTT
721    ----------+---------+---------+---------+---------+---------+   780
        S  R  A  A  R  V  S  I  Q  E  P  Q  D  Y  T  E  P  V  E  L
       CTGGCTGTGCGAATTCAGCTGGAAAATGTGACACTGCTGAACCCGGATCCTGCAGAGGGC
781    ----------+---------+---------+---------+---------+---------+   840
        L  A  V  R  I  Q  L  E  N  V  T  L  L  N  P  D  P  A  E  G
       CCCAAGCCTAGACCGGCGGTGTGGCTCAGCTGGAAGGTCAGTGGCCCTGCTGCGCCTGCC
841    ----------+---------+---------+---------+---------+---------+   900
        P  K  P  R  P  A  V  W  L  S  W  K  V  S  G  P  A  A  P  A
       CAATCTTACACGGCCTTGTTCAGGACCCAGACTGCCCCGGGAGGCCAGGGAGCTCCGTGG
901    ----------+---------+---------+---------+---------+---------+   960
        Q  S  Y  T  A  L  F  R  T  Q  T  A  P  G  G  Q  G  A  P  W
       GCAGAGGAGCTGCTGGCCGGCTGGCAGAGCGCAGAGCTTGGAGGCCTCCACTGGGGCCAA
961    ----------+---------+---------+---------+---------+---------+   1020
        A  E  E  L  L  A  G  W  Q  S  A  E  L  G  G  L  H  W  G  Q
       GACTACGAGTTCAAAGTGAGACCATCCTCTGGCCGGGCTCGAGGCCCTGACAGCAACGTG
1021   ----------+---------+---------+---------+---------+---------+   1080
        D  Y  E  F  K  V  R  P  S  S  G  R  A  R  G  P  D  S  N  V
```

Figure 12 (page 2 of 4)

```
     CTGCTCCTGAGGCTGCCGGAAAAAGTGCCCAGTGCCCCACCTCAGGAAGTGACTCTAAAG
1081 ---------+---------+---------+---------+---------+---------+ 1140
      L  L  L  R  L  P  E  K  V  P  S  A  P  P  Q  E  V  T  L  K
     CCTGGCAATGGCACTGTCTTTGTGAGCTGGGTCCCACCACCTGCTGAAAACCACAATGGC
1141 ---------+---------+---------+---------+---------+---------+ 1200
      P  G  N  G  T  V  F  V  S  W  V  P  P  P  A  E  N  H  N  G
     ATCATCCGTGGCTACCAGGTCTGGAGCCTGGGCAACACATCACTGCCACCAGCCAACTGG
1201 ---------+---------+---------+---------+---------+---------+ 1260
      I  I  R  G  Y  Q  V  W  S  L  G  N  T  S  L  P  P  A  N  W
     ACTGTAGTTGGTGAGCAGACCCAGCTGGAAATCGCCACCCATATGCCAGGCTCCTACTGC
1261 ---------+---------+---------+---------+---------+---------+ 1320
      T  V  V  G  E  Q  T  Q  L  E  I  A  T  H  M  P  G  S  Y  C
     GTGCAAGTGGCTGCAGTCACTGGTGCTGGAGCTGGGGAGCCCAGTAGACCTGTCTGCCTC
1321 ---------+---------+---------+---------+---------+---------+ 1380
      V  Q  V  A  A  V  T  G  A  G  A  G  E  P  S  R  P  V  C  L
     CTTTTAGAGCAGGCCATGGAGCGAGCCACCCAAGAACCCAGTGAGCATGGTCCCTGGACC
1381 ---------+---------+---------+---------+---------+---------+ 1440
      L  L  E  Q  A  M  E  R  A  T  Q  E  P  S  E  H  G  P  W  T
     CTGGAGCAGCTGAGGGCTACCTTGAAGCGGCCTGAGGTCATTGCCACCTGCGGTGTTGCA
1441 ---------+---------+---------+---------+---------+---------+ 1500
      L  E  Q  L  R  A  T  L  K  R  P  E  V  I  A  T  C  G  V  A
     CTCTGGCTGCTGCTTCTGGGCACCGCCGTGTGTATCCACCGCCGGCGCCGAGCTAGGGTG
1501 ---------+---------+---------+---------+---------+---------+ 1560
      L  W  L  L  L  G  T  A  V  C  I  H  R  R  R  R  A  R  V
     CACCTGGGCCCAGGTCTGTACAGATATACCAGTGAGGATGCCATCCTAAAACACAGGATG
1561 ---------+---------+---------+---------+---------+---------+ 1620
      H  L  G  P  G  L  Y  R  Y  T  S  E  D  A  I  L  K  H  R  M
     GATCACAGTGACTCCCAGTGGTTGGCAGACACTTGGCGTTCCACCTCTGGCTCTCGGGAC
1621 ---------+---------+---------+---------+---------+---------+ 1680
      D  H  S  D  S  Q  W  L  A  D  T  W  R  S  T  S  G  S  R  D
     CTGAGCAGCAGCAGCAGCCTCAGCAGTCGGCTGGGGGCGGATGCCCGGGACCCACTAGAC
1681 ---------+---------+---------+---------+---------+---------+ 1740
      L  S  S  S  S  S  L  S  S  R  L  G  A  D  A  R  D  P  L  D
     TGTCGTCGCTCCTTGCTCTCCTGGGACTCCCGAAGCCCCGGCGTGCCCCTGCTTCCAGAC
1741 ---------+---------+---------+---------+---------+---------+ 1800
      C  R  R  S  L  L  S  W  D  S  R  S  P  G  V  P  L  L  P  D
     ACCAGCACTTTTTATGGCTCCCTCATCGCTGAGCTGCCCTCCAGTACCCCAGCCAGGCCA
1801 ---------+---------+---------+---------+---------+---------+ 1860
      T  S  T  F  Y  G  S  L  I  A  E  L  P  S  S  T  P  A  R  P
     AGTCCCCAGGTCCCAGCTGTCAGGCGCCTCCCACCCCAGCTGGCCCAGCTCTCCAGCCCC
1861 ---------+---------+---------+---------+---------+---------+ 1920
      S  P  Q  V  P  A  V  R  R  L  P  P  Q  L  A  Q  L  S  S  P
     TGTTCCAGCTCAGACAGCCTCTGCAGCCGCAGGGGACTCTCTTCTCCCCGCTTGTCTCTG
1921 ---------+---------+---------+---------+---------+---------+ 1980
      C  S  S  S  D  S  L  C  S  R  R  G  L  S  S  P  R  L  S  L
     GCCCCTGCAGAGGCTTGGAAGGCCAAAAAGAAGCAGGAGCTGCAGCATGCCAACAGTTCC
1981 ---------+---------+---------+---------+---------+---------+ 2040
      A  P  A  E  A  W  K  A  K  K  K  Q  E  L  Q  H  A  N  S  S
     CCACTGCTCCGGGGCAGCCACTCCTTGGAGCTCCGGGCCTGTGAGTTAGGAAATAGAGGT
2041 ---------+---------+---------+---------+---------+---------+ 2100
      P  L  L  R  G  S  H  S  L  E  L  R  A  C  E  L  G  N  R  G
     TCCAAGAACCTTTCCCAAAGCCCAGGAGCTGTGCCCCAAGCTCTGGTTGCCTGGCGGGCC
2101 ---------+---------+---------+---------+---------+---------+ 2160
      S  K  N  L  S  Q  S  P  G  A  V  P  Q  A  L  V  A  W  R  A
     CTGGGACCGAAACTCCTCAGCTCCTCAAATGAGCTGGTTACTCGTCATCTCCCTCCAGCA
2161 ---------+---------+---------+---------+---------+---------+ 2220
      L  G  P  K  L  L  S  S  S  N  E  L  V  T  R  H  L  P  P  A
```

Figure 12 (page 3 of 4)

```
      CCCCTCTTTCCTCATGAAACTCCCCCAACTCAGAGTCAACAGACCCAGCCTCCGGTGGCA
2221  ---------+---------+---------+---------+---------+---------+  2280
       P  L  F  P  H  E  T  P  P  T  Q  S  Q  Q  T  Q  P  P  V  A
      CCACAGGCTCCCTCCTCCATCCTGCTGCCAGCAGCCCCCATCCCCATCCTTAGCCCCTGC
2281  ---------+---------+---------+---------+---------+---------+  2340
       P  Q  A  P  S  S  I  L  L  P  A  A  P  I  P  I  L  S  P  C
      AGTCCCCCTAGCCCCCAGGCCTCTTCCCTCTCTGGCCCCAGCCCAGCTTCCAGTCGCCTG
2341  ---------+---------+---------+---------+---------+---------+  2400
       S  P  P  S  P  Q  A  S  S  L  S  G  P  S  P  A  S  S  R  L
      TCCAGCTCCTCACTGTCATCCCTGGGGAGGATCAAGACAGCGTGCTGACCCCTGAGGAG
2401  ---------+---------+---------+---------+---------+---------+  2460
       S  S  S  S  L  S  S  L  G  E  D  Q  D  S  V  L  T  P  E  E
      GTAGCCCTGTGCTTGGAACTCAGTGAGGGTGAGGAGACTCCCAGGAACAGCGTCTCTCCC
2461  ---------+---------+---------+---------+---------+---------+  2520
       V  A  L  C  L  E  L  S  E  G  E  E  T  P  R  N  S  V  S  P
      ATGCCAAGGGCTCCTTCACCCCCCACCACCTATGGGTACATCAGCGTCCCAACAGCCTCA
2521  ---------+---------+---------+---------+---------+---------+  2580
       M  P  R  A  P  S  P  P  T  T  Y  G  Y  I  S  V  P  T  A  S
      GAGTTCACGGACATGGGCAGGACTGGAGGAGGGGTGGGGCCCAAGGGGGGAGTCTTGCTG
2581  ---------+---------+---------+---------+---------+---------+  2640
       E  F  T  D  M  G  R  T  G  G  G  V  G  P  K  G  G  V  L  L
      TGCCCACCTCGGCCCTGCCTCACCCCCACCCCCAGCGAGGGCTCCTTAGCCAATGGTTGG
2641  ---------+---------+---------+---------+---------+---------+  2700
       C  P  P  R  P  C  L  T  P  T  P  S  E  G  S  L  A  N  G  W
      GGCTCAGCCTCTGAGGACAATGCCGCCAGCGCCAGAGCCAGCCTTGTCAGCTCCTCCGAT
2701  ---------+---------+---------+---------+---------+---------+  2760
       G  S  A  S  E  D  N  A  A  S  A  R  A  S  L  V  S  S  S  D
      GGCTCCTTCCTCGCTGATGCTCACTTTGCCCGGGCCCTGGCAGTGGCTGTGGATAGCTTT
2761  ---------+---------+---------+---------+---------+---------+  2820
       G  S  F  L  A  D  A  H  F  A  R  A  L  A  V  A  V  D  S  F
      GGTTTCGGTCTAGAGCCCAGGGAGGCAGACTGCGTCTTCATAGATGCCTCATCACCTCCC
2821  ---------+---------+---------+---------+---------+---------+  2880
       G  F  G  L  E  P  R  E  A  D  C  V  F  I  D  A  S  S  P  P
      TCCCCACGGGATGAGATCTTCCTGACCCCCAACCTCTCCCTGCCCCTGTGGGAGTGGAGG
2881  ---------+---------+---------+---------+---------+---------+  2940
       S  P  R  D  E  I  F  L  T  P  N  L  S  L  P  L  W  E  W  R
      CCAGACTGGTTGGAAGACATGGAGGTCAGCCACACCCAGCGGCTGGGAAGGGGGATGCCT
2941  ---------+---------+---------+---------+---------+---------+  3000
       P  D  W  L  E  D  M  E  V  S  H  T  Q  R  L  G  R  G  M  P
      CCCTGGCCCCCTGAACTCTCAGATCTCTTCCCAGAGAAGTCAGCTCCACTGTCGTATGCC
3001  ---------+---------+---------+---------+---------+---------+  3060
       P  W  P  P  E  L  S  D  L  F  P  E  K  S  A  P  L  S  Y  A
      CAAGGCTGGTGCTTCTCCTGTAGATTACTCCTGAACCGTGTCCCTGAGACTTCCCAGACG
3061  ---------+---------+---------+---------+---------+---------+  3120
       Q  G  W  C  F  S  C  R  L  L  N  R  V  P  E  T  S  Q  T
      GGAATCAGAACCACTTCTCCTGTTCCACCCACAAGACCTGGGCTGTGGTGTGTGGGTCTT
3121  ---------+---------+---------+---------+---------+---------+  3180
       G  I  R  T  T  S  P  V  P  P  T  R  P  G  L  W  C  V  G  L
      GGCCTGTGTTTCTCTGCAGCTGGGGTCCACCTTCCCAAGCCTCCAGAGAGTTCTCCCTCC
3181  ---------+---------+---------+---------+---------+---------+  3240
       G  L  C  F  S  A  A  G  V  H  L  P  K  P  P  E  S  S  P  S
      ACGATTGTGAAAACAAATGAAAACAAAATTAGAGCAAAGCTGACCTGGAGCCCTCAGGGA
3241  ---------+---------+---------+---------+---------+---------+  3300
       T  I  V  K  T  N  E  N  K  I  R  A  K  L  T  W  S  P  Q  G
      GCAAAACATCATCTCCACCTGACTCCTAGCCACTGCTTTCTCCTCTGTGCCATCCACTCC
3301  ---------+---------+---------+---------+---------+---------+  3360
       A  K  H  H  L  H  L  T  P  S  H  C  F  L  L  C  A  I  H  S
```

Figure 12 (page 4 of 4)

```
         CACCACCAGGTTGTTTTGGCCTGAGGAGCAGCCCTGCCTGCTGCTCTTCCCCCACCATTT
3361     ---------+---------+---------+---------+---------+---------+  3420
         H  H  Q  V  V  L  A  *
         GGATCACAGGAAGTGGAGGAGCCAGAGGTGCCTTTGTGGAGGACAGCAGTGGCTGCTGGG
3421     ---------+---------+---------+---------+---------+---------+  3480

AGAGGGCTGTGGAGGAAGGAGCTTCTCGGAGCCCCCTCTCAGCCTTACCTGGGCCCCTCC
3481     ---------+---------+---------+---------+---------+---------+  3540

TCTAGAGAAGAGCTCAACTCTCTCCCAACCTCACCATGGAAAGAAAATAATTATGAATGC
3541     ---------+---------+---------+---------+---------+---------+  3600

CACTGAGGCACTGAGGCCCTACCTCATGCCAAACAAAGGGTTCAAGGCTGGGTCTAGCGA
3601     ---------+---------+---------+---------+---------+---------+  3660

GGATGCTGAAGGAAGGGAGGTATGAGACCCGTAGGTCAAAAGCACCATCCTCGTA
3661     ---------+---------+---------+---------+---------+-----  3715
```

Figure 13 (page 1 of 7)

```
(Linear) MAP of: /home/lif/icrt/mehtar/MuMR.seq   check: 370   from: 1
to: 3688

REFORMAT of: MuMR.seq   check: 370   from: 1   to: 3688   February 16,
2001 14:25
(No documentation)

February 16, 2001 15:01 ..
(Linear) MAP of: /home/lif/icrt/mehtar/MuMR.seq   check: 370   from: 1
to: 3688

REFORMAT of: MuMR.seq   check: 370   from: 1   to: 3688   February 16,
2001 14:25
(No documentation)

February 16, 2001 15:01 ..

agtgtatgggacaaggagaggagccgagagcagccatgggctctggaggaacgggcctcc
    1 ---------+---------+---------+---------+---------+---------+ 60
       tcacatacccctgttcctctcctcggctctcgtcggtacccgagacctccttgcccggagg c         M  G  Q  G  E  E  P  R  A  A  M  G  S  G  G  T  G  L  L  - tggggacggagtggcctctgcctctgctgctgcttttcatcatgggaggtgaggctctgg
   61 ---------+---------+---------+---------+---------+---------+ 120
       accccctgcctcaccggagacggagacgacgacgaaaagtagtaccctccactccgagacc c         G  T  E  W  P  L  P  L  L  L  F  I  M  G  G  E  A  L  D  - attctccacccccagatcctagttcaccccaggaccagctacttcagggctctggcccag
  121 ---------+---------+---------+---------+---------+---------+ 180
       taagaggtggggtctaggatcaagtgggggtcctggtcgatgaagtcccgagaccgggtc c         S  P  P  Q  I  L  V  H  P  Q  D  Q  L  L  Q  G  S  G  P  A  - ccaagatgaggtgcagatcatccggccaaccacctcccactatccgctggctgctgaatg
  181 ---------+---------+---------+---------+---------+---------+ 240
       ggttctactccacgtctagtaggccggttggtggagggtgataggcgaccgacgacttac c         K  M  R  C  R  S  S  G  Q  P  P  P  T  I  R  W  L  L  N  G  - ggcagcccctcagcatggccaccccagacctacattaccttttgccggatgggacccctcc
  241 ---------+---------+---------+---------+---------+---------+ 300
       ccgtcggggagtcgtaccggtggggtctggatgtaatggaaaacggcctaccctgggagg c         Q  P  L  S  M  A  T  P  D  L  H  Y  L  L  P  D  G  T  L  L  - tgttacatcggccctctgtccagggacggccacaagatgaccagaacatcctctcagcaa
  301 ---------+---------+---------+---------+---------+---------+ 360
       acaatgtagccgggagacaggtccctgccggtgttctactggtcttgtaggagagtcgtt c         L  H  R  P  S  V  Q  G  R  P  Q  D  D  Q  N  I  L  S  A  I  - tcctgggtgtctacacatgtgaggccagcaaccggctgggcacagcagtgagccggggtg
  361 ---------+---------+---------+---------+---------+---------+ 420
       aggacccacagatgtgtacactccggtcgttggccgacccgtgtcgtcactcggccccac
```

Figure 13 (page 2 of 7)

```
c        L   G   V   Y   T   C   E   A   S   N   R   L   G   T   A   V   S   R   G   A - ctaggctgtctgtggctgtcctccaggaggacttccagatccaacctcgggacacagtgg
   421   ----------+---------+---------+---------+---------+---------+  480
         gatccgacagacaccgacaggaggtcctcctgaaggtctaggttggagccctgtgtcacc c        R   L   S   V   A   V   L   Q   E   D   F   Q   I   Q   P   R   D   T   V   A - ccgtggtgggagagagcttggttcttgagtgtggtcctccctggggctacccaaaaccct
   481   ----------+---------+---------+---------+---------+---------+  540
         ggcaccaccctctctcgaaccaagaactcacaccaggagggaccccgatgggttttggga c        V   V   G   E   S   L   V   L   E   C   G   P   P   W   G   Y   P   K   P   S - cggtctcatggtggaaagacgggaaacccctggtcctccagccagggaggcgcacagtat
   541   ----------+---------+---------+---------+---------+---------+  600
         gccagagtaccacctttctgcccttggggaccaggaggtcggtccctccgcgtgtcata c        V   S   W   W   K   D   G   K   P   L   V   L   Q   P   G   R   R   T   V   S - ctggggattccctgatggtgtcaagagcagagaagaatgactcggggacctatatgtgta
   601   ----------+---------+---------+---------+---------+---------+  660
         gaccccctaagggactaccacagttctcgtctcttcttactgagcccctggatatacat c        G   D   S   L   M   V   S   R   A   E   K   N   D   S   G   T   Y   M   C   M - tggccaccaacaatgctgggcaacgggagagccgagcagccagggtgtctatccaggaat
   661   ----------+---------+---------+---------+---------+---------+  720
         accggtggttgttacgacccgttgccctctcggctcgtcggtcccacagataggtcctta c        A   T   N   N   A   G   Q   R   E   S   R   A   A   R   V   S   I   Q   E   S - cccaggaccacaaggaacatctagagcttctggctgttcgcattcagctggaaaatgtga
   721   ----------+---------+---------+---------+---------+---------+  780
         gggtcctggtgttccttgtagatctcgaagaccgacaagcgtaagtcgaccttttacact c        Q   D   H   K   E   H   L   E   L   L   A   V   R   I   Q   L   E   N   V   T - ccctgctaaaccccgaacctgtaaaggtcccaagcctgggccatccgtgtggctcagct
   781   ----------+---------+---------+---------+---------+---------+  840
         gggacgatttggggcttggacattttccaggttcggacccggtaggcacaccgagtcga c        L   L   N   P   E   P   V   K   G   P   K   P   G   P   S   V   W   L   S   W - ggaaggtgagcggccctgctgcacctgctgagtcatacacagctctgttcaggactcaga
   841   ----------+---------+---------+---------+---------+---------+  900
         ccttccactcgccgggacgacgtggacgactcagtatgtgtcgagacaagtcctgagtct c        K   V   S   G   P   A   A   P   A   E   S   Y   T   A   L   F   R   T   Q   R - ggtcccccagggaccaaggatctccatggacagaggtgctgctgcgtggcttgcagagtg
   901   ----------+---------+---------+---------+---------+---------+  960
         ccaggggtccctggttcctagaggtacctgtctccacgacgacgcaccgaacgtctcac c        S   P   R   D   Q   G   S   P   W   T   E   V   L   L   R   G   L   Q   S   A -
```

Figure 13 (page 3 of 7)

```
       caaagcttgggggtctccactgggccaagactatgaattcaaagtgagaccgtcctccg
  961 ---------+---------+---------+---------+---------+---------+ 1020
       gtttcgaacccccagaggtgaccccggttctgatacttaagtttcactctggcaggaggc c    K  L  G  G  L  H  W  G  Q  D  Y  E  F  K  V  R  P  S  S  G - gccgggctcgaggccctgacagcaatgtgttgctcctgaggctgcctgaacaggtgccca
 1021 ---------+---------+---------+---------+---------+---------+ 1080
       cggcccgagctccgggactgtcgttacacaacgaggactccgacggacttgtccacgggt c    R  A  R  G  P  D  S  N  V  L  L  R  L  P  E  Q  V  P  S - gtgccccacctcaaggagtgaccttaagatctggcaacggtagtgtctttgtgagttggg
 1081 ---------+---------+---------+---------+---------+---------+ 1140
       cacggggtggagttcctcactggaattctagaccgttgccatcacagaaacactcaaccc c    A  P  P  Q  G  V  T  L  R  S  G  N  G  S  V  F  V  S  W  A - ctccaccacctgctgaaagccataatggtgtcatccgtggttaccaggtctggagcctgg
 1141 ---------+---------+---------+---------+---------+---------+ 1200
       gaggtggtggacgactttcggtattaccacagtaggcaccaatggtccagacctcggacc c    P  P  P  A  E  S  H  N  G  V  I  R  G  Y  Q  V  W  S  L  G - gcaatgcctcattgcctgctgccaactggaccgtagtgggtgaacagacccagctggaga
 1201 ---------+---------+---------+---------+---------+---------+ 1260
       cgttacggagtaacggacgacggttgacctggcatcacccacttgtctgggtcgacctct c    N  A  S  L  P  A  A  N  W  T  V  V  G  E  Q  T  Q  L  E  I - tcgccacacgactgccaggctcctattgtgtgcaagtggctgcagtcactggagctggtg
 1261 ---------+---------+---------+---------+---------+---------+ 1320
       agcggtgtgctgacggtccgaggataacacacgttcaccgacgtcagtgacctcgaccac c    A  T  R  L  P  G  S  Y  C  V  Q  V  A  A  V  T  G  A  G  A - ctggagaactcagtacccctgtctgcctccttttagagcaggccatggagcaatcagcac
 1321 ---------+---------+---------+---------+---------+---------+ 1380
       gacctcttgagtcatggggacagacggaggaaaatctcgtccggtacctcgttagtcgtg c    G  E  L  S  T  P  V  C  L  L  E  Q  A  M  E  Q  S  A  R - gagaccccaggaaacatgttccctggaccctggaacagctgagggccaccttgagacgac
 1381 ---------+---------+---------+---------+---------+---------+ 1440
       ctctggggtcctttgtacaagggacctgggaccttgtcgactcccggtggaactctgctg c    D  P  R  K  H  V  P  W  T  L  E  Q  L  R  A  T  L  R  R  P - cagaagtcattgccagtagtgctgtcctactctggttgctgctactaggcattactgtgt
 1441 ---------+---------+---------+---------+---------+---------+ 1500
       gtcttcagtaacggtcatcacgacaggatgagaccaacgacgatgatccgtaatgacaca c    E  V  I  A  S  S  A  V  L  L  W  L  L  L  G  I  T  V  C - gtatctacagacgacgcaaagctggggtgcacctgggcccaggtctgtacagatacacca
 1501 ---------+---------+---------+---------+---------+---------+ 1560
       catagatgtctgctgcgtttcgaccccacgtggacccgggtccagacatgtctatgtggt
```

Figure 13 (page 4 of 7)

```
c      I  Y  R  R  R  K  A  G  V  H  L  G  P  G  L  Y  R  Y  T  S -
       gcgaggacgccattctaaaacacaggatggaccacagtgactccccatggctggcagaca
1561   ---------+---------+---------+---------+---------+---------+ 1620
       cgctcctgcggtaagattttgtgtcctacctggtgtcactgaggggtaccgaccgtctgt c      E  D  A  I  L  K  H  R  M  D  H  S  D  S  P  W  L  A  D  T -
       cctggcgttccacctctggctctcgagacctgagcagcagcagcagccttagtagtcggc
1621   ---------+---------+---------+---------+---------+---------+ 1680
       ggaccgcaaggtggagaccgagagctctggactcgtcgtcgtcgtcggaatcatcagccg c      W  R  S  T  G  S  R  D  L  S  S  S  S  S  L  S  S  R  L -
       tgggattggaccctcgggacccactagagggcaggcgctccttgatctcctgggaccctc
1681   ---------+---------+---------+---------+---------+---------+ 1740
       accctaacctgggagccctgggtgatctcccgtccgcgaggaactagaggaccctgggag c      G  L  D  P  R  D  P  L  E  G  R  R  S  L  I  S  W  D  P  R -
       ggagccccggtgtaccccctgcttccagacacgagcacgttttacggctccctcattgcag
1741   ---------+---------+---------+---------+---------+---------+ 1800
       cctcggggccacatggggacgaaggtctgtgctcgtgcaaaatgccgagggagtaacgtc c      S  P  G  V  P  L  L  P  D  T  S  T  F  Y  G  S  L  I  A  E -
       agcagccttccagccctccagtccggccaagccccaagacaccagctgctaggcgctttc
1801   ---------+---------+---------+---------+---------+---------+ 1860
       tcgtcggaaggtcgggaggtcaggccggttcggggttctgtggtcgacgatccgcgaaag c      Q  P  S  S  P  P  V  R  P  S  P  K  T  P  A  A  R  R  F  P -
       catccaagttggctggaacctccagcccctgggctagctcagatagtctctgcagccgca
1861   ---------+---------+---------+---------+---------+---------+ 1920
       gtaggttcaaccgaccttggaggtcggggacccgatcgagtctatcagagacgtcggcgt c      S  K  L  A  G  T  S  S  P  W  A  S  S  D  S  L  C  S  R  R -
       ggggactctgttccccacgcatgtctctgaccctacagaggcttggaaggccaaaaaga
1921   ---------+---------+---------+---------+---------+---------+ 1980
       cccctgagacaaggggtgcgtacagagactggggatgtctccgaaccttccggttttttct c      G  L  C  S  P  R  M  S  L  T  P  T  E  A  W  K  A  K  K  K -
       agcaggaattgcaccaagctaacagctccccactgctccggggcagccaccccatggaaa
1981   ---------+---------+---------+---------+---------+---------+ 2040
       tcgtccttaacgtggttcgattgtcgaggggtgacgaggccccgtcggtggggtacctttt c      Q  E  L  H  Q  A  N  S  S  P  L  L  R  G  S  H  P  M  E  I -
       tctgggcctgggagttgggaagcagagcctccaagaacctttctcaaagcccaggagaag
2041   ---------+---------+---------+---------+---------+---------+ 2100
       agacccggaccctcaacccttcgtctcggaggttcttggaaagagtttcgggtcctcttc c      W  A  W  E  L  G  S  R  A  S  K  N  L  S  Q  S  P  G  E  A -
```

Figure 13 (page 5 of 7)

```
      cgccccgagccgtggtatcctggcgtgctgtgggaccacaacttcaccgcaactccagtg
2101  ---------+---------+---------+---------+---------+---------+  2160
      gcggggctcggcaccataggaccgcacgacaccctggtgttgaagtggcgttgaggtcac c      P  R  A  V  V  S  W  R  A  V  G  P  Q  L  H  R  N  S  S  E  - agctggcatctcgtccactccctccaacaccccttctcttcgtggagcttccagtcatg
2161  ---------+---------+---------+---------+---------+---------+  2220
      tcgaccgtagagcaggtgagggaggttgtggggaagagaagcacctcgaaggtcagtac c      L  A  S  R  P  L  P  P  T  P  L  S  L  R  G  A  S  S  H  D  - acccacagagccagtgtgtggagaagctccaagctccctcctctgacccactgccagcag
2221  ---------+---------+---------+---------+---------+---------+  2280
      tgggtgtctcggtcacacacctcttcgaggttcgagggaggagactgggtgacggtcgtc c      P  Q  S  Q  C  V  E  K  L  Q  A  P  S  S  D  P  L  P  A  A  - cccctctctccgtcctcaactcttccagaccttccagcccccaggcctcttcctctcct
2281  ---------+---------+---------+---------+---------+---------+  2340
      ggggagagaggcaggagttgagaaggtctggaaggtcggggggtccggagaaaggagagga c      P  L  S  V  L  N  S  S  R  P  S  S  P  Q  A  S  F  L  S  C  - gtcctagcccatcctccagcaacctgtccagctcctcgctgtcatccttagaggaggagg
2341  ---------+---------+---------+---------+---------+---------+  2400
      caggatcgggtaggaggtcgttggacaggtcgaggagcgacagtaggaatctcctcctcc c      P  S  P  S  S  S  N  L  S  S  S  S  L  S  S  L  E  E  E  E  - aggatcaggacagcgtgctcaccccgaggaggtagccctgtgtctggagctcagtgatg
2401  ---------+---------+---------+---------+---------+---------+  2460
      tcctagtcctgtcgcacgagtgggggctcctccatcgggacacagacctcgagtcactac c      D  Q  D  S  V  L  T  P  E  E  V  A  L  C  L  E  L  S  D  G  - gggaggagacacccacgaacagtgtatctcctatgccaagagctccttccccgccaacaa
2461  ---------+---------+---------+---------+---------+---------+  2520
      ccctcctctgtgggtgcttgtcacatagaggatacggttctcgaggaaggggcggttgtt c      E  E  T  P  T  N  S  V  S  P  M  P  R  A  P  S  P  P  T  T  - cctatggctatatcagcataccaacctgctcaggactggcagacatgggcagagctggcg
2521  ---------+---------+---------+---------+---------+---------+  2580
      ggataccgatatagtcgtatggttggacgagtcctgaccgtctgtacccgtctcgaccgc c      Y  G  Y  I  S  I  P  T  C  S  G  L  A  D  M  G  R  A  G  G  - ggggcgtggggtctgaggttgggaacttactgtatccacctcggccctgccccaccccta
2581  ---------+---------+---------+---------+---------+---------+  2640
      ccccgcaccccagactccaaccccttgaatgacataggtggagccgggacggggtgggat c      G  V  G  S  E  V  G  N  L  L  Y  P  P  R  P  C  P  T  P  T  - cacccagcgagggctccctggccaatggttggggctcagcttctgaggacaatgtccca
2641  ---------+---------+---------+---------+---------+---------+  2700
      gtgggtcgctcccgagggaccggttaccaaccccgagtcgaagactcctgttacagggt
```

Figure 13 (page 6 of 7)

```
c      P  S  E  G  S  L  A  N  G  W  G  S  A  S  E  D  N  V  P  S  -
       gcgccagggccagcctggttagctcttctgatggctccttcctcgctgatactcactttg
2701   ---------+---------+---------+---------+---------+---------+ 2760
       cgcggtcccggtcggaccaatcgagaagactaccgaggaaggagcgactatgagtgaaac c      A  R  A  S  L  V  S  S  S  D  G  S  F  L  A  D  T  H  F  A  -
       ctcgtgccctggcagtggctgtggatagctttggcctcagtctggatcccagggaagctg
2761   ---------+---------+---------+---------+---------+---------+ 2820
       gagcacgggaccgtcaccgacacctatcgaaaccggagtcagacctagggtcccttcgac c      R  A  L  A  V  A  V  D  S  F  G  L  S  L  D  P  R  E  A  D  -
       actgtgtcttcactgatgcctcatcacctccctcccctcggggtgatctctccctgaccc
2821   ---------+---------+---------+---------+---------+---------+ 2880
       tgacacagaagtgactacggagtagtggagggaggggagccccactagagagggactggg c      C  V  F  T  D  A  S  S  P  P  S  P  R  G  D  L  S  L  T  R  -
       gaagcttctctctgcctttgtgggagtggaggccagactggttggaagatgctgagatca
2881   ---------+---------+---------+---------+---------+---------+ 2940
       cttcgaagagagacggaaacaccctcacctccggtctgaccaaccttctacgactctagt c      S  F  S  L  P  L  W  E  W  R  P  D  W  L  E  D  A  E  I  S  -
       gccacacccagaggctggggaggggctgcctccctggcctcctgattctagggcctctt
2941   ---------+---------+---------+---------+---------+---------+ 3000
       cggtgtgggtctccgacccctcccccgacggagggaccggaggactaagatcccggagaa c      H  T  Q  R  L  G  R  G  L  P  P  W  P  P  D  S  R  A  S  S  -
       cccagcgaagttggctaactggtgctgtgcccaaggctggtgattcctcctgaattgtcc
3001   ---------+---------+---------+---------+---------+---------+ 3060
       gggtcgcttcaaccgattgaccacgacacgggttccgaccactaaggaggacttaacagg c      Q  R  S  W  L  T  G  A  V  P  K  A  G  D  S  S  *        -
       ctgagaaggccagaagagcacccagaccactctcctgtctgtcccctggctttctcacat
3061   ---------+---------+---------+---------+---------+---------+ 3120
       gactcttccggtcttctcgtgggtctggtgagaggacagacaggggaccgaaagagtgta c                                                                 -
       gtggaggtcttggcctatgcttctctgtaatagaagtccaccgtcactaggcttctggag
3121   ---------+---------+---------+---------+---------+---------+ 3180
       cacctccagaaccggatacgaagagacattatcttcaggtggcagtgatccgaagacctc c                                                                 -
       agctctgtcattgggattgttaaaataaatgaaagcaaaccaaaatatgatcacgggagt
3181   ---------+---------+---------+---------+---------+---------+ 3240
       tcgagacagtaaccctaacaattttatttactttcgtttggttttatactagtgccctca c                                                                 -
```

Figure 13 (page 7 of 7)

```
     cttggattcccactgagaacaagacagcatcttcaggacagcagactctccacaaccaga
3241 ---------+---------+---------+---------+---------+---------+ 3300
     gaacctaagggtgactcttgttctgtcgtagaagtcctgtcgtctgagaggtgttggtct c                                                               - acctttggcctaagtaagcctggctccggagctcccacctaagtggatcatggaaagaag
3301 ---------+---------+---------+---------+---------+---------+ 3360
     tggaaaccggattcattcggaccgaggcctcgagggtggattcacctagtacctttcttc c                                                               - ggaagccaaccaggtcttcaggaaggacagaaatgttttttggtgagggctatggtggag
3361 ---------+---------+---------+---------+---------+---------+ 3420
     ccttcggttggtccagaagtccttcctgtctttacaaaaaaccactcccgataccacctc c                                          M  F  F  G  E  G  Y  G  G  G - gacctgtggaagagccctctcatatctacttggactcctcccttagaggccagctcaacc
3421 ---------+---------+---------+---------+---------+---------+ 3480
     ctggacaccttctcgggagagtatagatgaacctgaggagggaatctccggtcgagttgg c     P  V  E  E  P  S  H  I  Y  L  D  S  S  L  R  G  Q  L  N  P - ctttccccagtcacaccatgcaaggaaactaaaggagaaaggtcgtggatgcagtgggcc
3481 ---------+---------+---------+---------+---------+---------+ 3540
     gaaaggggtcagtgtggtacgttcctttgatttcctctttccagcacctacgtcacccgg c     F  P  S  H  T  M  Q  G  N  *                              - ctatacagcgtcacagtcaatgcttcaaagtgagatcaatggaggagactgaaggaaagg
3541 ---------+---------+---------+---------+---------+---------+ 3600
     gatatgtcgcagtgtcagttacgaagtttcactctagttacctcctctgacttcctttcc c                                          M  E  E  T  E  G  K  D - acgcagggaaacagggaaccaatgcgctattctcattctaccgccactctgagcttaagg
3601 ---------+---------+---------+---------+---------+---------+ 3660
     tgcgtcccttTgtcccttggttacgcgataagagtaagatggcggtgagactcgaattcc c     A  G  K  Q  G  T  N  A  L  F  S  F  Y  R  H  S  E  L  K  E - aacttaattctataaaactgtaaagacg
3661 ---------+---------+-------- 3688
     ttgaattaagatattttgacatttctgc c     L  N  S  I  K  L  *                  -
```

Figure 14 (page 1 of 3)

```
BESTFIT OF: MR.PEP  CHECK: 5275  FROM: 1  TO: 1104

TO: MUMR_1030818.PEP  CHECK: 6771  FROM: 1  TO: 1228

TRANSLATE OF: MUMR.SEQ CHECK: 370 FROM: 3 TO: 3688
GENERATED SYMBOLS 1 TO: 1228.
REFORMAT OF: MUMR.SEQ  CHECK: 370  FROM: 1  TO: 3688
SYMBOL COMPARISON TABLE:
/MOLBIO0/SOFTWARE/GCG/GCGCORE/DATA/RUNDATA/BLOSUM62.CMP
COMPCHECK: 6430

GAP WEIGHT:       8      AVERAGE MATCH:    2.912
    LENGTH WEIGHT:       2      AVERAGE MISMATCH: -2.003

QUALITY:    4035              LENGTH:    1081
            RATIO:   3.764                GAPS:       7
PERCENT SIMILARITY: 77.392    PERCENT IDENTITY:  74.390

MATCH DISPLAY THRESHOLDS FOR THE ALIGNMENT(S):
                   | = IDENTITY
                   : = 2
                   . = 1

MR.PEP X MUMR.PEP

1 MGSGGDSLLGGRGSLPLLLLLIMGGMAQDSPPQILVHPQDQLFQGPGPAR  50
     |||||  |||      ||||||  ||||  |  |||||||||||||||| ||  |||:
  12 MGSGGTGLLGTEWPLPLLLLFIMGGEALDSPPQILVHPQDQLLQGSGPAK  61

51 MSCQASGQPPPTIRWLLNGQPLSMVPPDPHHLLPDGTLLLLQPPARGHAH 100
     | |..|||||||||||||||||||||  ||  |:||||||||  .|   .|
  62 MRCRSSGQPPPTIRWLLNGQPLSMATPDLHYLLPDGTLLLHRPSVQGRPQ 111

101 DGQ.ALSTDLGVYTCEASNRLGTAVSRGARLSVAVLREDFQIQPRDMVAV 149
     | |   ||  ||||||||||||||||||||||||||||.||||||||| |||
 112 DDQNILSAILGVYTCEASNRLGTAVSRGARLSVAVLQEDFQIQPRDTVAV 161

150 VGEQFTLECGPPWGHPEPTVSWWKDGKPLALQPGRHTVSGGSLLMARAEK 199
     |||     |||||||:|.|.||||||||||   |||||  ||||  ||:..||||
 162 VGESLVLECGPPWGYPKPSVSWWKDGKPLVLQPGRRTVSGDSLMVSRAEK 211

200 SDEGTYMCVATNSAGHRESRAARVSIQEPQDYTEPVELLAVRIQLENVTL 249
     .|  |||||.|||.||  ||||||||||| ||: |  .|||||||||||||||
 212 NDSGTYMCMATNNAGQRESRAARVSIQESQDHKEHLELLAVRIQLENVTL 261
```

Figure 14 (page 2 of 3)

```
250 LNPDPAEGPKPRPAVWLSWKVSGPAAPAQSYTALFRTQTAPGGQGAPWAE 299
    |||:| .|||| |.|||||||||||||:||||||||:|| .| ||.|| |
262 LNPEPVKGPKPGPSVWLSWKVSGPAAPAESYTALFRTQRSPRDQGSPWTE 311

300 ELLAGWQSAELGGLHWGQDYEFKVRPSSGRARGPDSNVLLLRLPEKVPSA 349
    || | |||.|||||||||||||||||||||||||||||||||||.||||
312 VLLRGLQSAKLGGLHWGQDYEFKVRPSSGRARGPDSNVLLLRLPEQVPSA 361

350 PPQEVTLKPGNGTVFVSWVPPPAENHNGIIRGYQVWSLGNTSLPPANWTV 399
    ||| |||: |||.||||| |||||.|||:|||||||||| ||| |||||
362 PPQGVTLRSGNGSVFVSWAPPPAESHNGVIRGYQVWSLGNASLPAANWTV 411

400 VGEQTQLEIATHMPGSYCVQVAAVTGAGAGEPSRPVCLLLEQAMERATQE 449
    ||||||||||| :|+|||||||||||||||| | ||||||||||.. .:
412 VGEQTQLEIATRLPGSYCVQVAAVTGAGAGELSTPVCLLLEQAMEQSARD 461

450 PSEHGPWTLEQLRATLKRPEVIATCGVALWLLLLGTAVCIHRRRRARVHL 499
    | .| |||||||||||:||||||. | |||||||| |||:|||:| |||
462 PRKHVPWTLEQLRATLRRPEVIASSAVLLWLLLLGITVCIYRRRKAGVHL 511

500 GPGLYRYTSEDAILKHRMDHSDSQWLADTWRSTGSRDLSSSSSLSSRLG 549
    ||||||||||||||||||||||| |||||||||||||||||||||||||
512 GPGLYRYTSEDAILKHRMDHSDSPWLADTWRSTGSRDLSSSSSLSSRLG 561

550 ADARDPLDCRRSLLSWDSRSPGVPLLPDTSTFYGSLIAELPSSTPARPSP 599
    | ||||: ||||:||| ||||||||||||||||||||| ||| | ||||
562 LDPRDPLEGRRSLISWDPRSPGVPLLPDTSTFYGSLIAEQPSSPVRPSP 611

600 QVPAVRRLPPQLAQLSSPCSSSDSLCSRRGLSSPRLSLAPAEAWKAKKKQ 649
    . || || | .|| ||| .|||||||||| |||:|| | ||||||||
612 KTPAARRFPSKLAGTSSPWASSDSLCSRRGLCSPRMSLTPTEAWKAKKKQ 661

650 ELQHANSSPLLRGSHSLELRACELGNRGSKNLSQSPGAVPQALVAWRALG 699
    || |||||||||| :|: | |||.| ||||||||| |.|.|.|||.|
662 ELHQANSSPLLRGSHPMEIWAWELGSRASKNLSQSPGEAPRAVVSWRAVG 711

700 PKLLSSSNELVTRHLPPAPLFPHETPPTQSQQTQPPVAPQAPSSILLPAA 749
    |.| .|.|| .| ||| || . |.| ||||| ||||
712 PQLHRNSSELASRPLPPTPL.SLRGASSHDPQSQCVEKLQAPSSDPLPAA 760

750 PIPILSPCSPPSPQASSLSGPSPASSRLSSSSLSSL..GEDQDSVLTPEE 797
    |: :|. | ||||| || |||.|| ||||||||| |||||||||||
761 PLSVLNSSRPSSPQASFLSCPSPSSSNLSSSSLSSLEEEEDQDSVLTPEE 810
```

Figure 14 (page 3 of 3)

```
 798 VALCLELSEGEETPRNSVSPMPRAPSPPTTYGYISVPTASEFTDMGRTGG  847
     ||||||||:||||| |||||||||||||||||||||:|| |    |||| ||
 811 VALCLELSDGEETPTNSVSPMPRAPSPPTTYGYISIPTCSGLADMGRAGG  860

848 GVGPKGGVLLCPPRPCLTPTPSEGSLANGWGSASEDNAASARASLVSSSD  897
     ||| . | || ||||| |||||||||||||||||||| ||||||||||
 861 GVGSEVGNLLYPPRPCPTPTPSEGSLANGWGSASEDNVPSARASLVSSSD  910

898 GSFLADAHFARALAVAVDSFGFGLEPREADCVFIDASSPPSPRDEIFLTP  947
     |||||| |||||||||||||  |:|||||||| ||||||||| :: ||
 911 GSFLADTHFARALAVAVDSFGLSLDPREADCVFTDASSPPSPRGDLSLTR  960

948 NLSLPLWEWRPDWLEDMEVSHTQRLGRGMPPWPPELSDLFPEKSAPLSYA  997
     . ||||||||||||| |:|||||||||:|||||:          |. |:
 961 SFSLPLWEWRPDWLEDAEISHTQRLGRGLPPWPPD.....SRASSQRSWL 1005

998 QGWCFSCRLLLNRVPETSQTGIRTTSPVPPTRPG.LWCVGLGLCFSAAGV 1046
     |         ||| ..   |  |.   || | ||||||| |
1006 TGAVPKAGDSS*IVPEKAR...RAPRPLSCLSPGFLTCGGLGLCFSVIEV 1052

1047 ..HLPKPPESSPSTIVKTNENKIRAKLTWSP 1075
       |             | : || .: .| |
1053 HRH*ASGELCHWDC*NK*KQTKI*SRESWIP 1083
```

Figure 15 (page 1 of 8)

```
BESTFIT of: MR.seq   check: 650   from: 1   to: 3715

REFORMAT of: MR.seq   check: 650   from: 1   to: 3715   February
15, 2001 13:54
(No documentation)

to: MuMR.seq   check: 370   from: 1   to: 3688

REFORMAT of: MuMR.seq   check: 370   from: 1   to: 3688
February 16, 2001 14:25
(No documentation)

Symbol comparison table:
/molbio0/software/gcg/gcgcore/data/rundata/swgapdna.cmp
 CompCheck: 2335

Gap Weight:      50      Average Match:   10.000
      Length Weight:       3      Average Mismatch: -9.000

Quality:   20259             Length:    3672
              Ratio:   5.617              Gaps:      23
 Percent Similarity:  79.169     Percent Identity:  79.169

Match display thresholds for the alignment(s):
                     | = IDENTITY
                     : = 5
                     . = 1

HuMR.seq x MuMR.seq              February 16, 2001 14:38  ..

34 AGTGCTCGGGACAAGGACATAGGGCTGAGAGTAGCCATGGGCTCTGGAGG 83
       ||||    ||||||||| |   | ||  |||||| ||||||||||||||||
     1 AGTGTATGGGACAAGGAGA.GGAGCCGAGAGCAGCCATGGGCTCTGGAGG 49

84 AGACAGCCTCCTGGGGGGCAGGGGTTCCCTGCCTCTGCTGCTCCTGCTCA 133
       |   ||||||||||      |  |  | ||||||||||||| ||   |||
    50 AACGGGCCTCCTGGGGACGGAGTGGCCTCTGCCTCTGCTGCTGCTTTTCA 99

134 TCATGGGAGGCATGGCTCAGGACTCCCCGCCCCAGATCCTAGTCCACCCC 183
       |||||||||     ||||| ||| || || || |||||||||||| |||||
   100 TCATGGGAGGTGAGGCTCTGGATTCTCCACCCCAGATCCTAGTTCACCCC 149

184 CAGGACCAGCTGTTCCAGGGCCCTGGCCCTGCCAGGATGAGCTGCCAAGC 233
       ||||||||||  | |||||| |||||| |||||||||| |||| || | |
   150 CAGGACCAGCTACTTCAGGGCTCTGGCCCAGCCAAGATGAGGTGCAGATC 199
```

Figure 15 (page 2 of 8)

```
234 CTCAGGCCAGCCACCTCCCACCATCCGCTGGTTGCTGAATGGGCAGCCCC 283
    || ||||| |||||||||||| |||||||| |||||||||||||||||||
200 ATCCGGCCAACCACCTCCCACTATCCGCTGGCTGCTGAATGGGCAGCCCC 249

284 TGAGCATGGTGCCCCCAGACCCACACCACCTCCTGCCTGATGGGACCCTT 333
    | |||||||  |||||||||| |||  ||||  ||||  |||||||||||
250 TCAGCATGGCCACCCCAGACCTACATTACCTTTTGCCGGATGGGACCCTC 299

334 CTGCTGCTACAGCCCCCTGCCCGGGGACATGCCCACGATGGCCAG...GC 380
    |||  |  |  |||| |||  ||  |||||    |  ||||  ||||
300 CTGTTACATCGGCCCTCTGTCCAGGGACGGCCACAAGATGACCAGAACAT 349

381 CCTGTCCACAGACCTGGGTGTCTACACATGTGAGGCCAGCAACCGGCTTG 430
    ||| ||  ||  |||||||||||||||||||||||||||||||||||| |
350 CCTCTCAGCAATCCTGGGTGTCTACACATGTGAGGCCAGCAACCGGCTGG 399

431 GCACGGCAGTCAGCAGAGGCGCTCGGCTGTCTGTGGCTGTCCTCCGGGAG 480
    |||| |||||  ||| | || ||| ||||||||||||||||||| ||||
400 GCACAGCAGTGAGCCGGGGTGCTAGGCTGTCTGTGGCTGTCCTCCAGGAG 449

481 GATTTCCAGATCCAGCCTCGGGACATGGTGGCTGTGGTGGGTGAGCAGTT 530
    || |||||||||| ||||||||||| |||||||  ||||| |||  | |
450 GACTTCCAGATCCAACCTCGGGACACAGTGGCCGTGGTGGGAGAGAGCTT 499

531 TACTCTGGAATGTGGGCCGCCCTGGGGCCACCCAGAGCCCACAGTCTCAT 580
       ||| || ||||| || |||||||||| ||||| | ||| |||||||
500 GGTTCTTGAGTGTGGTCCTCCCTGGGGCTACCCAAAACCCTCGGTCTCAT 549

581 GGTGGAAAGATGGGAAACCCCTGGCCCTCCAGCCCGGAAGGCACACAGTG 630
    ||||||||||| |||||||||||| ||||||||| ||||||| ||||||
550 GGTGGAAAGACGGGAAACCCCTGGTCCTCCAGCCAGGGAGGCGCACAGTA 599

631 TCCGGGGGGTCCCTGCTGATGGCAAGAGCAGAGAAGAGTGACGAAGGGAC 680
    || ||||  ||||||| || || ||||||||||||||| ||||  |||||
600 TCTGGGGATTCCCTGATGGTGTCAAGAGCAGAGAAGAATGACTCGGGGAC 649

681 CTACATGTGTGTGGCCACCAACAGCGCAGGACATAGGGAGAGCCGCGCAG 730
    ||| |||||| ||||||||||||  || || || .|||||||||| ||||
650 CTATATGTGTATGGCCACCAACAATGCTGGGCAACGGGAGAGCCGAGCAG 699

731 CCCGGGTTTCCATCCAGGAGCCCCAGGACTACACGGAGCCTGTGGAGCTT 780
    || |||| || |||||||| |||||||| ||| ||| | | | ||||||
700 CCAGGGTGTCTATCCAGGAATCCCAGGACCACAAGGAACATCTAGAGCTT 749
```

Figure 15 (page 3 of 8)

```
 781 CTGGCTGTGCGAATTCAGCTGGAAAATGTGACACTGCTGAACCCGGATCC  830
     ||||||| || ||||||||||||||||||| ||||| ||||| || ||
 750 CTGGCTGTTCGCATTCAGCTGGAAAATGTGACCCTGCTAAACCCCGAACC  799

831 TGCAGAGGGCCCCAAGCCTAGACCGGCGGTGTGGCTCAGCTGGAAGGTCA  880
     || | | || |||||||||  | ||   |  |||||||||||||||||| |
 800 TGTAAAAGGTCCCAAGCCTGGGCCATCCGTGTGGCTCAGCTGGAAGGTGA  849

881 GTGGCCCTGCTGCGCCTGCCCAATCTTACACGGCCTTGTTCAGGACCCAG  930
     | |||||||||| |||||   | || ||||| || |||||||||| |||
 850 GCGGCCCTGCTGCACCTGCTGAGTCATACACAGCTCTGTTCAGGACTCAG  899

931 ACTGCCCCGGGAGGCCAGGGAGCTCCGTGGGCAGAGGAGCTGCTGGCCGG  980
     |   ||||  | |  |||  ||| ||||  ||||||  ||||||||  ||
 900 AGGTCCCCCAGGGACCAAGGATCTCCATGGACAGAGGTGCTGCTGCGTGG  949

981 CTGGCAGAGCGCAGAGCTTGGAGGCCTCCACTGGGGCCAAGACTACGAGT  1030
     || |||||| ||| ||||||| ||   |||||||||||||||||||| | |
 950 CTTGCAGAGTGCAAAGCTTGGGGGTCTCCACTGGGGCCAAGACTATGAAT  999

1031 TCAAAGTGAGACCATCCTCTGGCCGGGCTCGAGGCCCTGACAGCAACGTG  1080
     |||||||||||| ||| |||||||||||||||||||||||||||| |||
1000 TCAAAGTGAGACCGTCCTCCGGCCGGGCTCGAGGCCCTGACAGCAATGTG  1049

1081 CTGCTCCTGAGGCTGCCGGAAAAAGTGCCCAGTGCCCCACCTCAGGAAGT  1130
     |||||||||||||||||  ||| | ||||||||||||||||||||| |||
1050 TTGCTCCTGAGGCTGCCTGAACAGGTGCCCAGTGCCCCACCTCAAGGAGT  1099

1131 GACTCTAAAGCCTGGCAATGGCACTGTCTTTGTGAGCTGGGTCCCACCAC  1180
     ||| ||| ||||||| || | |||||||||||||||| |||| |||||||
1100 GACCTTAAGATCTGGCAACGGTAGTGTCTTTGTGAGTTGGGCTCCACCAC  1149

1181 CTGCTGAAAACCACAATGGCATCATCCGTGGCTACCAGGTCTGGAGCCTG  1230
     |||||||| ||| |||||  | ||||||||| ||||||||||||||||||
1150 CTGCTGAAAGCCATAATGGTGTCATCCGTGGTTACCAGGTCTGGAGCCTG  1199

1231 GGCAACACATCACTGCCACCAGCCAACTGGACTGTAGTTGGTGAGCAGAC  1280
     ||||| | ||| ||||  | ||||||||||| ||||| ||||| |||||
1200 GGCAATGCCTCATTGCCTGCTGCCAACTGGACCGTAGTGGGTGAACAGAC  1249

1281 CCAGCTGGAAATCGCCACCCATATGCCAGGCTCCTACTGCGTGCAAGTGG  1330
     ||||||||| |||||||||| | |||||||||||||| || |||||||||
1250 CCAGCTGGAGATCGCCACACGACTGCCAGGCTCCTATTGTGTGCAAGTGG  1299
```

Figure 15 (page 4 of 8)

```
1331 CTGCAGTCACTGGTGCTGGAGCTGGGGAGCCCAGTAGACCTGTCTGCCTC 1380
     |||||||||||| ||||| ||||| || | ||||| ||||||||||||
1300 CTGCAGTCACTGGAGCTGGTGCTGGAGAACTCAGTACCCTGTCTGCCTC 1349

1381 CTTTTAGAGCAGGCCATGGAGCGAGCCACCCAAGAACCCAGTGAGCATGG 1430
     |||||||||||||||||||||||| || | | ||| ||||| | ||||
1350 CTTTTAGAGCAGGCCATGGAGCAATCAGCACGAGACCCCAGGAAACATGT 1399

1431 TCCCTGGACCCTGGAGCAGCTGAGGGCTACCTTGAAGCGGCCTGAGGTCA 1480
     ||||||||||||| ||||||||||| |||||| || || || ||||
1400 TCCCTGGACCCTGGAACAGCTGAGGGCCACCTTGAGACGACCAGAAGTCA 1449

1481 TTGCCACCTGCGGTGTTGCACTCTGGCTGCTGCTTCTGGGCACCGCCGTG 1530
     |||||| | | ||| ||||||| ||||||| || |||| | |||
1450 TTGCCAGTAGTGCTGTCCTACTCTGGTTGCTGCTACTAGGCATTACTGTG 1499

1531 TGTATCCACCGCCGGCGCCGAGCTAGGGTGCACCTGGGCCCAGGTCTGTA 1580
     |||||| || | || ||| |||| ||||||||||||||||||||||||
1500 TGTATCTACAGACGACGCAAAGCTGGGGTGCACCTGGGCCCAGGTCTGTA 1549

1581 CAGATATACCAGTGAGGATGCCATCCTAAAACACAGGATGGATCACAGTG 1630
     |||||| ||||| ||||| ||||| |||||||||||||||| |||||||
1550 CAGATACACCAGCGAGGACGCCATTCTAAAACACAGGATGGACCACAGTG 1599

1631 ACTCCCAGTGGTTGGCAGACACTTGGCGTTCCACCTCTGGCTCTCGGGAC 1680
     |||||| ||| ||||||||| |||||||||||||||||||||||| |||
1600 ACTCCCCATGGCTGGCAGACACCTGGCGTTCCACCTCTGGCTCTCGAGAC 1649

1681 CTGAGCAGCAGCAGCAGCCTCAGCAGTCGGCTGGGGGCGGATGCCCGGGA 1730
     |||||||||||||||||||| || |||||||||||| ||| | |||||
1650 CTGAGCAGCAGCAGCAGCCTTAGTAGTCGGCTGGGATTGGACCCTCGGGA 1699

1731 CCCACTAGACTGTCGTCGCTCCTTGCTCTCCTGGGACTCCCGAAGCCCCG 1780
     |||||||| | | |||||||| |||||||||| | || ||||||||
1700 CCCACTAGAGGGCAGGCGCTCCTTGATCTCCTGGGACCCTCGGAGCCCCG 1749

1781 GCGTGCCCCTGCTTCCAGACACCAGCACTTTTTATGGCTCCCTCATCGCT 1830
     | || ||||||||||||||||| ||||| ||||| |||||||||| ||
1750 GTGTACCCCTGCTTCCAGACACGAGCACGTTTTACGGCTCCCTCATTGCA 1799

1831 GAGCTGCCCTCCAGTACCCCAGCCAGGCCAAGTCCCCAGGTCCCAGCTGT 1880
     |||| ||| ||||| | |||| | ||||||| ||| || |||||||
1800 GAGCAGCCTTCCAGCCCTCCAGTCCGGCCAAGCCCCAAGACACCAGCTGC 1849
```

Figure 15 (page 5 of 8)

```
1881 CAGGCGCCTCCCACCCCAGCTGGCCCAGCTCTCCAGCCCCTGTTCCAGCT 1930
     ||||||  |  |||  ||  ||  ||||         ||||||||||||  |  ||||
1850 TAGGCGCTTTCCATCCAAGTTGGCTGGAACCTCCAGCCCCTGGGCTAGCT 1899

1931 CAGACAGCCTCTGCAGCCGCAGGGGACTCTCTTCTCCCCGCTTGTCTCTG 1980
     ||||  ||  |||||||||||||||||||||||||  |||  ||  |||  ||||||||
1900 CAGATAGTCTCTGCAGCCGCAGGGGACTCTGTTCCCCACGCATGTCTCTG 1949

1981 GCCCCTGCAGAGGCTTGGAAGGCCAAAAAGAAGCAGGAGCTGCAGCATGC 2030
     |||||  ||||||||||||||||||||||||||||||||||||||  ||||  ||  ||
1950 ACCCCTACAGAGGCTTGGAAGGCCAAAAAGAAGCAGGAATTGCACCAAGC 1999

2031 CAACAGTTCCCCACTGCTCCGGGGCAGCCACTCCTTGGAGCTCCGGGCCT 2080
     |||||  ||||||||||||||||||||||||||||||||  ||  ||||     ||  ||||||
2000 TAACAGCTCCCCACTGCTCCGGGGCAGCCACCCCATGGAAATCTGGGCCT 2049

2081 GTGAGTTAGGAAATAGAGGTTCCAAGAACCTTTCCCAAAGCCCAGGAGCT 2130
     |  ||||||  ||||    ||||   ||||||||||||||  ||||||||||||||
2050 GGGAGTTGGGAAGCAGAGCCTCCAAGAACCTTTCTCAAAGCCCAGGAGAA 2099

2131 GTGCCCCAAGCTCTGGTTGCCTGGCGGGCCCTGGGACCGAAACTCCTCAG 2180
     |  ||||||  |||    ||||    |||||||  ||   |||||||    ||||    |    |    |
2100 GCGCCCCGAGCCGTGGTATCCTGGCGTGCTGTGGGACCACAACTTCACCG 2149

2181 CTCCTCAAATGAGCTGGTTACTCGTCATCTCCCTCCAGCACCCCTCTTTC 2230
     |    |||  |  ||||||||     ||||||  ||||||||  |||||||  |  ||
2150 CAACTCCAGTGAGCTGGCATCTCGTCCACTCCCTCCAACACCCCTTTCTC 2199

2231 CTCATGAAACTCCCCCAACTCAGAGTCAACAGACCCAGCCTCCGGTGGCA 2280
     ||  ||  |  ||  ||    |  |||         |  ||||||  ||||    |    ||  |
2200 TTCGTGGAGCTTCC...AGTCATGACCCACAGAGCCAGTGTGTGGAGAAG 2246

2281 CCACAGGCTCCCTCCTCCATCCTGCTGCCAGCAGCCCCCATCCCCATCCT 2330
     |    ||  ||||||||||     ||     |||||||||||||    ||  ||  ||||
2247 CTCCAAGCTCCCTCCTCTGACCCACTGCCAGCAGCCCCTCTCTCCGTCCT 2296

2331 TAGCCCCTGCAGTCCCCCTAGCCCCCAGGCCTCTTCCCTCTCTGGCCCCA 2380
     |  |  |  |  |||  ||  |  |||||||||||||||||  ||||||  |  ||  |
2297 CAACTCTTCCAGACCTTCCAGCCCCAGGCCTCTTTCCTCTCCTGTCCTA 2346

2381 GCCCAGCTTCCAGTCGCCTGTCCAGCTCCTCACTGTCATCCCT......G 2424
     |||||  |  |||||     ||||||||||||||||  ||||||||||  |                |
2347 GCCCATCCTCCAGCAACCTGTCCAGCTCCTCGCTGTCATCCTTAGAGGAG 2396
```

Figure 15 (page 6 of 8)

```
2425 GGGGAGGATCAAGACAGCGTGCTGACCCCTGAGGAGGTAGCCCTGTGCTT 2474
     | ||||||||| ||||||||||| ||||| ||||||||||||||||| |
2397 GAGGAGGATCAGGACAGCGTGCTCACCCCCGAGGAGGTAGCCCTGTGTCT 2446

2475 GGAACTCAGTGAGGGTGAGGAGACTCCCAGGAACAGCGTCTCTCCCATGC 2524
     ||| |||||||| || |||||||| |||| |||||| || ||||| ||||
2447 GGAGCTCAGTGATGGGGAGGAGACACCCACGAACAGTGTATCTCCTATGC 2496

2525 CAAGGGCTCCTTCACCCCCCACCACCTATGGGTACATCAGCGTCCCAACA 2574
     |||| |||||||| || || || |||||||| || |||||| | |||||
2497 CAAGAGCTCCTTCCCCGCCAACAACCTATGGCTATATCAGCATACCAACC 2546

2575 GCCTCAGAGTTCACGGACATGGGCAGGACTGGAGGAGGGGTGGGGCCCAA 2624
         |||||    |   |  |||||||||||  |||| || || ||||||  |   |
2547 TGCTCAGGACTGGCAGACATGGGCAGAGCTGGCGGGGGCGTGGGTCTGA 2596

2625 GGGGGGAGTCTTGCTGTGCCCACCTCGGCCCTGCCTCACCCCCACCCCCA 2674
     ||  ||   |||  ||||    ||||||||||||||||| |||||| || ||||
2597 GGTTGGGAACTTACTGTATCCACCTCGGCCCTGCCCCACCCCTACACCCA 2646

2675 GCGAGGGCTCCTTAGCCAATGGTTGGGGCTCAGCCTCTGAGGACAATGCC 2724
     |||||||||| | |||||||||||||||||||||| |||||||||||| |
2647 GCGAGGGCTCCCTGGCCAATGGTTGGGGCTCAGCTTCTGAGGACAATGTC 2696

2725 GCCAGCGCCAGAGCCAGCCTTGTCAGCTCCTCCGATGGCTCCTTCCTCGC 2774
     ||||||||| |||||||| || ||||| || ||||||||||||||||||
2697 CCCAGCGCCAGGGCCAGCCTGGTTAGCTCTTCTGATGGCTCCTTCCTCGC 2746

2775 TGATGCTCACTTTGCCCGGGCCCTGGCAGTGGCTGTGGATAGCTTTGGTT 2824
     |||| ||||||||| || |||||||||||||||||||||||||||||||
2747 TGATACTCACTTTGCTCGTGCCCTGGCAGTGGCTGTGGATAGCTTTGGCC 2796

2825 TCGGTCTAGAGCCCAGGGAGGCAGACTGCGTCTTCATAGATGCCTCATCA 2874
     || |||| || |||||||| || ||||| ||||||| ||||||||||||
2797 TCAGTCTGGATCCCAGGGAAGCTGACTGTGTCTTCACTGATGCCTCATCA 2846

2875 CCTCCCTCCCCACGGGATGAGATCTTCCTGACCCCCAACCTCTCCCTGCC 2924
     |||||||||| |||| |||  ||| |||||||| | | |||| |||||
2847 CCTCCCTCCCCTCGGGGTGATCTCTCCCTGACCCGAAGCTTCTCTCTGCC 2896

2925 CCTGTGGGAGTGGAGGCCAGACTGGTTGGAAGACATGGAGGTCAGCCACA 2974
     ||||||||||||||||||||||||||||||||||     |||  |||||||||
2897 TTTGTGGGAGTGGAGGCCAGACTGGTTGGAAGATGCTGAGATCAGCCACA 2946
```

Figure 15 (page 7 of 8)

```
2975 CCCAGCGGCTGGGAAGGGGGATGCCTCCCTGGCCCCCTGAACTCTCAGAT 3024
     |||||  ||||||||  ||||||  |||||||||||||  ||||  |  |||  |
2947 CCCAGAGGCTGGGGAGGGGGCTGCCTCCCTGGCCTCCTG.ATTCTAGGGC 2995

3025 CTCTTCCCAGAGAAGTCAGCTCCACTGTCGTATGCCCAAGGCTGGTGCTT 3074
     ||||||||||  |||||   |||       ||   |  ||||||||||||||||||
2996 CTCTTCCCAGCGAAGTTGGCTAACTGGTGCTGTGCCCAAGGCTGG.... 3041

3075 CTCCTGTAGATTACTCCTGAACCGTGTCCCTGAGACTTCCCAGACGGGAA 3124
             ||||  ||||||||      ||||||||||       |||||  |  |  |
3042 ........GATTCCTCCTGAA..TTGTCCCTGAGA.AGGCCAGAAGAGCA 3080

3125 TCAGAACCACTTCTCCTGTTCCACCCACAAGACCTGG...GCTGTGGTGT 3171
       |   |||||  ||||||||         ||            |||||          ||         |||
3081 CCCAGACCAC.TCTCCTGTCTGTCC.......CCTGGCTTTCTCACATGT 3122

3172 GTGGGTCTTGGCCTGTGTTTCTCTGCAGCTGGGGTCCACCTTC.CCAAGC 3220
       |   ||||||||||| ||  |||||||| |    |   ||||||| ||  |  |  ||
3123 GGAGGTCTTGGCCTATGCTTCTCTGTAATAGAAGTCCACCGTCACTAGGC 3172

3221 CTCCAGAGAGTTCTCCCTCCACGATTGTGAAAACAAATG.....AAAACA 3265
     ||  |||||  |||    |    ||||||  ||||  |||||      |||  ||
3173 TTCTGGAGAGCTCTGTCATTGGGATTGTTAAAATAAATGAAAGCAAACCA 3222

3266 AAATTAGAGCAAAGCTGACCTGGA.GCCCTCAGGGAGCAAAACATCATCT 3314
     ||||   ||  ||   |   |   ||||   ||| |  |  ||  |||  |||  |||  |||||
3223 AAATATGATCACGGGAGTCTTGGATTCCCACTGAGAACAAGACAGCATCT 3272

3315 CCACCTGACTCCTAGCCACTGCTTTCTCCTCTGTGCCATCCACTCCCACC 3364
     ||                        ||  ||     |||                  |||||     |||
3273 TCA............GGACAGCAGACTC..........TCCACAACCAGA 3300

3365 ACCAGGTTGTTTTGGCCTGAGGAGCAGCCCTGCCTGCTGCTCTTCCCCCA 3414
     |||·              ||||||||      ||  |    ||||  ||  |  |    ||      |||
3301 ACC.......TTTGGCCT...AAGTAAGCCTGGCTCCGGAGCT..CCCAC 3338

3415 CCATTTGGATCACAGGAAGTGGAGGAGCCAGAGGTGCCTTTGTGGAGGAC 3464
     |  |  |||||||  |  |||   |  |  ||||||       |  |||    |  ||||||
3339 CTAAGTGGATCATGGAAAGAAGGGAAGCCAACCAGGTCTTCAGGAAGGAC 3388

3465 AGCAGTGGCTGCTGGGAGAGGGCTGTGGAGGAAGGAGCTTCTCGGAGCCC 3514
     ||  |  ·|  |  |  ||  ||||||||  |||  |||    |    |  |  |  |  ||   |
3389 AGAAAT.GT.TTTTGGTGAGGGCTATGGTGGA...GGACCTGTGGAAGAGC 3435
```

Figure 15 (page 8 of 8)

```
3515 CCTCTCAGCCTTACCTGGGCCCCTCCTCTAGAGAAGAGCTCAACTCTCT. 3563
     |||||||    ||| ||| | |||||  |||||    |||||||| || |
3436 CCTCTCATATCTACTTGGACTCCTCCCTTAGAGGCCAGCTCAACCCTTTC 3485

3564 CCCAACCTCACCATGGAAAGAAAAT.AATTATGAATGCCACTGAGGCACT 3612
     ||||  | ||||||| || |||| | ||   ||  |   || ||| |
3486 CCCAGTCACACCATGCAAGGAAACTAAAGGAGAAAGGTCGTGGATGCAGT 3535

3613 GAGGCCCTACCTCATGCCAAACAAAGGGTTCAAGGCTGGGTCTAGCGAGG 3662
     | | ||   |    | |  || | |||||| |   | || |  ||||
3536 GGGCCCTATACAGCGTCACAGTCAATGCTTCAAAGTGAGATCAATGGAGG 3585

3663 ATGCTGAAGGAAGGGAGGTATG 3684
     |  |||||||||  ||| | | |
3586 AGACTGAAGGAAAGGACGCAGG 3607
```

Figure 19
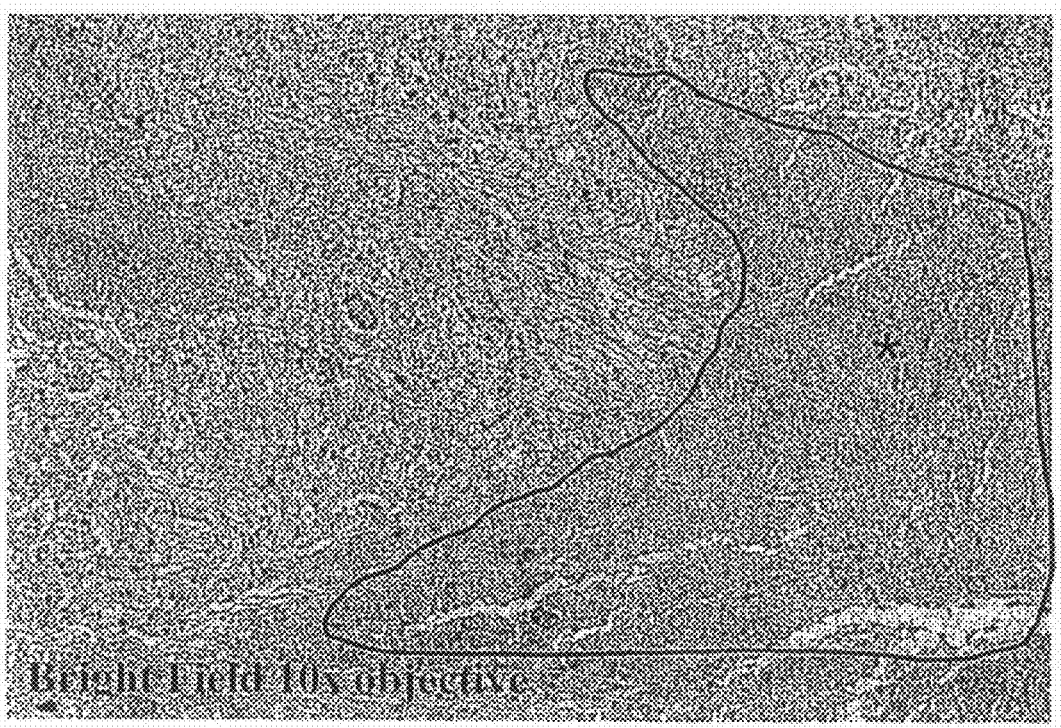
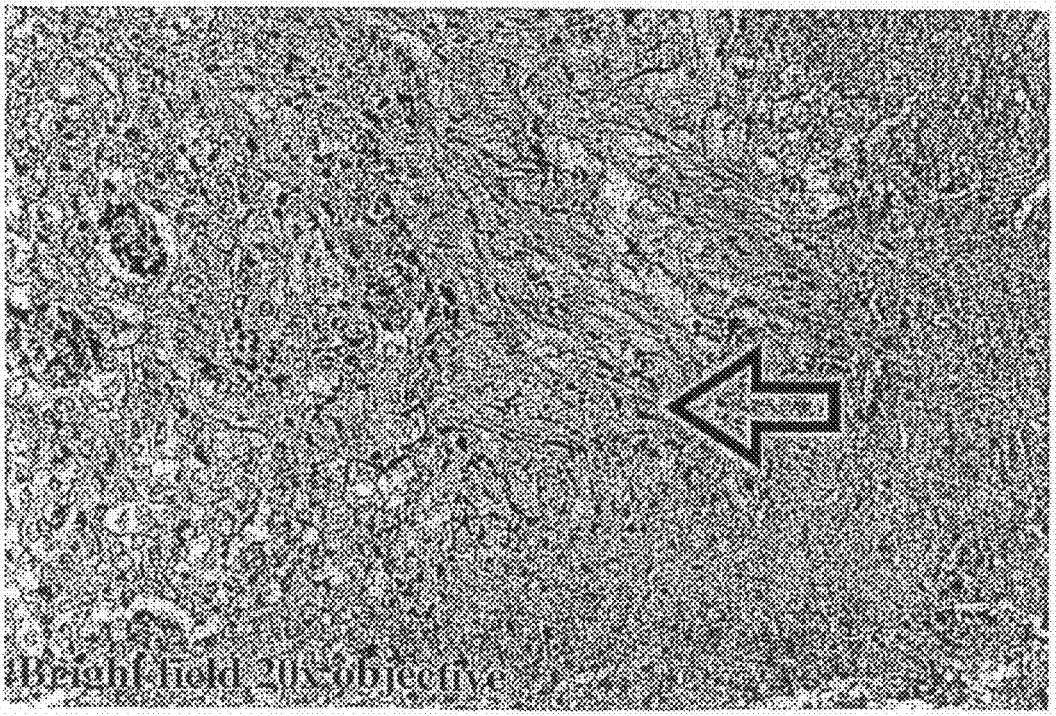

Figure 20
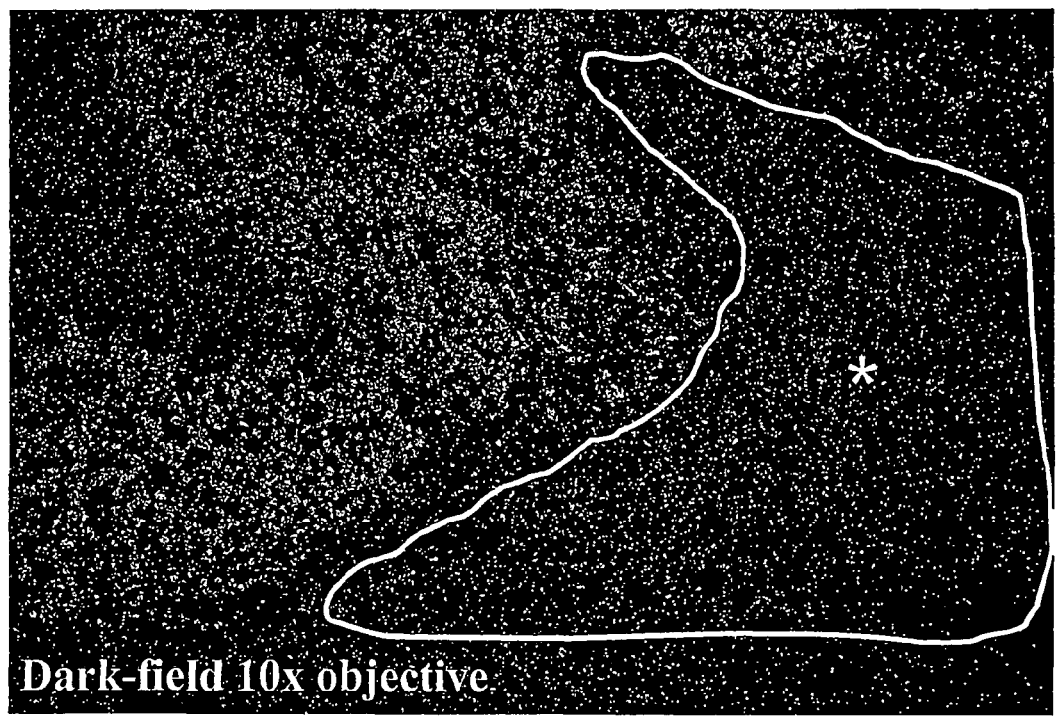
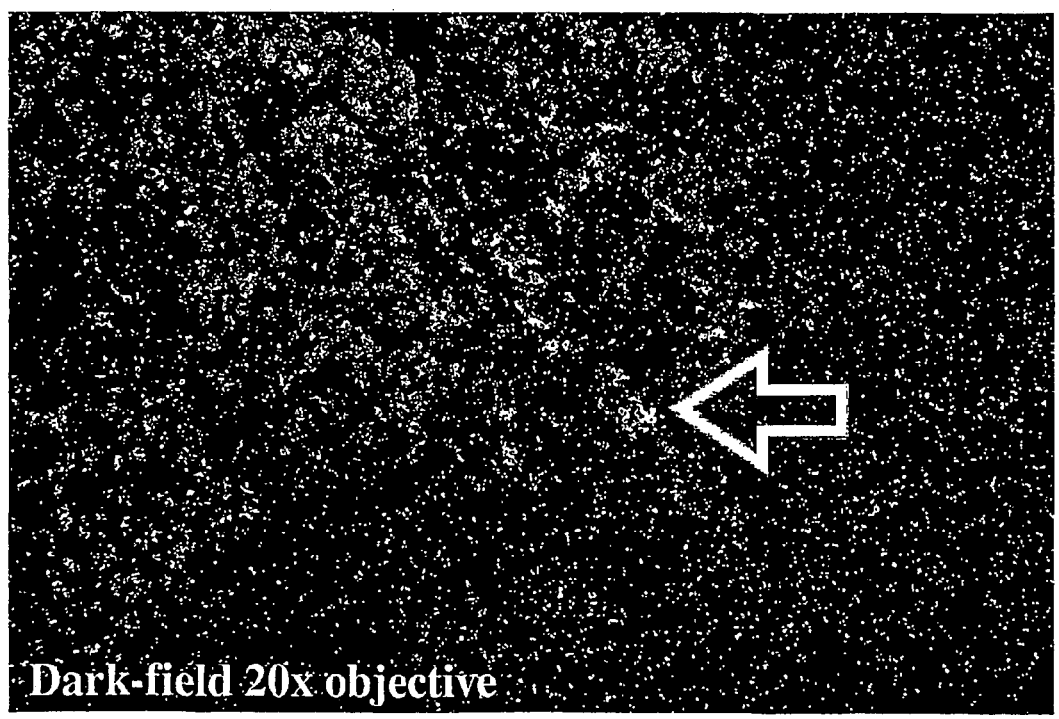

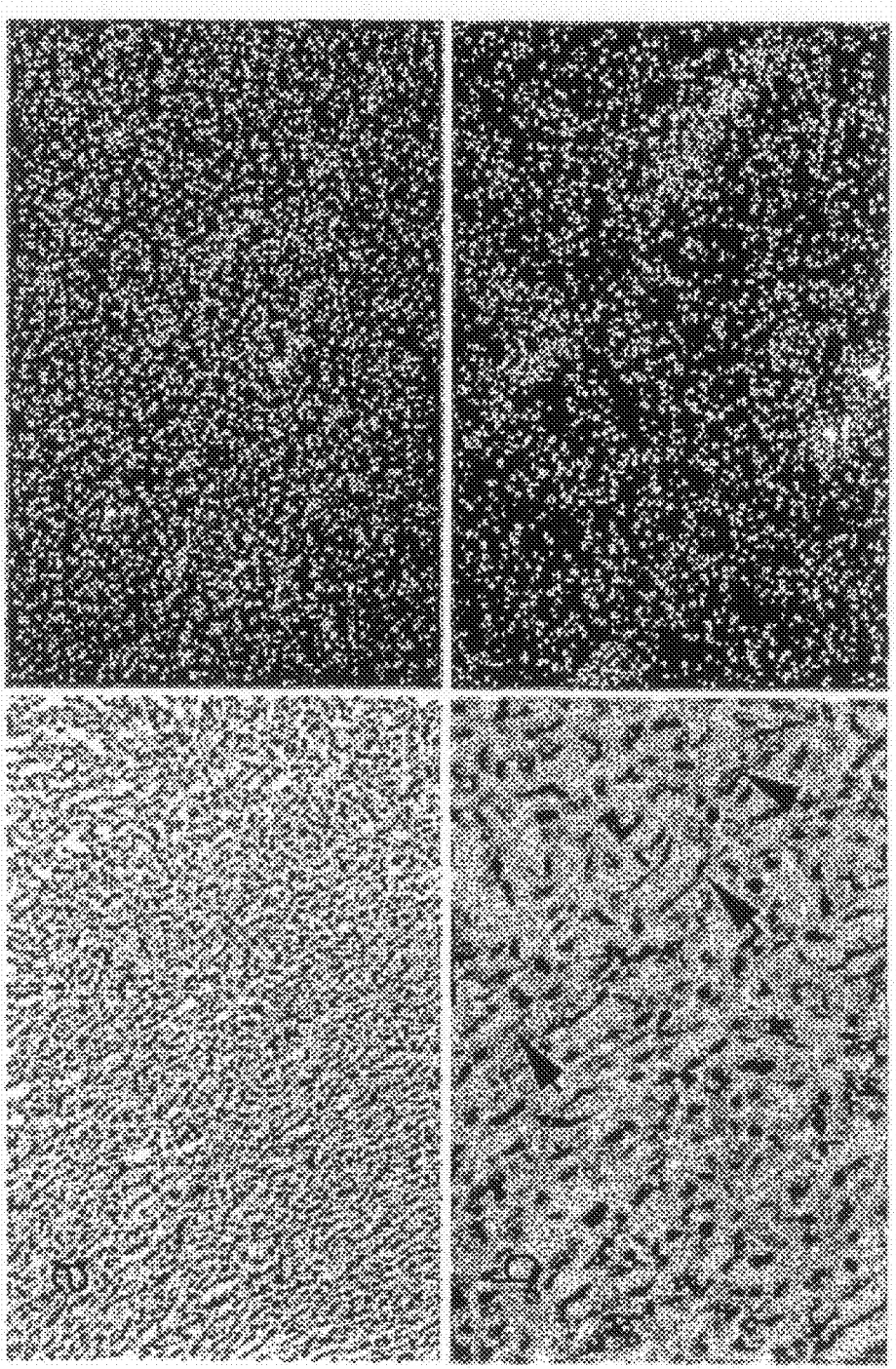
Figure 27 (page 1 of 2)

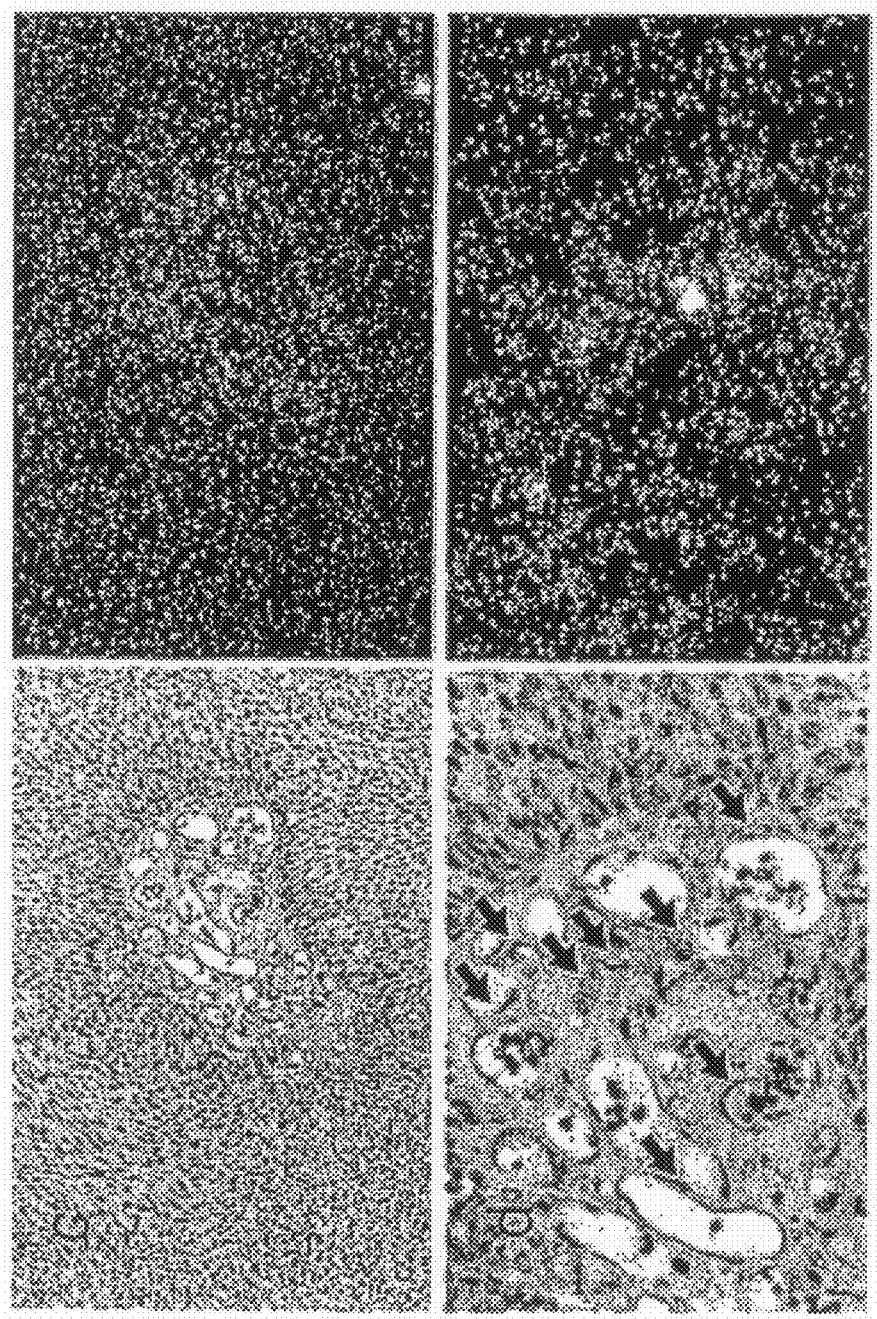
Figure 27 (page 2 of 2)

IMAGING, DIAGNOSIS AND TREATMENT OF DISEASE

CROSS-REFERENCE TO RELATED APPLICATIONS

This application is a Continuation of application Ser. No. 11/429,627, filed on May 4, 2006 now U.S. Pat No. 7,582,440, which is a Continuation of application Ser. No. 10/416,090, filed on Oct. 15, 2003 now U.S. Pat. No. 7,498,034, which is a national stage filing under 35 U.S.C. §371 of PCT International application PCT/GB2001/04906 designating the United States of America, and filed Nov. 6, 2001, the entire contents of which are hereby incorporated herein by reference. This application also claims the benefit under 35 U.S.C. §119(e) to U.S. Provisional Application Ser. Nos. 60/245,566, filed on Nov. 6, 2000 and 60/273,662, filed on Mar. 7, 2001, the entire contents of which are hereby incorporated by reference.

The present invention relates to genes whose expression is selective for the endothelium and use of these genes or gene products, or molecules which bind thereto, in imaging, diagnosis and treatment of conditions involving the vascular endothelium.

The endothelium plays a central role in many physiological and pathological processes and it is known to be an exceptionally active transcriptional site. Approximately 1,000 distinct genes are expressed in an endothelial cell. In contrast red blood cells were found to express 8, platelets 22 and smooth muscle 127 separate genes (Adams et al, 1995). Known endothelial specific genes attract much attention from both basic research and the clinical community. For example, the endothelial specific tyrosine kinases Tie, TIE2/TEK, KDR, and flt1 are crucial players in the regulation of vascular integrity, endothelium-mediated inflammatory processes and angiogenesis (Sato et al, 1993, Sato et al, 1995, Fong et al, 1995, Shalaby et al, 1995, Alello et al, 1995). Angiogenesis is now widely recognised as a rate-limiting process for the growth of solid tumours. It is also implicated in the formation of atherosclerotic plaques and restenosis. Finally endothelium plays a central role in the complex and dynamic system regulating coagulation and hemostasis.

Of the many distinct genes expressed in an endothelial cell, not all are entirely endothelial cell selective and so the genes and their products, and molecules which bind thereto are not generally useful in the imaging, diagnosis and treatment of disease. Thus, there remains a need for endothelial cell specific or selective molecules.

We report here identification of two highly endothelial selective genes which we have called: endothelial cell-specific molecule 1 (ECSM1) and magic roundabout (endothelial cell-specific molecule 4; ECSM4). The terms ECSM1 and ECSM4 are also used to indicate, as the context will make clear, the cDNA and polypeptides encoded by the genes. These genes, and especially ECSM4, are surprisingly specific in their cell expression profile. ECSM4, for example, shows similar endothelial-cell selectivity to the marker currently accepted in the art as the best endothelial cell marker (von Willibrand Factor). Clearly, such a high level of endothelial cell specificity is both unprecedented and unexpected.

ECSM1 (UniGene entry Hs.13957) has no protein or nucleotide homologues. It is most likely to code for a small protein of 103 aa (the longest and most up-stream open reading frame which was identified in the contig sequence). ECSM1 contains two sequence tagged sites which are unique and definite within the genome (STS sites; dbSTS G26129 and G28043) and localise to chromosome 19. A polynucleotide comprising the complement of part of the ECSM1 gene is described in WO 99/06423 (Human Genome Sciences) (termed "gene 22"; page 31-32) as being expressed primarily in umbilical cord endothelial cells and to a lesser extent in human adipose tissue. However, WO 99/06423 discloses an open reading frame (ORF) in the polynucleotide which encodes a polypeptide of only 45 amino acids. According to our analyses, this does not represent the correct polypeptide of 103 amino acids, as the actual start codon in ECSM1 is further 5' than the one identified in WO 99/06423.

The human magic roundabout (ECSM4) cDNA clone with a long ORF of more than 417 aa (GenBank Accession No AK000805) and described in WO 99/46281 as a 3716 nucleotide sequence was identified by BLAST searches for the Hs.111518 contig. This sequence is rich in prolines and has several regions of low amino acid complexity. BLAST PRODOM search (protein families database at HGMP, UK) identified a 120 bp region of homology to the cytoplasmic domain conserved family of transmembrane receptors involved in repulsive axon guidance (ROBO1 DUTT1 protein family, E=4e-07). Homology was extended to 468 aa (E=1.3e-09) when a more rigorous analysis was performed using ssearch (Smith and Waterman 1981) but the region of similarity was still contained to the cytoplasmic domain. The ROBO1 DUTT1 family comprises the human roundabout homologue 1 (ROBO1), the mouse gene DUTT1 and the rat ROBO1 (Kidd et al, 1998, Brose et al, 1999). Because of this region of homology we called the gene represented by Hs. 111518 "magic roundabout" (ECSM4). Additionally, BLAST SBASE (protein domain database at HGMP) suggested a region of similarity to the domain of the intracellular neural cell adhesion molecule long domain form precursor (E=2e-11). It should be noted that the true protein product for magic roundabout is likely to be larger than the 417 aa coded in the AK000805 clone since the ORF has no apparent up-stream limit, and size comparison to human roundabout 1 (1651 aa) suggests a much bigger protein. This is confirmed in FIG. 3 which shows the translation product of human ECSM4 to be around 118 kDa. However, ECSM4 is smaller than other members of the roundabout family, sharing only two of the five Ig domains and two of the three fibronectin domains in the extracellular region. The intracellular putative proline rich region that is homologous to those in roundabout are thought to couple to c-abl. FIG. 12 shows the full length amino acid sequence of human ECSM4 (1105aa), and the sequence of the mouse homologue is shown in FIG. 13. Nucleotide coding sequences which display around 99% identity to the ECSM4 nucleotide sequence given in FIG. 12 are disclosed in WO 99/11293 and WO 99/53051.

Additional sequences which display homology to the ECSM4 polypeptide or polynucleotide sequence are disclosed in EP 1 074 617, WO 00/53756, WO 99/46281, WO 01/23523 and WO 99/11293. However, none of these publications disclose that the sequences are selectively expressed in the vascular endothelium, nor suggest that they may be so expressed.

Recently intriguing associations between neuronal differentiation genes and endothelial cells have been discovered. For example, a neuronal receptor for vascular endothelial growth factor (VEGF) neuropilin 1 (Soker et al, 1998) was identified. VEGF was traditionally regarded as an exclusively endothelial growth factor. Processes similar to neuronal axon guidance are now being implicated in guiding migration of endothelial cells during angiogenic capillary sprouting. Thus ephrinB ligands and EphB receptors are involved in demarcation of arterial and venous domains (Adams et al, 1999). It is possible that magic roundabout (ECSM4) may be an endothelial specific homologue of the human roundabout 1 involved in endothelial cell repulsive guidance, presumably with a different ligand since similarity is contained within the cytoplasmic i.e. effector region and guidance receptors are known to have highly modular architecture (Bashaw and Goodman 1999).

However, to date there has been no mention of the existence of an endothelial counterpart, nor the expression pattern of the magic roundabout (ECSM4) gene being restricted to endothelial cells especially angiogeneic endothelial cells, nor of any function of the encoded polypeptide.

It should be noted that a surprising result of our RT-PCR analysis, described in Example 1, was that genes identified here appear to show endothelial specificity (FIG. 1) comparable with the classic endothelial marker von Willebrand factor (vWF). Expression of known endothelial specific genes is not usually 100% restricted to the endothelial cell. Data presented herein shows the quite unanticipated finding that ECSM4 is not expressed at detectable levels (at least using the methods described in the examples) in cell types other than endothelial cells, given the less than 100% selectivity of known endothelial cell markers. Ribonuclease protection analysis has confirmed and extended this observation (FIG. 14a). ECSM4 expression was seen to be restricted to endothelium (three different isolates) and absent from fibroblast, carcinoma and neuronal cells. KDR and FLT1 are both expressed in the male and female reproductive tract: on spermatogenic cells (Obermair et al, 1999), trophoblasts, and in decidua (Clark et al, 1996). KDR has been shown to define haematopoietic stem cells (Ziegler et al, 1999). FLT1 is also present on monocytes. In addition to endothelial cells vWF is strongly expressed in megakaryocytes (Sporn et al, 1985, Nichols et al, 1985), and in consequence present on platelets. Similarly, multimerin is present both in endothelial cells (Hayward et al, 1993) and platelets (Hayward et al, 1998).

Generally speaking, endothelial and haematopoietic cells descend from same embryonic precursors: haemangioblasts and many cellular markers are shared between these two cell lineages (for review see Suda et al, 2000). Hence, the finding that the genes ECSM1 and ECSM4 are not expressed in cells other than those of the vascular endothelium is highly surprising.

Determination of genes whose expression is selective for the vascular endothelium allows selective targeting to these cells and thereby the specific delivery of molecules for imaging, diagnosis, prognosis, treatment, prevention and evaluation of therapies for conditions associated with normal or aberrant vascular growth.

A first aspect of the invention provides a compound comprising (i) a moiety which selectively binds the polypeptide ECSM4 and (ii) a further moiety.

By "the polypeptide ECSM4" we include a polypeptide whose sequence comprises or consists of the amino acid sequence given in FIG. 4 or 5 or 7 or 12 or 13 or whose sequence is encoded by the nucleotide sequence given in FIG. 4 between nucleotides 1 and 1395 or between nucleotides 2 and 948 of FIG. 5 or FIG. 7 or between nucleotides 71 and 3442 of FIG. 12 or between nucleotides 6 and 3050 of FIG. 13 and natural variants thereof. Preferably, the ECSM4 polypeptide is one whose amino acid sequence comprises the sequence given in FIG. 4 or FIG. 12.

By "the polypeptide ECSM4" we include a polypeptide represented by SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293, or the polypeptide represented by SEQ ID No 18084 or 5096 of EP 1 074 617, SEQ ID No 210 of WO 00/53756 or WO 99/46281, or SEQ ID Nos 22, 23, 96 or 98 of WO 01/23523 or SEQ ID No 31 of WO 99/11293.

By "the polypeptide ECSM4" we also include any naturally occurring polypeptide which comprises a consecutive 50 amino acid residue portion or natural variants thereof of the polypeptide sequence given in FIG. 4 or 5 or 7 or 12 or 13. Preferably, the polypeptide is a human polypeptide.

Embodiments and features of this aspect of the invention are as described in more detail below.

A second aspect of the invention provides a compound comprising (i) a moiety which selectively binds the polypeptide ECSM1 and (ii) a further moiety.

Preferably, in the first and second aspects of the invention, the binding moiety and further moiety are covalently attached.

By "the polypeptide ECSM1" we include a polypeptide whose amino acid sequence comprises or consists of the sequence given in FIG. 2 and natural variants thereof.

By "the polypeptide ECSM1" we also include any naturally occurring polypeptides which comprises a consecutive 50 amino acid residue portion or natural variants thereof of the polypeptide sequence given in FIG. 2. Preferably, the polypeptide is a human polypeptide.

Preferably, the polypeptide ECSM1 amino acid sequence comprises the sequence given in FIG. 2 but does not comprise the amino acid sequence encoded by ATCC deposit No 209145 made on Jul. 17, 1997 for the purposes of WO 99/06423.

By "natural variants" we include, for example, allelic variants. Typically, these will vary from the given sequence by only one or two or three, and typically no more than 10 or 20 amino acid residues. Typically, the variants have conservative substitutions.

In a preferred embodiment of the first or second aspects of the invention, the moiety capable of selectively binding to the specified polypeptide is an antibody.

Preferably, an antibody which selectively binds ECSM1 or a natural variant thereof is not one which binds a polypeptide encoded by SEQ ID No 32 of WO 99/06423 or encoded by the nucleic acid of ATCC deposit No 209145 made on Jul. 17, 1997 for the purposes of WO 99/06423.

Preferably, an antibody which selectively binds ECSM1 is one which binds a polypeptide whose amino acid sequence comprises the sequence given in FIG. 2 or a natural variant thereof but which polypeptide does not comprise the amino acid sequence encoded by ATCC deposit No 209145 made on Jul. 17, 1997.

Preferably, an antibody which selectively binds ECSM4 is one which selectively binds a polypeptide with the sequence GGDSLLGGRGSL, LLQPPARGHAHDGQALSTDL, EPQDYTEPVE, TAPGGQGAPWAEE or ERATQEPSEHGP or a sequence which is located in the extracellular portion of ECSM4. As described in more detail below, these sequences represent amino acid sequences which are only found in the human ECSM4 and are not found in the mouse ECSM4 polypeptide sequence.

Preferably, the moiety which selectively binds ECSM4, such as an antibody, is one which binds a polypeptide whose amino acid sequence comprises the sequence given in any one of FIGS. 4, 5, 7, 12 or 13 or a natural variant thereof but does not bind the polypeptide represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293, or encoded by any one of the nucleotide sequences represented by SEQ ID No 18084 or 5096 of EP 1 074 617, SEQ ID No 210 of WO 00 53756 or WO 99/46281, or SEQ ID Nos 22, 23, 96 or 98 of WO 01/23523 and SEQ ID No 31 of WO 99/11293.

By "antibody" we include not only whole immunoglobulin molecules but also fragments thereof such as Fab, F(ab')2, Fv and other fragments thereof that retain the antigen-binding site. Similarly the term "antibody" includes genetically engineered derivatives of antibodies such as single chain Fv molecules (scFv) and domain antibodies (dAbs). The term also includes antibody-like molecules which may be produced using phage-display techniques or other random selection techniques for molecules which bind to ECSM1 or ECSM4.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dabs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')2 fragments have two antigen combining sites. In contrast, Fab, Fv, ScFv and dAb fragments are monovalent, having only one antigen combining site.

Although the antibody may be a polyclonal antibody, it is preferred if it is a monoclonal antibody. In some circumstance, particularly if the antibody is going to be administered repeatedly to a human patient, it is preferred if the monoclonal antibody is a human monoclonal antibody or a humanised monoclonal antibody.

Suitable monoclonal antibodies which are reactive as said may be prepared by known techniques, for example those disclosed in *"Monoclonal Antibodies; A manual of techniques"*, H Zola (CRC Press, 1988) and in *"Monoclonal Hybridoma Antibodies: Techniques and Application"*, SGR Hurrell (CRC Press, 1982). Polyclonal antibodies may be produced which are polypepcific or monospecific. It is preferred that they are monospecific.

Chimaeric antibodies are discussed by Neuberger et al (1998, 8$^{th}$ *International Biotechnology Symposium* Part 2, 792-799).

Suitably prepared non-human antibodies can be "humanised" in known ways, for example by inserting the CDR regions of mouse antibodies into the framework of human antibodies.

The antibodies may be human antibodies in the sense that they have the amino acid sequence of human anti-ECSM1 or -ECSM4 antibodies but they may be prepared using methods known in the art that do not require immunisation of humans. For example, transgenic mice are available which contain, in essence, human immunoglobulin genes (see Vaughan et al (1998) *Nature Biotechnol.* 16, 535-539.

In an alternative embodiment, the moiety capable of selectively binding to a polypeptide is a peptide. The ECSM4/magic roundabout polypeptide shows homology with the *Drosophila*, mouse and human roundabout proteins, which are cell surface receptors for secreted Slit proteins (Li et al (1996) *Cell* 96:807-818). Any cognate ligand for ECSM4/magic roundabout which is capable of selectively binding the region of the polypeptide which is located extracellularly may be useful. The extracellular region of ECSM4 is likely to be located within residues 1-467 of the ECSM4 polypeptide sequence given in FIG. 12. It is believed that certain peptides may be cognate ligands for ECSM4. Such a peptide will be a suitable moiety for selectively binding ECSM4/magic roundabout. Peptides binding ECSM4 can be identified by means of a screen. A suitable method or screen for identifying peptides or other molecules which selectively bind ECSM4 may comprise contacting the ECSM4 polypeptide with a test peptide or other molecule under conditions where binding can occur, and then determining if the test molecule or peptide has bound ECSM4. Methods of detecting binding between two moieties are well known in the art of biochemistry. Preferably, the known technique of phage display is used to identify peptides or other ligand molecules which bind to ECSM4. An alternative method includes the yeast two hybrid system.

Peptides or other agents which selectively bind ECSM4 include those which modulate or block the function of ECSM4.

Suitable peptides may be synthesised as described in more detail below.

The further moiety may be any further moiety which confers on the compound a useful property with respect to the treatment or imaging or diagnosis of diseases or other conditions or states which involve undesirable neovasculature formation. Such diseases or other conditions or states are described in more detail below. In particular, the further moiety is one which is useful in killing or imaging neovasculature associated with the growth of a tumour. Preferably, the further moiety is one which is able to kill the endothelial cells to which the compound is targeted.

In a preferred embodiment of the invention the further moiety is directly or indirectly cytotoxic. In particular the further moiety is preferably directly or indirectly toxic to cells in neovasculature or cells which are in close proximity to and associated with neovasculature.

By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it.

In one embodiment the cytotoxic moiety is a cytotoxic chemotherapeutic agent. Cytotoxic chemotherapeutic agents are well known in the art.

Cytotoxic chemotherapeutic agents, such as anticancer agents, include: alkylating agents including nitrogen mustards such as mechlorethanine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, M1H); and adrenocortical suppressant such as mitotane (o,p'-DDD) and aminoglutethimide; taxol and analogues/derivatives; and hormone agonists/antagonists such as flutamide and tamoxifen.

Various of these agents have previously been attached to antibodies and other target site-delivery agents, and so compounds of the invention comprising these agents may readily be made by the person skilled in the art. For example, carbodiimide conjugation (Bauminger & Wilchek (1980) *Methods Enzymol.* 70, 151-159; incorporated herein by reference) may be used to conjugate a variety of agents, including doxorubicin, to antibodies or peptides.

Carbodiimides comprise a group of compounds that have the general formula R—N═C═N—RN, where R and RN can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups.

The water soluble carbodiimide, 1-ethyl-3-(3-dimethylaminopropyl)carbodiimide (EDC) is particularly useful for conjugating a functional moiety to a binding moiety and may be used to conjugate doxorubicin to tumor homing peptides. The conjugation of doxorubicin and a binding moiety requires the presence of an amino group, which is provided by doxorubicin, and a carboxyl group, which is provided by the binding moiety such as an antibody or peptide.

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger & Wilchek, supra, 1980).

Other methods for conjugating a functional moiety to a binding moiety also can be used. For example, sodium periodate oxidation followed by reductive alkylation of appropriate reactants can be used, as can glutaraldehyde cross-linking. However, it is recognised that, regardless of which method of producing a conjugate of the invention is selected, a determination must be made that the binding moiety maintains its targeting ability and that the functional moiety maintains its relevant function.

In a further embodiment of the invention, the cytotoxic moiety is a cytotoxic peptide or polypeptide moiety by which we include any moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. The use of ricin as a cytotoxic agent is described in Burrows & Thorpe (1993) *Proc. Natl. Acad. Sci. USA* 90, 8996-9000, incorporated herein by reference, and the use of tissue factor, which leads to localised blood clotting and infarction of a tumour, has been described by Ran et al (1998) *Cancer Res.* 58, 4646-4653 and Huang et al (1997) *Science* 275, 547-550. Tsai et al (1995) *Dis. Colon Rectum* 38, 1067-1074 describes the abrin A chain conjugated to a monoclonal antibody and is incorporated herein by reference. Other ribosome inactivating proteins are described as cytotoxic agents in WO 96/06641. *Pseudomonas* exotoxin may also be used as the cytotoxic polypeptide moiety (see, for example, Aiello et al (1995) *Proc. Natl. Acad. Sci. USA* 92, 10457-10461; incorporated herein by reference).

Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the binding moiety in known ways. For example EDTA or another chelating agent may be attached to the binding moiety and used to attach $^{111}$In or $^{90}$Y. Tyrosine residues may be labelled with $^{125}$I or $^{131}$I.

The cytotoxic moiety may be a suitable indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody this type of system is often referred to as ADEPT (Antibody-Directed Enzyme Prodrug Therapy). The system requires that the targeting moiety locates the enzymatic portion to the desired site in the body of the patient (ie the site expressing ECSM1 or ECSM4, such as new vascular tissue associated with a tumour) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (see Senter, P. D. et al (1988) "Anti-tumor effects of antibody-alkaline phosphatase conjugates in combination with etoposide phosphate" *Proc. Natl. Acad. Sci. USA* 85, 4842-4846; Bagshawe (1987) *Br. J. Cancer* 56, 531-2; and Bagshawe, K.

D. et al (1988) "A cytotoxic agent can be generated selectively at cancer sites" *Br. J. Cancer.* 58, 700-703.)

Clearly, any ECSM1 or ECSM4 binding moiety may be used in place of an anti-ECSM1 or anti-ECSM4 antibody in this type of directed enzyme prodrug therapy system.

The enzyme and prodrug of the system using an ECSM1 or ECSM4 targeted enzyme as described herein may be any of those previously proposed. The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include: a phenol mustard prodrug activated by an *E. coli* β-glucuronidase (Wang et al, 1992 and Roffler et al, 1991); a doxorubicin prodrug activated by a human β-glucuronidase (Bosslet et al, 1994); further doxorubicin prodrugs activated by coffee bean α-galactosidase (Azoulay et al, 1995); daunorubicin prodrugs, activated by coffee bean α-D-galactosidase (Gesson et al, 1994); a 5-fluorouridine prodrug activated by an *E. coli* β-D-galactosidase (Abraham et al, 1994); and methotrexate prodrugs (eg methotrexate-alanine) activated by carboxypeptidase A (Kuefner et al, 1990, Vitols et al, 1992 and Vitols et al, 1995). These and others are included in the following table.

| Enzyme | Prodrug |
|---|---|
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate<br>Mitomycin phosphate |
| Beta-glucuronidase | p-Hydroxyaniline mustard-glucuronide<br>Epirubicin-glucuronide |
| Penicillin-V-amidase | Adriamycin-N phenoxyacetyl |
| Penicillin-G-amidase | N-(4'-hydroxyphenyl acetyl) palytoxin<br>Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-gluco-pyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

(This table is adapted from Bagshawe (1995) *Drug Dev. Res.* 34, 220-230, from which full references for these various systems may be obtained; the taxol derivative is described in Rodrigues, M. L. et al (1995) *Chemistry & Biology* 2, 223).

Suitable enzymes for forming part of the enzymatic portion of the invention include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as eg thrombolysin (for thrombin prodrugs); hydrolases, such as phosphatases (eg alkaline phosphatase) or sulphatases (eg aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

The prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

When each moiety of the compound is a polypeptide, the two portions may be linked together by any of the conventional ways of cross-linking polypeptides, such as those generally described in O'Sullivan et al (1979) *Anal. Biochem.* 100, 100-108. For example, the ECSM1 or ECSM4 binding moiety may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, the compound may be produced as a fusion compound by recombinant DNA techniques whereby a length of DNA comprises respect-ive regions encoding the two moieties of the compound of the invention either adjacent one another or separated by a region encoding a linker peptide which does not destroy the desired properties of the compound. Conceivably, the two portions of the compound may overlap wholly or partly.

The DNA is then expressed in a suitable host to produce a polypeptide comprising the compound of the invention.

The invention also provides a kit of parts (or a therapeutic system) comprising (1) a compound of the invention wherein the further moiety which is able to convert a relatively non-toxic prodrug into a cytotoxic drug and (2) a relatively non-toxic prodrug. The kit of parts may comprise any of the compounds of the invention and appropriate prodrugs as herein disclosed.

The invention also provides a kit of parts (or a therapeutic system) comprising (1) a compound of the invention wherein the further moiety is able to bind selectively to a directly or indirectly cytotoxic moiety or to a readily detectable moiety and (2) any one of a directly or indirectly cytotoxic or a readily detectable moiety to which the further moiety of the compound is able to bind.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst.* 88, 1193-11203; Shewach & Lawrence (1996) *Invest. New Drugs* 14, 257-263; Horsman (1995) *Acta Oncol.* 34, 571-587; Shenoy & Singh (1992) *Clin. Invest.* 10, 533-551; Mitchell et al (1989) *Int. J. Radiat. Biol.* 56, 827-836; Iliakis & Kurtzman (1989) *Int. J. Radiat. Oncol. Biol. Phys.* 16, 1235-1241; Brown (1989) *Int. J. Radiat. Oncol. Biol. Phys.* 16, 987-993; Brown (1985) *Cancer* 55, 2222-2228).

Also, delivery of genes into cells can radiosensitise them, for example delivery of the p53 gene or cyclin D (Lang et al (1998) *J. Neurosurg.* 89, 125-132; Coco Martin et al (1999) *Cancer Res.* 59, 1134-1140).

The further moiety may be one which becomes cytotoxic, or releases a cytotoxic moiety, upon irradiation. For example, the boron-10 isotope, when appropriately irradiated, releases α particles which are cytotoxic (see for example, U.S. Pat. No. 4,348,376 to Goldenberg; Primus et al (1996) *Bioconjug. Chem.* 7, 532-535).

Similarly, the cytotoxic moiety may be one which is useful in photodynamic therapy such as photofrin (see, for example, Dougherty et al (1998) *J. Natl. Cancer Inst.* 90, 889-905).

The further moiety may comprise a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis.

Examples of suitable oligonucleotides include those directed at bcl-2 (Ziegler et al (1997) *J. Natl. Cancer Inst.* 89, 1027-1036), and DNA polymerase a and topoisomerase Ia (Lee et al (1996) *Anticancer Res.* 16, 1805-1811.

Peptide nucleic acids may be useful in place of conventional nucleic acids (see Knudsen & Nielsen (1997) *Anticancer Drugs* 8, 113-118).

In a further embodiment, the binding moiety may be comprised in a delivery vehicle for delivering nucleic acid to the target. The delivery vehicle may be any suitable delivery vehicle. It may, for example, be a liposome containing nucleic acid, or it may be a virus or virus-like particle which is able to deliver nucleic acid. In these cases, the moiety which selectively binds to ECSM1 or ECSM4 is typically present on the surface of the delivery vehicle. For example, the moiety which selectively binds to ECSM1 or ECSM4, such as a suitable antibody fragment, may be present in the outer surface of a liposome and the nucleic acid to be delivered may be present in the interior of the liposome. As another example, a viral vector, such as a retroviral or adenoviral vector, is engineered so that the moiety which selectively binds to ECSM1 or ECSM4 is attached to or located in the surface of the viral particle thus enabling the viral particle to be targeted to the desired site. Targeted delivery systems are also known such as the modified adenovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Targeted retroviruses are also available for use in the invention; for example, sequences conferring specific binding affinities may be engineered into preexisting viral env genes (see Miller & Vile (1995) *Faseb J* 9, 190-199 for a review of this and other targeted vectors for gene therapy).

Immunoliposomes (antibody-directed liposomes) may be used in which the moiety which selectively binds to ECSM1 or ECSM4 is an antibody. For the preparation of immunoliposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the anti-ECSM1 or -ECSM4 antibody, or fragment thereof, to the liposomal surface. The liposome is conveniently loaded with the DNA or other genetic construct for delivery to the target cells, for example, by forming the said liposomes in a solution of the DNA or other genetic construct, followed by sequential extrusion through polycarbonate membrane filters with 0.6 μm and 0.2 μm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour.

The nucleic acid delivered to the target site may be any suitable DNA which leads, directly or indirectly, to cytotoxicity. For example, the nucleic acid may encode a ribozyme which is cytotoxic to the cell, or it may encode an enzyme which is able to convert a substantially non-toxic prodrug into a cytotoxic drug (this latter system is sometime called GDEPT: Gene Directed Enzyme Prodrug Therapy).

Ribozymes which may be encoded in the nucleic acid to be delivered to the target are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference. Suitable targets for ribozymes include transcription factors such as c-fos and c-myc, and bcl-2. Durai et al (1997) *Anticancer Res.* 17, 3307-3312 describes a hammerhead ribozyme against bcl-2.

EP 0 415 731 describes the GDEPT system. Similar considerations concerning the choice of enzyme and prodrug apply to the GDEPT system as to the ADEPT system described above.

The nucleic acid delivered to the target site may encode a directly cytotoxic polypeptide.

Alternatively, the further portion may comprise a polypeptide or a polynucleotide encoding a polypeptide which is not either directly or indirectly cytotoxic but is of therapeutic benefit. Examples of such polypeptides include anti-proliferative or anti-inflammatory cytokines which could be of benefit in artherosclerosis, and anti-proliferative, immunomodulatory or factors influencing blood clotting may be of benefit in treating cancer.

The further moiety may usefully be an inhibitor of angiogenesis such as the peptides angiostatin or endostatin. The further moiety may also usefully be an enzyme which converts a precursor polypeptide to angiostatin or endostatin. Human matrix metallo-proteases such as macrophage elastase, gelatinase and stromolysin convert plasminogen to angiostatin (Cornelius et al (1998) *J. Immunol.* 161, 6845-6852). Plasminogen is a precursor of angiostatin.

In a further embodiment of the invention, the further moiety comprised in the compound of the invention is a readily detectable moiety.

By a "readily detectable moiety" we include the meaning that the moiety is one which, when located at the target site following administration of the compound of the invention into a patient, may be detected, typically non-invasively from outside the body and the site of the target located. Thus, the compounds of this embodiment of the invention are useful in imaging and diagnosis.

Typically, the readily detectable moiety is or comprises a radioactive atom which is useful in imaging. Suitable radioactive atoms include technetium-99m or iodine-123 for scintigraphic studies. Other readily detectable moieties include, for example, spin labels for magnetic resonance imaging (MRI) such as iodine-123 again, iodine-131, indium-111, fluorine-19, carbon-13, nitrogen-15, oxygen-17, gadolinium, manganese or iron. Clearly, the compound of the invention must have sufficient of the appropriate atomic isotopes in order for the molecule to be readily detectable.

The radio- or other labels may be incorporated in the compound of the invention in known ways. For example, if the binding moiety is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker er al (1978) *Biochem. Biophys. Res. Comm.* 80, 49-57) can be used to incorporate iodine-123. Reference ("Monoclonal Antibodies in Immunoscintigraphy", J-F Chatal, CRC Press, 1989) describes other methods in detail.

In a further preferred embodiment of the invention the further moiety is able to bind selectively to a directly or indirectly cytotoxic moiety or to a readily detectable moiety. Thus, in this embodiment, the further moiety may be any moiety which binds to a further compound or component which is cytotoxic or readily detectable.

The further moiety may, therefore be an antibody which selectively binds to the further compound or component, or it may be some other binding moiety such as streptavidin or biotin or the like. The following examples illustrate the types of molecules that are included in the invention; other such molecules are readily apparent from the teachings herein.

A bispecific antibody wherein one binding site comprises the moiety which selectively binds to ECSM1 or ECSM4 and the second binding site comprises a moiety which binds to, for example, an enzyme which is able to convert a substantially non-toxic prodrug to a cytotoxic drug.

A compound, such as an antibody which selectively binds to ECSM1 or ECSM4, to which is bound biotin. Avidin or streptavidin which has been labelled with a readily detectable label may be used in conjunction with the biotin labelled antibody in a two-phase imaging system wherein the biotin labelled antibody is first localised to the target site in the patient, and then the labelled avidin or streptavidin is administered to the patient. Bispecific antibodies and biotin/streptavidin (avidin) systems are reviewed by Rosebrough (1996) *Q J Nucl. Med.* 40, 234-251.

In a preferred embodiment of the invention, the moiety which selectively binds to ECSM1 or ECSM4 and the further moiety are polypeptides which are fused.

The compounds of the first and second aspects of the invention are useful in treating, imaging or diagnosing disease, particularly diseases in which there may be undesirable neovasculature formation, as described in more detail below.

In a preferred embodiment of the first and second aspects of the invention, the compounds are suitable for use in medicine.

A third aspect of the invention provides a nucleic acid molecule encoding a compound of either the first or second aspects of the invention wherein the selective binding moiety and the further moiety are polypeptides which are fused.

Methods of linking polynucleotides are described in more detail below.

A fourth aspect of the invention provides a pharmaceutical composition comprising a compound according to the invention and a pharmaceutically acceptable carrier. The compound of the invention includes those described in the first, second and third aspects. The invention also includes pharmaceutical composition comprising any of an antibody, polypeptide, peptide, polynucleotide, expression vector or other agent which may be delivered to an individual as described below and a pharmaceutically acceptable carrier.

By "pharmaceutically acceptable" is included that the formulation is sterile and pyrogen free. Suitable pharmaceutical carriers are well known in the art of pharmacy.

The carrier(s) must be "acceptable" in the sense of being compatible with the compound of the invention and not deleterious to the recipients thereof. Typically, the carriers will be water or saline which will be sterile and pyrogen free; however, other acceptable carriers may be used.

Typically the pharmaceutical compositions or formulations of the invention are for parenteral administration, more particularly for intravenous administration.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

A fifth aspect of the invention provides a method of imaging vascular endothelium in the body of an individual the method comprising administering to the individual an effective amount of a compound according to either of the first or second aspects of the invention wherein the further moiety is a readily detectable moiety.

Typically the vascular endothelium is associated with angiogenesis.

As discussed above in relation to the first and second aspects of the invention, the moiety of the compound which selectively binds ECSM4 or ECSM1 may be an antibody. Preferred antibodies are as outlined above.

In a preferred embodiment of this aspect of the invention, the method of imaging the vascular endothelium in an individual comprises the further step of detecting the location of the compound in the individual.

Detecting the compound or antibody can be achieved using methods well known in the art of clinical imaging and diagnostics. The specific method required will depend on the type of detectable label attached to the compound or antibody. For example, radioactive atoms may be detected using autoradiography or in some cases by magnetic resonance imaging (MRI) as described above.

Imaging the vascular endothelium in the body is useful because it can provide information about the health of the body. It is particularly useful when the vascular endothelium is diseased, or is proliferating due to a cancerous growth. Imaging cancer in a patient is especially useful, because it can be used to determine the size of a tumour and whether it is responding to treatment. Since metastatic disease involves new blood vessel formation, the method is useful in assessing whether metastasis has occurred.

Hence, in a preferred embodiment of the fifth aspect of the invention, the vascular endothelium is neovasculature, such as that produced in cancer.

A sixth aspect of the invention provides a method of diagnosing or prognosing in an individual a condition which involves the vascular endothelium the method comprising administering to the individual an effective amount of a compound according to either of the first or second aspects of the invention wherein the further moiety is a readily detectable moiety.

The condition may be one which involves aberrant or excessive growth of vascular endothelium, such as cancer, artherosclerosis, restenosis, diabetic retinopathy, arthritis, psoriasis, endometriosis, menorrhagia, haemangiomas and venous malformations.

As discussed in relation to the first and second aspects of the invention, the compound may comprise an antibody. The antibody may be any antibody which selectively binds the polypeptide ECSM1 or ECSM4 as required. Preferred antibodies which bind the polypeptide ECSM4 are as outlined above.

The method may be one which is an aid to diagnosis.

In a preferred embodiment of this aspect of the invention, the method of diagnosing, or aiding diagnosis of, a condition involving the vascular endothelium in an individual comprises the further step of detecting the location of the compound in the individual. Preferably the endothelium is in neovasculature; ie, angiogenic vasculature.

The function of ECSM4 or ECSM1 may not be to promote proliferation of vascular endothelial cells. Therefore the level of expression of these polypeptides within an endothelial cell may not be informative about the health of the vascular endothelium. However, the location of expression of the polypeptides may be informative, as they represent the growth of blood vessels. Abnormal cell proliferation such as cancer may be diagnosed by the detection of new vasculature.

A seventh aspect of the invention provides a method of treating an individual in need of treatment, the method comprising administering to the individual an effective amount of a compound according to the first or second aspects of the invention wherein the further moiety is a cytotoxic or therapeutic moiety.

In one embodiment of this aspect, the patient in need of treatment has a proliferative disease or a condition involving the vascular endothelium.

A number of diseases and conditions involve undesirable neovasculature formation. Neovasculature formation is associated with cancer, psoriasis, atherosclerosis, menorrhagia, arthritis (both inflammatory and rheumatoid), macular degeneration, Paget's disease, retinopathy and its vascular complications (including proliferative and of prematurity, and diabetic), benign vascular proliferations and fibroses.

By cancer is included Kaposi's sarcoma, leukaemia, lymphoma, myeloma, solid carcinomas (both primary and secondary (metastasis), vascular tumours including haemangioma (both capillary and juvenile (infantile)), haemangiomatosis and haemagioblastoma.

Thus, the invention comprises a method of treating a patient who has a disease in which angiogenesis contributes to pathology the method comprising the step of administering to the patient an effective amount of a compound of the first or second aspect of the invention wherein the further moiety of the compound is one which either directly or indirectly is of therapeutic benefit to the patient.

Typically, the disease is associated with undesirable neovasculature formation and the treatment reduces this to a useful extent.

The tumours that may be treated by the methods of the invention include any tumours which are associated with new blood vessel production.

The term "tumour" is to be understood as referring to all forms of neoplastic cell growth, including tumours of the lung, liver, blood cells, skin, pancreas, stomach, colon, prostate, uterus, breast, lymph glands and bladder. Solid tumours are especially suitable. However, blood cancers, including leukaemias and lymphomas are now also believed to involve new blood vessel formation and may be treated by the methods of the invention.

Typically in the above-mentioned methods of treatment, the further moiety is one which destroys or slows or reverses the growth of the neovasculature.

It will readily be appreciated that, depending on the particular compound used in imaging, diagnosis or treatment, the timing of administration may vary and the number of other components used in therapeutic systems disclosed herein may vary.

For example, in the case where the compound of the invention comprises a readily detectable moiety or a directly cytotoxic moiety, it may be that only the compound, in a suitable formulation, is administered to the patient. Of course, other agents such as immunosuppressive agents and the like may be administered.

In respect of compounds which are detectably labelled, imaging takes place once the compound has localised at the target site.

However, if the compound is one which requires a further component in order to be useful for treatment, imaging or diagnosis, the compound of the invention may be administered and allowed to localise at the target site, and then the further component administered at a suitable time thereafter.

For example, in respect of the ADEPT and ADEPT-like systems above, the binding moiety-enzyme moiety compound is administered and localises to the target site. Once this is done, the prodrug is administered.

Similarly, for example, in respect of the compounds wherein the further moiety comprised in the compound is one which binds a further component, the compound may be administered first and allowed to localise at the target site, and subsequently the further component is administered.

Thus, in one embodiment a biotin-labelled anti-ECSM1 or -ECSM4 antibody is administered to the patient and, after a suitable period of time, detectably labelled streptavidin is administered. Once the streptavidin has localised to the sites where the antibody has localised (ie the target sites) imaging takes place.

Where the compound whose moiety which selectively binds is an antibody, the antibody may be any antibody which selectively binds the polypeptide ECSM1 or ECSM4 as required. Preferred antibodies are as outlined in the first and second aspects of the invention.

It is believed that the compounds of the invention wherein the further moiety is a readily detectable moiety may be useful in determining the angiogenic status of tumours or other disease states in which angiogenesis contributes to pathology. This may be an important factor influencing the nature and outcome of future therapy.

An eighth aspect of the invention provides a method of introducing genetic material selectively into vascular endothelial cells the method comprising contacting the cells with a compound according to either of the first or second aspects of the invention as described above wherein the further moiety is a nucleic acid.

The vascular endothelial cells may be any vascular endothelial cells such as those in tissue culture or in a living organism. It is preferred if the cells are in a living organism. It is further preferred if the organism is a human. It is still more preferred if the vascular endothelial cells are those in neovasculature, ie they are angiogenic endothelial cells.

Preferably, the binding moiety is an antibody. The antibody may be any antibody which selectively binds the polypeptide ECSM1 or ECSM4 as required. Preferably, the antibody is one as defined above in relation to the first or second aspects of the invention. Typically, the binding moiety is comprised in a delivery vehicle and preferably, the delivery vehicle is a liposome, as described in further detail above. In this embodiment, the further moiety is nucleic acid and is comprised within the liposome, also as described above. Typically, the method is used in gene therapy, and the genetic material is therapeutically useful. Therapeutically useful genetic material includes that which encodes a therapeutic protein.

A ninth aspect of the invention provides a use of a compound according to either of the first or second aspects of the invention wherein the further moiety is a readily detectable label in the manufacture of a diagnostic or prognostic agent for a condition which involves the vascular endothelium.

As discussed above, the compound may comprise an antibody as the moiety which selectively binds. The antibody may be any antibody which selectively binds the polypeptide ECSM1 or ECSM4 as required.

A tenth aspect of the invention provides a use of a compound according to either of the first or second aspects of the invention wherein the further moiety is a cytotoxic or therapeutic moiety in the manufacture of a medicament for treating a condition involving the vascular endothelium.

Conditions which involve the vascular endothelium are described above.

As described above, the compound may comprise an antibody as the moiety which selectively binds. The antibody may be any suitable antibody which selectively binds the polypeptide ECSM1 or ECSM4 as required.

An eleventh aspect of the invention provides a polypeptide comprising or consisting of a fragment or variant or fusion of the ECSM4 polypeptide or a fusion of said fragment or variant provided that it is not a polypeptide consisting of the amino acid sequence given between residues 49 and 466 of FIG. 4.

The ECSM4 polypeptide includes a polypeptide comprising or consisting of the amino acid sequence given in FIG. 4 or FIG. 5 or FIG. 7 or FIG. 12 or FIG. 13 or the polypeptide encoded by the nucleotide sequence of either FIG. 4 between positions 1 and 1395 or FIG. 5 between positions 2 and 948 or FIG. 7 or FIG. 12 or FIG. 13 is that of the ECSM4 polypeptide. Preferably, the ECSM4 polypeptide of the invention comprises but does not consist of the amino acid sequence given in FIG. 4.

Preferably, the ECSM4 polypeptide of the invention does not consist of any of the amino acid sequences represented by SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293, or any of the amino acid sequences encoded by SEQ ID No 18084 or 5096 of EP 1 074 617, SEQ ID No 210 of WO 00 53756 or WO 99/46281, or SEQ ID Nos 22, 23, 96 or 98 of WO 01/23523 or SEQ ID No 31 of WO 99/11293.

A twelfth aspect of the invention provides a polypeptide comprising or consisting of the ECSM1 polypeptide or a fragment or variant or fusion thereof or a fusion of said fragment or variant.

The ECSM1 polypeptide includes a polypeptide comprising or consisting of the amino acid sequence given in FIG. 2. Preferably, the ECSM1 polypeptide or fragment is not a polypeptide whose sequence is given in SEQ ID No 120 of WO 99/06423 or which is encoded by SEQ ID No 32 of WO 99/06423 or encoded by the nucleic acid of ATCC deposit No 209145 made on Jul. 17, 1997 for the purposes of WO 99/06423.

The invention includes peptides which are derived from the ECSM4 or ECSM1 polypeptides. These peptides may be considered "fragments" of the ECSM4 or ECSM1 polypeptides but may be produced by de novo synthesis or by fragmentation of the polypeptide.

"Fragments" of the ECSM4 or ECSM1 polypeptide include polypeptides which comprise at least five consecutive amino acids of the ECSM4 or ECSM1 polypeptide. Preferably, a fragment of the polypeptide comprises an amino acid sequence which is useful, for example, a fragment which retains activity of the polypeptide, or a fragment for use in a binding assay or is useful as a peptide for producing an antibody which is specific for the ECSM4 or ECSM1 polypeptide. An activity of the ECSM4 polypeptide may be in endothelial cell repulsive guidance. Repulsive guidance may be tested in vivo by constructing appropriate transgenic or knock-out animal models, for example mice or zebrafish. It may also be tested in vivo on cell migration assays such as Boyden chamber or video microscopy. Typically, the fragments have at least 8 consecutive amino acids, preferably at least 10, more preferably at least 12 or 15 or 20 or 30 or 40 or 50 consecutive amino acids of the ECSM4 or ECSM1 polypeptide. Preferably, fragments of the ECSM4 polypeptide comprise but do not consist of the amino acid sequence given in FIG. 4 or FIG. 5 or FIG. 7 or FIG. 12 or FIG. 13. Preferably, fragments of the ECSM4 polypeptide comprise but do not consist of any of the amino acid sequences represented by SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293, or any of the amino acid sequences encoded by SEQ ID No 18084 or 5096 of EP 1 074 617, SEQ ID No 210 of WO 00 53756 or WO 99/46281, or SEQ ID Nos 22, 23, 96 or 98 of WO 01/23523 or SEQ ID No 31 of WO 99/11293.

Typically, the fragments of ECSM4 polypeptide are ones which have portions of the amino acid sequence shown in FIG. 4 or FIG. 12.

Typically, the fragments of ECSM1 polypeptide are ones which have portions of the amino acid sequence shown in FIG. 2.

In a preferred embodiment of the thirteenth aspect of the invention, a fragment of the ECSM4 polypeptide is a fragment which has the sequence LSQSPGAVPQALVAWRA (SEQ ID NO:6), DSVLTPEEVALCLEL (SEQ ID NO:7), TYGYISVPTA (SEQ ID NO:8), KGGVLLCPPRPCLTPT (SEQ ID NO:9), WLADTW (SEQ ID NO:10), WLADTWRSTSGSRD (SEQ ID NO:11), SPPTTYGYIS (SEQ ID NO:12), GSLANGWGSASEDNAASARASLVSSSDGSFLAD (SEQ ID NO:13) or FARALAVAVD (SEQ ID NO:14) or has a sequence of at least 5 or 8 or 10 residues of any of these sequences. These peptides correspond to amino acids 213-229, 322-336, 359-368, 384-399, 56-61, 56-69, 355-364, 403-435 and 438-447 respectively of the human ECSM4 polypeptide shown in FIG. 4. Peptides WLADTW (SEQ ID NO:10), WLADTWRSTSGSRD (SEQ ID NO:11), SPPTTYGYIS (SEQ ID NO:12), GSLANGWGSASEDNAASARASLVSSSDGSFLAD (SEQ ID NO:13) and FARALAVAVD (SEQ ID NO:14) represent conserved regions between the mouse and human homologues of the ECSM4 polypeptide, and between the ECSM4 polypeptide and the mouse duttl protein. The peptides LSQSPGAVPQALVAWRA (SEQ ID NO:6), DSVLTPEEVALCLEL (SEQ ID NO:7), TYGYISVPTA (SEQ ID NO:8) and KGGVLLCPPRPCLTPT (SEQ ID NO:9) may be useful in raising antibodies.

Preferred peptides are peptides of at least 5 or 8 or 10 or 12 or 15 or 20 consecutive amino acid residues from these conserved sequences. Peptides of ECSM4 which affect cell migration and/or growth and/or vascular development are particularly preferred. They can be identified in suitable screening systems.

In a further preferred embodiment of this aspect of the invention, a fragment of the ECSM4 polypeptide is a fragment which has the sequence GGDSLLGGRGSL, LLQP-PARGHAHDGQALSTDL, EPQDYTEPVE, TAPGGQ-GAPWAEE or ERATQEPSEHGP or has a sequence of at least 5 or 8 or 10 residues of any of these sequences. These peptides correspond to regions of the human ECSM4 polypeptide (located at residues 4-16, 91-109, 227-236, 288-300 and 444-455 respectively in the sequence given in FIG. 12) which are not, or are poorly, conserved in the mouse homologue (see FIG. 14). As described below, such peptides may be particularly useful in raising antibodies to the human ECSM4 polypeptide.

According to the transmembrane domain predicting software program called PRED-TMR (available at the Biophys.Biol. internet site) and an amino acid sequence alignment with the human protein Robo1 (whose transmembrane region is known), residues 1-467 as shown in FIG. 12 are likely to be extracellular, and in addition to being extracellularly exposed, may include the binding site of the natural ligand. Hence fragments of ECSM4 which include or consist of a sequence within the extracellular domain of residues 1-467 of FIG. 12 may represent useful fragments for raising antibodies selective for cells expressing ECSM4 on their surface and which may also be useful in modulating the activity of the polypeptide ECSM4.

Hence, preferred fragments of the ECSM4 polypeptide are those fragments of the polypeptide sequence of FIG. 12 which comprise at least 1, 3 or 5, amino acid residues which are not conserved when compared to the mouse ECSM4 (as shown in FIG. 13). More preferably at least 7, 9, 11 or 13 amino acid residues in the fragment are not conserved between human ECSM4 and mouse ECSM4, and still more preferably at least 15, 17, 19 or 21 residues of the fragment are not conserved between human ECSM4 and mouse ECSM4. The sequence of such fragments may be determined from the alignment of the human and mouse amino acid sequences shown in FIG. 14.

It will be appreciated that fragments of the ECSM4 or ECSM1 polypeptide of the invention are particularly useful when fused to other polypeptides, such as glutathione-S-transferase (GST), green fluorescent protein (GFP), vesicular stomatitis virus glycoprotein (VSVG) or keyhole limpet haemacyanin (KLH). Fusions of the polypeptide, or fusions of fragments or variants of the polypeptide of the invention are included in the scope of the invention.

Other useful fragments of ECSM4 are those which are able to bind a ligand selective for ECSM4. Suitable methods for identification of ligands such as peptides or other molecules which bind ECSM4 is discussed in more detail above. Such peptides or other ECSM4-binding molecules can be used to identify the amino acid sequences present in ECSM4 which are responsible for ligand binding. Identification of those fragments of ECSM4 which, when isolated from the rest of the molecule, are still able to bind a ligand of ECSM4 can be achieved by means of a screen. Typically, such a screen will comprise contacting a ligand of ECSM4 with a test fragment of the ECSM4 polypeptide and determining if the test fragment binds the ligand. Fragments of ECSM4 are within the scope of the invention, and may be particularly useful in medicine. A fragment of ECSM4 which binds the natural ECSM4 ligand may neutralise the effect of the ligand and thereby affect endothelial cell migration, growth and/or vascular development. Hence, administration of fragments of ECSM4 may be useful in the treatment of diseases or conditions where endothelial cell migration, growth and/or vascular development need to be modulated. Examples of such diseases include cancer and artherosclerosis.

A "fusion" of the ECSM4 or ECSM1 polypeptide or a fragment or variant thereof provides a molecule comprising a polypeptide of the invention and a further portion. It is preferred that the said further portion confers a desirable feature on the said molecule; for example, the portion may useful in detecting or isolating the molecule, or promoting cellular uptake of the molecule. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the molecule or the interacting polypeptide, as known to those skilled in the art.

A "variant" of the ECSM4 or ECSM1 polypeptide includes natural variants, including allelic variants and naturally-occurring mutant forms and variants with insertions, deletions and substitutions, either conservative or non-conservative, where such changes do not substantially alter the activity of the said polypeptide. In the case of the ECSM4 polypeptide, as an endothelial specific homologue of the human roundabout 1 it may well be involved in endothelial cell repulsive guidance. In addition, polypeptides which are elongated as a result of an insertion or which are truncated due to deletion of a region are included in the scope of the invention. For example, deletion of cytoplasmically-located regions may be useful in creation of "dominant negative" or "dominant positive" forms of the polypeptide. Similarly, deletion of a transmembrane region of the polypeptide may produce such forms.

By "conservative substitution" is intended combinations such as Gly, Ala; Val, Ile, Leu; Asp, Glu; Asn, Gln; Ser, Thr; Lys, Arg; and Phe, Tyr.

By "non-conservative substitution" we include other substitutions, such as those where the substituted residue mimics a particular modification of the replaced residue, for example a phosphorylated tyrosine or serine may be replaced by aspartate or glutamate due to the similarity of the aspartate or glutamate side chain to a phosphorylated residue (ie they carry a negative charge at neutral pH).

Further non-conservative substitutions which are included in the term "variants" are point mutations which alter one, sometimes two, and usually no more than three amino acids. Such mutations are well known in the art of biochemistry and are usually designed to insert or remove a defined characteristic of the polypeptide. Another type of non-conservative mutation is the alteration or addition of a residue to a cysteine or lysine residue which can then be used with maleimide or succinimide cross-linking reagents to covalently conjugate the polypeptide to another moiety. Non-glycosylated proteins may be mutated to convert an asparagine to the recognition motif N—X—S/T for N-linked glycosylation. Such a modification may be useful to create a tag for purification of the polypeptide using Concanavalin A-linked beads.

Such variants may be made using the methods of protein engineering and site-directed mutagenesis well known in the art.

Variants of the ECSM4 polypeptide include polypeptides comprising a sequence with at least 65% identity to the amino acid sequence given in FIG. 4 or FIG. 7 or FIG. 12 or FIG. 13, preferably at least 70% or 80% or 85% or 90% identity to said sequence, and more preferably at least 95% or 98% identity to said amino acid sequence.

Variants of the ECSM1 polypeptide include polypeptides comprising a sequence with at least 65% identity to the amino acid sequence given in FIG. 2, preferably at least 70% or 80% or 85% or 90% identity to said sequence, and more preferably at least 95% or 98% identity to said amino acid sequence.

Percent identity can be determined by, for example, the LALIGN program (Huang and Miller, *Adv. Appl. Math.* (1991) 12:337-357) at the Expasy facility internet site using as parameters the global alignment option, scoring matrix BLOSUM62, opening gap penalty -14, extending gap penalty -4.

A thirteenth aspect of the invention provides a polynucleotide encoding the ECSM4 polypeptide of the invention, or the complement thereof or a polynucleotide which selectively hybridises to either of these which polynucleotide is not any one of the clones corresponding to GenBank Accession No AK000805 or the ESTs whose GenBank Accession Nos are given in Table 11 or Table 12.

GenBank Accession No AK000805 corresponds to a cDNA sequence cloned in the vector pME18SFL3. ESTs listed in Table 11 represent nucleotide sequences which can be assembled into the contig sequence shown in FIG. 5. ESTs listed in Table 12 represent nucleotide sequences which can be assembled into the mouse nucleotide cluster sequence (Mm.27782) given in FIG. 7.

Preferably, the polynucleotide of this aspect of the invention does not consist of any one of the nucleotide sequences represented by SEQ ID No 18084 or 5096 of EP 1 074 617, SEQ ID No 210 of WO 00 53756 or WO 99/46281, or SEQ ID Nos 22, 23, 96 or 98 of WO 01/23523 or SEQ ID No 31 of WO 99/11293, or their complement.

Also preferably, the polynucleotide of this aspect of the invention is not a polynucleotide which encodes a polypeptide consisting of the amino acid sequence represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293

Polynucleotides of the thirteenth aspect of the invention are described in more detail below.

A fourteenth aspect of the invention provides a polynucleotide encoding the ECSM1 polypeptide or the complement thereof or a polynucleotide which selectively hybridises to either of these, according to the twelfth aspect of the invention provided that the polynucleotide is not one present in ATCC deposit No 209145 or the clone corresponding to GenBank Accession No AC011526 or the ESTs whose GenBank Accession Nos are given in Table 10.

By "encoding a polypeptide according to the twelfth aspect of the invention" we mean that the polynucleotide is one which encodes an ECSM1 polypeptide of the invention and is not one which encodes a polypeptide whose sequence is given in SEQ ID No 120 of WO 99/06423 or which is encoded by SEQ ID No 32 or by the nucleic acid included in the microbiological deposit corresponding to American Type Culture Collection (ATCC) No. 209145 made on 17 Jul. 1997.

ATCC deposit No 209145 comprises a pSport1 vector which includes a 765 base nucleotide sequence.

The polynucleotide sequence given in SEQ ID No 32 of WO 99/06423 is similar to the nucleotide sequence shown in FIG. 2. The sequence of SEQ ID No 32 given in WO 99/06423 may be capable of encoding part of the ECSM1 polypeptide of the invention. Due to degeneracy of the genetic code however, a polynucleotide sequence may encode the ECSM1 polypeptide of the invention without having a nucleotide sequence as given in WO 99/06423. In a similar manner, a polynucleotide sequence may encode the (full length) ECSM4 polypeptide of the invention without having the same sequence as that given in FIG. 4 or FIG. 5 or FIG. 12. Such polynucleotides are within the scope of this invention.

Hence, it will be appreciated that a polynucleotide of the thirteenth aspect of the invention is preferably not one whose nucleotide sequence is given in FIG. 4, and that a polynucleotide of the fourteenth aspect of the invention is preferably not a polynucleotide which is disclosed in WO 99/06423, such as SEQ ID No 32 disclosed therein or its complement or variants or the corresponding cDNA sequence deposited under Accession No 209145 at the ATCC or a polynucleotide fragment capable of encoding a polypeptide whose amino acid sequence comprises the sequence given in SEQ ID No 120 of WO 99/06423.

A polynucleotide of the thirteenth or fourteenth aspects of the invention may encode a variant of the ECSM4 or ECSM1 polypeptide as described above. In addition, the insertions and/or deletions within the ECSM4 or ECSM1 polypeptide may lead to frameshift mutations which may encode truncated (or elongated) polypeptide products, and insertions, deletions or other mutations may lead to the introduction of stop codons which encode truncate polypeptide products.

The polynucleotide of the invention may be DNA or RNA. It is preferred if it is DNA.

The polynucleotide may or may not contain introns. It is preferred if it does not contain introns.

The polynucleotide may be single stranded or double stranded or a mixture of either.

The polynucleotide of the invention has at least 10 nucleotides, and preferably at least 15 nucleotides and more preferably at least 30 nucleotides. In a further preference, the polynucleotide is more than 50 nucleotides, more preferably at least 100 nucleotides, and still more preferably the polynucleotide is at least 500 nucleotides. The polynucleotide may be more than 1 kb, and may comprise more than 5 kb.

The invention also includes a polynucleotide which is able to selectively hybridise to a polynucleotide which encodes the ECSM4 or ECSM1 polypeptide or a fragment or variant or fusion thereof, or a fusion of said variant or fragment. Preferably, said polynucleotide is at least 10 nucleotides, more preferably at least 15 nucleotides and still more preferably at least 30 nucleotides in length. The said polynucleotide may be longer than 100 nucleotides and may be longer than 200 nucleotides, but preferably the said polynucleotide is not longer than 250 nucleotides. Such polynucleotides are useful in procedures as a detection tool to demonstrate the presence of the polynucleotide in a sample. Such a sample may be a sample of DNA, such as a bacterial colony, fixed on a membrane or filter.

Preferably, the polynucleotide which is capable of selectively hybridising as said is not any one of the nucleotide sequences represented by SEQ ID No 18084 or 5096 of EP 1 074 617, SEQ ID No 210 of WO 00 53756 or WO 99/46281, or SEQ ID Nos 22, 23, 96 or 98 of WO 01/23523 or SEQ ID No 31 of WO 99/11293.

By "selectively hybridise" we mean that the polynucleotide hybridises under conditions of high stringency. DNA-DNA, DNA-RNA and RNA-RNA hybridisation may be performed in aqueous solution containing between 0.1×SSC and 6×SSC and at temperatures of between 55° C. and 70° C. It is well known in the art that the higher the temperature or the lower the SSC concentration the more stringent the hybridisation conditions. By "high stringency" we mean 2×SSC and 65° C. 1×SSC is 0.15M NaCl/0.015M sodium citrate. Polynucleotides which hybridise at high stringency are included within the scope of the claimed invention.

In another embodiment, the polynucleotide can be used as a primer in the polymerase chain reaction (PCR), and in this capacity a polynucleotide of between 15 and 30 nucleotides is preferred. A polynucleotide of between 20 and 100 nucleotides is preferred when the fragment is to be used as a mutagenic PCR primer. It is particularly preferred if the PCR primer (when not being used to mutate a nucleic acid) contains about 15 to 30 contiguous nucleotides (ie perfect matches) from the nucleotide sequence given in FIG. 4 or FIG. 7 or FIG. 12 or FIG. 13 from the nucleotide sequence given in FIG. 2. Clearly, if the PCR primers are used for mutagenesis, differences compared to the sequence will be present.

Primers which are suitable for use in a polymerase chain reaction (PCR; Saiki et al (1988) *Science* 239, 487-491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artifactual product called "primer dimer". When the 3' ends of the two primers hybridize, they form a "primed template" complex, and primer extension results in a short duplex product called "primer dimer".

Internal secondary structure should be avoided in primers. For symmetric PCR, a 40-60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37-55° C. region, so primer extension will occur during the annealing step and the hybrid will be stabilised. The concentrations of the primers are equal in conventional (symmetric) PCR and, typically, within 0.1- to 1 nM range.

When a pair of suitable nucleic acids of the invention are used in a PCR it is convenient to detect the product by gel electrophoresis and ethidium bromide staining. As an alternative to detecting the product of DNA amplification using agarose gel electrophoresis and ethidium bromide staining of the DNA, it is convenient to use a labelled oligonucleotide capable of hybridising to the amplified DNA as a probe. When the amplification is by a PCR the oligonucleotide probe hybridises to the interprimer sequence as defined by the two primers. The probe may be labelled with a radionuclide such as $^{32}$P, $^{33}$P and $^{35}$S using standard techniques, or may be labelled with a fluorescent dye. When the oligonucleotide probe is fluorescently labelled, the amplified DNA product may be detected in solution (see for example Balaguer et al (1991) "Quantification of DNA sequences obtained by polymerase chain reaction using a bioluminescence adsorbent" *Anal. Biochem.* 195, 105-110 and Dilesare et al (1993) "A high-sensitivity electrochemiluminescence-based detection system for automated PCR product quantitation" *BioTechniques* 15, 152-157.

PCR products can also be detected using a probe which may have a fluorophore-quencher pair or may be attached to a solid support or may have a biotin tag or they may be detected using a combination of a capture probe and a detector probe.

Fluorophore-quencher pairs are particularly suited to quantitative measurements of PCR reactions (eg RT-PCR). Fluorescence polarisation using a suitable probe may also be used to detect PCR products.

Oligonucleotide primers can be synthesised using methods well known in the art, for example using solid-phase phosphoramidite chemistry.

A polynucleotide or oligonucleotide primer of the invention may contain one or more modified bases or may contain a backbone which has been modified for stability purposes or for other reasons. By modified we included for example, tritylated bases and unusual bases such as inosine. A variety of modifications can be made to DNA and RNA and these are included in the scope of the invention.

In a preferred embodiment, the polynucleotides of the invention are detectably labelled. Suitable detectable labels are described in detail above.

A fifteenth aspect of the invention provides an expression vector comprising a polynucleotide as described above. Typically, the polynucleotides are those which encode the polypeptides ECSM1 or ECSM4 or a fragment, variant or fusion thereof.

By "expression vector" we mean one which is capable, in an appropriate host, of expressing a polypeptide encoded by the polynucleotide.

Such vectors may be useful in expressing the encoded polypeptide in a host cell for production of useful quantities of the polypeptide, or may be useful in medicine. Expression vectors comprising a polynucleotide according to the thirteenth or fourteenth aspects of the invention which are suitable for use in gene therapy are within the scope of the invention. Administration of a gene therapy vector capable of expressing the ECSM4 polypeptide may be useful in modulating or inhibiting angiogenesis, since this polypeptide is likely to be a repulsive guidance receptor. Similarly, gene therapy vectors capable of expressing fragments or mutants of ECSM4 on the cell surface, which fragments or mutants are capable of binding the ECSM4 cognate ligand but are not able to convey the normal downstream signal (for example, because the necessary cytosolic portion of the polypeptide is deleted or mutated so as to not be functional or capable of binding normally interacting cellular proteins) may also be useful in modulating angiogenesis in an individual.

Hence, in a preferred embodiment, the vector is one which is suitable for use in gene therapy. Examples of suitable vectors and methods of their introduction into cells are given in more detail below. In particular, the gene therapy methods and vectors described in relation to the use of promoters of ECSM4 may also be used in relation to the use of ECSM4 coding sequences or antisense in gene therapy.

It will be appreciated that the polynucleotide comprised within the expression vector of this aspect of the invention may be one which encodes the polypeptide ECSM4 or ECSM1 or a fragment or variant thereof, or the polynucleotide may be one which is capable of selectively hybridising to the ECSM4 or ECSM1 coding region. Polynucleotides which are capable of hybridising to the ECSM4 or ECSM1 coding region are useful as antisense polynucleotides which may decrease the expression level of ECSM4 or ECSM1 within a target cell. The design of suitable and effective antisense polynucleotides based on a known coding sequence is known in the art of gene therapy.

Preferably, the expression vector of this aspect of the invention is one which does not contain a polynucleotide sequence represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293 or their complement. Also preferably, the said vector is one which does not contain a polynucleotide encoding a polypeptide whose amino acid sequence is represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293.

Both the amount of therapeutic protein or therapeutic polynucleotide produced and the duration of production are important issues in gene therapy. Consequently, the use of viral vectors capable of cellular gene integration (eg retroviral vectors) may be more beneficial than non-integrating alternatives (eg adenovirus derived vectors) when repeated therapy is undesirable for immunogenicity reasons.

By "therapeutic polynucleotide" or "therapeutic protein" we include ECSM4 and ECSM1 coding sequences, the polypeptide product encoded by said coding sequences, and ECSM4 antisense polynucleotides. The therapeutic effect of said polynucleotides or proteins may include pro-angiogenic or anti-angiogenic effects, depending on the precise therapeutic agent administered. For example, an expression vector suitable for gene therapy which comprises a polynucleotide which is antisense to at least part of the ECSM4 coding region may have anti-angiogenic activity when expressed in a host cell or patient if it suppresses expression of a molecule which is required for angiogenesis. If the polynucleotide comprised within the expression vector encodes a polypeptide which is required for inhibition of angiogenesis (for example, because said polypeptide has endothelial cell repulsive guidance activity), then expression of the antisense may also be anti-angiogenic.

Conversely, if said the expression vector comprises a polynucleotide of the invention which polynucleotide suppresses expression of a molecule whose activity is required to decrease vascular growth (for example, because said molecule is an endothelial cell repulsive guidance molecule) or encodes a polypeptide whose activity is required for angiogenesis, administration of the said vector may be pro-angiogenic.

Where the therapeutic gene is maintained extrachromosomally, the highest level of expression is likely to be achieved using viral promoters, for example, the Rous sarcoma virus long terminal repeat (Ragot et al (1993) *Nature* 361, 647-650; Hyde et al (1993) *Nature* 362, 250-255) and the adenovirus major late promoter. The latter has been used successfully to drive the expression of a cystic fibrosis transmembrane conductance regulator (CFTR) gene in lung epithelium (Rosenfeld et al (1992) *Cell* 68, 143-155). Since these promoters function in a broad range of tissues they may not be suitable to direct cell-type-specific expression unless the delivery method can be adapted to provide the specificity. However, somatic enhancer sequences could be used to give cell-type-specific expression in an extrachromosomal setting.

As described in more detail below, the ECSM4 regulatory/promoter region is an example of a regulatory region capable of conferring endothelial cell selective expression, preferably selective to endothelial cells of neovasculature (ie, angiogenic endothelial cells) on an operatively linked coding region. As outlined above, such a coding region may encode an antisense polynucleotide.

Where withdrawal of the gene-vector construct is not possible, it may be necessary to add a suicide gene to the system to abort toxic reactions rapidly. The herpes simplex virus thymidine kinase gene, when transduced into cells, renders them sensitive to the drug ganciclovir, creating the option of killing the cells quickly.

The use of ectotropic viruses, which are species specific, may provide a safer alternative to the use of amphotropic viruses as vectors in gene therapy. In this approach, a human homologue of the non-human, ectotropic viral receptor is modified in such a way so as to allow recognition by the virus. The modified receptor is then delivered to cells by constructing a molecule, the front end of which is specified for the targeted cells and the tail part being the altered receptor. Following delivery of the receptor to its target, the genetically engineered ectotropic virus, carrying the therapeutic gene, can be injected and will only integrate into the targeted cells.

Virus-derived gene transfer vectors can be adapted to recognise only specific cells so it may be possible to target to an endothelial cell, such as endothelial cells within a tumour. Similarly, it is possible to target expression of an therapeutic gene to the endothelial cell, using an endothelial cell-specific promoter such as that for the ECSM4 or ECSM1 genes.

One of the ECSM genes or a part of the genes or a polynucleotide comprising an antisense to the gene may be introduced into the cell in a vector such that the gene remains extrachromosomal. In such a situation, the gene will be expressed by the cell from the extrachromosomal location. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the ordinary skilled person. Cells transformed with the wild-type novel gene can be used as model systems to study cancer remission and drug treatments which promote such remission.

A variety of methods have been developed to operably link polynucleotides, especially DNA, to vectors, for example, via complementary cohesive termini. For instance, complementary homopolymer tracts can be added to the DNA segment to be inserted into the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a larger molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease site are commercially available from a number of sources including International Biotechnologies Inc., New Haven, Conn., USA.

A desirable way to modify the DNA encoding the polypeptide of the invention is to use PCR. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the polypeptide of the invention. Thus, the DNA encoding the polypeptide constituting the polypeptide of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859 issued 3 Apr. 1984 to Rutter et al, 4,530,901 issued 23 Jul. 1985 to Weissman, 4,582,800 issued 15 Apr. 1986 to Crowl, 4,677,063 issued 30 Jun. 1987 to Mark et al, 4,678,751 issued 7 Jul. 1987 to Goeddel, 4,704,362 issued 3 Nov. 1987 to Itakura et al, 4,710,463 issued 1 Dec. 1987 to Murray, 4,757,006 issued 12 Jul. 1988 to Toole, Jr. et al, 4,766,075 issued 23 Aug. 1988 to Goeddel et al and 4,810,648 issued 7 Mar. 1989 to Stalker, all of which are incorporated herein by reference.

The DNA (or in the case or retroviral vectors, RNA) encoding the polypeptide constituting the polypeptide of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the expression vector of the invention are then cultured for a sufficient time and under appropriate conditions known to those skilled in the art in view of the teachings disclosed herein to permit the expression of the polypeptide, which can then be recovered.

Many expression systems are known, including bacteria (for example, *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps).

Other vectors and expression systems are well known in the art for use with a variety of host cells.

A sixteenth aspect of the invention provides a recombinant host cell comprising a polynucleotide or vector of the invention.

The polynucleotide of the invention includes polynucleotides encoding a compound of the third aspect of the invention (where both the moiety which selectively binds and the further moiety are polypeptides which are fused) or an ECSM4 or ECSM1 polypeptide of the invention or a fragment or fusion or variant thereof as defined above.

The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No. ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CRL 1658 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) Molecular Cloning, A Laboratory Manual, Cold Spring Harbor Laboratory, Cold Spring Harbor, N.Y. Transformation of yeast cells is described in Sherman et al (1986) *Methods In Yeast Genetics*, A Laboratory Manual, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cells, bacterial cells, insect cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5 PEB using 6250V per cm at 25 µFD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well-known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity.

Samples of cells suspected of being transformed are harvested and assayed for the protein using suitable antibodies.

The host cell may be a host cell within an animal body. Thus, transgenic animals which express a polypeptide of the first or third aspects of the invention by virtue of the presence of the transgene are included. Preferably, the transgenic animal is a rodent such as a mouse. Transgenic animals can be made using methods well known in the art.

Polynucleotides encoding the polypeptide ECSM4 may be useful in generating transgenic non-human mammals wherein the ECSM4 is mutated in some way. For example, the mouse ECSM4 genomic coding region may be mutated in a mouse so as to produce an ECSM4 polypeptide which is incapable of binding its natural ligand, or incapable of correctly interacting with intracellular components. Such a mutated ECSM4 polypeptide may produce a disease in the mouse which is very similar to a disease involving abnormal vascularisation in humans.

Hence, non-human mammals, especially rodents such as mice and rats, are useful as models of diseases involving abnormal vascularisation.

Alternatively, mammals lacking the ECSM4 gene ("knock-outs") or lacking an ECSM4 genomic coding region which is capable of being transcribed or of expressing the ECSM4 polypeptide, may be useful in providing a means of generating antibodies selective for the human ECSM4 polypeptide. Such mammals, especially mice, are likely to be particularly useful since the high level of homology between the human and mouse ECSM4 polypeptides may prevent human ECSM4 polypeptide from being antigenic in mice who do express the ECSM4 polypeptide.

A potentially more accurate animal model of diseases involving abnormal vascularisation may be made by addition to the genome of a transgenic animal as described above, or replacing the genomic ECSM4 of an animal with, the gene for human ECSM4 which has been mutated. Suitably, the human ECSM4 inserted will be under control of an endothelial selective promoter and regulatory region. Preferably, the promoter and regulatory regions are those of the host animal ECSM4 gene. An animal who genome is modified in this way will express the dysfunctional human ECSM4, and therefore will be useful in testing the efficacy of drugs and antibodies in the diagnosis, prognosis and treatment of diseases involving abnormal vascularisation in humans.

Such knockout or transgenic mammals are within the scope of the invention and antibodies generated using such mammals and compounds comprising them are also included within the scope of the invention.

A seventeenth aspect of the invention provides a method of producing a polypeptide of the invention, the method comprising expressing a polynucleotide as described above or culturing a host cell as described herein.

It will be appreciated that in order to produce the ECSM1 polypeptide, the host cell may comprise a polynucleotide encoding a polypeptide whose amino acid sequence includes the sequence given in FIG. 2, and that in order to produce the ECSM4 polypeptide the host cell may comprise a polynucleotide encoding the polypeptide whose amino acid sequence is given in FIG. 4 or FIG. 7 or FIG. 12 and so on.

Preferably, the polynucleotide expressed does not consist of any one of the nucleotide sequences represented by SEQ ID No 18084 or 5096 of EP 1 074 617, SEQ ID No 210 of WO 00/53756 or WO 99/46281, or SEQ ID Nos 22, 23, 96 or 98 of WO 01/23523 and SEQ ID No 31 of WO 99/11293.

Also preferably, the polypeptide produced is not one with an amino acid sequence consisting of the sequence represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293.

Methods of cultivating host cells and isolating recombinant proteins are well known in the art. It will be appreciated that, depending on the host cell, the ECSM1 or ECSM4 polypeptides produced may differ from that which can be isolated from nature. For example, certain host cells, such as yeast or bacterial cells, either do not have, or have different, post-translational modification systems which may result in the production of forms of ECSM1 or ECSM4 which may be post-translationally modified in a different way to ECSM1 or ECSM4 isolated from nature. In order to obtain ECSM1 or ECSM4 which is post-translationally modified in a different way to human ECSM1 or ECSM4 it is preferred if the host cell is a non-human host cell; more preferably it is not a mammalian cell.

It is preferred that the ECSM1 or ECSM4 polypeptide is produced in a eukaryotic system, such as an insect cell.

According to a less preferred embodiment, the ECSM1 or ECSM4 polypeptide can be produced in vitro using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation. Conveniently, where the expressed polypeptide comprises one or more transmembrane domains, the translation system can be supplemented with a source of endoplasmic reticulum-derived membranes and folding chaperones, such as dog pancreatic microsomes, to allow synthesis of the polypeptide in a native conformation.

Preferably, the production method of this aspect of the invention comprises a further step of isolating the ECSM1 or ECSM4 produced from the host cell or from the in vitro translation mix. Preferably, the isolation employs an antibody which selectively binds the expressed polypeptide of the invention.

It will be understood that the invention comprises the ECSM1 or ECSM4 polypeptides or the variants or fragments or fusions thereof, or a fusion of said variants or fragments obtainable by the methods herein disclosed, provided that the ECSM4 polypeptide is not one which consists of the amino acid sequence given in FIG. 4. Preferably, the polypeptide is not one which consists of an amino acid sequence represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293. Preferably, the ECSM1 polypeptide produced by the methods herein disclosed is not one which is encoded by SEQ ID No 32 of WO 99/06423 or encoded by the nucleic acid of ATCC deposit No. 209145 made on Jul. 17, 1997 for the purposes of WO 99/06423.

An eighteenth aspect of the invention provides an antibody capable of selectively binding to either ECSM4 or ECSM1 as defined above.

Preferably, an antibody which selectively binds ECSM1 is not one which binds a polypeptide encoded by SEQ ID No 32 of WO 99/06423 or encoded by the nucleic acid of ATCC deposit No 209145 made on Jul. 17, 1997 for the purposes of the international patent application PCT/US98/15949.

Preferably, an antibody which selectively binds ECSM1 is one which binds a polypeptide whose amino acid sequence comprises the sequence given in FIG. 2 or a natural variant thereof but does not comprise the amino acid sequence encoded by ATCC deposit No 209145 made on Jul. 17, 1997.

Preferably, an antibody which selectively binds ECSM4 is one which binds a polypeptide whose amino acid sequence comprises the sequence given in any one of FIGS. 4, 5, 7, 12 or 13 or a natural variant thereof but does not bind the polypeptide represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293, or encoded by any one of the nucleotide sequences represented by SEQ ID No 18084 or 5096 of EP 1 074 617, SEQ ID No 210 of WO 00/53756 or WO 99/46281, or SEQ ID Nos 22, 23, 96 or 98 of WO 01/23523 and SEQ ID No 31 of WO 99/11293.

By "selectively bind" we include antibodies which bind at least 10-fold more strongly to a polypeptide of the invention (such as ECSM4 or ECSM1) than to another polypeptide; preferably at least 50-fold more strongly and more preferably at least 100-fold more strongly. Such antibodies may be made by methods well known in the art using the information concerning the differences in amino acid sequence of ECSM4 or ECSM1 and another polypeptide which is not a polypeptide of the invention.

Antibodies which selectively bind ECSM4 may also modulate the function of the ECSM4 polypeptide. Antibodies which mimic the effect of binding of the cognate ligand by stimulating or activating ECSM4, or which bind and thereby prevent subsequent binding and activation or stimulation of ECSM4 by the cognate ligand, and such function-modulating antibodies are included in the scope of the invention. It will be appreciated that antibodies which modulate the function are useful as a tool in research, for example in studying the effects of ECSM4 stimulation or activation, or downstream processes triggered by such stimulation. Such antibodies are also useful in medicine, for example in modulating angiogenesis in an individual. Specifically, modulation of angiogenesis by administration of such an antibody may be useful in the treatment of a disease in an individual where modulation of angiogenesis would be beneficial, such as cancer.

The following peptides may be useful as immunogens in the generation of antibodies, such as rabbit polyclonal sera: LSQSPGAVPQALVAWRA (SEQ ID NO:6), DSVLTPEEVALCLEL (SEQ ID NO:7), TYGYISVPTA (SEQ ID NO:8) and KGGVLLCPPRPCLTPT (SEQ ID NO:9).

In a preferred embodiment of this aspect, the antibody of the invention selectively binds an amino acid sequence with the sequence GGDSLLGGRGSL (SEQ ID NO:1), LLQPPARGHAHDGQALSTDL (SEQ ID NO:2), EPQDYTEPVE (SEQ ID NO:3), TAPGGQGAPWAEE (SEQ ID NO:4) or ERATQEPSEHGP (SEQ ID NO:5). These sequences represent amino acid sequences which are not identical between the human and mouse ECSM4 polypeptide sequences. Generally, the human and mouse ECSM4 polypeptides display a high degree of identity, which makes the production of mouse antibodies to the human ECSM4 particularly difficult due to the lack of immunogenicity of much of the human ECSM4 sequence in mouse. Amino acid sequences which are absent from the mouse ECSM4 are more likely to more be immunogenic in a mouse than those sequences which are present in the mouse ECSM4 (an alignment of the human and mouse ECSM4 amino acid sequences is shown in FIG. 14). Hence, polypeptide fragments which contain sequences which are unique to human ECSM4 as described above are more useful than ECSM4 polypeptides whose sequence is found in both human and mouse ECSM4, in the production of antibodies which selectively bind the human ECSM4 polypeptide.

Antibodies generated as a result of use of amino acid sequences which are located in the extracellular portion of the ECSM4 polypeptide are likely to be useful as endothelial cell targeting molecules. Therefore, it is particularly preferred if the antibody of the invention is raised to, and preferably selectively binds, an amino acid sequence which is unique to the human ECSM4 polypeptide, which sequence is located towards the N-terminal end of the polypeptide and is found in the extracellular portion located between residues 1 and 467 of the amino acid sequence given in FIG. 12. An example of an amino acid sequence which is suitable for raising antibody molecules selective for the ECSM4 extracellular region is given in FIG. 12.

Although the amino acid sequences which are unique to the human ECSM4 may be used to produce polyclonal antibodies, it is preferred if they are used to produce monoclonal antibodies.

Peptides in which one or more of the amino acid residues are chemically modified, before or after the peptide is synthesised, may be used providing that the function of the peptide, namely the production of specific antibodies in vivo, remains substantially unchanged. Such modifications included forming salts with acids or bases, especially physiologically acceptable organic or in organic acids and bases, forming an ester or amid of a terminal carboxyl group, and attaching amino acid protecting groups such as N-t-butoxycarbonyl. Such modifications may protect the peptide from in vivo metabolism. The peptides may be present as single copies or as multiples, for example tandem repeats. Such tandem or multiple repeats may be sufficiently antigenic themselves to obviate the use of a carrier. It may be advantageous for the peptide to be formed as a loop, with the N-terminal and C-terminal ends joined together, or to add one or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

According to current immunological theories, a carrier function should be present in any immunogenic formulation in order to stimulate, or enhance stimulation of, the immune system. It is though that the best carriers embody (or, together with the antigen, create) a T-cell epitope. The peptides may be associated, for example by cross-linking, with a separate carrier, such as serum albumins, myoglobins, bacterial toxoids and keyhole limpit haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys, β-galactosidase and the 163-171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitably cross-linking agents include those listed as such in the Sigma and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present).

If the peptide is prepared by expression of a suitable nucleotide sequence in a suitable host, then it may be advantageous to express the peptide as a fusion product with a peptide sequence which acts as a carrier. Kabigen's "Ecosec" system is an example of such an arrangement.

Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix.

Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography.

Analysis of peptides may be carried out using thin layer chromatography, reverse-phase high performance liquid chromatography, amino-acid analysis after acid hydrolysis and by fast atom bombardment (FAB) mass spectrometric analysis.

The peptide of the invention may be linked to other antigens to provide a dual effect.

Included in the scope of the invention is a method of producing an antibody according to this aspect of the invention.

Antibodies can be raised in an animal by immunising with an appropriate peptide. Appropriate peptides are described herein. Alternatively, with today's technology, it is possible to make antibodies as defined herein without the need to use animals. Such techniques include, for example, antibody phage display technology as is well known in the art. Appropriate peptides, as described herein, may be used to select antibodies produced in this way.

It will be appreciated that, with the advancements in antibody technology, it may not be necessary to immunise an animal in order to produce an antibody. Synthetic systems, such as phage display libraries, may be used. The use of such systems is included in the methods of the invention and the products of such systems are "antibodies" for the purposes of the invention.

It will be appreciated that such antibodies which recognise ECSM1 or ECSM4 and variants or fragments thereof are useful research reagents and therapeutic agents, particularly when prepared as a compound of the invention as described above. Suitably, the antibodies of the invention are detectably labelled, for example they may be labelled in such a way that they may be directly or indirectly detected. Conveniently, the antibodies are labelled with a radioactive moiety or a coloured moiety or a fluorescent moiety, or they may be linked to an enzyme. Typically, the enzyme is one which can convert a non-coloured (or non-fluorescent) substrate to a coloured (or fluorescent) product. The antibody may be labelled by biotin (or streptavidin) and then detected indirectly using streptavidin (or biotin) which has been labelled with a radioactive moiety or a coloured moiety or a fluorescent moiety, or the like or they may be linked to any enzyme of the type described above.

A nineteenth aspect of the invention provides a method of detecting endothelial damage or activation in an individual comprising obtaining a fluid sample from the individual and detecting the presence of fragments of ECSM1 or ECSM4 in the sample.

Preferably, the fluid sample is blood. Typically, the presence of peptide fragments derived from ECSM1 or ECSM4 are detected.

In a preferred embodiment of this aspect, the presence of peptide fragments of the ECSM1 or ECSM4 polypeptides are detected using an antibody selective for a polypeptide whose amino acid sequence comprises a sequence given in either one of FIG. 2 or FIG. 4 or FIG. 12 or fragments thereof. Preferably, the antibody is an antibody according to the eighteenth aspect of the invention. Typically, such an antibody would be detectably labelled.

Detecting or diagnosing endothelial cell damage in an individual is useful in diagnosing cancer or aiding diagnosis of cardiac disease, endometriosis or artheroslcerosis in that individual. It may be that certain levels of apparent cell damage are detected in individuals who do not have cancer, cardiac disease, endometriosis or artheroslcerosis. It may be necessary to compare the amount of endothelial cell damage detected with amounts or levels observed in individuals who are known to have cancer, cardiac disease, endometriosis or artheroslcerosis with the "normal" levels of apparent damage in the individual who does not have cancer, cardiac disease, endometriosis or artheroslcerosis.

Hence, detection of endothelial damage or activation in an individual may be useful as a means of detecting the presence or extent or growth rate of a tumour in that individual. The detection of vessel damage is an indirect report of the formation of tumour neovasculature. In this way, ECSM4 or ECSM1 may be surrogate markers of angiogenesis. The presence of ECSM4 or ECSM1 fragments in a sample from the individual, or more ECSM4 or ECSM1 polypeptide fragments than in an individual who does not have a tumour, may be a means of detecting a tumour, or growth of a known tumour, in that individual.

Furthermore, it will be appreciated that detection of neovasculature by means of detecting the presence of, or a certain level of, ECSM4 or ECSM1 in a sample from an individual may be useful in determining if a treatment in that individual is being effective, and/or to what extent the treatment is effective. Preferably the therapy is to treat a tumour or cancer in the individual.

Hence, an aspect of the invention provides a method of detecting a tumour or tumour neovasculature or cardiac disease or endometriosis or artherosclerosis in an individual comprising obtaining a fluid sample from the individual and detecting the presence of fragments of ECSM1 or ECSM4 in the sample.

As described above in relation to detecting or diagnosing endothelial cell damage, detection of the disease (such as a tumour or cardiac disease etc) by means of detecting the presence of, or a certain level of, ECSM4 or ECSM1 in a sample from an individual may be useful in determining the efficacy of a treatment in that individual.

In one embodiment, the therapy is gene therapy.

Preferably, the efficacy of the a treatment in an individual is determined using the amount of fragments of ECSM1 or ECSM4 found in the fluid sample of the individual and comparing it to either to the amount of ECSM1 or ECSM4 fragments in a sample from an individual who does not have cancer, cardiac disease, endometriosis or artherosclerosis and/or to the amount in a sample from the individual prior to commencement of said treatment. The comparison indicates the efficacy of treatment of the individual, wherein if there is no change in the amount of fragments determined before and during/after treatment this is indicative of poor efficacy of the treatment. A decrease in the amount of fragments found during or after treatment compared to the amount found before treatment was started indicates some efficacy of the treatment in ameliorating the condition of the individual.

Current methods of assessing the efficacy of various anti-angiogenic therapies being tested in clinical trials are invasive. The selective expression of ECSM4 on endothelial cells of angiogenic blood vessels means that detecting the presence, absence, increase or decrease in the level of ECSM1 or ECSM4 in a subject undergoing therapy is a means of determining the efficacy of the therapy in that subject without the need, or with a reduced need, for invasive biopsies, scans and the such like.

Hence, determination of the level of ECSM1 and or ECSM4 fragments in the blood of an individual undergoing an anti-angiogenic therapy (such as cancer therapy) may act as a "surrogate marker of angiogenesis".

By "peptide fragments derived from ECSM1 or ECSM4" we mean peptides which have at least 5 consecutive amino acids of the ECSM4 or ECSM1 polypeptide. Typically, the fragments have at least 8 consecutive amino acids, preferably at least 10, more preferably at least 12 or 15 or 20 or 30 or 40 or 50 consecutive amino acids of the ECSM4 or ECSM1 polypeptide.

Methods for detecting the presence of fragments of peptides derived from larger polypeptides are known in the art.

A further aspect of the invention provides a method of modulating angiogenesis in an individual, the method comprising administering to the individual ESCM4 or a peptide fragment of ECSM4 or a ligand of ECSM4 or an antibody which selectively binds to ECSM4 or ECSM1.

Preferably, the peptide fragment or ligand or antibody is one which modulates the activity or function, either directly or indirectly, of the ECSM4 polypeptide of the individual.

Preferred antibodies are those as described in more detail above.

The production of antibodies which modulate the function of a polypeptide exposed on the cell surface is known in the art and is discussed in more detail above. Such antibodies may modulate the function by imitating the function of the natural ligand and stimulating the polypeptide into activity or function, or may modulate the polypeptide function by preventing stimulation of the polypeptide by the ligand by sterically obscuring the ligand binding site thereby preventing binding of the natural ligand.

Delivery of a ligand to magic roundabout might be an angiogenic inhibitor useful in therapy of cancer or other diseases involving hyper-angiogenesis. Also, introduction of the ECSM4 polypeptide to endothelial cells by gene therapy using the ECSM4 encoding polynucleotide might alter growth and migration.

A still further aspect of the invention provides a method of diagnosing a condition which involves aberrant or excessive growth of vascular endothelium in an individual comprising obtaining a sample containing nucleic acid from the individual and contacting said sample with a polynucleotide which selectively hybridises to a nucleic acid which encodes the ECSM4 polypeptide or the ECSM1 polypeptide or a fragment or natural variant thereof.

The method may be used for aiding diagnosis.

A condition which involves aberrant or excessive growth of vascular endothelium such as cancer, artherosclerosis, restenosis, diabetic retinopathy, arthritis, psoriasis, endometriosis, menorrhagia, haemangiomas and venous malformations may be caused by a mutation in the nucleic acid which encodes the ECSM1 or ECSM4 polypeptides.

By "selectively hybridising" is meant that the nucleic acid has sufficient nucleotide sequence similarity with the said human DNA or cDNA that it can hybridise under moderately or highly stringent conditions. As is well known in the art, the stringency of nucleic acid hybridization depends on factors such as length of nucleic acid over which hybridisation occurs, degree of identity of the hybridizing sequences and on factors such as temperature, ionic strength and CG or AT content of the sequence. Thus, any nucleic acid which is capable of selectively hybridising as said is useful in the practice of the invention.

Nucleic acids which can selectively hybridise to the said human DNA or cDNA include nucleic acids which have >95% sequence identity, preferably those with >98%, more preferably those with >99% sequence identity, over at least a portion of the nucleic acid with the said human DNA or cDNA. As is well known, human genes usually contain introns such that, for example, a mRNA or cDNA derived from a gene within the said human DNA would not match perfectly along its entire length with the said human DNA but would nevertheless be a nucleic acid capable of selectively hybridising to the said human DNA. Thus, the invention specifically includes nucleic acids which selectively hybridise to an ECSM4 or ECSM1 cDNA but may not hybridise to an ECSM4 or ECSM1 gene, or vice versa. For example, nucleic acids which span the intron-exon boundaries of the ECSM4 or ECSM1 gene may not be able to selectively hybridise to the ECSM4 or ECSM1 cDNA.

Typical moderately or highly stringent hybridisation conditions which lead to selective hybridisation are known in the art, for example those described in *Molecular Cloning, a laboratory manual,* 2nd edition, Sambrook et al (eds), Cold Spring Harbor Laboratory Press, Cold Spring Harbor, N.Y., USA, incorporated herein by reference.

An example of a typical hybridisation solution when a nucleic acid is immobilised on a nylon membrane and the probe nucleic acid is >500 bases or base pairs is:
6×SSC (saline sodium citrate)
0.5% sodium dodecyl sulphate (SDS)
100 μg/ml denatured, fragmented salmon sperm DNA The hybridisation is performed at 68° C. The nylon membrane, with the nucleic acid immobilised, may be washed at 68° C. in 1×SSC or, for high stringency, 0.1×SSC.

20×SSC may be prepared in the following way. Dissolve 175.3 g of NaCl and 88.2 g of sodium citrate in 800 ml of $H_2O$. Adjust the pH to 7.0 with a few drops of a 10 N solution of NaOH. Adjust the volume to 1 litre with $H_2O$. Dispense into aliquots. Sterilize by autoclaving.

An example of a typical hybridisation solution when a nucleic acid is immobilised on a nylon membrane and the probe is an oligonucleotide of between 15 and 50 bases is:
3.0 M trimethylammonium chloride (TMACl)
0.01 M sodium phosphate (pH 6.8)
1 mm EDTA (pH 7.6)
0.5% SDS
100 μg/ml denatured, fragmented salmon sperm DNA
0.1% nonfat dried milk The optimal temperature for hybridization is usually chosen to be 5° C. below the $T_i$ for the given chain length. $T_i$ is the irreversible melting temperature of the hybrid formed between the probe and its target sequence. Jacobs et al (1988) *Nucl. Acids Res.* 16, 4637 discusses the determination of $T_i$s. The recommended hybridization temperature for 17-mers in 3 M TMACl is 48-50° C.; for 19-mers, it is 55-57° C.; and for 20-mers, it is 58-66° C.

By "nucleic acid which selectively hybridises" is also included nucleic acids which will amplify DNA from the said region of human DNA by any of the well known amplification systems such as those described in more detail below, in particular the polymerase chain reaction (PCR). Suitable conditions for PCR amplification include amplification in a suitable 1× amplification buffer:

10× amplification buffer is 500 mM KCl; 100 mM Tris.Cl (pH 8.3 at room temperature); 15 mM $MgCl_2$; 0.1% gelatin.

A suitable denaturing agent or procedure (such as heating to 95° C.) is used in order to separate the strands of double-stranded DNA.

Suitably, the annealing part of the amplification is between 37° C. and 60° C., preferably 50° C.

Although the nucleic acid which is useful in the methods of the invention may be RNA or DNA, DNA is preferred. Although the nucleic acid which is useful in the methods of the invention may be double-stranded or single-stranded, single-stranded nucleic acid is preferred under some circumstances such as in nucleic acid amplification reactions.

The sample may be directly derived from the patient, for example, by biopsy of a tissue which may be associated with aberrant vascular development, or it may be derived from the patient from a site remote from the tissue, for example because cells from the tissue have migrated from the tissue to other parts of the body. Alternatively, the sample may be indirectly derived from the patient in the sense that, for example, the tissue or cells therefrom may be cultivated in vitro, or cultivated in a xenograft model; or the nucleic acid sample may be one which has been replicated (whether in vitro or in vivo) from nucleic acid from the original source from the patient. Thus, although the nucleic acid derived from the patient may have been physically within the patient, it may alternatively have been copied from nucleic acid which was physically within the patient. When aberrant vascular development is believed to be associated with a tumour, tumour tissue may be taken from the primary tumour or from metastases.

It will be appreciated that a useful method of the invention includes the analysis of mutations in, or the detection of the presence or absence of, the ECSM4 or ECSM1 gene in any suitable sample. The sample may suitably be a freshly-obtained sample from the patient, or the sample may be an historic sample, for example a sample held in a library of samples.

Conveniently, the nucleic acid capable of selectively hybridising to the said human DNA and which is used in the methods of the invention further comprises a detectable label.

By "detectable label" is included any convenient radioactive label such as $^{32}P$, $^{33}P$ or $^{35}S$ which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless O-nitrophenylphosphate into coloured o-nitrophenol). Conveniently, the nucleic acid probe may occupy a certain position in a fixed assay and whether the nucleic acid hybridises to the said region of human DNA can be determined by reference to the position of hybridisation in the fixed assay. The detectable label may also be a fluorophore-quencher pair as described in Tyagi & Kramer (1996) *Nature Biotechnology* 14, 303-308.

Conveniently, in this method of diagnosis of a condition in which vascular development is aberrant the nucleic acid which is capable of the said selective hybridisation (whether labelled with a detectable label or not) is contacted with a nucleic acid derived from the patient under hybridising conditions. Suitable hybridising conditions include those described above.

This method of diagnosing a condition in which vascular development is aberrant may involve sequencing of DNA at one or more of the relevant positions within the relevant region, including direct sequencing; direct sequencing of PCR-amplified exons; differential hybridisation of an oligonucleotide probe designed to hybridise at the relevant positions within the relevant region (conveniently this uses immobilised oligonucleotide probes in, so-called, "chip" systems which are well known in the art); denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; heteroduplex analysis; selective DNA amplification using oligonucleotides; fluorescent in-situ hybridisation (FISH) of interphase chromosomes; ARMS-PCR (Amplification Refractory Mutation System-PCR) for specific mutations; cleavage at mismatch sites in hybridised nucleic acids (the cleavage being chemical or enzymic); SSCP single strand conformational polymorphism or DGGE (discontinuous or denaturing gradient gel electrophoresis); analysis to detect mismatch in annealed normal/mutant PCR-amplified DNA; and protein truncation assay (translation and transcription of exons—if a mutation introduces a stop codon a truncated protein product will result). Other methods may be employed such as detecting changes in the secondary structure of single-stranded DNA resulting from changes in the primary sequence, for example, using the cleavase I enzyme. This system is commercially available from GibcoBRL, Life Technologies, 3 Fountain Drive, Inchinnan Business Park, Paisley PA4 9RF, Scotland.

It will be appreciated that the methods of the invention may also be carried out on "DNA chips". Such "chips" are described in U.S. Pat. No. 5,445,934 (Affymetrix; probe arrays), WO 96/31622 (Oxford; probe array plus ligase or polymerase extension), and WO 95/22058 (Affymax; fluorescently marked targets bind to oligomer substrate, and location in array detected); all of these are incorporated herein by reference.

Detailed methods of mutation detection are described in "Laboratory Protocols for Mutation Detection" 1996, ed. Landegren, Oxford University Press on behalf of HUGO (Human Genome Organisation).

It is preferred if RFLP is used for the detection of fairly large (>500 bp) deletions or insertions. Southern blots may be used for this method of the invention.

PCR amplification of smaller regions (maximum 300 bp) to detect small changes greater than 3-4 bp insertions or deletions may be preferred. Amplified sequence may be analysed on a sequencing gel, and small changes (minimum size 3-4 bp) can be visualised. Suitable primers are designed as herein described.

In addition, using either Southern blot analysis or PCR restriction enzyme variant sites may be detected. For example, for analysing variant sites in genomic DNA restriction enzyme digestion, gel electrophoresis, Southern blotting, and hybridisation specific probe (for example any suitable fragment derived from the ECSM4 or ECSM1 cDNA or gene).

For example, for analysing variant sites using PCR DNA amplification, restriction enzyme digestion, gel detection by ethidium bromide, silver staining or incorporation of radionucleotide or fluorescent primer in the PCR.

Other suitable methods include the development of allele specific oligonucleotides (ASOs) for specific mutational events. Similar methods are used on RNA and cDNA for the suitable tissue.

Whilst it is useful to detect mutations in any part of the ECSM4 or ECSM1 gene, it is preferred if the mutations are detected in the exons of the gene and it is further preferred if the mutations are ones which change the coding sense. The detection of these mutations is a preferred aspect of the invention.

The methods of the invention also include checking for loss-of-heterozygosity (LOH; shows one copy lost). LOH may be a sufficient marker for diagnosis; looking for mutation/loss of the second allele may not be necessary. LOH of the gene may be detected using polymorphisms in the coding sequence, and introns, of the gene.

Particularly preferred nucleic acids for use in the aforementioned methods of the invention are those selected from the group consisting of primers suitable for amplifying nucleic acid.

Suitably, the primers are selected from the group consisting of primers which hybridise to the nucleotide sequences shown in any of the Figures which show ECSM4 or ECSM1 gene or cDNA sequences. It is particularly preferred if the primers hybridise to the introns of the ECSM4 or ECSM1 gene or if the primers are ones which will prime synthesis of DNA from the ECSM4 or ECSM1 gene or cDNA but not from other genes or cDNAs.

Primers which are suitable for use in a polymerase chain reaction (PCR; Saiki et al (1988) *Science* 239, 487-491) are preferred. Suitable PCR primers and methods of detecting products of PCR reactions are described in detail above.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991) *Nature* 350, 91-92 and AIDS (1993), Vol 7 (Suppl 2), S108 or SDA (strand displacement amplification) can be used as described in Walker et al (1992) *Nucl. Acids Res.* 20, 1691-1696. The polymerase chain reaction is particularly preferred because of its simplicity.

The present invention provides the use of a nucleic acid which selectively hybridises to the human-derived DNA of genomic clones as described in Table 8 of Example 1 or to the ECSM4 or ECSM1 gene, or a mutant allele thereof, or a nucleic acid which selectively hybridises to ECSM4 or ECSM1 cDNA or a mutant allele thereof, or their complement in a method of diagnosing a condition in which vascular development is aberrant; or in the manufacture of a reagent for carrying out these methods.

Preferred polynucleotides which selectively hybridise to the ECSM4 gene or cDNA are as described above in relation to a method of diagnosis.

Also, the present invention provides a method of determining the presence or absence, or mutation in, the said ECSM4 or ECSM1 gene. Preferably, the method uses a suitable sample from a patient.

The methods of the invention include the detection of mutations in the ECSM4 or ECSM1 gene.

The methods of the invention may make use of a difference in restriction enzyme cleavage sites caused by mutation. A non-denaturing gel may be used to detect differing lengths of fragments resulting from digestion with an appropriate restriction enzyme.

An "appropriate restriction enzyme" is one which will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence which occurs only rarely.

In another method, a pair of PCR primers are used which match (ie hybridise to) either the wild-type genotype or the mutant genotype but not both. Whether amplified DNA is produced will then indicate the wild-type or mutant genotype (and hence phenotype). However, this method relies partly on a negative result (ie the absence of amplified DNA) which could be due to a technical failure. It therefore may be less reliable and/or requires additional control experiments.

A preferable method employs similar PCR primers but, as well as hybridising to only one of the wild-type or mutant sequences, they introduce a restriction site which is not otherwise there in either the wild-type or mutant sequences.

The nucleic acids which selectively hybridise to the ECSM4 or ECSM1 gene or cDNA, or which selectively hybridise to the genomic clones containing ECSM4 or ECSM1 as listed in Table 8 of Example 1 are useful for a number of purposes. They can be used in Southern hybridization to genomic DNA and in the RNase protection method for detecting point mutations already discussed above. The probes can be used to detect PCR amplification products. They may also be used to detect mismatches with the ECSM4 or ECSM1 gene or mRNA in a sample using other techniques. Mismatches can be detected using either enzymes (eg S1 nuclease or resolvase), chemicals (eg hydroxylamine or osmium tetroxide and piperidine), or changes in electrophoretic mobility of mismatched hybrids as compared to totally matched hybrids. These techniques are known in the art. Generally, the probes are complementary to the ECSM4 or ECSM1 gene coding sequences, although probes to certain introns are also contemplated. A battery of nucleic acid probes may be used to compose a kit for detecting loss of or mutation in the wild-type ECSM4 or ECSM1 gene. The kit allows for hybridization to the entire ECSM4 or ECSM1 gene. The probes may overlap with each other or be contiguous.

If a riboprobe is used to detect mismatches with mRNA, it is complementary to the mRNA of the human ECSM4 or ECSM1 gene. The riboprobe thus is an anti-sense probe in that it does not code for the protein encoded by the ECSM4 or ECSM1 gene because it is of the opposite polarity to the sense strand. The riboprobe generally will be labelled, for example, radioactively labelled which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the ECSM4 or ECSM1 gene. These are useful to detect similar mutations in other patients on the basis of hybridization rather than mismatches. As mentioned above, the ECSM4 or ECSM1 gene probes can also be used in Southern hybridizations to genomic DNA to detect gross chromosomal changes such as deletions and insertions.

Particularly useful methods of detecting a mutation in the ECSM1 or ECSM4 genes include single strand conformation polymorphism (SSCP), hetero duplex analysis, polymerase chain reaction, using DNA chips and sequencing.

Any sample containing nucleic acid derived from the individual is useful in the methods of the invention. It is preferred if the nucleic acid in the sample is DNA. Thus, samples from cells may be obtained as is well known in the art, for example from blood samples or cheek cells or the like. Where the methods are being used to determine the presence or absence of a mutation in an unborn child, it is preferred if the sample is a maternal sample containing nucleic acid from the unborn child. Suitable maternal samples include the amniotic fluid of the mother, chorionic villus samples and blood samples from which foetal cells can be isolated.

A further aspect of the invention provides a method of reducing the expression of the ECSM4 or ECSM1 polynucleotide in an individual, comprising administering to the individual an agent which selectively prevents expression of ECSM4 or ECSM1.

In a preferred embodiment, the agent which selectively prevents expression of ECSM4 or ECSM1 is an antisense nucleic acid.

Preferably, the antisense nucleic acid is not one (or is not antisense to one) whose sequence consists of the sequence represented by SEQ ID No 18084 or 5096 of EP 1 074 617, SEQ ID No 210 of WO 00/53756 or WO 99/46281, or SEQ ID Nos 22, 23, 96 or 98 of WO 01/23523 or SEQ ID No 31 of WO 99/11293 or their complement, or a nucleic acid sequence which encodes a polypeptide whose amino acid sequence is represented by any one of SEQ ID No 18085 of EP 1 074 617, SEQ ID No 211 of either WO 00/53756 or WO99/46281, SEQ ID Nos 24-27, 29, 30, 33, 34, 38 or 39 of WO 01/23523, or SEQ ID No 86 of WO 99/11293.

A further aspect thereof includes administering an antisense nucleic acid to a cell in order to prevent expression of ECSM4 or ECSM1. Typically, the cell is in the body of an individual in need of prevention of expression of ESCM4 or ECSM1.

The ECSM4 or ECSM1 polynucleotide which is bound by an antisense molecule may be DNA or RNA.

Preferred antisense molecules are as described above.

Diseases which may be treated by reducing ECSM4 or ECSM1 expression include diseases involving aberrant or excessive vascularisation as described above.

Antisense nucleic acids are well known in the art and are typically single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A) addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci.* (*USA*) 85(15), 5507-11). The Goodchild study showed that oligonucleotides that were most effective were complementary to the poly(A) signal; also effective were those targeted at the 5N end of the RNA, particularly the cap and 5N untranslated region, next to the primer binding site and at the primer binding site. The cap, 5N untranslated region, and poly(A) signal lie within the sequence repeated at the ends of retrovirus RNA (R region) and the oligonucleotides complementary to these may bind twice to the RNA.

Typically, antisense oligonucleotides are 15 to 35 bases in length. For example, 20-mer oligonucleotides have been shown to inhibit the expression of the epidermal growth factor receptor mRNA (Witters et al, *Breast Cancer Res Treat* 53:41-50 (1999)) and 25-mer oligonucleotides have been shown to decrease the expression of adrenocorticotropic hormone by greater than 90% (Frankel et al, *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079-7083 showed increased inhibition in tissue culture of HIV-1 using oligonucleotide phosphoramidates and phosphorothioates. Sarin et al (1988) *Proc. Natl. Acad. Sci. USA* 85, 7448-7451 demonstrated increased inhibition of HIV-1 using oligonucleotide methylphosphonates. Agrawal et al (1989) *Proc. Natl. Acad. Sci. USA* 86, 7790-7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430-3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res.* 19, 747-750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesizing oligonucleoside phosphorothioates is provided in Agrawal and Tang (1990) *Tetrahedron Letters* 31, 7541-7544, the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) *Tetrahedron Letters* 28, 3401; Bannwarth (1988) *Helv. Chim. Acta.* 71, 1517; Crosstick and Vyle (1989) *Tetrahedron Letters* 30, 4693; Agrawal et al (1990) *Proc. Natl. Acad. Sci. USA* 87, 1401-1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesized and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747-750 and Agrawal et al (1991) *Proc. Natl. Acad. Sci. USA* 88(17), 7595-7599, the teachings of which are hereby incorporated herein by reference.

A further method of making oligonucleotides resistant to nuclease attack is for them to be "self-stabilized" as described by Tang et al (1993) *Nucl. Acids Res.* 21, 2729-2735 incorporated herein by reference. Self-stabilized oligonucleotides have hairpin loop structures at their 3' ends, and show increased resistance to degradation by snake venom phosphodiesterase, DNA polymerase I and fetal bovine serum. The self-stabilized region of the oligonucleotide does not interfere in hybridization with complementary nucleic acids, and pharmacokinetic and stability studies in mice have shown increased in vivo persistence of self-stabilized oligonucleotides with respect to their linear counterparts.

In accordance with the invention, the antisense compound may be administered systemically. Alternatively the inherent binding specificity of antisense oligonucleotides characteristic of base pairing is enhanced by limiting the availability of the antisense compound to its intended locus in vivo, permitting lower dosages to be used and minimising systemic effects. Thus, oligonucleotides may be applied locally to achieve the desired effect. The concentration of the oligonucleotides at the desired locus is much higher than if the oligonucleotides were administered systemically, and the therapeutic effect can be achieved using a significantly lower total amount. The local high concentration of oligonucleotides enhances penetration of the targeted cells and effectively blocks translation of the target nucleic acid sequences.

The oligonucleotides can be delivered to the locus by any means appropriate for localised administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus.

The oligonucleotides may be administered via a hydrogel material. The hydrogel is non-inflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10% to about 80% by weight ethylene oxide and from about 20% to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warms, it solidifies to form a gel, and the oligonucleotides diffuse out of the gel into the surrounding cells over a period of time defined by the exact composition of the gel.

It will be appreciated that the oligonucleotides or other agents may be administered after surgical removal of a tumour, and may be administered to the area from which the tumour has been removed, and surrounding tissue, for example using cytoscopy to guide application of the oligonucleotides or other agents.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerised or solidified, using melt or solvent evaporation techniques, or mechanically mixed with the material. In one embodiment, the oligonucleotides are mixed into or applied onto coatings for implantable devices such as dextran coated silica beads, stents, or catheters.

The dose of oligonucleotides is dependent on the size of the oligonucleotides and the purpose for which is it administered. In general, the range is calculated based on the surface area of tissue to be treated. The effective dose of oligonucleotide is somewhat dependent on the length and chemical composition of the oligonucleotide but is generally in the range of about 30 to 3000 µg per square centimetre of tissue surface area.

The oligonucleotides may be administered to the patient systemically for both therapeutic and prophylactic purposes. The oligonucleotides may be administered by any effective method, for example, parenterally (eg intravenously, subcutaneously, intramuscularly) or by oral, nasal or other means which permit the oligonucleotides to access and circulate in the patient's bloodstream. Oligonucleotides administered systemically preferably are given in addition to locally administered oligonucleotides, but also have utility in the absence of local administration. A dosage in the range of from about 0.1 to about 10 grams per administration to an adult human generally will be effective for this purpose.

It will be appreciated that antisense agents also include larger molecules which bind to said ECSM4 or ECSM1 mRNA or genes and substantially prevent expression of said ECSM4 or ECSM1 mRNA or genes and substantially prevent expression of said ECSM4 or ECSM1 protein. Thus, expression of an antisense molecule which is substantially complementary to said ECSM4 or ECSM1 mRNA is envisaged as part of the invention.

The said larger molecules may be expressed from any suitable genetic construct as is described below and delivered to the patient. Typically, the genetic construct which expresses the antisense molecule comprises at least a portion of the said ECSM4 or ECSM1 cDNA or gene operatively linked to a promoter which can express the antisense molecule in a cell. Promoters that may be active in endothelial cells are described below.

Although the genetic construct can be DNA or RNA it is preferred if it is DNA.

Preferably, the genetic construct is adapted for delivery to a human cell.

Means and methods of introducing a genetic construct into a cell in an animal body are known in the art. For example, the constructs of the invention may be introduced into proliferating endothelial cells by any convenient method, for example methods involving retroviruses, so that the construct is inserted into the genome of the endothelial cell. For example, in Kuriyama et al (1991) *Cell Struc. and Func.* 16, 503-510 purified retroviruses are administered. Retroviruses provide a potential means of selectively infecting proliferating endothelial cells because they can only integrate into the genome of dividing cells; most endothelial cells are in a quiescent, non-receptive stage of cell growth or, at least, are dividing much less rapidly than angiogenic cells. Retroviral DNA constructs which encode said antisense agents may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo$^R$ gene). Independent colonies are isolated and expanded and the culture supernatant removed, filtered through a 0.45 µm pore-size filter and stored at −70°. For the introduction of the retrovirus into the tumour cells, it is convenient to inject directly retroviral supernatant to which 10 µg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992) *Science* 256, 1550-1552, cells which produce retroviruses are injected into specific tissue. The retrovirus-producing cells so introduced are engineered to actively produce retroviral vector particles so that continuous productions of the vector occurred within the tumour mass in situ. Thus, proliferating endothelial cells can be successfully transduced in vivo if mixed with retroviral vector-producing cells.

Targeted retroviruses are also available for use in the invention; for example, sequences conferring specific binding affinities may be engineered into pre-existing viral env genes (see Miller & Vile (1995) *Faseb J* 9, 190-199 for a review of this and other targeted vectors for gene therapy).

Other methods involve simple delivery of the construct into the cell for expression therein either for a limited time or, following integration into the genome, for a longer time. An example of the latter approach includes (preferably endothelial-cell-targeted) liposomes (N≡ssander et al (1992) *Cancer Res.* 52, 646-653).

Immunoliposomes (antibody-directed liposomes) are especially useful in targeting to endothelial cell types which express a cell surface protein for which antibodies are available.

Other methods of delivery include adenoviruses carrying external DNA via an antibody-polylysine bridge (see Curiel *Prog. Med. Virol.* 40, 1-18) and transferrin-polycation conjugates as carriers (Wagner et al (1990) *Proc. Natl. Acad. Sci. USA* 87, 3410-3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalised into the cell and carries into the cell with it the DNA construct of the invention. It is preferred if the polycation is polylysine.

The DNA may also be delivered by adenovirus wherein it is present within the adenovirus particle, for example, as described below.

In the second of these methods, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the endothelial cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) *Proc. Natl. Acad. Sci. USA* 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It may be desirable to locally perfuse a tumour with the suitable delivery vehicle comprising the genetic construct for a period of time; additionally or alternatively the delivery vehicle or genetic construct can be injected directly into accessible tumours.

It will be appreciated that "naked DNA" and DNA complexed with cationic and neutral lipids may also be useful in introducing the DNA of the invention into cells of the patient to be treated. Non-viral approaches to gene therapy are described in Ledley (1995) *Human Gene Therapy* 6, 1129-1144.

Alternative targeted delivery systems are also known such as the modified adenovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Mutant adenoviruses which replicate selectively in p53-deficient human tumour cells, such as those described in Bischoff et al (1996) *Science* 274, 373-376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

In a further embodiment the agent which selectively prevents the function of ECSM4 or ECSM1 is a ribozyme capable of cleaving targeted ECSM4 or ECSM1 RNA or DNA. A gene expressing said ribozyme may be administered in substantially the same and using substantially the same vehicles as for the antisense molecules.

Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053; Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

It will be appreciated that it may be desirable that the antisense molecule or ribozyme is expressed from a cell-specific promoter element.

The genetic constructs of the invention can be prepared using methods well known in the art.

A further aspect of the invention is a method of screening for a molecule that binds to ECSM4 or a suitable variant, fragment or fusion thereof, or a fusion of a said fragment or fusion thereof, the method comprising 1) contacting a) the ECSM4 polypeptide with b) a test molecule 2) detecting the presence of a complex containing the ECSM4 polypeptide and a test molecule, and optionally 3) identifying any test molecule bound to the ECSM4 polypeptide.

Preferably the ECSM4 polypeptide is one as described above in respect of the eleventh aspect of the invention.

In a preferred embodiment, the test molecule is a polypeptide.

In a further preferred embodiment, the method is used to identify natural ligands of ECSM4. Thus, in this embodiment the test molecule includes the natural ligand of ECSM4. A particularly useful technique for the identification of natural ligands of polypeptide molecules is the yeast two-hybrid technique. This technique is well known in the art and relies on binding between a molecule and its cognate ligand to bring together two parts of a transcription complex (which are fused one to the molecule in question and other to the test ligand) which, when together, promote transcription of a reporter gene.

Hence, a preferred embodiment of this aspect of the invention comprises use of the screening method, preferably the yeast two-hybrid system, to identify natural ligands of the ECSM4 polypeptide.

A molecule which is identifiable as binding the ECSM4 polypeptide is a further aspect of the invention.

It will be appreciated that a molecule which binds to ESCM4 may modulate the activation of ECSM4.

Suitable peptide ligands that will bind to ECSM4 may be identified using methods known in the art.

One method, disclosed by Scott and Smith (1990) *Science* 249, 386-390 and Cwirla et al (1990) *Proc. Natl. Acad. Sci. USA* 87, 6378-6382, involves the screening of a vast library of filamentous bacteriophages, such as M13 or fd, each member of the library having a different peptide fused to a protein on the surface of the bacteriophage. Those members of the library that bind to ECSM4 are selected using an iterative binding protocol, and once the phages that bind most tightly have been purified, the sequence of the peptide ligands may be determined simply by sequencing the DNA encoding the surface protein fusion. Another method that can be used is the NovaTope™ system commercially available from Novagen, Inc., 597 Science Drive, Madison, Wis. 53711. The method is based on the creation of a library of bacterial clones, each of which stably expresses a small peptide derived from a candidate protein in which the ligand is believed to reside. The library is screened by standard lift methods using the antibody or other binding agent as a probe. Positive clones can be analysed directly by DNA sequencing to determine the precise amino acid sequence of the ligand.

Further methods using libraries of beads conjugated to individual species of peptides as disclosed by Lam et al (1991) *Nature* 354, 82-84 or synthetic peptide combinatorial libraries as disclosed by Houghten et al (1991) *Nature* 354, 84-86 or matrices of individual synthetic peptide sequences on a solid support as disclosed by Pirrung et al in U.S. Pat. No. 5,143,854 may also be used to identify peptide ligands.

It will be appreciated that screening assays which are capable of high throughput operation will be particularly preferred. Examples may include cell based assays and protein-protein binding assays. An SPA-based (Scintillation Proximity Assay; Amersham International) system may be used. For example, an assay for identifying a compound capable of modulating the activity of a protein kinase may be performed as follows. Beads comprising scintillant and a polypeptide that may be phosphorylated may be prepared. The beads may be mixed with a sample comprising the protein kinase and $^{32}$P-ATP or $^{33}$P-ATP and with the test compound. Conveniently this is done in a 96-well format. The plate is then counted using a suitable scintillation counter, using known parameters for $^{32}$P or $^{33}$P SPA assays. Only $^{32}$P or $^{33}$P that is in proximity to the scintillant, i.e. only that bound to the polypeptide, is detected. Variants of such an assay, for example in which the polypeptide is immobilised on the scintillant beads via binding to an antibody, may also be used.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

Alternative methods of detecting binding of a polypeptide to macromolecules, for example DNA, RNA, proteins and phospholipids, include a surface plasmon resonance assay, for example as described in Plant et al (1995) *Analyt Biochem* 226(2), 342-348. Methods may make use of a polypeptide that is labelled, for example with a radioactive or fluorescent label.

A further method of identifying a compound that is capable of binding to the ECSM4 polypeptide is one where the polypeptide is exposed to the compound and any binding of the compound to the said polypeptide is detected and/or measured. The binding constant for the binding of the compound to the polypeptide may be determined. Suitable methods for detecting and/or measuring (quantifying) the binding of a compound to a polypeptide are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips or arrays have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Biological chips or arrays are useful in a variety of screening techniques for obtaining information about either the probes or the target molecules. For example, a library of peptides can be used as probes to screen for drugs. The peptides can be exposed to a receptor, and those probes that bind to the receptor can be identified. See U.S. Pat. No. 5,874,219 issued 23 Feb. 1999 to Rava et al.

Another method of targeting proteins that modulate the activity of ECSM4 is the yeast two-hybrid system, where the polypeptides of the invention can be used to "capture" ECSM4 protein binding proteins. The yeast two-hybrid system is described in Fields & Song, *Nature* 340:245-246 (1989).

It will be understood that it will be desirable to identify compounds that may modulate the activity of the polypeptide in vivo. Thus it will be understood that reagents and conditions used in the method may be chosen such that the interactions between the said and the interacting polypeptide are substantially the same as between a said naturally occurring polypeptide and a naturally occurring interacting polypeptide in vivo.

It will be appreciated that in the method described herein, the ligand may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

Alternatively, the methods may be used as "library screening" methods, a term well known to those skilled in the art. Thus, for example, the method of the invention may be used to detect (and optionally identify) a polynucleotide capable of expressing a polypeptide activator of ECSM4. Aliquots of an expression library in a suitable vector may be tested for the ability to give the required result.

Hence, an embodiment of this aspect of the invention provides a method of identifying a drug-like compound or lead compound for the development of a drug-like compound that modulates the activity of the polypeptide ECSM4, the method comprising contacting a compound with the polypeptide or a suitable variant, fragment, derivative or fusion thereof or a fusion of a variant, fragment or derivative thereof and determining whether, for example, the enzymic activity of the said polypeptide is changed compared to the activity of the said polypeptide or said variant, fragment, derivative or fusion thereof or a fusion of a variant, fragment or derivative thereof in the absence of said compound.

Preferably, the ECSM4 polypeptide is as described above in respect of the eleventh aspect of the invention.

It will be understood that it will be desirable to identify compounds that may modulate the activity of the polypeptide in vivo. Thus it will be understood that reagents and conditions used in the method may be chosen such that the interactions between the said polypeptide and its substrate are substantially the same as in vivo.

In one embodiment, the compound decreases the activity of said polypeptide. For example, the compound may bind substantially reversibly or substantially irreversibly to the active site of said polypeptide. In a further example, the compound may bind to a portion of said polypeptide that is not the active site so as to interfere with the binding of the said polypeptide to its ligand. In a still further example, the compound may bind to a portion of said polypeptide so as to decrease said polypeptide's activity by an allosteric effect. This allosteric effect may be an allosteric effect that is involved in the natural regulation of the said polypeptide's activity, for example in the activation of the said polypeptide by an "upstream activator".

A still further aspect of the invention provides a polynucleotide comprising a promoter and/or regulatory portion of any one of the ECSM1 or ECSM4 genes.

By "ECSM1 or ECSM4 genes" we mean the natural genomic sequence which when transcribed is capable of encoding a polypeptide comprising the ECSM1 or ECSM4 polypeptide sequence as defined herein. The natural genomic sequence of the ECSM1 or ECSM4 genes may contain introns.

The polynucleotide of this aspect of the invention is preferably one which has transcriptional promoter activity. A promoter is an expression control element formed by a DNA sequence that permits binding of RNA polymerase and transcription to occur. Preferably the transcriptional promoter activity is present in mammalian cells and more preferably the polynucleotide has transcriptional promoter activity in endothelial cells. In a preferred embodiment, the transcriptional promoter activity is present in endothelial cells and not in other cell types.

Preferably, the promoter and/or regulatory portion is one which can direct endothelial cell selective expression.

Preferably, the promoter or regulatory region of the ECSM4 gene is one which is capable of promoting transcription of an operatively-linked coding sequence in response to hypoxic conditions. More preferably, the level of transcription of the coding sequence is up-regulated in hypoxic conditions compared to the level of transcription in the absence of hypoxia. By "hypoxic conditions" we include the physiological conditions of cancer where the inappropriate cell proliferation deprives surrounding tissue of oxygen, cardiac disease where for example a vessel occlusion may restrict the delivery of oxygen to certain tissues, and tissue necrosis where destruction of vascular tissue cells results in a reduced supply of oxygen to surrounding tissue and the consequent death of that surrounding tissue. Hypoxia is described in more detail in Hockel and Vaupel (2001) *J. Nat. Can. Inst.* 93: 266-276.

Hence, in a preferred embodiment, the ECSM4 promoter or regulatory region is comprised in a vector suitable for use in gene therapy for driving expression of a therapeutic gene to treat a hypoxic condition. Preferably, the hypoxic condition is cancer or cardiac disease. A "therapeutic gene" may be any gene which provides a desired therapeutic effect.

It will be appreciated that use of the said ECSM4 promoter to treat a hypoxic condition, for example by gene therapy, is included within the scope of the present invention.

Methods for the determination of the sequence of the promoter region of a gene are well known in the art. The presence of a promoter region may be determined by identification of known motifs, and confirmed by mutational analysis of the identified sequence. Preferably, the promoter sequence is located in the region 5 kb upstream of the genomic coding region of ECSM1 or ECSM4. More preferably, it is located in the region 3 kb or 2 kb or 1 kb or 500 bp upstream, and still more preferably it is located within 210 bp of the transcription start site.

Regulatory regions, or transcriptional elements such as enhancers are less predictable than promoters in their location relative to a gene. However, many motifs indicative of regulatory regions are well characterised and such regions affecting the level of transcription of the relevant gene can usually be identified on the basis of these motifs. The function of such a region can be demonstrated by well-known methods such as mutational analysis and in vitro DNA-binding assays including DNA footprinting and gel mobility shift assays.

Regulatory regions influencing the transcription of the ECSM1 or ECSM4 genes are likely to be located within the region 20 kb or 10 kb or 7 kb 5 kb or 3 kb, or more preferably 1 kb 5' upstream of the relevant genomic coding region or can be located within introns of the gene.

Sequence tagged sites and mapping intervals will be helpful in localising promoter regions, regulatory regions and physical clones.

In a further preferred embodiment, the polynucleotide comprising the promoter and/or regulatory portion is operatively linked to a polynucleotide encoding a polypeptide. Methods for linking promoter polynucleotides to polypeptide coding sequences are well known in the art.

Preferably the polypeptide is a therapeutic polypeptide. A therapeutic polypeptide may be any polypeptide which it is medically useful to express selectively in endothelial cells. Examples of such therapeutic polypeptides include anti-proliferative, immunomodulatory or blood clotting-influencing factors, or anti-proliferative or anti-inflammatory cytokines. They may also comprise anti-cancer polypeptides.

In one embodiment of this aspect of the invention, the polynucleotide is one suitable for use in medicine. Thus, the invention includes the polynucleotide packaged and presented for use in medicine. It will be appreciated that such polynucleotides will be especially useful in gene therapy, especially where it is desirable to express a therapeutic polypeptide selectively an endothelial cell. It is preferred if the polynucleotide is one suitable for use in gene therapy.

Gene therapy may be carried out according to generally accepted methods, for example, as described by Friedman, 1991. A virus or plasmid vector (see further details below), containing a copy of the gene to be expressed linked to expression control elements such as promoters and other regulatory elements influencing transcription of ECSM1 or ECSM4 as described above and capable of replicating inside endothelial cells, is prepared. Suitable vectors are known, such as disclosed in U.S. Pat. No. 5,252,479 and WO 93/07282. The vector is then injected into the patient, either locally or systemically. If the transfected gene is not permanently incorporated into the genome of each of the targeted endothelial cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, eg SV40 (Madzak et al, 1992), adenovirus (Berkner, 1992; Berkner et al, 1988; Gorziglia and Kapikian, 1992; Quantin et al, 1992; Rosenfeld et al, 1992; Wilkinson et al, 1992; Stratford-Perricaudet et al, 1990), vaccinia virus (Moss, 1992), adeno-associated virus (Muzyczka, 1992; Ohi et al, 1990), herpesviruses including HSV and EBV (Margolskee, 1992; Johnson et al, 1992; Fink et al, 1992; Breakfield and Geller, 1987; Freese et al, 1990), and retroviruses of avian (Brandyopadhyay and Temin, 1984; Petropoulos et al., 1992), murine (Miller, 1992; Miller et al, 1985; Sorge et al, 1984; Mann and Baltimore, 1985; Miller et al, 1988), and human origin (Shimada et al, 1991; Helseth et al, 1990; Page et al, 1990; Buchschacher and Panganiban, 1992). To date most human gene therapy protocols have been based on disabled murine retroviruses.

Nonviral gene transfer methods known in the art include chemical techniques such as calcium phosphate coprecipitation (Graham and van der Eb, 1973; Pellicer et al, 1980); mechanical techniques, for example microinjection (Anderson et al, 1980; Gordon et al, 1980; Brinster et al, 1981; Constantini and Lacy, 1981); membrane fusion-mediated transfer via liposomes (Felgner et al, 1987; Wang and Huang, 1989; Kaneda et al, 1989; Stewart et al, 1992; Nabel et al, 1990; Lim et al, 1992); and direct DNA uptake and receptor-mediated DNA transfer (Wolff et al, 1990; Wu et al, 1991; Zenke et al, 1990; Wu et al, 1989b; Wolff et al, 1991; Wagner et al, 1990; Wagner et al, 1991; Cotten et al, 1990; Curiel et al, 1991a; Curiel et al, 1991b).

Other suitable systems include the retroviral-adenoviral hybrid system described by Feng et al (1997) *Nature Biotechnology* 15, 866-870, or viral systems with targeting ligands such as suitable single chain Fv fragments.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumour deposits, for example, following direct in situ administration (Nabel, 1992).

Gene transfer techniques which target DNA directly to tissues, eg endothelial cells, is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. In the case of endothelial cells, a suitable receptor is ECSM4. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

In the case where replacement gene therapy using a functionally wild-type gene is used, it may be useful to monitor the treatment by detecting the presence of replacement gene mRNA or encoded replacement polypeptide, or functional gene product, at various sites in the body, including the endothelial cells, blood serum, and bodily secretions/excretions, for example urine.

A further aspect of the present invention provides a method of treating an individual with cancer, cardiac disease, a hypoxic condition, endometriosis or artherosclerosis comprising administering to the individual a polynucleotide according to the invention, which polynucleotide comprises a promoter or regulatory region of the invention operatively linked to a polynucleotide encoding a therapeutic polypeptide.

A still further aspect of the invention provides a method of modulating angiogenesis in an individual comprising administering to the individual a polynucleotide according to the invention, which polynucleotide comprises a promoter or regulatory region of the invention operatively linked to a polynucleotide encoding a therapeutic polypeptide or a polynucleotide which is capable of expressing ECSM4 or a fragment or variant thereof or which comprises an ECSM4 antisense nucleic acid.

The therapeutic polypeptide may be any therapeutic polypeptide which is useful in treating the individual. Preferably, the therapeutic polypeptide is any one or more of immunomodulatory, anti-cancer, a blood-clotting-influencing factor or an anti-proliferative or anti-inflammatory cytokine.

Antisense nucleic acid is discussed in more detail above. Briefly, the function of an antisense nucleic acid is to inhibit the translation of a specific mRNA to which the antisense nucleic acid is complementary and able to hybridise to within a cell, at least in part. The design of optimal antisense nucleic acid molecules is well known in the art of molecular biology.

The present invention also provides a use of a polynucleotide according to the invention, which polynucleotide comprises a promoter or regulatory region of the invention operatively linked to a polynucleotide encoding a therapeutic polypeptide in the manufacture of a medicament for treating cancer, cardiac disease, a hypoxic condition, endometriosis or artherosclerosis.

The invention will now be described in more detail by reference to the following Examples and Figures herein

FIG. 1.

Experimental verification by reverse transcription PCR. Candidate endothelial specific genes predicted by the combination of the UniGene/EST screen and xProfiler SAGE differential analysis (Table 8) were checked for expression in three endothelial and nine non-endothelial cell cultures. Endothelial cultures were as follows: HMVEC (human microvascular endothelial cells), HUVEC (human umbilical vein endothelial cells) confluent culture and HUVEC proliferating culture. Non-endothelial cultures were as follows: normal endometrial stromal (NES) cells grown in normoxia and NES grown in hypoxia, MDA 453 and MDA 468 breast carcinoma cell lines, HeLa, FEK4 fibroblasts cultured in normoxia and FEK4 fibroblasts cultured in hypoxia, and SW480, HCT116-two colorectal epithelium cell lines. ECSM1 showed complete endothelial specificity, while magic roundabout/ECSM4 was very strongly preferentially expressed in the endothelium. Interestingly, both these novel genes appear more endothelial specific than the benchmark endothelial specific gene: von Willebrand factor.

FIG. 2.

Phrap generated contig sequence (SEQ ID NO:21) for ECSM1 and amino acid sequence (SEQ ID NO:22) of the translation product. The ESTs used to generate this contig are shown in Table 10.

FIG. 3.

ECSM4 in vitro transcription/translation. The cDNA coding for full length ECSM4 was cloned into pBluescript plasmid vector. Circular and HindIII digested plasmid were subjected to in vitro transcription/translation using TNT® T7 Quick Coupled Transcription/Translation System (Promega Corporation) incorporating $^{35}$S Methionine as per manufacturer's instructions. The reaction products were resolved by SDS PAGE and visualised by autoradiography. The Luciferase plasmid was utilised as a positive control for the reaction. The numbers on the left indicate the position of molecular size markers for reference. The size of the band denoting ECSM4 is consistent with the calculated molecular weight of the polypeptide of 118 kDa.

FIG. 4.

cDNA and computer translation of GenBank AK000805 (human ECSM4/magic roundabout (SEQ ID NOs:23 and 24)).

FIG. 5.

Phrap generated contig sequence for human ECSM4 (magic roundabout) ESTs (SEQ ID NO:25) and translation of the encoded polypeptide (SEQ ID NO:26). The DNA sequence is shown in the orientation as if it were a cDNA, which is opposite to that in which it was originally generated. The ESTs used to generate the contig are shown in Table 11. Translation start in this sequence is at position 2 of the contig sequence, and translation finish is at position 948.

FIG. 6.

An alignment of the GenBank Accession No AK000805 ("magic.seq") (SEQ ID NO:27) and Phrap ("hs. 111518") generated nucleic acid sequences of human ECSM4 (SEQ ID NO:28) given in FIGS. 4 and 5.

FIG. 7.

Mouse ECSM4 contig nucleotide sequence (SEQ ID NO:29) and amino acid sequence (SEQ ID NO:30).

FIG. 8.

An alignment of the amino acid sequences of the mouse Robo1 protein ("T30805") (SEQ ID NO:32) and human ECSM4 ("magic.pep") (SEQ ID NO:31).

FIG. 9.

An alignment of the amino acid sequences of mouse Robo1 protein ("T30805") (SEQ ID NO:33) and mouse ECSM4 ("mousemagic.pep") (SEQ ID NO:30).

FIG. 10.

An alignment of the amino acid sequences of human ("magic.pep") (SEQ ID NO:35) and mouse ("mousemagic.pep") ECSM4 proteins (SEQ ID NO.34). Residues in bold indicate well conserved sequences. The mouse protein sequence is shown on top and the human sequence is below.

FIG. 11.

Expression of magic roundabout in vitro. (a) Ribonuclease protection analysis. Top, two probes to different regions (nucleotides 1 to 355 and 3333 to 3679) of magic roundabout were used in the analysis (shown left and right). RNase protection assay was performed with U6 small nuclear RNA as control (shown bottom) (Maxwell et al (1999) *Nature* 399: 271). Human cell lines and primary isolates: MRC-5, fibroblast cell line, MCF-7, breast carcinoma cell line, Neuro, SY-SH-5Y neuroblastoma cell line, HUVEC, umbilical vein endothelial isolate, HDMEC, dermal microvascular endothelial isolate and HMME2, mammary microvascular endothelial cell line. N, normoxia, H, hypoxia, P. proliferating. (b) Western analysis of cell lysates. A band at ~110 kD corresponds to MR and was stronger in cells exposed to hypoxia for 18 h. The experiment was repeated twice with similar results. Immunoblotting was carried out as described in Brown et al (2000) *Cancer Res.* 60: 6298. Polyclonal rabbit anti-sera was raised against the following peptides coupled to keyhole limpet haemocyanin: amino acids 165-181 (LSQSP-GAVPQALVAWRA (SEQ ID NO:6)) and 274-288 (DSVLT-PEEVALCLEL (SEQ ID NO:7)) (anti-sera 1) or peptides 311-320 (TYGYISVPTA (SEQ ID NO:8)) and 336-351 (KG-GVLLCPPRPCLTPT (SEQ ID NO:9)) (anti-sera 2). Both anti-sera gave identical results. For western analysis, anti-sera was affinity purified on a "Hi-Trap NHS-activated HP" column (Amersham) to which the peptides used to raise anti-sera 1 were coupled.

FIG. 12.

Human ECSM4 full-length cDNA (SEQ ID NO:36) and encoded protein sequence (SEQ ID NO:37).

FIG. 13.

Mouse ECSM4 full-length cDNA (MuMR.seq) (SEQ ID NOs:38 and 39) and encoded protein sequences (SEQ ID NOs:40-42).

FIG. 14.

Alignment of human ECSM4 (top) (SEQ ID NO:43) and mouse ECSM4 (bottom) amino acid sequences (SEQ ID NO:48 and SEQ ID NOs:45-47).

FIG. 15.

Alignment of human ECSM4 ("HuMR.seq"; top (SEQ ID NO:49)) and mouse ECSM4 ("MuMR.seq"; bottom (SEQ ID NO:50)) cDNA sequences.

FIG. 16.

In situ hybridisation analysis of human placental tissue using ECSM4 as probe. A bright field view of 10× magnification of thin section of placental tissue. The arrow indicates a large blood vessel.

FIG. 17.

In situ hybridisation analysis of human placental tissue using ECSM4 as probe. A higher magnification of the bright-field view of thin section of placental tissue shown in FIG. 16, focussing on the blood vessel. The arrow points to endothelial cells lining the lumen of the vessel.

FIG. 18.

In situ hybridisation analysis of human placental tissue using ECSM4 as probe. A higher magnification of the thin section of placental tissue shown in FIG. 16, focussing on the blood vessel and shown here in dark-field. The arrow depicts positive staining of endothelial cells lining the lumen of the vessel.

FIG. 19.

In situ hybridisation analysis of colorectal liver metastatic tissue using ECSM4 as probe. A bright-field view of a section of colorectal liver metastatic tissue magnified with (A) 10× and (B) 20× objective. The area marked by the boundary (encircling * A) depicts the normal liver tissue. The arrow in (B) shows one of the blood vessels within the metastatic tumour tissue.

FIG. 20.

In situ hybridisation analysis of colorectal liver metastatic tissue using ECSM4 as a probe. This is a dark field view of a section of colorectal liver metastatic tissue magnified with (A) 10× and (B) 20× objective. The area marked by the boundary (encircling *) depicts the normal liver tissue. The arrow in (B) shows one of the blood vessels within the metastatic tumour tissue corresponding to the vessel shown in FIG. 19B. Expression of ECSM4 is restricted to endothelial cells of the tumour blood vessels. Note that there is little expression in the surrounding normal tissue (*).

FIG. 21.

Western Blot using the rabbit antibody MGO-5 as primary antibody. Dilutions of the peptides ECSM4-derived peptides MR 165, MR 311, MR 366 and the control polypeptide Bovine Serum Albumin (BSA) were resolved by SDS polyacrylamide gel electrophoresis and blotted onto Immobilon P membrane. The blot was probed with MGO-5 antibody and visualised using anti-rabbit antibody coupled with alkaline phosphatase.

FIG. 22.

Immunostaining of frozen placental section. A frozen thin section of human placenta was analysed by immunohistochemistry without any primary antibody (negative control) and visualised using anti-rabbit antibody coupled with alkaline phosphatase. Little background staining is observed.

FIG. 23.

Immunostaining of frozen placental section. A frozen thin section of human placenta was analysed by immunohistochemistry using a primary antibody recognising von Willibrand Factor (positive control), and visualised using an anti-rabbit secondary antibody coupled with alkaline phosphatase. The arrows show high levels of expression of vWF restricted to the vascular endothelial cells.

FIG. 24.

Figure 22:
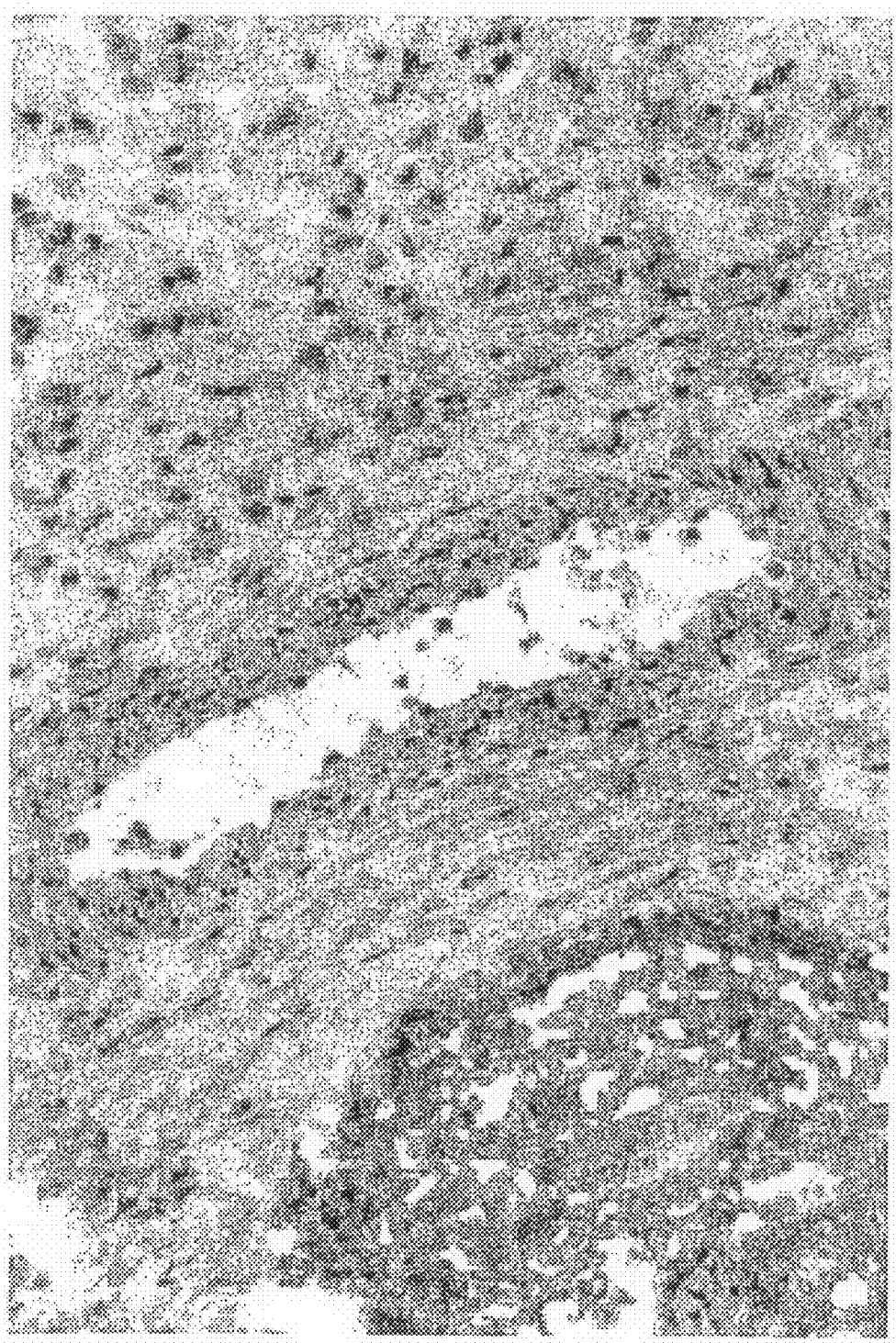
Figure 23:
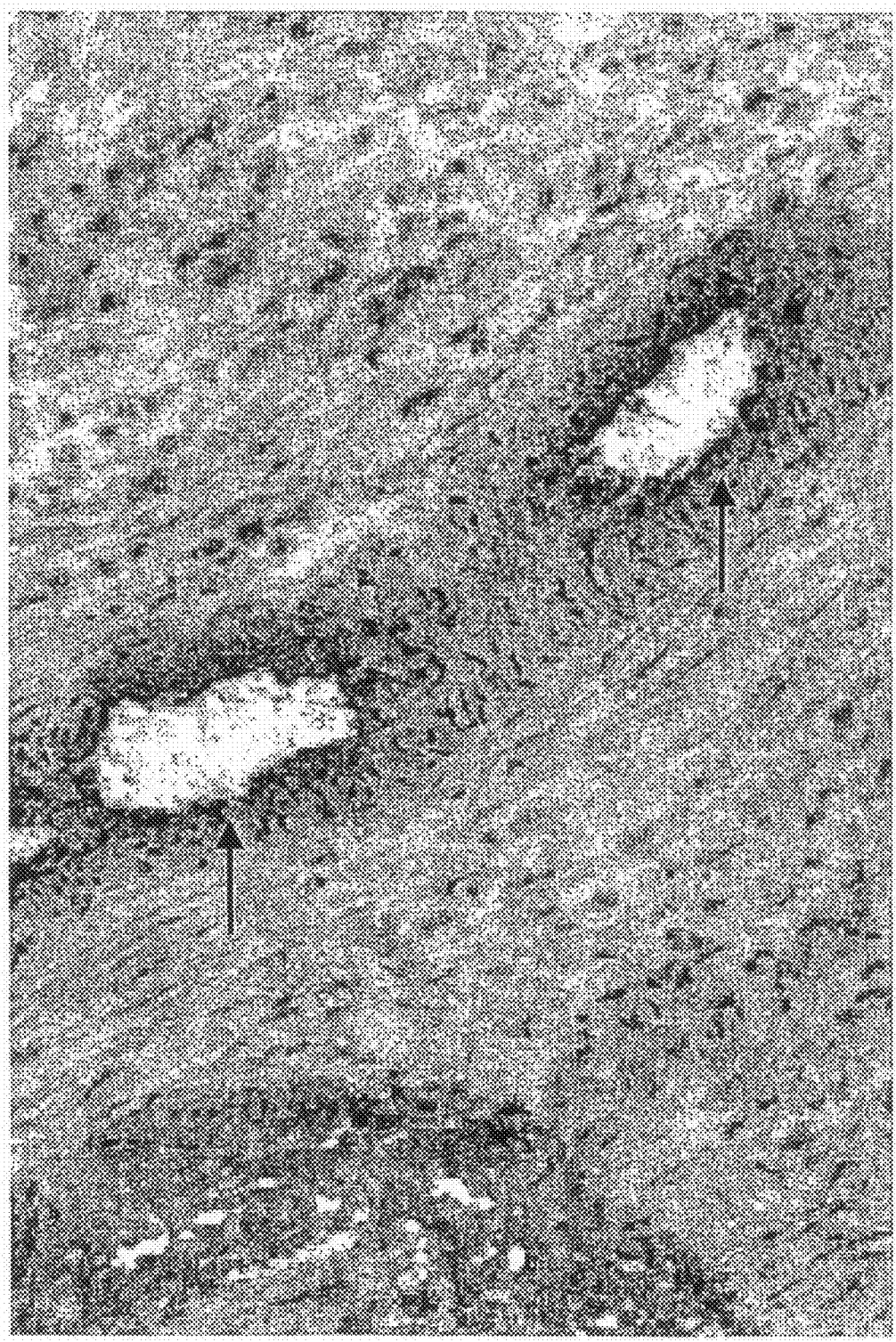
Figure 24:
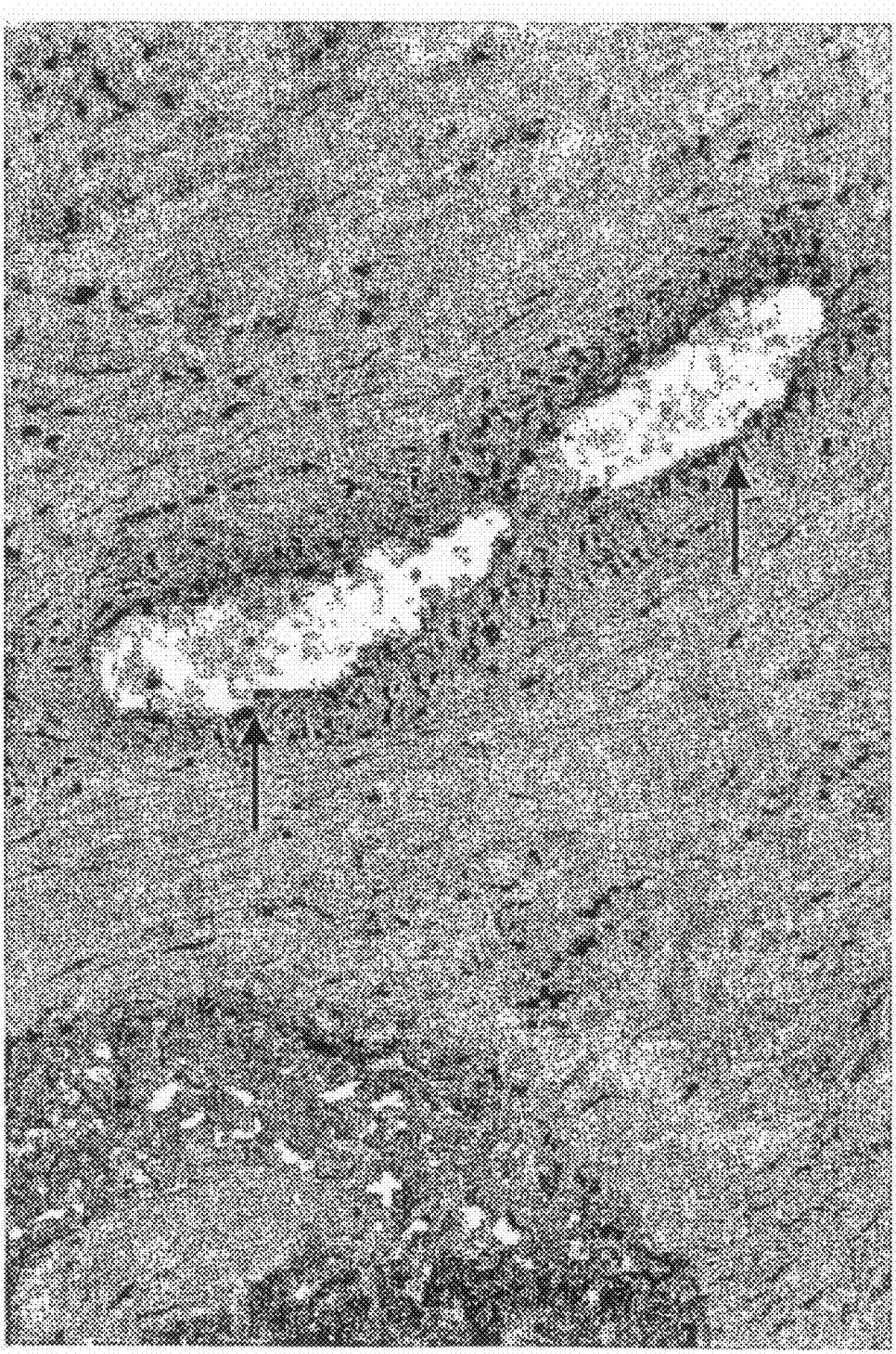
Figure 25:
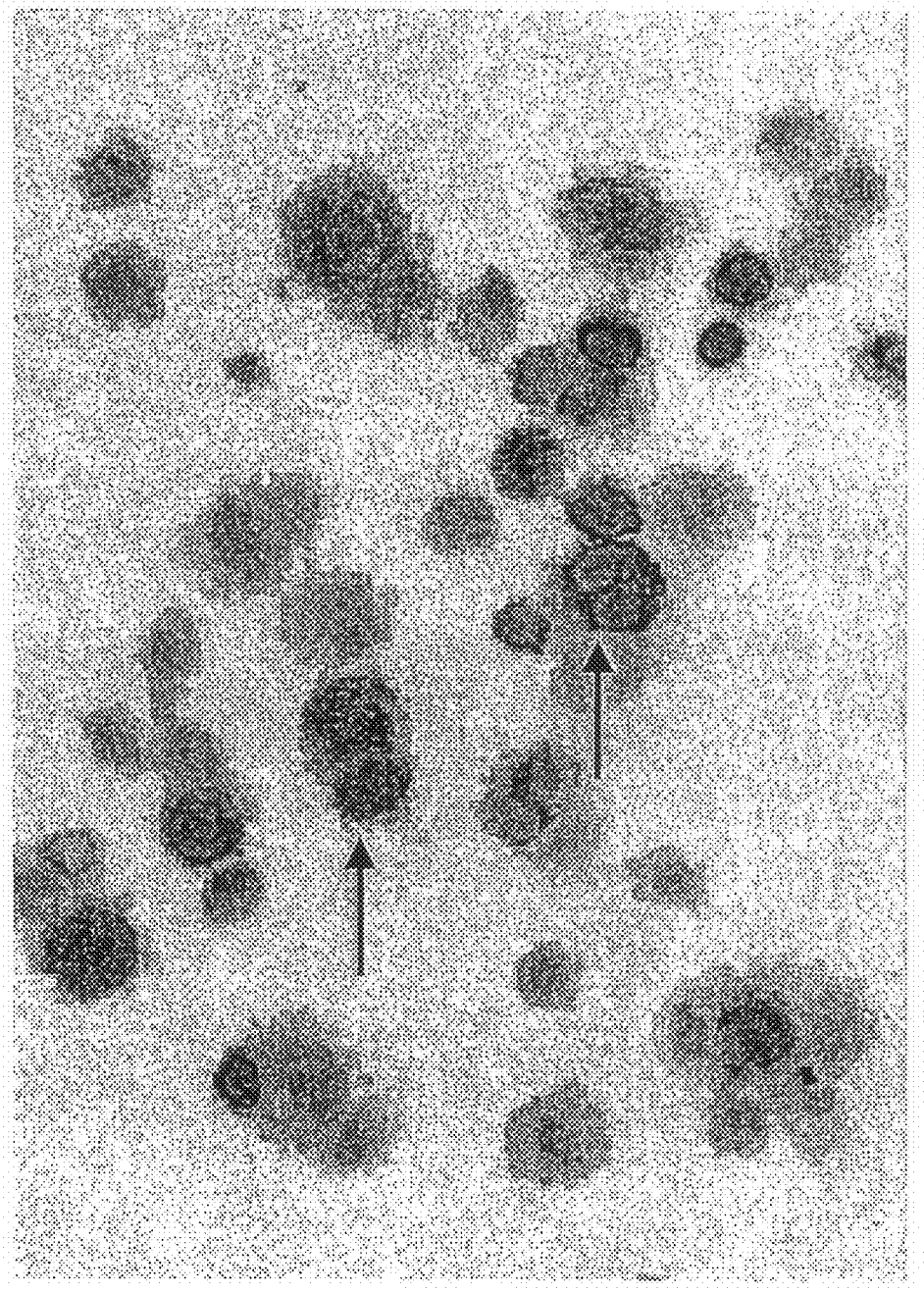
Figure 26:
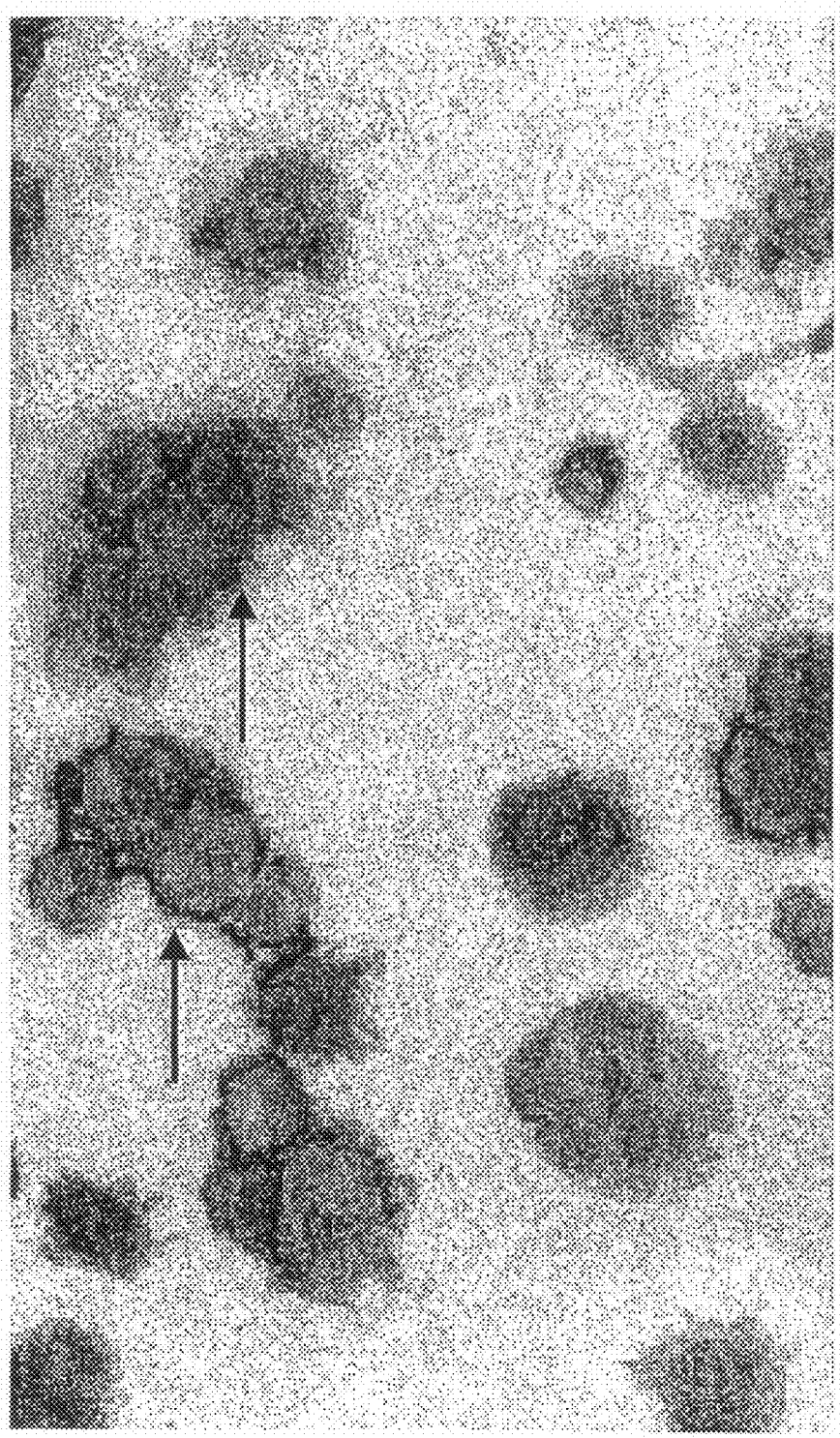

Immunostaining of frozen placental section. A frozen thin section of human placenta was analysed by immunohistochemistry using MGO-5 (a rabbit polyclonal antibody raised against peptide MR 165) as the primary antibody, and visualised using anti-rabbit secondary antibody coupled with alkaline phosphatase. The arrows show high levels of expression of ECSM4 restricted to the vascular endothelial cells. Note that the surrounding tissue shows little staining. Comparison with FIGS. 22 and 23 shows that the expression of ECSM4 colocalises with that of vWF, a known marker for vascular endothelial cells.

FIG. 25.

Immunohistochemical analysis of HUVEC cells: von Willibrand Factor (VWF). HUVEC cells were immobilised and analysed by immunohistochemistry using an antibody recognising von Willibrand Factor (a marker for endothelial cells) as the primary antibody and visualised using anti-rabbit antibody coupled with alkaline phosphatase. The arrows show expression of vWF in a subset of the HUVEC cells.

FIG. 26.

Immunohistochemical analysis of HUVEC cells using the antibody MGO-7. HUVEC cells were immobilised and analysed by immunohistochemistry using MGO-7 antibody (a rabbit polyclonal antibody raised against peptides MR 311 and MR 336) as the primary antibody and visualised using anti-rabbit antibody coupled with alkaline phosphatase. The arrows show expression of ECSM4 in a subset of the HUVEC cells. Note that the staining is localised primarily to the cell surface of the cells.

FIG. 27. Expression of magic roundabout in vivo.

(A) Expression of MR detected by in situ hybridisation in of a placental arteriole (a) and venule (b) (left, light field and right, dark field). (c) Immunohistochemical staining of magic roundabout in a placental arteriole. Left, von Willibrand factor control and right, magic roundabout. (B) Expression of MR in tumour endothelium. Ganglioglioma (a) x20 and (b) x50. Left, light field; right, dark field. Arrows highlight a vessel running diagonally down the section with an erythrocyte within it. Endothelial cells are strongly positive for MR expression. Papillary bladder carcinoma (c) x20 and (d) x50. The vascular core of the papilla of the tumour is strongly positive, particularly the 'flat' endothelial cells indicated by arrows. A magic roundabout antisense in situ probe was generated using T3 polymerase from IMAGE EST clone 1912098 (GenBank acc. AI278949). The plasmid was linearised with Eco RI prior to probe synthesis. In situ analysis was then performed as described in Poulsom et al (1998) Eur. J. Histochemistry 42:121-132.

EXAMPLE 1

In Silico Cloning of Novel Endothelial Specific Genes

We describe the use of two independent strategies for differential expression analysis combined with experimental verification to identify genes specifically or preferentially expressed in vascular endothelium.

The first strategy was based the EST cluster expression analysis in the human UniGene gene index (Schuler et al, 1997). Recurrent gapped BLAST searches (Altschul et al, 1997) were performed at very high stringency against expressed sequence tags (ESTs) grouped in two pools. These two pools comprised endothelial cell and non-endothelial cell libraries derived from dbEST (Boguski et al, 1995). The second strategy employed a second datamining tool: SAGEmap xprofiler. XProfiler is a freely available on-line tool, which is a part of the NCBI's Cancer Genome Anatomy Project (CGAP) (Strausberg et al, 1997, Cole et al, 1995). While these two approaches alone were producing a discouragingly high number of false positives, when both strategies were combined, predictions proved exceptionally reliable and two novel candidate endothelial-specific genes have been identified. Full-length cDNAs have been identified in sequence databases. Another gene (EST cluster) corresponds to a partial cDNA sequence from a large-scale cDNA sequencing project and contains a region of similarity to the intracellular domain of human roundabout homologue 1 (ROBO1).

UniGene/EST Gene Index Screen

A pool of endothelial and a pool of non-endothelial sequences were extracted using Sequence Retrieval System (SRS) version 5 from dbEST. The endothelial pool consisted of 11,117 ESTs from nine human endothelial libraries (Table 1). The non-endothelial pool included 173,137 ESTs from 108 human cell lines and microdissected tumour libraries (Table 2). ESTs were extracted from dbEST release April 2000. Multiple FASTA files were transformed into a BLAST searchable database using the pressdb programme. Table 3 shows the expression status of five known endothelial cell-specific genes in these two pools.

Subsequently, the longest, representative sequence in each UniGene cluster (UniGene Build #111 May 2000, multiple FASTA file hs.seq.uniq) was searched using very high stringency BLAST against these two pools. If such representative sequence reported no hits, the rest of the sequences belonging to the cluster (UniGene multiple-FASTA file hs.seq) were used as BLAST queries. Finally, clusters with no hits in the non-endothelial pool and at least one hit in the endothelial pool were selected.

Optimising the BLAST E-value was crucial for the success of BLAST identity-level searches. Too high an E-value would result in gene paralogues being reported. On the other hand, too low (stringent) an E-parameter would result in many false negatives, i.e. true positives would not be reported due to sequencing errors in EST data: ESTs are large-scale low-cost single pass sequences and have high error rate (Aaronson et al, 1996). In this work an E-value of 10e-20 was used in searches against non-endothelial EST pool and a more stringent 10e-30 value in searches against the smaller endothelial pool. These values were deemed optimal after a series of test BLAST searches.

SAGE Data and SAGEmap xProfiler Differential Analysis

Web-based SAGE library subtraction (available at the National Center for Biotechnology Information SAGEmap xProfiler internet site) was utilised as the second datamining strategy for the identification of novel endothelial specific or preferentially endothelial genes. Two endothelial SAGE libraries (SAGE_Duke_HMVEC and SAGE_Duke_HMVEC+VEGF with a total of 110,790 sequences) were compared to twenty-four non-endothelial, cell line libraries (full list in Table 4, total of 733,461 sequences). Table 5 shows the status of expression of five known endothelial specific genes: von Willebrand's factor (vWF), two vascular endothelial growth factor receptors: fms-like tyrosine kinase 1 (flt1) and kinase insert domain receptor (KDR), tyrosine kinase receptor type tie (TIE 1) and tyrosine kinase receptor type tek (TIE2/TEK), in these two SAGE pools.

Combined Data Gives Highly Accurate Predictions

Twenty known genes were selected in the UniGene/EST screen (Table 6). These genes had no hits in the non-endothelial pool and at least one hit in the endothelial pool. The list contained at least four endothelial specific genes: TIE1, TIE2/TEK, LYVE1 and multimerin, indicating ~20% accuracy of prediction. Other genes on the list, while certainly preferentially expressed in the endothelial cells, might not be endothelial specific. To improve on the prediction accuracy we decided to combine UniGene/EST screen with the xProfiler SAGE analysis. The xProfiler output consisted of a list of genes with a ten times higher number of tags in the endothelial than in the non-endothelial pool sorted according to the certainty of prediction. A 90% certainty threshold was applied to this list. Table 7 shows how data from the two approaches were combined. Identity-level BLAST searches were performed on mRNAs (known genes) or phrap computed contigs (EST clusters representing novel genes) to investigate how these genes were represented in the endothelial and non-endothelial pool. Subsequent experimental verification by RT-PCR (FIG. 1) proved that the combined approach was 100% accurate, i.e. genes on the xProfiler list which had no matches the non-endothelial EST pool and at least one match in the endothelial pool were indeed endothelial specific.

Discussion

There have been several reports of computer analysis of tissue transcriptosomes. Usually an expression profile is constructed, based on the number of tags assigned to a given gene or a class of genes (Bernstein et al, 1996, Welle et al, 1999, Bortoluzzi et al, 2000). An attempt can be made to identify tissue-specific transcripts, for example Vasmatzis et al, (1997) described three novel genes expressed exclusively in the prostate by in silico subtraction of libraries from the dbEST collection. Purpose made cDNA libraries may also be employed. Ten candidate granulocyte-specific genes have been identified by extensive sequence analysis of cDNA libraries derived from granulocytes and eleven other tissue samples, namely a hepatocyte cell line, foetal liver, infant liver, adult liver, subcutaneous fat, visceral fat, lung, colonic mucosa, keratinocytes, cornea and retina (Itoh et al, 1998).

An analysis similar to the dbEST-based approach taken by Vasmatzis et al, is complicated by the fact that endothelial cells are present in all tissues of the body and endothelial-ESTs are contaminating all bulk tissue libraries. To validate this we used three well-known endothelial specific genes: KDR, FLT1, and TIE-2 as queries for BLAST searches against dbEST. Transcripts were present in a wide range of tissues with multiple hits in well vascularised tissues (e.g. placenta, retina), embryonic (liver, spleen) or infant (brain) tissues. Additionally, we found that simple subtraction of endothelial EST libraries against all other dbEST libraries failed to identify any specific genes (data not shown).

Two very different types of expression data resources were used in our datamining efforts. The UniGene/EST screen was based on expressed sequence tag libraries from dbEST. There are 9 human endothelial libraries in the current release of dbEST with a relatively small total number of ESTs: ~11,117. Some well-known endothelial specific genes are not represented in this dataset (Table 3). This limitation raised our concerns that genes with low levels of expression would be overlooked in our analysis. Therefore, we utilised another type of computable expression data: CGAP SAGE libraries. SAGE tags are sometimes called small ESTs (usually 10-11 bp in length). Their major advantage is that they can be unambiguously located within the cDNA: they are immediately adjacent to the most 3' NlaIII restriction site. Though, there are only two endothelial CGAP SAGE libraries available at the moment, they contain an impressive total of ~111, 000 tags—an approximately 10 times bigger dataset than the ~11,117 sequences in the endothelial EST pool. The combined approach proved very accurate (Table 8, FIG. 1) when verified by RT-PCR.

We report here identification of two novel highly endothelial specific genes: endothelial cell-specific molecule 1 (ECSM1—UniGene entry Hs.13957) and magic roundabout (UniGene entry Hs. 111518). For a comprehensive summary of data available on these genes see Table 8.

Our combined datamining approach together with experimental verification is a powerful functional genomics tool. This type of analysis can be applied to many cell types not just endothelial cells. The challenge of identifying the function of discovered genes remains, but bioinformatics tools such as structural genomics, or homology and motif searches can offer insights that can then be verified experimentally.

In summary, this screening approach has allowed the identification of novel endothelial cell specific genes and known genes whose expression was not known to be specific to endothelial cells. This identification both advances our understanding of endothelial cell biology and provides new pharmaceutical targets for imaging, diagnosing and treating medical conditions involving the endothelium.

Methods

PERL Scripts

A number of PERL scripts were generated to facilitate large scale sequence retrieval, BLAST search submissions, and automatic BLAST output analysis.

Database Sequence Retrieval

Locally stored UniGene files (Build #111, release date May 2000) were used in the preparation of this report. The UniGene website can be accessed on the National Center for Biotechnology Information internet site, and UniGene files can be downloaded from the ftp repository: ftp://ncbi.nlm.nih.gov/repository/unigene/. Representative sequences for the human subset of UniGene (the longest EST within the cluster) are stored in the file Hs.seq.uniq, while all ESTs belonging to the cluster are stored in a separate file called Hs.seq.

Sequences were extracted from the dbEST database accessed locally at the HGMP centre using the Sequence Retrieval System (SRS version 5) getz command. This was done repeatedly using a PERL script for all the libraries in the endothelial and non-endothelial subsets, and sequences were merged into two multiple-FASTA files.

Selection Criteria for Non-endothelial EST Libraries

Selection of 108 non-endothelial dbEST libraries was largely manual. Initially the list of all available dbEST libraries, which is available at the National Center for Biotechnology Information internet site was searched using the keyword 'cells' and the phrase 'cell line'. While this searched identified most of the libraries, additional keywords had to be added for the list to be full: 'melanocyte', 'macrophage', 'HeLa', 'fibroblast'. In some cases, detailed library description was consulted to confirm that library is derived from a cell line/primary culture. We also added a number of CGAP microdissected tumour libraries. For that, Library Browser, available at the National Center for Biotechnology Information internet site, was used to search for the keyword 'microdissected'.

UniGene Gene Index Screen

The UniGene gene transcript index was screened against the EST division of GenBank, dbEST. Both UniGene and dbEST were developed at the National Centre for Biotechnology Information (NCBI). UniGene is a collection of EST clusters corresponding to putative unique genes. It currently consists of four datasets: human, mouse, rat and zebrafish. The human dataset is comprised of approximately 90,000 clusters (UniGene Build #111 May 2000). By means of very high stringency BLAST identity searches, we aimed to identify those UniGene genes that have transcripts in the endothelial and not in the non-endothelial cell-type dbEST libraries. Throughout the project, University of Washington blast2 which is a gapped version was used as BLAST implementation. The E-value was set to 10e-20 in searches against the non-endothelial EST pool and to 10e-30 in searches against the smaller endothelial pool.

While UniGene does not provide consensus sequences for its clusters, the longest sequence within the cluster is identified. Thus, this longest representative sequence (multiple FASTA file Hs.seq.uniq) was searched using very high stringency BLAST against the endothelial and non-endothelial EST pool. If such representative sequence reported no matches, the rest of the sequences belonging to the cluster (UniGene multiple-FASTA file Hs.seq) followed as BLAST queries. Finally, clusters with no matches in the non-endothelial pool and at least one match in the endothelial pool were selected using PERL scripts analysing BLAST textual output.

xProfiler SAGE Subtraction xProfiler enables an on-line user to perform a differential comparison of any combination of forty seven serial analysis of gene expression (SAGE) libraries with a total of~2,300,000 SAGE tags using a dedicated statistical algorithm (Chen et al, 1998). xProfiler can be accessed on the National Center for Biotechnology Information internet site SAGE itself is a quantitative expression technology in which genes are identified by typically a 10 or 11 bp sequence tag adjacent to the cDNA's most 3' NlaIII restriction site (Velculescu et at, 1995).

The two available endothelial cell libraries (SAGE_Duke_HMVEC and SAGE_Duke_HMVEC+VEGF) defined pool A and twenty-four (see Table 4 for list) non-endothelial libraries together built pool B. The approach was verified by establishing the status of expression of the five reference endothelial specific genes in the two SAGE pools (Table 5) using Gene to Tag Mapping, available on the National Center for Biotechnology Information internet site Subsequently, xProfiler was used to select genes differentially expressed between the pools A and B. The xProfiler output consisted of a list of genes with a ten fold difference in the number of tags in the endothelial compared to the non-endothelial pool sorted according to the certainty of prediction. A 90% certainty threshold was applied to this list.

The other CGAP's on-line differential expression analysis tool, Digital Differential Display (DDD), relies on EST expression data (source library info) instead of using SAGE tags. We attempted to utilise this tool similarly to SAGEmap xProfiler but have been unable to obtain useful results. Five out of nine endothelial and sixty-four out of hundred and eight non-endothelial cell libraries used in our BLAST-oriented approach were available for on-line analysis using DDD, available at the National Center for Biotechnology Information internet site. When such analysis was performed the following were fifteen top scoring genes: annexin A2, actin gamma 1, ribosomal protein large P0, plasminogen activator inhibitor type I, thymosin beta 4, peptidylprolyl isomerase A, ribosomal protein L13a, laminin receptor 1 (ribosomal protein SA), eukaryotic translation elongation factor 1 alpha 1, vimentin, ferritin heavy polypeptide, ribosomal protein L3, ribosomal protein S18, ribosomal protein L19, tumour protein translationally-controlled 1. This list was rather surprising, did not include any well-known endothelial specific genes, did not have any overlap with SAGE results (Table 8), and contained many genes, that in the literature are reported to be ubiquitously expressed (ribosomal proteins, actin, vimentin, ferritin). A major advantage of our UniGene/EST screen is that instead of relying on source library data and fallible EST clustering algorithms it actually performs identity-level BLAST comparisons in search of transcripts corresponding to a gene.

Mining Data on UniGene Clusters

To quickly access information about UniGene entries (e.g. literature references, STS sites, homologues, references to function) on-line resources were routinely used: NCBI's UniGene and LocusLink interfaces and Online Mendelian Inheritance in Man.

ESTs in UniGene clusters are not assembled into contigs, so before any sequence analysis, contigs were created using phrap assembler (for documentation on phrap see the bozeman.mbt internet site).

To analyse genomic contig AC005795 (44,399) bp containing ECSM1, NIX Internet interface for multi-application analysis of large unknown nucleotide sequences was used. For further information on NIX see the hgmp.mrc internet site. Alignment of ECSM1 against AC005795 was obtained using the NCBI interface to the Human Genome Interface: the NCBI Map Viewer. For further information on the NCBI Map Viewer see the National Center for Biotechnology Information internet site.

To search for possible transmembrane domains and signal sequences in translated nucleotide sequences three Internet based applications were used: DAS (Cserzo et al, 1997), TopPred2 (Heijne 1992), and SignalP (Nielsen et al, 1997).

PERL Scripts

A number of PERL scripts were generated to facilitate large scale sequence retrieval, BLAST search submissions, and automatic BLAST output analysis.

Experimental Verification

To experimentally verify specificity of expression we used the reverse transcription polymerase chain reaction (RT-PCR). RNA was extracted from three endothelial and seven non-endothelial cell types cultured in vitro. Endothelial cultures were as follows: HMVEC (human microvascular endothelial cells), HUVEC (human umbilical vein endothelial cells) confluent culture and HUVEC proliferating culture. Non-endothelial cultures were as follows: normal endometrial stromal (NES) cells grown in normoxia and NES grown in hypoxia, MDA 453 and MDA 468 breast carcinoma cell lines, HeLa, FEK4 fibroblasts cultured in normoxia and FEK4 fibroblasts cultured in hypoxia, and SW480, HCT116—two colorectal epithelium cell lines.

If a sequence tagged site (STS) was available, dbSTS PCR primers were used and cycle conditions suggested in the dbSTS entry followed. Otherwise, primers were designed using the Primer3 programme. Primers are listed in Table 9.

Tissue Culture Media, RNA Extraction and cDNA Synthesis

Cell-lines were cultured in vitro according to standard tissue culture protocols. In particular, endothelial media were supplemented with ECGS (endothelial cell growth supplement—Sigma), and heparin (Sigma) to promote growth. Total RNA was extracted using the RNeasy Minikit (Qiagen) and cDNA synthesised using the Reverse-IT $1^{st}$ Strand Synthesis Kit (ABgene).

REFERENCES

Aaronson J. S., B. Eckman, R. A. Blevins, J. A. Borkowski, J. Myerson, S. Imran, and K. O. Elliston. 1996. Toward the development of a gene index to the human genome: an assessment of the nature of high-throughput EST sequence data. Genome Res. 6: 829-45.

Adams M. D., A. R. Kerlavage, R. D. Fleischmann, R. A. Fuldner, C. J. Bult, N. H. Lee, E. F. Kirkness, K. G. Weinstock, J. D. Gocayne, O. White, et al, 1995. Initial assessment of human gene diversity and expression patterns based upon 83 million nucleotides of cDNA sequence. Nature. 377(6547 Suppl): 3-174.

Adams R. H., G. A. Wilkinson, C. Weiss, F. Diella, N. W. Gale, U. Deutsch, W. Risau, and R. Klein. 1999. Roles of ephrinB ligands and EphB receptors in cardiovascular development: demarcation of arterial/venous domains, vascular morphogenesis, and sprouting angiogenesis. Genes Dev. 13(3): 295-306.

Aiello L. P., E. A. Pierce, E. D. Foley, H. Takagi, H. Chen, L. Riddle, N. Ferrara, G. L. King, and L. E. H. Smith. 1995. Suppression of retinal neovascularization in vivo by inhibition of vascular endothelial growth factor (VEGF) using soluble VEGF-receptor chimeric proteins. Proc. Natl. Acad. Sci. USA. 92: 10457-10461.

Altschul S. F., T. L. Madden, A. A. Schäffer, J. Zhang, Z. Zhang, W. Miller, and D. J. Lipman. 1997. Gapped BLAST and PSI-BLAST: a new generation of protein database search programs. Nucleic Acids Res. 25: 3389-3402.

Banerji S., J. Ni, S. X. Wang, S. Clasper, J. Su, R. Tammi, M. Jones, and D. G. Jackson. 1999. LYVE-1, a new homologue of the CD44 glycoprotein, is a lymph-specific receptor for hyaluronan. J Cell Biol. 144(4): 789-801.

Bashaw G. J., and C. S. Goodman. 1999. Chimeric axon guidance receptors: the cytoplasmic domains of slit and netrin receptors specify attraction versus repulsion. Cell. 97(7):917-26.

Bates E. E., O. Ravel, M. C. Dieu, S. Ho, C. Guret, J. M. Bridon, S. Ait-Yahia, F. Briere, C. Caux, J. Banchereau, and S. Lebecque. 1997. Identification and analysis of a novel member of the ubiquitin family expressed in dendritic cells and mature B cells. Eur J Immunol. 27(10): 2471-7.

Bernstein S. L., D. E. Borst, M. E. Neuder, and P. Wong. 1996. Characterization of the human fovea cDNA library and regional differential gene expression in the human retina. Genomics 32: 301-308.

Boguski M. S. 1999. Biosequence exegesis. Science. 286: 453-5.

Boguski M. S. and G. D. Schuler. 1995. ESTablishing a human transcript map. Nature Genetics: 10, 369-371.

Bortoluzzi S., F. d'Alessi, C. Romualdi, and G. A. Danieli. 2000. The human adult skeletal muscle transcriptional profile reconstructed by a novel computational approach. Genome Research. 10: 344-349.

Brose K., K. S. Bland, K. H. Wang, D. Arnott, W. Henzel, C. S. Goodman, M. Tessier-Lavigne, and T. Kidd. 1999. Slit proteins bind Robo receptors and have an evolutionarily conserved role in repulsive axon guidance. Cell. 96(6): 795-806.

Chen H., M. Centola, S. F. Altschul, and H. Metzger. 1998. Characterization of gene expression in resting and activated mast cells. J Exp Med. 188(9): 1657-68.

Clark D. E., S. K. Smith, A. M. Sharkey, and D. S. Chamock-Jones. 1996 Localisation of VEGF and expression of its receptors flt and KDR in human placenta throughout pregnancy. Human Reproduction. 11(5): 1090-1098.

Cole K. A., D. B. Krizman, and M. R. Emmert-Buck. 1999. The Genetics of Cancer—A 3D Model. Nat Genet 21(1): 38-41.

Cserzo M., E. Wallin, I. Simon, G. von Heijne, and A. Elofsson. 1997. Prediction of transmembrane alpha-helices in prokaryotic membrane proteins: the Dense Alignment Surface method; Prot. Eng. 6: 673-676.

Dillon N., and P. Sabbattini. 2000. Functional gene expression domains: defining the functional unit of eukaryotic gene regulation. BioEssays. 7: 657-665.

Felbor U., A. Gehrig, C. G. Sauer, A. Marquardt, M. Kohler, M. Schmid, and B. H. F. Weber. 1998. Genomic organization and chromosomal localization of the interphotoreceptor matrix proteoglycan-1 (IMPG1) gene: a candidate for 6q-linked retinopathies. Cytogenet Cell Genet. 81: 12-17.

Fong G. H., J. Rossant, and M. L. Breitman. 1995. Role of the Flt-1 receptor tyrosine kinase in regulating the assembly of vascular endothelium. Nature. 376: 65-69.

Gerhold D., and C. T. Caskey. 1996. It's the genes! EST access to human genome content. Bioessays. 18:973-81

Ginsburg, R. I. Handin, D. T. Bonthron, T. A. Donlon, G. A. Bruns, S. A. Latt, and S. H. Orkin. 1985. Human von Willebrand factor (vWF): isolation of complementary DNA (cDNA) clones and chromosomal localization. Science. 228:1401-6.

Hayward C. P. M., G. E Rivard., W. H. Kane, J. Drouin, S. Zheng, J. C. Moore, and J. G. Kelton. 1996. An autosomal dominant, qualitative platelet disorder associated with multimerin deficiency, abnormalities in platelet factor V, thrombospondin, von Willebrand factor, and fibrinogen and an epinephrine aggregation defect. Blood. 87: 4967-4978.

Hayward C. P., D. F. Bainton, J. W. Smith, P. Horsewood, R. H. Stead, T. J. Podor, T. E. Warkentin, and J. G. Kelton. 1993. Multimerin is found in the alpha-granules of resting platelets and is synthesized by a megakaryocytic cell line. J Clin Invest. 91(6): 2630-9.

Hayward C. P., E. M. Cramer, Z. Song, S. Zheng, R. Fung, J. M. Masse, R. H. Stead, and T. J. Podor. 1998. Studies of multimerin in human endothelial cells. Blood. 91(4): 1304-17.

Heijne G. Membrane Protein Structure Prediction, Hydrophobicity Analysis and the Positive-inside Rule. 1992. J. Mol. Biol. 225: 487-494.

Itoh K., K. Okubo, H. Utiyama, T. Hirano, J. Yoshii, and K. Matsubara. (1998). Expression profile of active genes in granulocytes. Blood. 15: 1432-41

Kidd T., K. Brose, K. J. Mitchell, R. D. Fetter, M. Tessier-Lavigne, C. S. Goodman, and G. Tear. 1998. Roundabout controls axon crossing of the CNS midline and defines a novel subfamily of evolutionarily conserved guidance receptors. Cell. 92(2): 205-15.

Matthews W., C. T. Jordan, M. Gavin, N. A. Jenkins, N. G. Copeland, and I. R. Lemischka. 1991. A receptor tyrosine kinase cDNA isolated from a population of enriched primitive hematopoietic cells and exhibiting close genetic linkage to c-kit. Proc Natl Acad Sci USA. 88(20): 9026-30.

Nichols W. L., D. A. Gastineau, L. A. Solberg, and K. G. Jr Mann. 1985. Identification of human megakaryocyte coagulation factor V. Blood. 65(6): 1396-406.

Nielsen H., J. Engelbrecht, S. Brunak, and G. Heijne. 1997. Identification of prokaryotic and eukaryotic signal peptides and prediction of their cleavage sites. Protein Engineering 10: 1-6.

Obermair A., A. Obruca, M. Pohl, A. Kaider, A. Vales, S. Leodolter, J. Wojta, and W. Feichtinger. 1999. Vascular endothelial growth factor and its receptors in male fertility. Fert. Ster. 72(2): 269-275.

Partanen J., E. Armstrong, T. P. Makela, J. Korhonen, M. Sandberg, R. Renkonen, S. Knuutila, K. Huebner, K. and Alitalo. 1992. A novel endothelial cell surface receptor tyrosine kinase with extracellular epidermal growth factor homology domains. Mol Cell Biol. 12(4):1698-707.

Petrenko O., A. Beavis, M. Klaine, R. Kittappa, I. Godin, I. R. and Lemischka. 1999. The molecular characterization of the fetal stem cell marker AA4. Immunity. 10(6): 691-700.

Sato T. N, Y. Qin, C. A. Kozak, and K. L. Audus. 1993. Tie-1 and tie-2 define another class of putative receptor tyrosine kinase genes expressed in early embryonic vascular system. Proc. Nat. Acad. Sci. 90: 9355-9358.

Sato T. N., Y. Tozawa, U. Deutsch, K. Wolburg-Buchholz, Y. Fujiwara, M. Gendron-Maguire, T. Gridley, H. Wolburg, W. Risau, and Y. Qin. 1995. Distinct roles of the receptor tyrosine kinases Tie-1 and Tie-2 in blood vessel formation. Nature. 376: 70-74.

Schuler G. D. 1997. Pieces of the puzzle: expressed sequence tags and the catalog of human genes. J Mol Med. 75(10): 694-8.

Shalaby F., J. Rossant, T. P. Yamaguchi, M. Gertsenstein, X. F. Wu, M. L. Breitman, and A. C. Schuh. 1995. Failure of blood-island formation and vasculogenesis in Flk-1-deficient mice. Nature 376: 62-65.

Shibayama S., J. Hirano, and H. Ono. 1997. cDNA encoding novel polypeptide from human umbilical vein endothelial cell. European Patent Office. Publication number: 0 682 113 A2.

Shibuya M., S. Yamaguchi, A. Yamane, T. Ikeda, A. Tojo, H. Matsushime, and M. Sato. 1990. Nucleotide sequence and expression of a novel human receptor-type tyrosine kinase gene (flt) closely related to the fms family. Oncogene. 5(4): 519-24.

Smith T. F., and M. S. Waterman. 1981. Identification of common molecular subsequences. J Mol Biol. 147: 195-197.

Soker S., S. Takashima, H. Q. Miao, G. Neufeld, and M. Klagsbrun. 1998. Neuropilin-1 is expressed by endothelial and tumor cells as an isoform-specific receptor for vascular endothelial growth factor. Cell. 92(6): 735-45.

Sporn L. A., S. I. Chavin, V. J. Marder, and D. D. Wagner. 1985. Biosynthesis of von Willebrand protein by human megakaryocytes. J Clin Invest. 76(3): 1102-6

Strausberg R. L., C. A. Dahl, and R. D. Klausner. 1997. New Opportunities for Uncovering the Molecular Basis of Cancer. Nat Genet. 15: 415-6.

Suda T., N. Takakura, and Y. Oike. 2000. Hematopoiesis and angiogenesis. Int J Hematol. 71(2): 99-107

Tamura N., H. Itoh, Y. Ogawa, O. Nakagawa, M. Harada, T. H. Chun, T. Suga, T. Yoshimasa, and K. Nakao, 1996. cDNA cloning and gene expression of human type I-alpha cGMP-dependent protein kinase. Hypertension. 27: 552-557.

Vasmatzis G., M. Essand, U. Brinkmann, L. Byungkook, and I. Pastan. 1997. Discovery of three genes specifically expressed in human prostate by expressed sequence tag database analysis. Proc. Natl. Acad. Sci. USA. 95: 300-304.

Velculescu V. E., L. Zhang, B. Vogelstein, and K. W. Kinzler. 1995. Serial analysis of gene expression. Science. 270: 484-7.

Vikkula M., L. M. Boon, K. L. Carraway 3rd, J. T. Calvert, A. J. Diamonti, B. Goumnerov, K. A. Pasyk, D. A. Marchuk, M. L. Warman, L. C. Cantley, J. B. Mulliken, and B. R. Olsen. 1996. Vascular dysmorphogenesis caused by an activating mutation in the receptor tyrosine kinase TIE2. Cell. 87(7):1181-90.

Walker M. G., and Volkmuth W. 2000. Matrix-remodelling associated genes identified by co-expression. Personal communication.

Welle S., K. Bhatt, and C. A. Thornton. 1999. Inventory of high-abundance mRNAs in skeletal muscle of normal men. Genome Res. May; 9(5): 506-13.

Ziegler B. L., M. Valtieri, G. A. Porada, R. De Maria, R. Muller, B. Masella, M. Gabbianelli, I. Casella, E. Pelosi, T. Bock, E. D. Zanjani, and C. Peschle. 1999. KDR receptor: a key marker defining hematopoietic stem cells. Science 285: 1553-1558.

TABLE 1

Nine human endothelial libraries from dbEST

Human aortic endothelium, 20 sequences, in vitro culture
Human endothelial cells, 346 sequences, primary isolate
Human endothelial cell (Y. Mitsui), 3 sequences, in vitro culture

TABLE 1-continued

Nine human endothelial libraries from dbEST

Stratagene endothelial cell 937223, 7171 sequences, primary isolate
Aorta endothelial cells, 1245 sequences, primary isolate
Aorta endothelial cells, TNF treated, 1908 sequences, primary isolate
Umbilical vein endothelial cells I, 9 sequences
HDMEC cDNA library, 11 sequences, in vitro culture
Umbilical vein endothelial cells II, 404 sequences

TABLE 2

Non-endothelial dbEST libraries.

1. Activated T-cells I
2. Activated T-cells II
3. Activated T-cells III
4. Activated T-cells IV
5. Activated T-cells IX
6. Activated T-cells V
7. Activated T-cells VI
8. Activated T-cells VII
9. Activated T-cells VIII
10. Activated T-cells X
11. Activated T-cells XI
12. Activated T-cells XII
13. Activated T-cells XX
14. CAMA1Ee cell line I
15. CAMA1Ee cell line II
16. CCRF-CEM cells, cyclohexamide treated I
17. CdnA library of activated B cell line 3D5
18. Chromosome 7 HeLa cDNA Library
19. Colon carcinoma (Caco-2) cell line I
20. Colon carcinoma (Caco-2) cell line II
21. Colon carcinoma (HCC) cell line
22. Colon carcinoma (HCC) cell line II
23. HCC cell line (matastasis to liver in mouse)
24. HCC cell line (matastasis to liver in mouse) II
25. HeLa cDNA (T. Noma)
26. HeLa SRIG (Synthetic retinoids induced genes)
27. Homo sapiens monocyte-derived macrophages
28. HSC172 cells I
29. HSC172 cells II
30. Human 23132 gastric carcinoma cell line
31. Human breast cancer cell line Bcap 37
32. Human cell line A431 subclone
33. Human cell line AGZY-83a
34. Human cell line PCI-O6A
35. Human cell line PCI-O6B
36. Human cell line SK-N-MC
37. Human cell line TF-1 (D. L. Ma)
38. Human exocervical cells (CGLee)
39. Human fibrosarcoma cell line HT1080
40. Human fibrosarcoma cell line HT1080-6TGc5
41. Human gastric cancer SGC-7901 cell line
42. Human GM-CSF-deprived TF-1 cell line (Liu, Hongtao)
43. Human HeLa (Y. Wang)
44. Human HeLa cells (M. Lovett)
45. Human Jurkat cell line mRNA (Thiele, K.)
46. Human K562 erythroleukemic cells
47. Human lung cancer cell line A549.A549
48. Human nasopharyngeal carcinoma cell line HNE1

TABLE 2-continued

Non-endothelial dbEST libraries.

49. Human neuroblastoma SK-ER3 cells (M. Garnier)
50. Human newborn melanocytes (T. Vogt)
51. Human pancreatic cancer cell line Patu 8988t
52. Human primary melanocytes mRNA (I. M. Eisenbarth)
53. Human promyelocytic HL60 cell line (S. Herblot)
54. Human retina cell line ARPE-19
55. Human salivary gland cell line HSG
56. Human White blood cells
57. Jurkat T-cells I
58. Jurkat T-cells II
59. Jurkat T-cells III
60. Jurkat T-cells V
61. Jurkat T-cells VI
62. Liver HepG2 cell line.
63. LNCAP cells I
64. Macrophage I
65. Macrophage II
66. Macrophage, subtracted (total CdNA)
67. MCF7 cell line
68. Namalwa B cells I
69. Namalwa B cells II
70. NCI_CGAP_Br4
71. NCI_CGAP_Br5
72. NCI_CGAP_CLL1
73. NCI_CGAP_GCB0
74. NCI_CGAP_GCB1
75. NCI_CGAP_HN1
76. NCI_CGAP_HN3
77. NCI_CGAP_HN4
78. NCI_CGAP_HSC1
79. NCI_CGAP_Li1
80. NCI_CGAP_Li2
81. NCI_CGAP_Ov5
82. NCI_CGAP_Ov6
83. NCI_CGAP_Pr1
84. NCI_CGAP_Pr10
85. NCI_CGAP_Pr11
86. NCI_CGAP_Pr16
87. NCI_CGAP_Pr18
88. NCI_CGAP_Pr2
89. NCI_CGAP_Pr20
90. NCI_CGAP_Pr24
91. NCI_CGAP_Pr25
92. NCI_CGAP_Pr3
93. NCI_CGAP_Pr4
94. NCI_CGAP_Pr4.1
95. NCI_CGAP_Pr5
96. NCI_CGAP_Pr6
97. NCI_CGAP_Pr7
98. NCI_CGAP_Pr8
99. NCI_CGAP_Pr9
100. Normal Human Trabecular Bone Cells
101. Raji cells, cyclohexamide treated I
102. Retinal pigment epithelium 0041 cell line
103. Retinoid treated HeLa cells
104. Soares melanocyte 2NbHM
105. Soares_senescent_fibroblasts_Nb HSF
106. Stratagene HeLa cell s3 937216
107. Supt cells
108. T, Human adult Rhabdomyosarcoma cell-line

TABLE 3

Five genes known to be endothelial specific genes in the dbEST pools.

| Known endothelial specific gene | Hits in the non-endothelial pool | Hits in the endothelial pool |
|---|---|---|
| von Willebrand factor (vWF) | 1 | 27 |
| flt1 VEGF receptor | — | — |
| KDR VEGF receptor | 1 | — |
| TIE1 tyrosine kinase | — | 5 |
| TIE2/TEK tyrosine kinase | — | 2 |

The number of ESTs in the endothelial pool is relatively small (~11,117) and not all known endothelial genes are represented

TABLE 4

Twenty-four non-endothelial cell SAGE-CGAP libraries.

| SYMBOL | DESCRIPTION |
|---|---|
| SAGE_HCT116 | Colon, cell line derived from colorectal carcinoma |
| SAGE_Caco_2 | Colon, colorectal carcinoma cell line |
| SAGE_Duke_H392 | Brain, Duke glioblastoma multiforme cell line |
| SAGE_SW837 | Colon, cancer cell line |
| SAGE_RKO | Colon, cancer cell line |
| SAGE_NHA(5th) | Brain, normal human astrocyte cells harvested at passage 5 |
| SAGE_ES2-1 | Ovarian Clear cell carcinoma cell line ES-2, poorly differentiated |
| SAGE_OVCA432-2 | Ovary, carcinoma cell line OVCA432 |
| SAGE_OV1063-3 | Ovary, carcinoma cell line OV1063 |
| SAGE_Duke_mhh-1 | Brain, c-myc negative medulloblastoma cell line mhh-1 |
| SAGE_Duke_H341 | Brain, c-myc positive medulloblastoma cell line H341 |
| SAGE_HOSE_4 | Ovary, normal surface epithelium |
| SAGE_OVP-5 | Ovary, pooled cancer cell lines |
| SAGE_LNCaP | Prostate, cell line. Androgen dependent |
| SAGE_HMEC-B41 | Cell culture HMEC-B41 of normal human mammary epithelial cells |
| SAGE_MDA453 | Cell line MDA-MB-453 of human breast carcinoma |
| SAGE_SKBR3 | ATCC cell line SK-BR-3. Human breast adenocarcinoma |
| SAGE_A2780-9 | Ovary, ovarian cancer cell line A2780 |
| SAGE_Duke_H247_normal | Brain, glioblastoma multiforme cell line, H247 |
| AGE_Duke_H247_Hypoxia | Brain, Duke glioblastoma multiforme cell line, H247, grown under 1.5% oxygen |
| SAGE_Duke_post_crisis_fibroblasts | Skin, post-crisis survival fibroblast cell-line |
| SAGE_Duke_precrisis_fibroblasts | Skin, large T antigen transformed human fibroblasts clones |
| SAGE_A | Prostate, cancer cell line. Induced with synthetic androgen |
| SAGE_IOSE29-11 | Ovary, surface epithelium line |

TABLE 5

Five known endothelial specific genes in the CGAP SAGE pools.

| Known endothelial specific gene | Tags in the non-endothelial sage libraries | Tags in the endothelial sage libraries |
|---|---|---|
| von Willebrand factor (VWF) | 1 (colon carcinoma cell line) | 80 |
| flt1 VEGF receptor | — | — |
| KDR VEGF receptor | 1 (IOSE29 ovarian surface epithelium cell line) | 6 |
| TIE1 tyrosine kinase | 17 (ovarian tumour and normal ovarian epithelium cell lines) | 27 |
| TIE2/TEK tyrosine kinase | 4 (ovarian carcinoma and glioblastoma multiforme cell lines) | 2 |

TIE1 and TIE2/TEK have multiple hits in the non-endothelial pool (most in normal or carcinoma cell lines of ovarian origin). vWF is most endothelial specific having 80 hits in the endothelial pool and only one hit in the non-endothelial pool.

TABLE 6

Results of the UniGene/EST screen.

| Description | UniGene ID | Endothelial hits |
|---|---|---|
| TIE1 receptor endothelial tyrosine kinase | Hs.78824 | 5 |
| Cytosolic phospholipase A2; involved in the metabolism of eicosanoids | Hs.211587 | 3 |
| Branched chain alpha-ketoacid dehydrogenase | Hs.1265 | 2 |
| CGMP-dependent protein kinase; cloned from aorta cDNA, strongly expressed in well vascularised tissues like aorta, heart, and uterus (Tamura et al, 1996) | Hs.2689 | 2 |
| Lymphatic vessel endothelial hyaluronan receptor 1-LYVE1 (Banerji et al, 1999) | Hs.17917 | 2 |
| TRAF interacting protein: TNF signalling pathway | Hs.21254 | 2 |
| Multimerin: a very big endothelial specific protein; binds platelet factor V, can also be found in platelets (Hayward et al, 1996) | Hs.32934 | 2 |
| Diubiquitin (a member of the ubiquitin family); reported in dendrytic and B lymphocyte cells; involved in antigen processing; this is first evidence that it is also present in endothelial cells (Bates et al, 1997) | Hs.44532 | 2 |
| Beta-transducin family protein; also a homolog of D. melanogaster gene notchless: a novel WD40 repeat containing protein that modulates Notch signalling activity | Hs.85570 | 2 |
| TIE2/TEK receptor endothelial tyrosine kinase | Hs.89640 | 2 |
| BCL2 associated X protein (BAX) | Hs.159428 | 2 |
| Sepiapterin reductase mRNA | Hs.160100 | 2 |
| Retinoic acid receptor beta (RARB) | Hs.171495 | 2 |
| ST2 receptor: a homolog of the interleukin 1 receptor | Hs.66 | 1 |
| Mitogen activated protein kinase 8 (MAPK8) | Hs.859 | 1 |
| ERG gene related to the ETS oncogene | Hs.45514 | 1 |
| PP35 similar to E. coli yhdg and R. Capsulatus nifR3 | Hs.97627 | 1 |
| Interphotoreceptor matrix proteoglycan; strongly expressed in retina and umbilical cord vein (Felbor et al, 1998) | Hs.129882 | 1 |
| Methylmalonate semialdehyde dehydrogenase gene, | Hs.170008 | 1 |
| HTLV-I related endogenous retroviral sequence | Hs.247963 | 1 |

Twenty known genes were selected in the UniGene/EST screen (no hits in the non-endothelial pool and minimum one hit in the endothelial pool). At least four of these genes are known endothelial specific genes: TIE1, TIE2/TEK, LYVE1 and multimerin, indicating ~ 20% prediction accuracy. Other genes, while certainly preferentially expressed in the endothelial cells, may not be endothelial specific.

TABLE 7 xProfiler differential analysis was combined with data from the UniGene/EST screen achieving 100% certainty of prediction.

| Unigene ID | Gene description | X profiler prediction certainty | Hits in endothelial EST pool | Hits in non-endothelial EST pool |
|---|---|---|---|---|
| Hs.13957 | ESTs-ECSM1 | 97% | 4 | 0 |
| Hs.111518 | magic roundabout, distant homology to human roundabout 1 | 100% | 4 | 0 |
| Hs.268107 | multimerin | 92% | 5 | 0 |
| Hs.155106 | calcitonin receptor-like receptor activity modifying protein 2 | 97% | 0 | 0 |
| Hs.233955 | ESTs | 96% | 0 | 0 |
| Hs.26530 | serum deprivation response (phosphatidylserine-binding protein) | 94% | 3 | 1 |
| Hs.83213 | fatty acid binding protein 4 | 100% | 3 | 1 |
| Hs.110802 | von Willebrand factor | 100% | 25 | 1 |
| Hs.76206 | cadherin 5, VE-cadherin (vascular endothelium) | 100% | 4 | 1 |
| Hs.2271 | endothelin 1 | 98% | 9 | 2 |
| Hs.119129 | collagen, type IV, alpha 1 | 100% | 4 | 6 |
| Hs.78146 | platelet/endothelial cell adhesion molecule (CD31 antigen) | 99% | 18 | 5 |
| Hs.76224 | EGF-containing fibulin-like extracellular matrix protein 1 | 100% | 37 | 9 |
| Hs.75511 | connective tissue growth factor | 100% | 34 | 48 | xProfiler's output lists genes with 10-times higher number of tags in the endothelial than in the non-endothelial pool of SAGE-CGAP libraries. Hits corresponding to these genes in the endothelial and non-endothelial EST pools were identified by identity-level BLAST searches for mRNA (known genes) or phrap computed contig sequences (EST clusters representing novel genes). Genes are sorted according to the number of hits in the non-endothelial EST pool. Known and predicted novel endothelial specific genes are in bold.

TABLE 8

Summary of available information on magic roundabout.

| | UniGene cluster ID and size | Full-length cDNA | Longest ORF | Transmembrane segments, signal peptide | Mapping information Genomic context Genomic clones | Description |
|---|---|---|---|---|---|---|
| ECSM1 | Hs.13957 1100 bp | confirmed with 5'RACE | 103 aa | | Genomic neighbour: Tropomyosin dbSTS G26129 and G28043 Chr. 19 Gene Map 98: Marker SGC33470, Marker stSG3414, IntervalD19S425-D19S418 AC005945, AC005795 (partial identity) | |

TABLE 8-continued

Summary of available information on magic roundabout.

| | UniGene cluster ID and size | Full-length cDNA | Longest ORF | Transmembrane segments, signal peptide | Mapping information Genomic context Genomic clones | Description |
|---|---|---|---|---|---|---|
| Magic roundabout | Hs.111518 2076 bp | Partial cDNA FLJ20798 fis, clone ADSU02031 (acc. AK000805) 1496 bp | 417 aa | One transmembrane domain predicted by TopPred2 and DAS. No signal peptide in the available 417 aa ORF (SignalP) however the true protein product is very likely to be larger | Genomic neighbour: integral transmembrane protein 1 (ITM1) dbSTS G14646 and G14937 Chr. 11, Gene Map 98: Marker SHGC-11739, Interval D11S1353-D11S93 | 468 aa region of homology to the cytoplasmic portion of the roundabout axon guidance protein family: human ROBO1, rat ROBO1 and mouse dutt1 (E = 1.3e−09) ORF has no apparent up-stream limit. This and size comparison to ROBO1 (1651 aa) suggests that true protein is very likely to be much larger Possible alternative polyA sites: the cDNA clone from adipocyte tissue seems to be polyadenylated in a different position to the sequence from the UniGene contig |

TABLE 9

List of primers used in RT-PCR reactions. dbSTS primers were used if a UniGene entry contained a sequence tagged site (STS). Otherwise, primers were designed using the Primer3 programme.

| Gene | Primers (sequence or GenBank Accession for the STS) |
|---|---|
| ECSM1-Hs.13957 | G26129 |
| Magic roundabout-Hs.111518 | G14937 |
| calcitonin receptor-like receptor activity modifying 2 | G26129 |
| Hs.233955 | G21261 |
| fatty acid binding protein 4 | 5'-TGC AGC TTC CTT CTC ACC TT-3' (SEQ ID NO: 15) 5'-TCA CAT CCC CAT TCA CAC TG-3' (SEQ ID NO: 16) |
| von Willebrand factor | 5'-TGT ACC ATG AGG TTC TCA ATG C-3' (SEQ ID NO: 17) 5'-TTA TTG TGG GCT CAG AAG GG-3' (SEQ ID NO: 18) |
| serum deprivation response protein | G21528 |
| collagen, type IV, alpha 1 | G07125 |
| EGF-containing fibulin-like extracellular matrix protein 1 | G06992 |
| connective tissue growth factor | 5'-CAA ATG CTT CCA GGT GAA AAA-3' (SEQ ID NO: 19) 5'-CGT TCA AAG CAT GAA ATG GA-3' (SEQ ID NO: 20) |

TABLE 10

ESTs belonging to ECSM1 contig sequence are as follows:

EST SEQUENCES(30)
AI540508, cDNAcloneIMAGE: 2209821, Uterus, 3'read, 2.1 kb
AI870175, cDNAcloneIMAGE: 2424998, Uterus, 3'read, 1.7 kb
AI978643, cDNAcloneIMAGE: 2491824, Uterus, 3'read, 1.3 kb
AI473856, cDNAcloneIMAGE: 2044374, Lymph, 3'read
AI037900, cDNAcloneIMAGE: 1657707, Wholeembryo, 3'read, 1.2 kb
AI417620, cDNAcloneIMAGE: 2115082, 3'read, 1.0 kb
AA147817, cDNAcloneIMAGE: 590062, 3'read
AA968592, cDNAcloneIMAGE: 1578323, 3'read, 0.7 kb
AW474729, cDNAcloneIMAGE: 2853635, Uterus, 3'read
R02352, cDNAcloneIMAGE: 124282, 3'read, 0.7 kb
R01889, cDNAcloneIMAGE: 124485, 5'read, 0.7 kb
AA446606, cDNAcloneIMAGE: 783693, Wholeembryo, 3'read
R02456, cDNAcloneIMAGE: 124282, 5'read, 0.7 kb
T72705, cDNAcloneIMAGE: 108686, 5'read, 0.7 kb
R01890, cDNAcloneIMAGE: 124485, 3'read, 0.7 kb
AA147925, cDNAcloneIMAGE: 590014, 5'read
AI131471, cDNAcloneIMAGE: 1709098, Heart, 3'read, 0.6 kb
AA733177, cDNAclone399421, Heart, 3'read
AI039489, cDNAcloneIMAGE: 1658903, Wholeembryo, 3'read, 0.6 kb
AI128585, cDNAcloneIMAGE: 1691245, Heart, 3'read, 0.6 kb
AI540506, cDNAcloneIMAGE: 2209817, Uterus, 3'read, 0.6 kb
AA894832, cDNAcloneIMAGE: 1502815, Kidney, 3'read, 0.5 kb
AW057578, cDNAcloneIMAGE: 2553014, Pooled, 3'read, 0.3 kb
AA729975, cDNAcloneIMAGE: 1257976, GermCell, 0.3 kb
AI131016, cDNAcloneIMAGE: 1706622, Heart, 3'read, 0.2 kb
AA147965, cDNAcloneIMAGE: 590062, 5'read
AA446735, cDNAcloneIMAGE: 783693, Wholeembryo, 5'read
AA147867, cDNAcloneIMAGE: 590014, 3'read
AI497866, cDNAcloneIMAGE: 2125892, Pooled, 3'read
T72636, cDNAcloneIMAGE: 108686, 3'read, 0.7 kb

TABLE 11

ESTs within the magic roundabout sequence:

EST sequences in magic roundabout (55):
AI803963, cDNAcloneIMAGE: 2069520, 3'read, 0.9 kb
W88669, cDNAcloneIMAGE: 417844, 3'read, 0.7 kb
AI184863, cDNAcloneIMAGE: 1565500, Pooled, 3'read, 0.6 kb
AA011319, cDNAcloneIMAGE: 359779, Heart, 3'read, 0.6 kb
AA302765, cDNAcloneATCC: 194652, Adipose, 3'read
AI278949, cDNAcloneIMAGE: 1912098, Colon, 3'read, 0.7 kb
AI265775, cDNAcloneIMAGE: 2006542, Ovary, 3'read
AA746200, cDNAcloneIMAGE: 1324396, Kidney, 0.5 kb
N78762, cDNAcloneIMAGE: 301290, Lung, 3'read
AI352263, cDNAcloneIMAGE: 1940638, Wholeembryo, 3'read, 0.6 kb
AA630260, cDNAcloneIMAGE: 854855, Lung, 3'read, 0.5 kb

TABLE 11-continued

ESTs within the magic roundabout sequence:

C20950, cDNAclone(no-name), 3'read
W88875, cDNAcloneIMAGE: 417844, 5'read, 0.7 kb
AA156022, cDNAcloneIMAGE: 590120, 3'read
N93972, cDNAcloneIMAGE: 309369, Lung, 3'read, 1.7 kb
AI217602, cDNAcloneIMAGE: 1732380, Heart, 3'read, 0.5 kb
AW294276, cDNAcloneIMAGE: 2726'347, 3'read
AA010931, cDNAcloneIMAGE: 359779, Heart, 5'read, 0.6 kb
AA303624, cDNAcloneATCC: 115215, Aorta, 5'read
AI366745, cDNAcloneIMAGE: 1935056, 3'read, 0.5 kb
AA327257, cDNAcloneATCC: 127927, Colon, 5'read
C06489, cDNAclonehbc5849, Pancreas
BE218677, cDNAcloneIMAGE: 3176164, lung, 3'read
AA335675, cDNAcloneATCC: 137498, Testis, 5'read
R84975, cDNAcloneIMAGE: 180552, Brain, 3'read, 2.1 kb
AI926445, cDNAcloneIMAGE: 2459442, Stomach, 3'read, 1.9 kb
H61208, cDNAcloneIMAGE: 236318, Ovary, 3'read, 1.9 kb
AA335358, cDNAcloneATCC: 137019, Testis, 5'read
AI129190, cDNAcloneIMAGE: 1509564, Pooled, 3'read, 0.8 kb
T59188, cDNAcloneIMAGE: 74634, Spleen, 5'read, 0.8 kb
T59150, cDNAcloneIMAGE: 74634, Spleen, 3'read, 0.8 kb
R53174, cDNAcloneIMAGE: 154350, Breast, 5'read, 0.8 kb
AA156150, cDNAcloneIMAGE: 590120, 5'read
AA302509, cDNAcloneATCC: 114727, Aorta, 5'read
R99429, cDNAcloneIMAGE: 201985, 5'read, 2.4 kb
AI813787, cDNAcloneIMAGE: 2421627, Pancreas, 3'read, 1.2 kb
H62113, cDNAcloneIMAGE: 236316, Ovary, 5'read, 1.0 kb
R16422, cDNAcloneIMAGE: 129313, 5'read, 0.7 kb
T48993, cDNAcloneIMAGE: 70531, Placenta, 5'read, 0.6 kb
T05694, cDNAcloneHFBDF13, Brain
R84531, cDNAcloneIMAGE: 180104, Brain, 5'read, 2.2 kb
AI903080, cDNAclone(no-name), breast
AI903083, cDNAclone(no-name), breast
AA302764, cDNAcloneATCC: 194652, Adipose, 5'read
AA341407, cDNAcloneATCC: 143064, Kidney, 5'read
W16503, cDNAcloneIMAGE: 301194, Lung, 5'read
AW801246, cDNAclone(no-name), uterus
AW959183, cDNAclone(no-name)
R85924, cDNAcloneIMAGE: 180104, Brain, 3'read, 2.2 kb
AA358843, cDNAcloneATCC: 162953, Lung, 5'read
BE161769, cDNAclone(no-name), head-neck
W40341, cDNAcloneIMAGE: 309369, Lung, 5'read, 1.7 kb
AA876225, cDNAcloneIMAGE: 1257188, GermCell, 3'read
R99441, cDNAcloneIMAGE: 202009, 5'read, 2.3 kb
W76132, cDNAcloneIMAGE: 344982, Heart, 5'read, 1.4 kb,

TABLE 12

110 ESTs in the mouse magic roundabout cluster (Mm.27782)

AI427548, cDNAcloneIMAGE: 521115, Muscle, 3'read
AV022394, cDNAclone1190026N09, 3'read
BB219221, cDNAcloneA530053H04, 3'read
AI604803, cDNAcloneIMAGE: 388336, Embryo, 3'read
AI504730, cDNAcloneIMAGE: 964027, Mammarygland, 3'read
AI430395, cDNAcloneIMAGE: 388336, Embryo, 5'read
AI181963, cDNAcloneIMAGE: 1451626, Liver, 3'read
AV020471, cDNAclone1190017N14, 3'read
BB219225, cDNAcloneA530053H12, 3'read
BB224304, cDNAcloneA530086A21, 3'read
BB527740, cDNAcloneD930042M18, 3'read
W66614, cDNAcloneIMAGE: 388336, Embryo, 5'read
BB097630, cDNAclone9430060E21, 3'read
AI152731, cDNAcloneIMAGE: 1478154, Uterus, 5'read
AW742708, cDNAcloneIMAGE: 2780289, innerear, 170pooled, 3'read
BB118169, cDNAclone9530064M17, 3'read
AI839154, cDNAcloneUI-M-AO0-ach-e-11-0-UI, 3'read
BB206388, cDNAcloneA430075J10, 3'read
BB381670, cDNAcloneC230015E01, 3'read
BB199721, cDNAcloneA430017A19, 3'read
AI593217, cDNAcloneIMAGE: 1177959, Mammarygland, 3'read
BB219411, cDNAcloneA530054L01, 3'read
BB220744, cDNAcloneA530061M19, 3'read
BB220944, cDNAcloneA530062O22, 3'read
BB390078, cDNAcloneC230066L23, 3'read

TABLE 12-continued

110 ESTs in the mouse magic roundabout cluster (Mm.27782)

BB220730, cDNAcloneA530061L13, 3'read
AI615527, cDNAcloneIMAGE: 964027, Mammarygland, 5'read
AI882477, cDNAcloneIMAGE: 1396822, Mammarygland, 5'read
AV025281, cDNAclone1200012D01, 3'read
BB470462, cDNAcloneD230033L23, 3'read
BB247620, cDNAcloneA730020G03, 3'read
BB555377, cDNAcloneE330019B13, 3'read
BB512960, cDNAcloneD730043I21
BB400157, cDNAcloneC330017F17, 3'read
BB320465, cDNAcloneB230385O10, 3'read
BB105670, cDNAclone9430096H10, 3'read
BB441462, cDNAcloneD030027B11, 3'read
BB137530, cDNAclone9830142O07, 3'read
AA553155, cDNAcloneIMAGE: 964027, Mammarygland, 5'read
BB319763, cDNAcloneB230382G07, 3'read
BB451051, cDNAcloneD130007I05, 3'read
BB504672, cDNAcloneD630049J11, 3'read
AI429453, cDNAcloneIMAGE: 569122, Embryo, 3'read
BB190585, cDNAcloneA330062J23, 3'read
BB257082, cDNAcloneA730076M18, 3'read
BB386699, cDNAcloneC230047P06, 3'read
BB295814, cDNAcloneB130042A09, 3'read
BB450972, cDNAcloneD130007A22, 3'read
AA718562, cDNAcloneIMAGE: 1177959, Mammarygland, 5'read
BB223775, cDNAcloneA530083K18, 3'read
AV020555, cDNAclone1190018G05, 3'read
BB226083, cDNAcloneA530095K11, 3'read
BB482105, cDNAcloneD430007O19, 3'read
BB381671, cDNAcloneC230015E02, 3'read
BB383758, cDNAcloneC230030C02, 3'read
BB257519, cDNAcloneA730080D13, 3'read
BB265667, cDNAcloneA830021I17, 3'read
BB254777, cDNAcloneA730063K20, 3'read
AV240775, cDNAclone4732443F15, 3'read
BB315010, cDNAcloneB230352H04, 3'read
BB390074, cDNAcloneC230066L16, 3'read
BB517605, cDNAcloneD830025B17, 3'read
BB484410, cDNAcloneD430025H01, 3'read
BB357583, cDNAcloneC030022J01, 3'read
AV225639, cDNAclone3830431D12, 3'read
BB554921, cDNAcloneE330016A12, 3'read
BB161650, cDNAcloneA130061H21, 3'read
BB106720, cDNAclone9530002M22, 3'read
BB535465, cDNAcloneE030043P14, 3'read
BB357738, cDNAcloneC030024B10, 3'read
AV285588, cDNAclone5031411M12
BB188339, cDNAcloneA330048H22, 3'read
AV337749, cDNAclone6430404F19, 3'read
BB065281, cDNAclone8030443H10, 3'read
BB148059, cDNAclone9930104N19, 3'read
AV252251, cDNAclone4833438P20, 3'read
BB184506, cDNAcloneA330012J24, 3'read
BB522445, cDNAcloneD930007M08, 3'read
BB520366, cDNAcloneD830041K23, 3'read
AV127290, cDNAclone2700047J01, 3'read
BB248651, cDNAcloneA730027F04, 3'read
BB008452, cDNAclone4732482M24, 3'read
BB550719, cDNAcloneE230024C07, 3'read
BB182033, cDNAcloneA230095N14, 3'read
BB480258, cDNAcloneD330045D17, 3'read
BB004855, cDNAclone4732463E03, 3'read
AV379748, cDNAclone9230013A19, 3'read
BB552137, cDNAcloneE230035B12, 3'read
BB288263, cDNAcloneIMAGE: 3490042, mammary, 5'read
BB215681, cDNAcloneA530026M11, 3'read
BB251356, cDNAcloneA730046B16, 3'read
BB503441, cDNAcloneD630043F10, 3'read
BB500571, cDNAcloneD630029E03, 3'read
BB199833, cDNAcloneA430017K13, 3'read
BB533549, cDNAcloneE030030K03, 3'read
BB098399, cDNAclone9430063L18, 3'read
BB213310, cDNAcloneA530009E09, 3'read
BB240699, cDNAcloneA630083B14, 3'read
BB217106, cDNAcloneA530040N24, 3'read
BB057432, cDNAclone7120459H22, 3'read
BB214645, cDNAcloneA530021N22, 3'read
BB218254, cDNAcloneA530048K12, 3'read

TABLE 12-continued

110 ESTs in the mouse magic roundabout cluster (Mm.27782)

BB319841, cDNAcloneB230382O06, 3'read
BB459759, cDNAcloneD130063G22, 3'read
BB485618, cDNAcloneD430032M09, 3'read
BB517699, cDNAcloneD830025J18, 3'read
BB535595, cDNAcloneE030044M09, 3'read
BB536291, cDNAcloneE030049D17, 3'read
BB552689, cDNAcloneE330001A16, 3'read
BB552709, cDNAcloneE33C001C16, 3'read

EXAMPLE 2

ECSM4 Expression is Restricted to Endothelial Cells

Figure 16:

In situ hybridisation (ISH) of tumour and normal tissues showed that the expression of ECSM4 is restricted to vascular endothelial cells in adult angiogenic vessels only. Analysis of normal tissues showed that expression of ECSM4 is detected in human placenta and umbilical cord foetal tissue 10.8 weeks menstrual age. As shown in FIG. 16, ECSM4 expression is highly specific for the vascular endothelial cells of the blood vessel in placenta. Furthermore, expression was absent throughout a number of other normal tissues that were analysed, including adult liver, brain cerebrum and large vessels, prostate, colon, small bowel, heart, eye (choroid and sclera), ovary, stomach, breast and foetal bladder, testis, kidney (15.8 weeks) and foetal heart, kidney, adrenal, intestine (11.3 weeks) foetal brain (10.6 weeks) and foetal eye (16.5 weeks) (data not shown).

Figure 17:
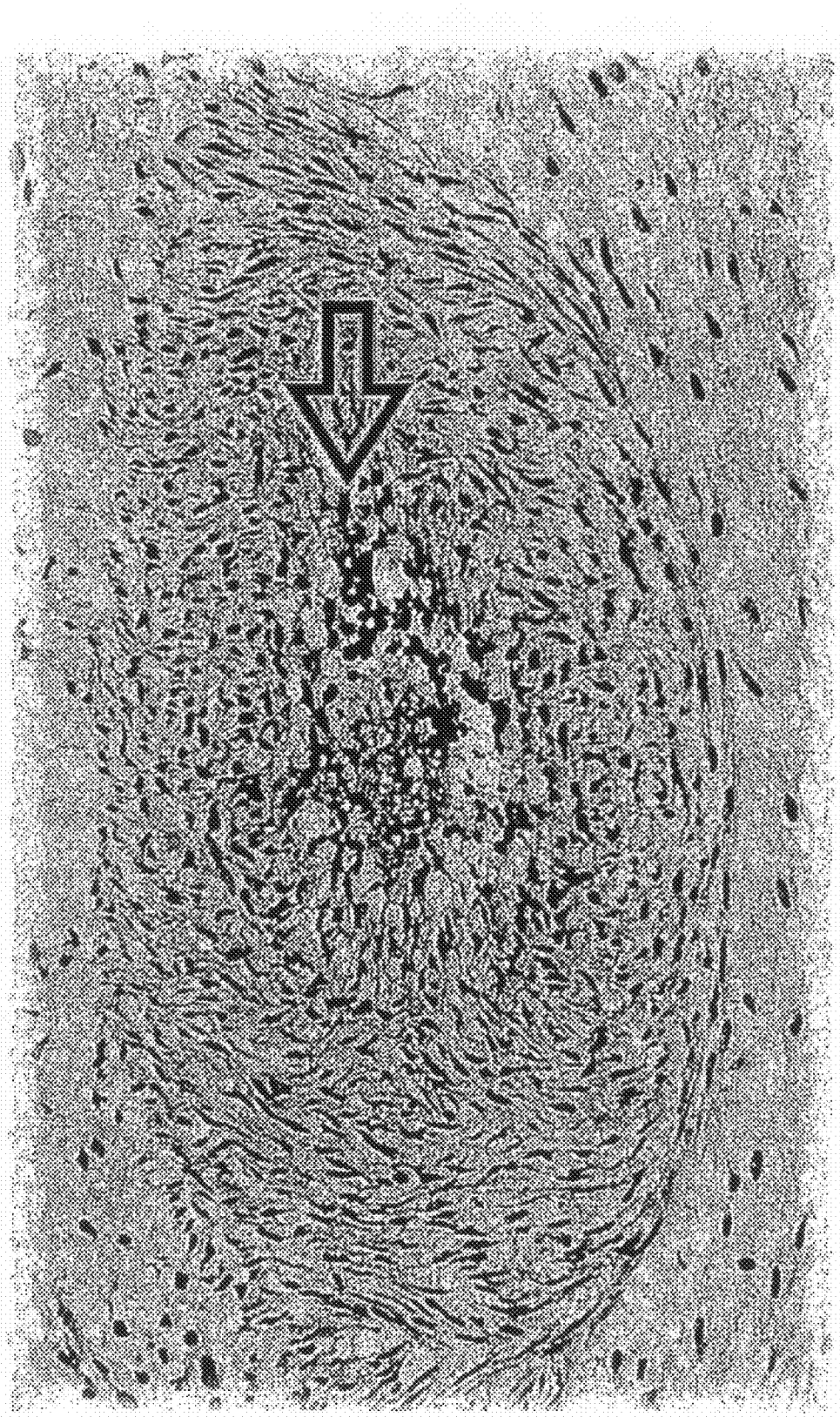
Figure 18:
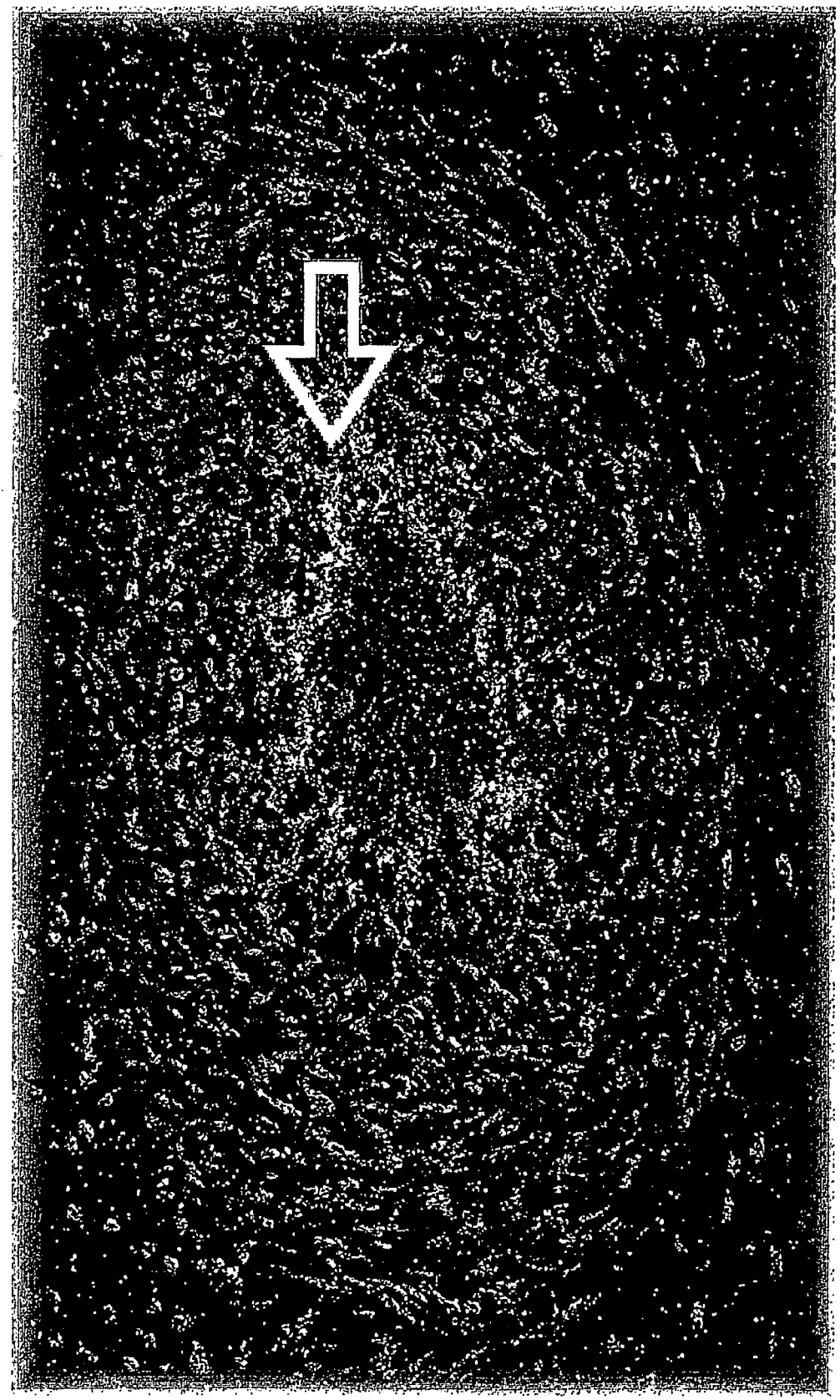
Figure 21:
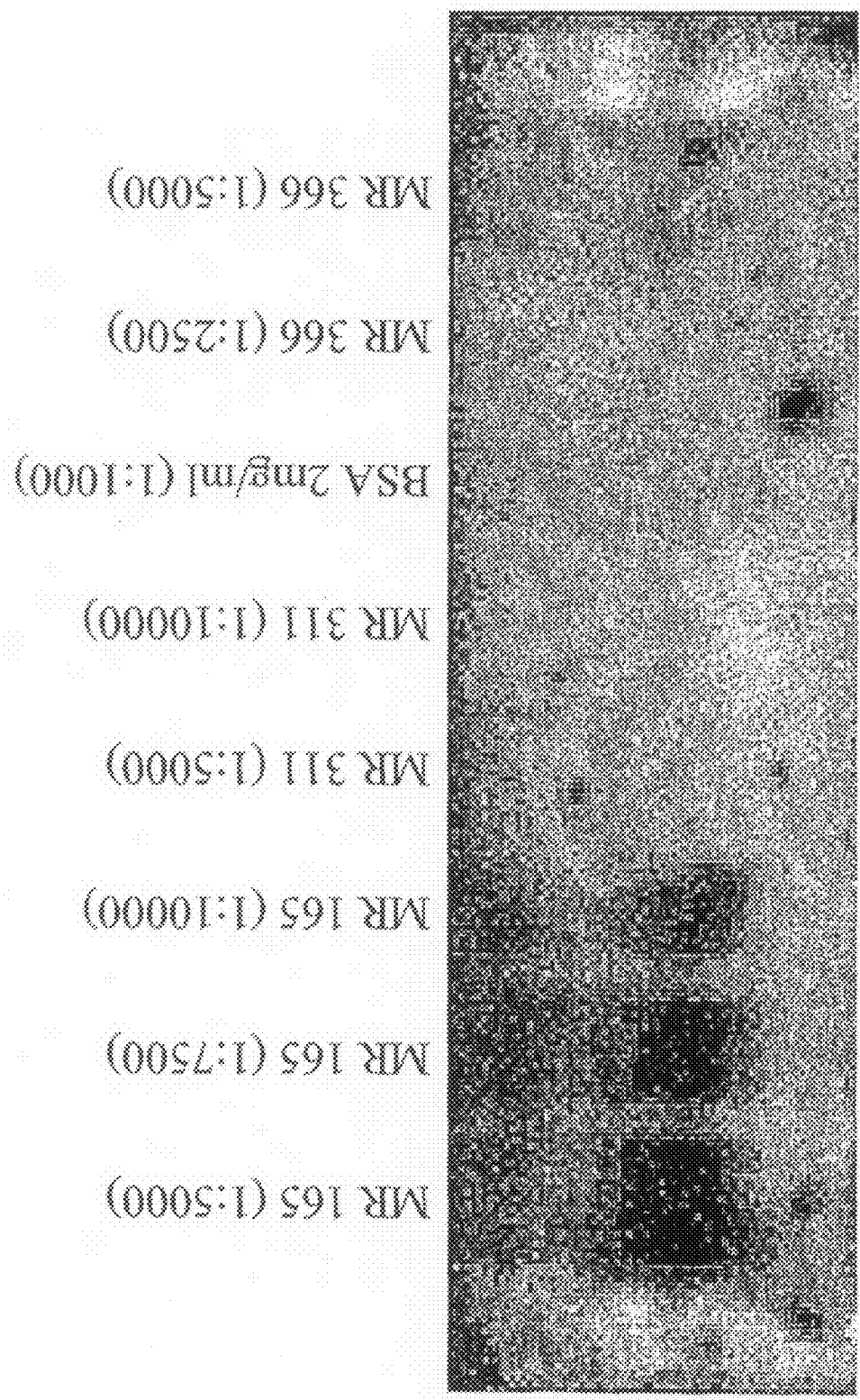

ISH analysis of colorectal liver metastasis biopsies showed that expression of ECSM4 was restricted to vascular endothelial cells of the tumour vessels only (FIGS. 17 and 18). No expression was detected in the surrounding normal tissue. Furthermore the enhanced expression in the vicinity of the necrotic tissues (FIG. 18, necrotic tissue is indicated by the bright signal labelled *) is indicative and consistent with induction of ECSM4 expression by hypoxia. As such, ECSM4 may be a novel hypoxia regulated gene.

The highly restricted expression pattern of ECSM4 in angiogenic vessels in normal and tumour tissues in adult is entirely consistent with the endothelial cell selective pattern of expression determined by the in silico analysis described in Example 1.

Methods

Blocks of formalin-fixed, paraffin-embedded tissues and tumours were obtained from the archives of the Imperial Cancer Research Fund Breast Pathology Group at Guys Hospital, London, UK. An antisense riboprobe to ECSM4 cDNA was prepared for specific localisation of the ECSM4 mRNA by in situ hybridisation. The methods for pretreatment, hybridisation, washing, and dipping of slides in Ilford K5 for autoradiography has been described previously (Poulsom, R., Longcroft, J. M., Jeffrey, R. E., Rogers, L., and Steel, J. H. (1998) Eur. J. Histochem. 42, 121-132). Films were exposed for 7 to 15 days before developing in Kodak D19 and counterstaining with Giemsa. Sections were examined under conventional or reflected light dark-field conditions (Olympus BH2 with epi-illumination) under a x5, x10 or x20 objective that allowed individual auto-radiographic silver grains to be seen as bright objects on a dark background.

EXAMPLE 3

ECSM4 Polypeptide is Detected Only in Endothelial Cells

Antibodies capable of selectively binding the ECSM4 polypeptide were generated and used in immunohistochemistry to demonstrate the presence of ECSM4 polypeptide in a range of cell types (FIGS. 21 to 26). Tissue samples were prepared by standard techniques in the art of immunohistochemistry.

Generation of Antibodies Recognising ECSM4.

The peptides MR 165, MR 311 and MR 336 were fused to Keyhole Limpet Haemocyanin (KLH) before immunisation of rabbits for production of polyclonal antibodies. The antibody MGO-5 was derived from rabbits immunised with the peptide MR 165, whereas MGO-7 was derived from rabbits immunised with a mixture of MR 311 and MR 336. The sequence of the peptides used to generated the polyclonal antibodies is shown below with their reference within the amino acid sequence of full length human ECSM4 as shown in FIG. 12.

MR 165 = LSQSPGAVPQALVAWRA   (681-697)  (SEQ ID NO: 6)

MR 274 = DSVLTPEEVALCLEL    (790-804)  (SEQ ID NO: 7)

MR 311 = TYGYISVPTA         (827-836)  (SEQ ID NO: 8)

MR 336 = KGGVLLCPPRPCLTPT   (852-867)  (SEQ ID NQ: 9)

EXAMPLE 4

The magic roundabout EST sequence identified in the bioinformatics search for endothelial specific transcripts was used to isolate a cDNA of 3800 base pairs in length from a human heart cDNA library. A screen using gene specific primers showed the gene to be present in libraries from heart, adult and foetal brain, liver, lung, kidney, muscle, placenta and small intestine but absent from peripheral blood leukocytes, spleen and testis. Highest expression was in the placental library. Comparison of the magic roundabout sequence to that of roundabout revealed a transmembrane protein with homology throughout but absence of some extracellular domains. Thus, MR has two immunoglobulin and two fibronectin domains in the extracellular domain compared to five immunoglobulin and two fibronectin domains in the extracellular domains of the neuronal specific roundabouts. A transmembrane domain was identified by (i) using the transmembrane predicting software PRED-TMR and (ii) using an alignment between human MR and human ROBO1 peptide sequences. Both methods identified the same residues as the transmembrane region of human MR as amino acids 468-490. Thus, aa 1-467 are extracellular and aa 491-1007 are intracellular. The intracellular domain contains a putative proline rich region that is homologous to those in roundabout that are thought to couple to c-abl (Bashaw et al (2000) Cell 101: 703-715).

Figure 3:
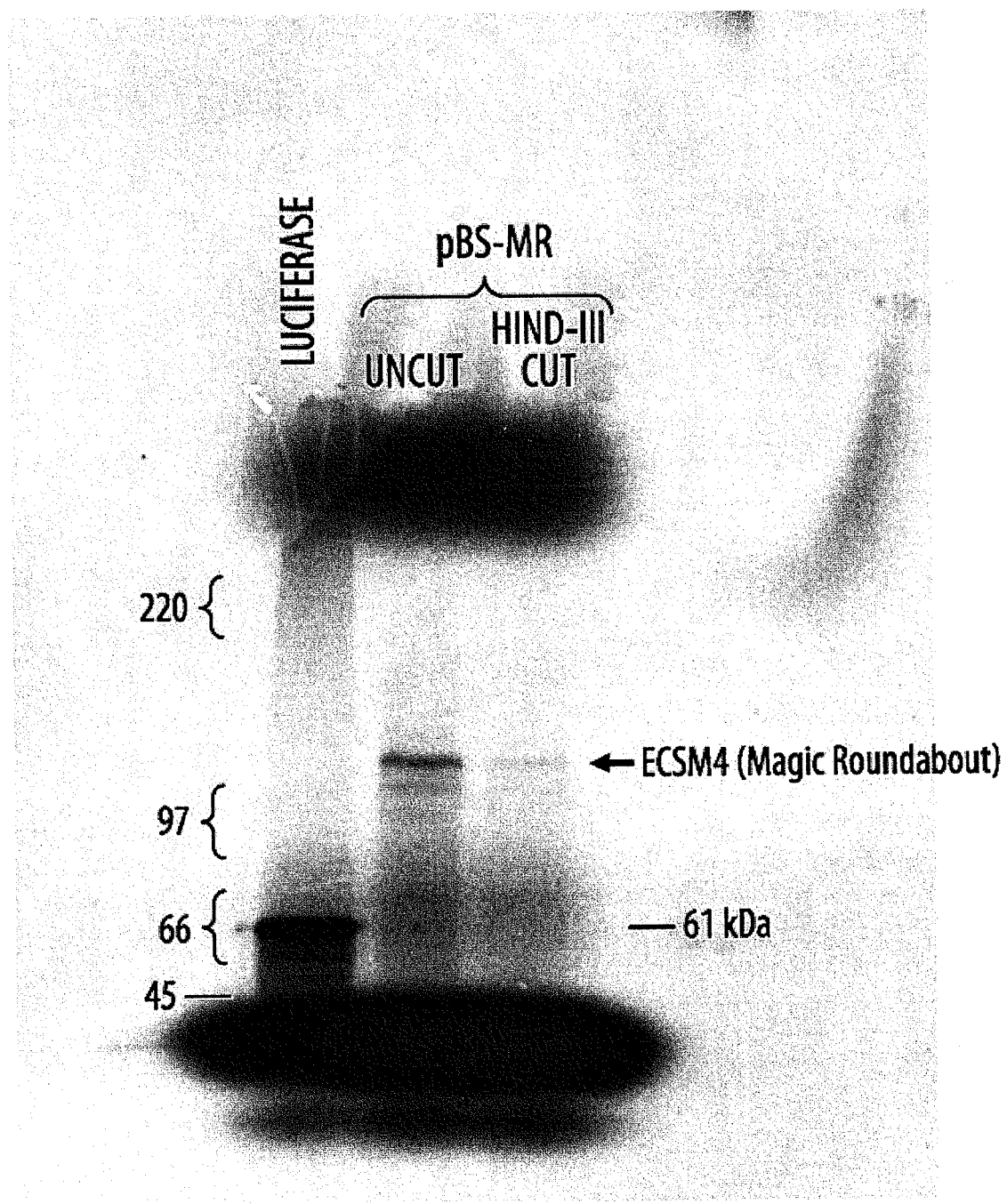

Human SHGC-11739 (GenBank acc. G14646) sequence tagged site (STS) was mapped to magic roundabout mRNA in a BLAST dbSTS search. This STSmaps to chromosome 11 on the Stanford G3 physical map (region 5647.00 cR10000 LOD 1.09 bin 129). Nevertheless, much sequence is missing and the genomic structure is not known. Search of the RIKEN database identified murine magic roundabout. The predicted molecular weight for the peptide core of human MR was 107,457 kDa. This was confirmed by in vitro translation (FIG. 3).

EXAMPLE 5

ECSM4 Expression is Detectable in Tumours

In situ hybridisation was used to characterise expression of ECSM4 in vivo. Expression of ECSM4 was found to be very restricted (Table 13), with no signal detectable in many tissues including neuronal tissue. In contrast, strong expression was detected in pacenta and a range of tumours including those of the brain, bladder and colonic metastasis to the liver (FIG. 27). Expression within tumours was restricted to the tumour vasculature. Immuno-histochemical staining of placenta confirmed endothelial specific expression of the protein.

A search of CGAP SAGE libraries for ECSM4 detected it only in endothelial and tumour libraries (Table 14). This was consistent with in situ hybridisation results in the adult showing that expression was restricted to tumour vessels (colon metastasis to liver, ganglioglioma, bladder and breast carcinoma).

TABLE 13

Expression of magic roundabout in human tissue in vivo.

Expression detected

Placenta and umbilical cord foetal tissue (10.8 weeks menstrual age)
Vessels in colorectal liver metastasis, ganglioglioma, bladder and breast carcinoma.

Expression not detected

Adult liver, brain cerebrum and large vessels, prostate, colon, small bowel, heart, eye choroid and sclera, ovary, stomach, breast

TABLE 14

CGAP SAGE libraries in which magic roundabout was found on the basis of gene to tag mapping

| Library | Tags/million Tags |
| --- | --- |
| HDMEC | 171 |
| HDMEC + VEGF | 224 |
| Medulloblastoma | 102 |
| Glioblastoma multiforme | 85 |
| Ovary, serous adenocarcinoma | 59 |
| Glioblastoma multiforme, pooled | 48 |

HDMEC, human dermal microvascular endothelial cells;
VEGF, vascular endothelial growth factor.

EXAMPLE 6

Induction of ECSM4 in Hypoxic Endothelial Cells

Figure 11A:
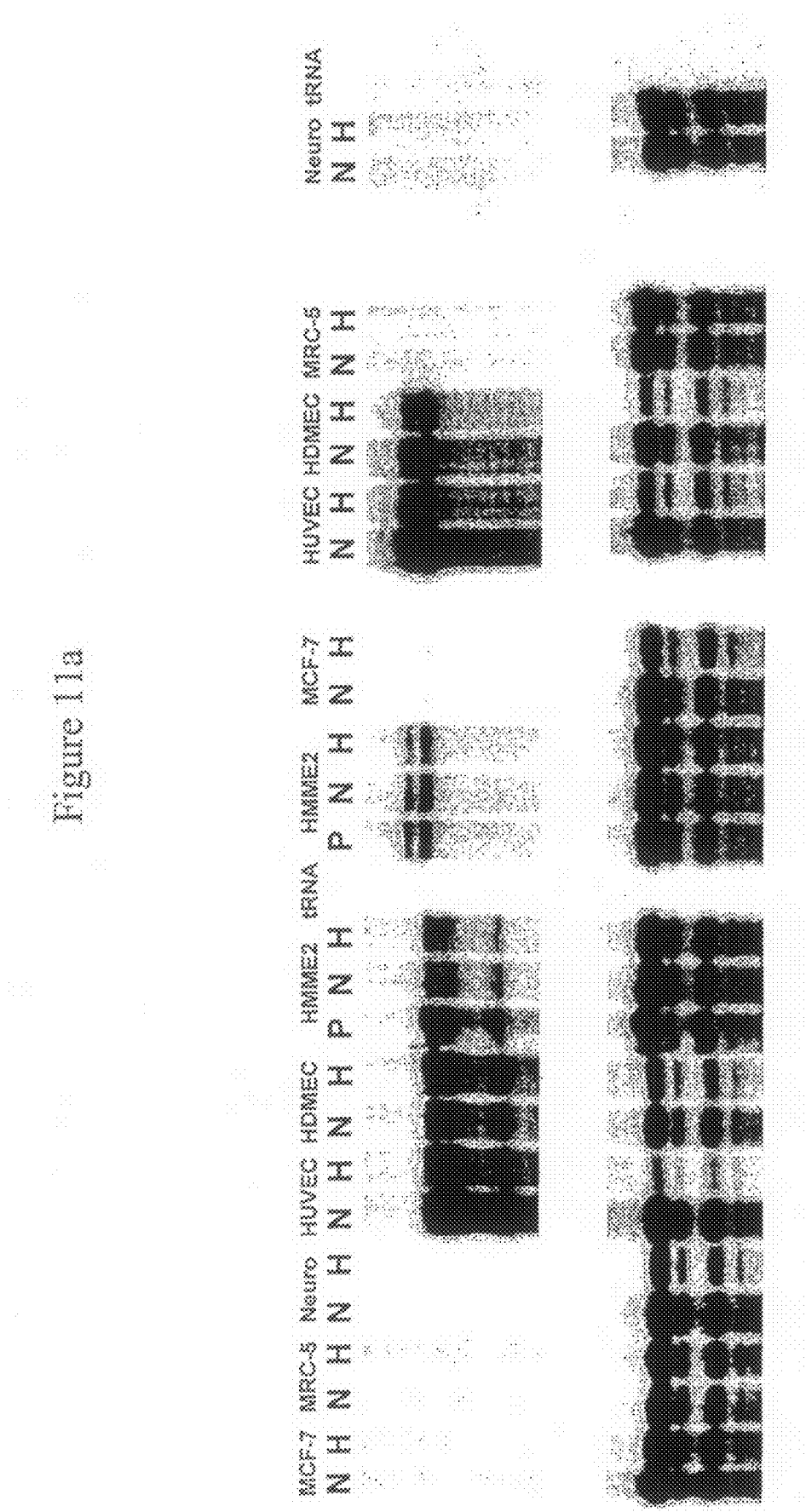

Initial RT-PCR detected ECSM4 expression in endothelial but not other cell lines such as fibroblasts (normal endometial and FEK4), colon carcinoma (SW480 and HCT116), breast carcinoma (MDA453 and MDA468) and HeLa cells. Ribonuclease protection analysis has confirmed and extended this (FIG. 11a). ECSM4 expression was seen to be restricted to endothelium (three different isolates) and absent from fibroblast, carcinoma and neuronal cells. Induction of ECSM4 in hypoxia in endothelial (but not non-endothelial cells) was seen when expression of ECSM4 was analysed using two different RNase protection probes. Expression was on average 5.5 and 2.6 fold higher in hypoxia for HUVEC and HDMEC respectively. Western analysis identified a weak band of 110 kD in human dermal microvascular endothelial cells (HDMEC) but absent from the non-endothelial cells types (FIG. 11b). The band was more intense when the HDMEC cells were epxosed to 18 h hyposia, consistent with ECSM4 being a hypoxically regulated gene.

The invention claimed is:

1. A method of imaging vascular endothelium in the body of an individual, the method comprising administering to the individual an effective amount of a compound comprising a moiety which selectively binds to a polypeptide having at least 90% identity to the amino acid sequence of SEQ ID NO:37 or SEQ ID NO:24, and a further moiety.

2. A method according to claim 1 wherein the vasculature is neovasculature.

3. A method of diagnosing or prognosing in an individual a condition which involves the vascular endothelium, the method comprising administering to the individual an effective amount of a compound comprising a moiety which selectively binds to a polypeptide having at least 90% identity to the amino acid sequence of SEQ ID NO:37 or SEQ ID NO:24, and a further moiety.

4. A method according to claim 3 further comprising the step of detecting the location of the compound in the individual.

5. A method according to claim 1 wherein the individual has cancer.

6. A method according to claim 2, wherein the individual has cancer.

7. A method according to claim 3, wherein the individual has cancer.

8. A method according to claim 4, wherein the individual has cancer.

9. A method according to claim 2, wherein the moiety which selectively binds is an antibody.

10. A method according to claim 2, wherein the further moiety is a detectable moiety.

11. A method according to claim 10, wherein the moiety is a detectable agent.

12. A method according to claim 1, further comprising the step of detecting the location of the compound in the individual.

13. A method according to claim 2, further comprising the step of detecting the location of the compound in the individual.

14. A method according to claim 1, wherein the moiety which selectively binds is an antibody.

15. A method according to claim 3, wherein the moiety which selectively binds is an antibody.

16. A method according to claim 2, wherein the moiety binds to SEQ ID NO:37 or SEQ ID NO:24.

17. A method according to claim 9, wherein the antibody binds to SEQ ID NO:37 or SEQ ID NO:24.

* * * * *

SEQUENCE LISTING

```
<160> NUMBER OF SEQ ID NOS: 50

<210> SEQ ID NO 1
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 1

Gly Gly Asp Ser Leu Leu Gly Gly Arg Gly Ser Leu
 1               5                  10

<210> SEQ ID NO 2
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 2

Leu Leu Gln Pro Pro Ala Arg Gly His Ala His Asp Gly Gln Ala Leu
 1               5                  10                  15
```

Ser Thr Asp Leu
            20

<210> SEQ ID NO 3
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 3

Glu Pro Gln Asp Tyr Thr Glu Pro Val Glu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 4

Thr Ala Pro Gly Gly Gln Gly Ala Pro Trp Ala Glu Glu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 5

Glu Arg Ala Thr Gln Glu Pro Ser Glu His Gly Pro
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 6

Leu Ser Gln Ser Pro Gly Ala Val Pro Gln Ala Leu Val Ala Trp Arg
1               5                   10                  15

Ala

<210> SEQ ID NO 7
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 7

Asp Ser Val Leu Thr Pro Glu Glu Val Ala Leu Cys Leu Glu Leu
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Synthetically generated peptide

```
<400> SEQUENCE: 8

Thr Tyr Gly Tyr Ile Ser Val Pro Thr Ala
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 9

Lys Gly Gly Val Leu Leu Cys Pro Pro Arg Pro Cys Leu Thr Pro Thr
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 10

Trp Leu Ala Asp Thr Trp
1               5

<210> SEQ ID NO 11
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 11

Trp Leu Ala Asp Thr Trp Arg Ser Thr Ser Gly Ser Arg Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 12

Ser Pro Pro Thr Thr Tyr Gly Tyr Ile Ser
1               5                   10

<210> SEQ ID NO 13
<211> LENGTH: 33
<212> TYPE: PRT
<213> ORGANISM: Artificial Sequence
<220> FEATURE:
<223> OTHER INFORMATION: Synthetically generated peptide

<400> SEQUENCE: 13

Gly Ser Leu Ala Asn Gly Trp Gly Ser Ala Ser Glu Asp Asn Ala Ala
1               5                   10                  15

Ser Ala Arg Ala Ser Leu Val Ser Ser Ser Asp Gly Ser Phe Leu Ala
            20                  25                  30

Asp

<210> SEQ ID NO 14
<211> LENGTH: 10
<212> TYPE: PRT
```

```
<213> ORGANISM: Artificial Sequence
<220> FEATURE:
<223> OTHER INFORMATION: Synthetically generated peptide

<400> SEQUENCE: 14

Phe Ala Arg Ala Leu Ala Val Ala Val Asp
 1               5                  10

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tgcagcttcc ttctcacctt                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcacatcccc attcacactg                                              20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
tgtaccatga ggttctcaat gc                                           22

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ttattgtggg ctcagaaggg                                              20

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
caaatgcttc caggtgaaaa a                                            21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
```

```
cgttcaaagc atgaaatgga                                              20

<210> SEQ ID NO 21
<211> LENGTH: 1100
<212> TYPE: DNA
<213> ORGANISM: Homo sapiens
<220> FEATURE:
<221> NAME/KEY: CDS
<222> LOCATION: (152)...(460)

<400> SEQUENCE: 21
tgtctgctta tgcggtggct cgctgctcag aacaggatgg cagagatgag caccaccatc    60
aaaaactcaa ggaccagtgc tgtgggtcca gtcatctgtt tcatggaatt caccagtctg   120
gtatcttcaa atccagaag gatgatggca g atg gca gga agg agg aag agg       172
                                  Met Ala Gly Arg Arg Lys Arg
                                   1               5 gta atc tgg aag agt ttc cgg acc tac tct gct gct gtg att aaa caa     220
Val Ile Trp Lys Ser Phe Arg Thr Tyr Ser Ala Ala Val Ile Lys Gln
         10                  15                  20 cca cca gga aat ttt gat gac act gtt ctc ctg agc tcc tcc ctt tcc    268
Pro Pro Gly Asn Phe Asp Asp Thr Val Leu Leu Ser Ser Ser Leu Ser
 25                  30                  35 tcg ggg aag aaa agc att gaa act aca aaa ata aag tgt tat ttg gct    316
Ser Gly Lys Lys Ser Ile Glu Thr Thr Lys Ile Lys Cys Tyr Leu Ala
 40                  45                  50                  55 gga gtg agg tct cat gtc tgc tta tgc ggt ggc tcg ctg ctc aga aca    364
Gly Val Arg Ser His Val Cys Leu Cys Gly Gly Ser Leu Leu Arg Thr
                 60                  65                  70 ggg aac cat tgg aga tac tca tta ctc ttt gaa ggc tta cag tgg aat    412
Gly Asn His Trp Arg Tyr Ser Leu Leu Phe Glu Gly Leu Gln Trp Asn
             75                  80                  85 gaa ttc aaa tac gac tta ttt gag gaa ttg aag ttg act tta tgg agc    460
Glu Phe Lys Tyr Asp Leu Phe Glu Glu Leu Lys Leu Thr Leu Trp Ser
         90                  95                 100 tgataagaat cttcttggag aaaaaaagac tggtacttct gaattaacca aaatcacagt   520
attctgaaga tgattctaca aagcctgctg tttctacaaa ggctgctgat gatttctaca   580
aagcctgctg tagtgttgct gtggcctctg cttaaaaaag tagaaaacac attgatgcag   640
catgttcacc ccaacctccc tgcctaaagg cctcaggggc ccctccttgg gaagagggaa   700
gggcgccgtg aggattggta agagcccga ttaggggggg gatgggagtg gtgggagaat    760
aaggggacac cttccatcct tgggatgctc accctgccca aattgacctt cctgatgaaa   820
ggccagctcc cagaaatgtg ccctacagtt acctactttc accctaaacc ctgcccttag   880
tcaaatcctt ttcttttttt aagcaatcaa cttcaattcc ttgtataacc cccagtataa   940
aagggctttt ataccattct atcctattgc atgtaagcct tgggtttggg aggtaacagt  1000
gtgggattcc cccatttcat ttccctgcca cccaaacatg cctgtttttt tttaagcaat  1060
attaaatgtt tgtacttcag aaaaaaaaaa aaaaaaaaa                         1100

<210> SEQ ID NO 22
<211> LENGTH: 103
<212> TYPE: PRT
<213> ORGANISM: Homo sapiens

<400> SEQUENCE: 22

Met Ala Gly Arg Arg Lys Arg Val Ile Trp Lys Ser Phe Arg Thr Tyr
 1               5                  10                  15

Ser Ala Ala Val Ile Lys Gln Pro Pro Gly Asn Phe Asp Asp Thr Val
```

```
                    20                  25                  30
Leu Leu Ser Ser Ser Leu Ser Ser Gly Lys Lys Ser Ile Glu Thr Thr
            35                  40                  45

Lys Ile Lys Cys Tyr Leu Ala Gly Val Arg Ser His Val Cys Leu Cys
        50                  55                  60

Gly Gly Ser Leu Leu Arg Thr Gly Asn His Trp Arg Tyr Ser Leu Leu
65                  70                  75                  80

Phe Glu Gly Leu Gln Trp Asn Glu Phe Lys Tyr Asp Leu Phe Glu Glu
                85                  90                  95

Leu Lys Leu Thr Leu Trp Ser
            100

<210> SEQ ID NO 23
<211> LENGTH: 1496
<212> TYPE: DNA
<213> ORGANISM: Homo sapiens
<220> FEATURE:
<221> NAME/KEY: CDS
<222> LOCATION: (1)...(1395)

<400> SEQUENCE: 23
```

| | | | | | | | | | | | | | | | | |
|---|---|---|---|---|---|---|---|---|---|---|---|---|---|---|---|---|
| aac | tgg | ttg | cga | cac | tgc | ggt | gtt | gca | ctc | tgg | ctg | ctg | ctt | ctg | ggc | 48 |
| Asn | Trp | Leu | Arg | His | Cys | Gly | Val | Ala | Leu | Trp | Leu | Leu | Leu | Leu | Gly | |
| 1 | | | | 5 | | | | | 10 | | | | | 15 | | |
| acc | gct | gtg | tgt | atc | cac | cgc | cgt | cgc | cga | gct | agg | gtg | ctt | ctg | ggc | 96 |
| Thr | Ala | Val | Cys | Ile | His | Arg | Arg | Arg | Arg | Ala | Arg | Val | Leu | Leu | Gly | |
| | | | 20 | | | | 25 | | | | | 30 | | | | |
| cca | ggt | ctg | tac | aga | tat | acc | agt | gag | gat | gcc | atc | cta | aaa | cac | agg | 144 |
| Pro | Gly | Leu | Tyr | Arg | Tyr | Thr | Ser | Glu | Asp | Ala | Ile | Leu | Lys | His | Arg | |
| | | 35 | | | | | 40 | | | | | 45 | | | | |
| atg | gat | cac | agt | gac | tcc | cag | tgg | ttg | gca | gac | act | tgg | cgt | tcc | acc | 192 |
| Met | Asp | His | Ser | Asp | Ser | Gln | Trp | Leu | Ala | Asp | Thr | Trp | Arg | Ser | Thr | |
| 50 | | | | | 55 | | | | | 60 | | | | | | |
| tct | ggc | tct | cgg | gac | ctg | agc | agc | agc | agc | ctc | agc | agt | cgg | ctg | | 240 |
| Ser | Gly | Ser | Arg | Asp | Leu | Ser | Ser | Ser | Ser | Leu | Ser | Ser | Arg | Leu | | |
| 65 | | | | | 70 | | | | | 75 | | | | | 80 | |
| ggg | gcg | gat | gcc | cgg | gac | cca | cta | gac | tgt | cgt | cgc | tcc | ttg | ctc | tcc | 288 |
| Gly | Ala | Asp | Ala | Arg | Asp | Pro | Leu | Asp | Cys | Arg | Arg | Ser | Leu | Leu | Ser | |
| | | | | 85 | | | | | 90 | | | | | 95 | | |
| tgg | gac | tcc | cga | agc | ccc | ggc | gtg | ccc | ctg | ctt | cca | gac | acc | agc | act | 336 |
| Trp | Asp | Ser | Arg | Ser | Pro | Gly | Val | Pro | Leu | Leu | Pro | Asp | Thr | Ser | Thr | |
| | | | 100 | | | | | 105 | | | | | 110 | | | |
| ttt | tat | ggc | tcc | ctc | atc | gct | gag | ctg | ccc | tcc | agt | acc | cca | gcc | agg | 384 |
| Phe | Tyr | Gly | Ser | Leu | Ile | Ala | Glu | Leu | Pro | Ser | Ser | Thr | Pro | Ala | Arg | |
| | | 115 | | | | | 120 | | | | | 125 | | | | |
| cca | agt | ccc | cag | gtc | cca | gct | gtc | agg | cgc | ctc | cca | ccc | cag | ctg | gcc | 432 |
| Pro | Ser | Pro | Gln | Val | Pro | Ala | Val | Arg | Arg | Leu | Pro | Pro | Gln | Leu | Ala | |
| | 130 | | | | | 135 | | | | | 140 | | | | | |
| cag | ctc | tcc | agc | ccc | tgt | tcc | agc | tca | gac | agc | ctc | tgc | agc | cgc | agg | 480 |
| Gln | Leu | Ser | Ser | Pro | Cys | Ser | Ser | Ser | Asp | Ser | Leu | Cys | Ser | Arg | Arg | |
| 145 | | | | | 150 | | | | | 155 | | | | | 160 | |
| gga | ctc | tct | tct | ccc | cgc | ttg | tct | ctg | gcc | cct | gca | gag | gct | tgg | aag | 528 |
| Gly | Leu | Ser | Ser | Pro | Arg | Leu | Ser | Leu | Ala | Pro | Ala | Glu | Ala | Trp | Lys | |
| | | | | 165 | | | | | 170 | | | | | 175 | | |
| gcc | aaa | aag | aag | cag | gag | ctg | cag | cat | gcc | aac | agt | tcc | cca | ctg | ctc | 576 |
| Ala | Lys | Lys | Lys | Gln | Glu | Leu | Gln | His | Ala | Asn | Ser | Ser | Pro | Leu | Leu | |
| | | | 180 | | | | | 185 | | | | | 190 | | | |
| cgg | ggc | agc | cac | tcc | ttg | gag | ctc | cgg | gcc | tgt | gag | tta | gga | aat | aga | 624 |
| Arg | Gly | Ser | His | Ser | Leu | Glu | Leu | Arg | Ala | Cys | Glu | Leu | Gly | Asn | Arg | |
| | | 195 | | | | | 200 | | | | | 205 | | | | |

| | | |
|---|---|---|
| ggt tcc aag aac ctt tcc caa agc cca ggg gct gtg ccc caa gct ctg<br>Gly Ser Lys Asn Leu Ser Gln Ser Pro Gly Ala Val Pro Gln Ala Leu<br>210                          215                        220 | | 672 |
| gtt gcc tgg cgg gcc ctg gga ccg aaa ctc ctc agc tcc tca aat gag<br>Val Ala Trp Arg Ala Leu Gly Pro Lys Leu Leu Ser Ser Ser Asn Glu<br>225                   230                 235                 240 | | 720 |
| ctg gtt act cgt cat ctc cct cca gca ccc ctc ttt cct cat gaa act<br>Leu Val Thr Arg His Leu Pro Pro Ala Pro Leu Phe Pro His Glu Thr<br>                  245                 250                 255 | | 768 |
| ccc cca act cag agt caa cag acc cag cct ccg gtg gca cca cag gct<br>Pro Pro Thr Gln Ser Gln Gln Thr Gln Pro Pro Val Ala Pro Gln Ala<br>    260                       265                 270 | | 816 |
| ccc tcc tcc atc ctg ctg cca gca gcc ccc atc ccc atc ctt agc ccc<br>Pro Ser Ser Ile Leu Leu Pro Ala Ala Pro Ile Pro Ile Leu Ser Pro<br>275                   280                 285 | | 864 |
| tgc agt ccc cct agc ccc cag gcc tct tcc ctc tct ggc ccc agc cca<br>Cys Ser Pro Pro Ser Pro Gln Ala Ser Ser Leu Ser Gly Pro Ser Pro<br>         290                   295                 300 | | 912 |
| gct tcc agt cgc ctg tcc agc tcc tca ctg tca tcc ctg ggg gag gat<br>Ala Ser Ser Arg Leu Ser Ser Ser Ser Leu Ser Ser Leu Gly Glu Asp<br>305                   310                 315                 320 | | 960 |
| caa gac agc gtg ctg acc cct gag gag gta gcc ctg tgc ttg gaa ctc<br>Gln Asp Ser Val Leu Thr Pro Glu Glu Val Ala Leu Cys Leu Glu Leu<br>                  325                 330                 335 | | 1008 |
| agt gag ggt gag gag act ccc agg aac agc gtc tct ccc atg cca agg<br>Ser Glu Gly Glu Glu Thr Pro Arg Asn Ser Val Ser Pro Met Pro Arg<br>              340                      345                 350 | | 1056 |
| gct cct tca ccc ccc acc acc tat ggg tac atc agc gtc cca aca gcc<br>Ala Pro Ser Pro Pro Thr Thr Tyr Gly Tyr Ile Ser Val Pro Thr Ala<br>355                   360                 365 | | 1104 |
| tca gag ttc acg gac atg ggc agg act gga gga ggg gtg ggg ccc aag<br>Ser Glu Phe Thr Asp Met Gly Arg Thr Gly Gly Gly Val Gly Pro Lys<br>    370                       375                 380 | | 1152 |
| ggg gga gtc ttg ctg tgc cca cct cgg ccc tgc ctc acc ccc acc ccc<br>Gly Gly Val Leu Leu Cys Pro Pro Arg Pro Cys Leu Thr Pro Thr Pro<br>385                   390                 395                 400 | | 1200 |
| agc gag ggc tcc tta gcc aat ggt tgg ggc tca gcc tct gag gac aat<br>Ser Glu Gly Ser Leu Ala Asn Gly Trp Gly Ser Ala Ser Glu Asp Asn<br>                  405                 410                 415 | | 1248 |
| gcc gcc agc gcc aga gcc agc ctt gtc agc tcc tcc gat ggc tcc ttc<br>Ala Ala Ser Ala Arg Ala Ser Leu Val Ser Ser Ser Asp Gly Ser Phe<br>             420                      425                 430 | | 1296 |
| ctc gct gat gct cac ttt gcc cgg gcc ctg gca gtg gct gtg gat agc<br>Leu Ala Asp Ala His Phe Ala Arg Ala Leu Ala Val Ala Val Asp Ser<br>435                   440                 445 | | 1344 |
| ttt ggt ttc ggt cta gag ccc agg gag gca gac tgc gtc ttc ata ggt<br>Phe Gly Phe Gly Leu Glu Pro Arg Glu Ala Asp Cys Val Phe Ile Gly<br>    450                       455                 460 | | 1392 |
| atg tgaggtctcc ccatcttact cctcactcat gcccttgcc tttctaacaa<br>Met<br>465 | | 1445 |
| ctgttatcat gtcatcattg ttaaaaaaaa aaaaaaaaa aaaaaaaaa a | | 1496 |

<210> SEQ ID NO 24
<211> LENGTH: 465
<212> TYPE: PRT
<213> ORGANISM: Homo sapiens

<400> SEQUENCE: 24

-continued

```
Asn Trp Leu Arg His Cys Gly Val Ala Leu Trp Leu Leu Leu Gly
  1               5                  10                  15

Thr Ala Val Cys Ile His Arg Arg Arg Ala Arg Val Leu Leu Gly
                 20                  25                  30

Pro Gly Leu Tyr Arg Tyr Thr Ser Glu Asp Ala Ile Leu Lys His Arg
             35                  40                  45

Met Asp His Ser Asp Ser Gln Trp Leu Ala Asp Thr Trp Arg Ser Thr
 50                  55                          60

Ser Gly Ser Arg Asp Leu Ser Ser Ser Ser Leu Ser Ser Arg Leu
 65                  70                  75                  80

Gly Ala Asp Ala Arg Asp Pro Leu Asp Cys Arg Arg Ser Leu Leu Ser
                 85                  90                  95

Trp Asp Ser Arg Ser Pro Gly Val Pro Leu Leu Pro Asp Thr Ser Thr
                100                 105                 110

Phe Tyr Gly Ser Leu Ile Ala Glu Leu Pro Ser Ser Thr Pro Ala Arg
            115                 120                 125

Pro Ser Pro Gln Val Pro Ala Val Arg Arg Leu Pro Pro Gln Leu Ala
    130                 135                 140

Gln Leu Ser Ser Pro Cys Ser Ser Asp Ser Leu Cys Ser Arg Arg
145                 150                 155                 160

Gly Leu Ser Ser Pro Arg Leu Ser Leu Ala Pro Ala Glu Ala Trp Lys
                165                 170                 175

Ala Lys Lys Lys Gln Glu Leu Gln His Ala Asn Ser Ser Pro Leu Leu
            180                 185                 190

Arg Gly Ser His Ser Leu Glu Leu Arg Ala Cys Glu Leu Gly Asn Arg
        195                 200                 205

Gly Ser Lys Asn Leu Ser Gln Ser Pro Gly Ala Val Pro Gln Ala Leu
    210                 215                 220

Val Ala Trp Arg Ala Leu Gly Pro Lys Leu Leu Ser Ser Ser Asn Glu
225                 230                 235                 240

Leu Val Thr Arg His Leu Pro Pro Ala Pro Leu Phe Pro His Glu Thr
                245                 250                 255

Pro Pro Thr Gln Ser Gln Gln Thr Gln Pro Pro Val Ala Pro Gln Ala
            260                 265                 270

Pro Ser Ser Ile Leu Leu Pro Ala Pro Ile Pro Ile Leu Ser Pro
    275                 280                 285

Cys Ser Pro Pro Ser Pro Gln Ala Ser Ser Leu Ser Gly Pro Ser Pro
290                 295                 300

Ala Ser Ser Arg Leu Ser Ser Ser Leu Ser Ser Leu Gly Glu Asp
305                 310                 315                 320

Gln Asp Ser Val Leu Thr Pro Glu Glu Val Ala Leu Cys Leu Glu Leu
                325                 330                 335

Ser Glu Gly Glu Glu Thr Pro Arg Asn Ser Val Ser Pro Met Pro Arg
        340                 345                 350

Ala Pro Ser Pro Pro Thr Thr Tyr Gly Tyr Ile Ser Val Pro Thr Ala
    355                 360                 365

Ser Glu Phe Thr Asp Met Gly Arg Thr Gly Gly Val Gly Pro Lys
370                 375                 380

Gly Gly Val Leu Leu Cys Pro Pro Arg Pro Cys Leu Thr Pro Thr Pro
385                 390                 395                 400

Ser Glu Gly Ser Leu Ala Asn Gly Trp Gly Ser Ala Ser Glu Asp Asn
                405                 410                 415

Ala Ala Ser Ala Arg Ala Ser Leu Val Ser Ser Ser Asp Gly Ser Phe
```

```
                 420             425              430
Leu Ala Asp Ala His Phe Ala Arg Ala Leu Ala Val Ala Val Asp Ser
        435                 440                445

Phe Gly Phe Gly Leu Glu Pro Arg Glu Ala Asp Cys Val Phe Ile Gly
    450                 455                460

Met
465

<210> SEQ ID NO 25
<211> LENGTH: 2076
<212> TYPE: DNA
<213> ORGANISM: Homo sapiens

<400> SEQUENCE: 25 agggggactct cttctccccg cttgtctctg gcccctgcag aggcttggaa ggccaaaaag    60
aaagcaggag ctgcagcatg ccaacagttc cccactgctc cggggcagcc actccttaga   120
gctccgggcc tgtgagttag aaatagagg ttccaagaac ctttcccaaa gcccaggagc   180
tgtgccccaa gctctggttg cctggcgggc cctgggaccg aaactcctca gctcctcaaa   240
tgagctggtt actcgtcatc tccctccagc accctctttt cctcatgaaa ctcccccaac   300
tcagagtcaa cagacccagc ctccggtggc accacaggct ccctcctcca tcctgctgcc   360
agcagccccc atccccatcc ttagcccctg cagtccccct agccccagg cctcttccct   420 ctctggcccc agcccagctt ccagtcgcct gtccagctcc tcactgtcat ccctggggga   480
ggatcaagac agcgtgctga cccctgagga ggtagccctg tgcttggaac tcagtgaggg   540
tgaggagact cccaggaaca gcgtctctcc catgccaagg gttccttcac cccccaccac   600
ctatgggtac atcagcgtcc aacagcctc agagttcacg gacatgggca ggactggagg   660
aggggtgggg cccaaggggg gagtcttgct gtgcccacct cggccctgcc tcaccccccac   720 ccccagcgag ggctccttag ccaatggttg gggctcagcc tctgaggaca atgccgccag   780
cgccagagcc agccttgtca gctcctccga tggctccttc ctcgctgatg ctcactttgc   840
ccgggccctg gcagtggctg tggatagctt tggtttcggt ctagagccca gggaggcaga   900
ctgcgtcttc atagatgcct catcacctcc ctccccacgg gattgagatc ttcctgaccc   960
ccaacctctc cctgccctg tgggaagtgg aggccagact ggttggaaga caatggaagg  1020
tcagccacac ccagcggctg gaaggggga tgcctccctg gcccctgac tctcagatct  1080 cttcccagag aagtcagctc cactgtcgta tgcccaaggg tgggtgcttc tcctgtagat  1140
tactcctgaa ccgtgtccct gagacttccc agacgggaat cagaaccact tctcctgtcc  1200
acccacaaga cctgggctgt ggtgtgtggg tcttggcctg tgtttctctg cagctggggt  1260
ccaccttccc aagcctccag agagttctcc ctccacgatt gtgaaaacaa atgaaaacaa  1320
aattagagca aagctgtacc tgggagccct cagggagcaa acatcatct ccacctgact  1380 cctagccact gctttctcct ctgtgccatc cactcccacc acccaggttg tttttggcct  1440
gaaggagcaa gccctgcctg ctggcttttc ccccaaccat tttgggattc acagggaagt  1500
gggagggagc ccagagggtg gccttttgtg ggagggacag cagtggctgc tgggggagag  1560
ggctgtggag gaaggagctt tcggagccc ctctcagcc ttacctgggc cctcctctca  1620
gagaagagct caactctctc ccaaccctca ccaatggaaa gaaataatt atgaatgccg  1680 actgaggcac tgaggcccct acctcatgcc caaacaaag gggttcaagg ctgggtctag  1740
cgaggatgct tgaaggaagg gaggtatgga gcccgtaggt caaaagcacc catcctcgta  1800
```

-continued

```
ctgttgtcac tatgagctta agaaatttga taccataaaa tggtaaagac ttgagttctg    1860
tgagatcatt ccccggagca ccatttttag gggagcacct ggagagatgg caagaatttc    1920
ctgagttagg cagggatcag gcattcattg acactcaggg agtgtcacac atttctgttc    1980
tgcaattaaa gggagaatga ggttcatcca ccaaatttta agcagaatat aggaagggca    2040
ggggtgggga gtttcagggt ctgctggtcc tgggca                              2076
```

<210> SEQ ID NO 26
<211> LENGTH: 314
<212> TYPE: PRT
<213> ORGANISM: Homo sapiens

<400> SEQUENCE: 26

```
Gly Asp Ser Leu Leu Pro Ala Cys Leu Trp Pro Leu Gln Arg Leu Gly
1               5                   10                  15

Arg Pro Lys Arg Lys Gln Glu Leu Gln His Ala Asn Ser Ser Pro Leu
            20                  25                  30

Leu Arg Gly Ser His Ser Leu Glu Leu Arg Ala Cys Glu Leu Gly Asn
        35                  40                  45

Arg Gly Ser Lys Asn Leu Ser Gln Ser Pro Gly Ala Val Pro Gln Ala
    50                  55                  60

Leu Val Ala Trp Arg Ala Leu Gly Pro Lys Leu Leu Ser Ser Ser Asn
65                  70                  75                  80

Glu Leu Val Thr Arg His Leu Pro Pro Ala Pro Leu Phe Pro His Glu
                85                  90                  95

Thr Pro Pro Thr Gln Ser Gln Gln Thr Gln Pro Val Ala Pro Gln
            100                 105                 110

Ala Pro Ser Ser Ile Leu Leu Pro Ala Ala Pro Ile Pro Ile Leu Ser
        115                 120                 125

Pro Cys Ser Pro Pro Ser Pro Gln Ala Ser Ser Leu Ser Gly Pro Ser
    130                 135                 140

Pro Ala Ser Ser Arg Leu Ser Ser Ser Ser Leu Ser Ser Leu Gly Glu
145                 150                 155                 160

Asp Gln Asp Ser Val Leu Thr Pro Glu Glu Val Ala Leu Cys Leu Glu
                165                 170                 175

Leu Ser Glu Gly Glu Glu Thr Pro Arg Asn Ser Val Ser Pro Met Pro
            180                 185                 190

Arg Val Pro Ser Pro Pro Thr Thr Tyr Gly Tyr Ile Ser Val Pro Thr
        195                 200                 205

Ala Ser Glu Phe Thr Asp Met Gly Arg Thr Gly Gly Gly Val Gly Pro
    210                 215                 220

Lys Gly Gly Val Leu Leu Cys Pro Pro Arg Pro Cys Leu Thr Pro Thr
225                 230                 235                 240

Pro Ser Glu Gly Ser Leu Ala Asn Gly Trp Gly Ser Ala Ser Glu Asp
                245                 250                 255

Asn Ala Ala Ser Ala Arg Ala Ser Leu Val Ser Ser Asp Gly Ser
            260                 265                 270

Phe Leu Ala Asp Ala His Phe Ala Arg Ala Leu Ala Val Ala Val Asp
        275                 280                 285

Ser Phe Gly Phe Gly Leu Glu Pro Arg Glu Ala Asp Cys Val Phe Ile
    290                 295                 300

Asp Ala Ser Ser Pro Pro Ser Pro Arg Asp
305                 310
```

<210> SEQ ID NO 27
<211> LENGTH: 1046
<212> TYPE: DNA
<213> ORGANISM: Homo sapiens

<400> SEQUENCE: 27

```
tccagctcag acagcctctg cagccgcagg ggactctctt ctccccgctt gtctctggcc     60
cctgcagagg cttggaaggc caaaagaag caggagctgc agcatgccaa cagttcccca    120
ctgctccggg gcagccactc cttggagctc cgggcctgtg agttaggaaa tagaggttcc    180
aagaaccttt cccaaagccc aggggctgtg ccccaagctc tggttgcctg gcggccctg    240
ggaccgaaac tcctcagctc ctcaaatgag ctggttactc gtcatctccc tccagcaccc    300
ctctttcctc atgaaactcc cccaactcag agtcaacaga cccagcctcc ggtggcacca    360
caggctccct cctccatcct gctgccagca gccccatcc ccatccttag ccctgcagt    420
ccccctagcc cccaggcctc ttccctctct ggccccagcc cagcttccag tcgcctgtcc    480
agctcctcac tgtcatccct gggggaggat caagacagcg tgctgacccc tgaggaggta    540
gccctgtgct tggaactcag tgagggtgag gagactccca ggaacagcgt ctctcccatg    600
ccaagggctc cttacccccc caccacctat gggtacatca gcgtcccaac agcctcagag    660
ttcacggaca tgggcaggac tggaggaggg gtggggccca agggggagt cttgctgtgc    720
ccacctcggc cctgcctcac ccccacccc agcgagggct ccttagccaa tggttggggc    780
tcagcctctg aggacaatgc cgccagcgcc agagccagcc ttgtcagctc tccgatggc    840
tccttcctcg ctgatgctca ctttgcccgg gccctggcag tggctgtgga tagctttggt    900
ttcggtctag agcccaggga ggcagactgc gtcttcatag gtatgtgagg tctccccatc    960
ttactcctca ctcatgcccc ttgccttcct aacaactgtt atcatgtcat cattgttaaa   1020
aaaaaaaaaa aaaaaaaaaa aaaaaa                                       1046
```

<210> SEQ ID NO 28
<211> LENGTH: 1023
<212> TYPE: DNA
<213> ORGANISM: Homo sapiens

<400> SEQUENCE: 28

```
aggggactct cttctccccg cttgtctctg gcccctgcag aggcttggaa ggccaaaaag     60
aaagcaggag ctgcagcatg ccaacagttc cccactgctc cggggcagcc actccttaga    120
gctccgggcc tgtgagttag gaaatagagg ttccaagaac cttcccaaa gcccaggagc    180
tgtgccccaa gctctggttg cctggcgggc cctgggaccg aaactcctca gctcctcaaa    240
tgagctggtt actcgtcatc tccctccagc accctctttt cctcatgaaa ctcccccaac    300
tcagagtcaa cagacccagc ctccggtggc accacaggct ccctcctcca tcctgctgcc    360
agcagccccc atccccatcc ttagcccctg cagtcccct agccccagg cctcttccct    420
ctctggcccc agcccagctt ccagtcgcct gtccagctcc tcactgtcat ccctggggga    480
ggatcaagac agcgtgctga cccctgagga ggtagccctg tgcttggaac tcagtgaggg    540
tgaggagact cccaggaaca gcgtctctcc catgccaagg gttccttcac ccccaccac    600
ctatgggtac atcagcgtcc caacagcctc agagttcacg gacatgggca ggactggagg    660
aggggtgggg cccaaggggg gagtcttgct gtgcccacct cggccctgcc tcaccccac    720
ccccagcgag ggctccttag ccaatggttg gggctcagcc tctgaggaca atgccgccag    780
cgccagagcc agccttgtca gctcctccga tggctccttc ctcgctgatg ctcactttgc    840
```

```
ccgggccctg gcagtggctg tggatagctt tggtttcggt ctagagccca gggaggcaga    900
ctgcgtcttc atagatgcct catcacctcc ctccccacgg gattgagatc ttcctgaccc    960
ccaacctctc cctgcccctg tgggaagtgg aggccagact ggttggaaga caatggaagg   1020
tca                                                                 1023
```

<210> SEQ ID NO 29
<211> LENGTH: 1271
<212> TYPE: DNA
<213> ORGANISM: Mus musculus

<400> SEQUENCE: 29

```
gggtctttac agttttatag aattaagttc cttaagctca gagtgggggt agaaatgaga     60 ataggaatt ggttccctgt cttcctgcgt ccttatcctt tcagtctcct ccaatgattt    120
cactttgaag gattgaatgt gaggctgtat aggggccagt gcatccagaa cgtttctcca    180
taagtttcct tggatggttg tgaatgggga aagggttgag ttggtgttgt aagggaggag    240
tccaagttaa tattagaggg gtcttccaca ggtccaccaa cagaggccct caccaaaaaa    300
catttctgtc cttcctgaag acctggttgg cttcccttct ttccatgatc cacttaggcg    360
ggagctccgg agccaggctt acttaggcca aaggttctgg ttgtggagag tctgctgtcc    420
tgaagatgct gtcttgttct cagtgggaat ccaagactcc cgtgatcata ttttggtttg    480
ctttcattta ttttaacaat cccaatgaca gagctctcca aagcctagt gacagtggac     540 ttctattaca gagaagcata ggccaagacc tccacatgtg agaaagccag ggacagaca     600 ggagagtggt ctgggtgctc ttctggcctt tcagggaca attcaggagg aatcacacag     660
ccttgggcac agcaccagtt agccaacttc gctgggaaga ggccctagaa tcaggaggcc    720
agggaggcag ccccctcccc agcctctggg tgtggctgat ctcagcatct tccaaccagt    780
ctggcctcca ctcccacaaa ggcagagaga agcttcgggt cagggagaga tcaccccgag    840
gggagggagg tgatgaggca tcagtgaaga cacagtcagc ttccctggga tccagactga    900
ggccaaagct atcccacagcc actgccaggg cacgagcaaa gtgagtatca gcgaggaagg    960
agccatcaga agagctaacc aggctggccc tggcgctggg gacattgtcc tcagaagctg   1020
agccccaacc attggccagg gagccctcgc tgggtgtagg ggtggggcag ggccgaggtg   1080
gatacagtaa gttcccaacc tcagacccca cgccccgcc agctctgccc atgtctgcca   1140
gtcctgagca ggttggtatg ctgatatagc cataggttgt tggcggggaa ggagctcttg   1200
gcataggaga tacactgttc gtgggtgtct cctccccatc actgagctcc agacacaggg   1260
ctacctcctc g                                                        1271
```

<210> SEQ ID NO 30
<211> LENGTH: 205
<212> TYPE: PRT
<213> ORGANISM: Mus musculus

<400> SEQUENCE: 30

```
Glu Glu Val Ala Leu Cys Leu Glu Leu Ser Asp Gly Glu Glu Thr Pro
 1               5                  10                  15

Thr Asn Ser Val Ser Pro Met Pro Arg Ala Pro Ser Pro Pro Thr Thr
            20                  25                  30

Tyr Gly Tyr Ile Ser Ile Pro Thr Cys Ser Gly Leu Ala Asp Met Gly
        35                  40                  45

Arg Ala Gly Gly Gly Val Gly Ser Glu Val Gly Asn Leu Leu Tyr Pro
    50                  55                  60
```

Pro Arg Pro Cys Pro Thr Pro Thr Pro Ser Glu Gly Ser Leu Ala Asn
65                  70                  75                  80

Gly Trp Gly Ser Ala Ser Glu Asp Asn Val Pro Ser Ala Arg Ala Ser
                85                  90                  95

Leu Val Ser Ser Ser Asp Gly Ser Phe Leu Ala Asp Thr His Phe Ala
            100                 105                 110

Arg Ala Leu Ala Val Ala Val Asp Ser Phe Gly Leu Ser Leu Asp Pro
            115                 120                 125

Arg Glu Ala Asp Cys Val Phe Thr Asp Ala Ser Ser Pro Pro Ser Pro
130                 135                 140

Arg Gly Asp Leu Ser Leu Thr Arg Ser Phe Ser Leu Pro Leu Trp Glu
145                 150                 155                 160

Trp Arg Pro Asp Trp Leu Glu Asp Ala Glu Ile Ser His Thr Gln Arg
                165                 170                 175

Leu Gly Arg Gly Leu Pro Pro Trp Pro Pro Asp Ser Arg Ala Ser Ser
            180                 185                 190

Gln Arg Ser Trp Leu Thr Gly Ala Val Pro Lys Ala Val
            195                 200                 205

<210> SEQ ID NO 31
<211> LENGTH: 417
<212> TYPE: PRT
<213> ORGANISM: Homo sapiens

<400> SEQUENCE: 31

Met Asp His Ser Asp Ser Gln Trp Leu Ala Asp Thr Trp Arg Ser Thr
1               5                   10                  15

Ser Gly Ser Arg Asp Leu Ser Ser Ser Ser Leu Ser Ser Arg Leu
            20                  25                  30

Gly Ala Asp Ala Arg Asp Pro Leu Asp Cys Arg Arg Ser Leu Leu Ser
            35                  40                  45

Trp Asp Ser Arg Ser Pro Gly Val Pro Leu Leu Pro Asp Thr Ser Thr
50                  55                  60

Phe Tyr Gly Ser Leu Ile Ala Glu Leu Pro Ser Thr Pro Ala Arg
65                  70                  75                  80

Pro Ser Pro Gln Val Pro Ala Val Arg Arg Leu Pro Pro Gln Leu Ala
                85                  90                  95

Gln Leu Ser Ser Pro Cys Ser Ser Ser Asp Ser Leu Cys Ser Arg Arg
            100                 105                 110

Gly Leu Ser Ser Pro Arg Leu Ser Leu Ala Pro Ala Glu Ala Trp Lys
            115                 120                 125

Ala Lys Lys Lys Gln Glu Leu Gln His Ala Asn Ser Ser Pro Leu Leu
130                 135                 140

Arg Gly Ser His Ser Leu Glu Leu Arg Ala Cys Glu Leu Gly Asn Arg
145                 150                 155                 160

Gly Ser Lys Asn Leu Ser Gln Ser Pro Gly Ala Val Pro Gln Ala Leu
                165                 170                 175

Val Ala Trp Arg Ala Leu Gly Pro Lys Leu Leu Ser Ser Ser Asn Glu
            180                 185                 190

Leu Val Thr Arg His Leu Pro Pro Ala Pro Leu Phe Pro His Glu Thr
            195                 200                 205

Pro Pro Thr Gln Ser Gln Gln Thr Gln Pro Pro Val Ala Pro Gln Ala
210                 215                 220

Pro Ser Ser Ile Leu Leu Pro Ala Ala Pro Ile Pro Ile Leu Ser Pro

```
                225                 230                 235                 240
Cys Ser Pro Pro Ser Pro Gln Ala Ser Ser Leu Ser Gly Pro Ser Pro
                    245                 250                 255
Ala Ser Ser Arg Leu Ser Ser Ser Leu Ser Ser Leu Gly Glu Asp
        260                 265                 270
Gln Asp Ser Val Leu Thr Pro Glu Glu Val Ala Leu Cys Leu Glu Leu
            275                 280                 285
Ser Glu Gly Glu Glu Thr Pro Arg Asn Ser Val Ser Pro Met Pro Arg
    290                 295                 300
Ala Pro Ser Pro Pro Thr Thr Tyr Gly Tyr Ile Ser Val Pro Thr Ala
305                 310                 315                 320
Ser Glu Phe Thr Asp Met Gly Arg Thr Gly Gly Val Gly Pro Lys
                325                 330                 335
Gly Gly Val Leu Leu Cys Pro Pro Arg Pro Cys Leu Thr Pro Thr Pro
            340                 345                 350
Ser Glu Gly Ser Leu Ala Asn Gly Trp Gly Ser Ala Ser Glu Asp Asn
                355                 360                 365
Ala Ala Ser Ala Arg Ala Ser Leu Val Ser Ser Asp Gly Ser Phe
370                 375                 380
Leu Ala Asp Ala His Phe Ala Arg Ala Leu Ala Val Ala Val Asp Ser
385                 390                 395                 400
Phe Gly Phe Gly Leu Glu Pro Arg Glu Ala Asp Cys Val Phe Ile Gly
                    405                 410                 415
Met
```

<210> SEQ ID NO 32
<211> LENGTH: 516
<212> TYPE: PRT
<213> ORGANISM: Mus musculus

<400> SEQUENCE: 32

```
Pro Thr Val Thr Tyr Gln Arg Gly Gly Glu Ala Val Ser Ser Gly Gly
1               5                   10                  15
Arg Pro Gly Leu Leu Asn Ile Ser Glu Pro Ala Thr Gln Pro Trp Leu
            20                  25                  30
Ala Asp Thr Trp Pro Asn Thr Gly Asn Asn His Asn Asp Cys Ser Ile
        35                  40                  45
Asn Cys Cys Thr Ala Gly Asn Gly Asn Ser Asp Ser Asn Leu Thr Thr
    50                  55                  60
Tyr Ser Arg Pro Ala Asp Cys Ile Ala Asn Tyr Asn Asn Gln Leu Asp
65                  70                  75                  80
Asn Lys Gln Thr Asn Leu Met Leu Pro Glu Ser Thr Val Tyr Gly Asp
                85                  90                  95
Val Asp Leu Ser Asn Lys Ile Asn Glu Met Lys Thr Phe Asn Ser Pro
            100                 105                 110
Asn Leu Lys Asp Gly Arg Phe Val Asn Pro Ser Gly Gln Pro Thr Pro
        115                 120                 125
Tyr Ala Thr Thr Gln Leu Ile Gln Ala Asn Leu Ser Asn Asn Met Asn
    130                 135                 140
Asn Gly Ala Gly Asp Ser Ser Glu Lys His Trp Lys Pro Pro Gly Gln
145                 150                 155                 160
Gln Lys Pro Glu Val Ala Pro Ile Gln Tyr Asn Ile Met Glu Gln Asn
                165                 170                 175
Lys Leu Asn Lys Asp Tyr Arg Ala Asn Asp Thr Ile Pro Pro Thr Ile
```

```
                180             185             190
Pro Tyr Asn Gln Ser Tyr Asp Gln Asn Thr Gly Gly Ser Tyr Asn Ser
            195                 200                 205

Ser Asp Arg Gly Ser Ser Thr Ser Gly Ser Gln Gly His Lys Lys Gly
210                 215                 220

Ala Arg Thr Pro Lys Ala Pro Lys Gln Gly Gly Met Asn Trp Ala Asp
225                 230                 235                 240

Leu Leu Pro Pro Pro Ala His Pro Pro His Ser Asn Ser Glu
                245                 250                 255

Glu Tyr Asn Met Ser Val Asp Glu Ser Tyr Asp Gln Glu Met Pro Cys
            260                 265                 270

Pro Val Pro Pro Ala Pro Met Tyr Leu Gln Gln Asp Glu Leu Gln Glu
                275                 280                 285

Glu Glu Asp Glu Arg Gly Pro Thr Pro Pro Val Arg Gly Ala Ala Ser
            290                 295                 300

Ser Pro Ala Ala Val Ser Tyr Ser His Gln Ser Thr Ala Thr Leu Thr
305                 310                 315                 320

Pro Ser Pro Gln Glu Glu Leu Gln Pro Met Leu Gln Asp Cys Pro Glu
                325                 330                 335

Asp Leu Gly His Met Pro His Pro Pro Asp Arg Arg Arg Gln Pro Val
                340                 345                 350

Ser Pro Pro Pro Pro Arg Pro Ile Ser Pro Pro His Thr Tyr Gly
            355                 360                 365

Tyr Ile Ser Gly Pro Leu Val Ser Asp Met Asp Thr Asp Ala Pro Glu
370                 375                 380

Glu Glu Glu Asp Glu Ala Asp Met Glu Val Ala Lys Met Gln Thr Arg
385                 390                 395                 400

Arg Leu Leu Leu Arg Gly Leu Glu Gln Thr Pro Ala Ser Ser Val Gly
                405                 410                 415

Asp Leu Glu Ser Ser Val Thr Gly Ser Met Ile Asn Gly Trp Gly Ser
                420                 425                 430

Ala Ser Glu Glu Asp Asn Ile Ser Ser Gly Arg Ser Ser Val Ser Ser
            435                 440                 445

Ser Asp Gly Ser Phe Phe Thr Asp Ala Asp Phe Ala Gln Ala Val Ala
        450                 455                 460

Ala Ala Ala Glu Tyr Ala Gly Leu Lys Val Ala Arg Arg Gln Met Gln
465                 470                 475                 480

Asp Ala Ala Gly Arg Arg His Phe His Ala Ser Gln Cys Pro Arg Pro
                485                 490                 495

Thr Ser Pro Val Ser Thr Asp Ser Asn Met Ser Ala Val Val Ile Gln
            500                 505                 510

Lys Ala Arg Pro
        515

<210> SEQ ID NO 33
<211> LENGTH: 297
<212> TYPE: PRT
<213> ORGANISM: Mus musculus

<400> SEQUENCE: 33

Thr Ala Thr Leu Thr Pro Ser Pro Gln Glu Glu Leu Gln Pro Met Leu
 1               5                  10                  15

Gln Asp Cys Pro Glu Asp Leu Gly His Met Pro His Pro Pro Asp Arg
                20                  25                  30
```

```
Arg Arg Gln Pro Val Ser Pro Pro Pro Arg Pro Ile Ser Pro
        35                  40                  45

Pro His Thr Tyr Gly Tyr Ile Ser Gly Pro Leu Val Ser Asp Met Asp
50                      55                  60

Thr Asp Ala Pro Glu Glu Glu Asp Glu Ala Asp Met Glu Val Ala
65                  70                  75                  80

Lys Met Gln Thr Arg Arg Leu Leu Leu Arg Gly Leu Glu Gln Thr Pro
                85                  90                  95

Ala Ser Ser Val Gly Asp Leu Glu Ser Ser Val Thr Gly Ser Met Ile
            100                 105                 110

Asn Gly Trp Gly Ser Ala Ser Glu Glu Asp Asn Ile Ser Ser Gly Arg
            115                 120                 125

Ser Ser Val Ser Ser Ser Asp Gly Ser Phe Phe Thr Asp Ala Asp Phe
        130                 135                 140

Ala Gln Ala Val Ala Ala Ala Glu Tyr Ala Gly Leu Lys Val Ala
145                 150                 155                 160

Arg Arg Gln Met Gln Asp Ala Ala Gly Arg Arg His Phe His Ala Ser
                165                 170                 175

Gln Cys Pro Arg Pro Thr Ser Pro Val Ser Thr Asp Ser Asn Met Ser
            180                 185                 190

Ala Val Val Ile Gln Lys Ala Arg Pro Ala Lys Lys Gln Lys His Gln
            195                 200                 205

Pro Gly His Leu Arg Arg Glu Ala Tyr Ala Asp Asp Leu Pro Pro Pro
        210                 215                 220

Pro Val Pro Pro Pro Ala Ile Lys Ser Pro Thr Val Gln Ser Lys Ala
225                 230                 235                 240

Gln Leu Glu Val Arg Pro Val Met Val Pro Lys Leu Ala Ser Ile Glu
                245                 250                 255

Ala Arg Thr Asp Arg Ser Ser Asp Arg Lys Gly Gly Ser Tyr Lys Gly
            260                 265                 270

Arg Glu Ala Leu Asp Gly Arg Gln Val Thr Asp Leu Arg Thr Asn Pro
        275                 280                 285

Ser Asp Pro Arg Glu Ala Gln Glu Gln
        290                 295

<210> SEQ ID NO 34
<211> LENGTH: 135
<212> TYPE: PRT
<213> ORGANISM: Mus musculus

<400> SEQUENCE: 34

Glu Glu Val Ala Leu Cys Leu Glu Leu Ser Asp Gly Glu Glu Thr Pro
1               5                   10                  15

Thr Asn Ser Val Ser Pro Met Pro Arg Ala Pro Ser Pro Pro Thr Thr
                20                  25                  30

Tyr Gly Tyr Ile Ser Ile Pro Thr Cys Ser Gly Leu Ala Asp Met Gly
            35                  40                  45

Arg Ala Gly Gly Gly Val Gly Ser Glu Val Gly Asn Leu Leu Tyr Pro
50                  55                  60

Pro Arg Pro Cys Pro Thr Pro Thr Pro Ser Glu Gly Ser Leu Ala Asn
65                  70                  75                  80

Gly Trp Gly Ser Ala Ser Glu Asp Asn Val Pro Ser Ala Arg Ala Ser
                85                  90                  95

Leu Val Ser Ser Ser Asp Gly Ser Phe Leu Ala Asp Thr His Phe Ala
            100                 105                 110
```

```
Arg Ala Leu Ala Val Ala Val Asp Ser Phe Gly Leu Ser Leu Asp Pro
        115                 120                 125

Arg Glu Ala Asp Cys Val Phe
        130                 135

<210> SEQ ID NO 35
<211> LENGTH: 135
<212> TYPE: PRT
<213> ORGANISM: Homo sapiens

<400> SEQUENCE: 35

Glu Glu Val Ala Leu Cys Leu Glu Leu Ser Glu Gly Glu Glu Thr Pro
 1               5                  10                  15

Arg Asn Ser Val Ser Pro Met Pro Arg Ala Pro Ser Pro Pro Thr Thr
                20                  25                  30

Tyr Gly Tyr Ile Ser Val Pro Thr Ala Ser Glu Phe Thr Asp Met Gly
            35                  40                  45

Arg Thr Gly Gly Gly Val Gly Pro Lys Gly Gly Val Leu Leu Cys Pro
        50                  55                  60

Pro Arg Pro Cys Leu Thr Pro Thr Pro Ser Glu Gly Ser Leu Ala Asn
65                  70                  75                  80

Gly Trp Gly Ser Ala Ser Glu Asp Asn Ala Ala Ser Ala Arg Ala Ser
                85                  90                  95

Leu Val Ser Ser Ser Asp Gly Ser Phe Leu Ala Asp Ala His Phe Ala
                100                 105                 110

Arg Ala Leu Ala Val Ala Val Asp Ser Phe Gly Phe Gly Leu Glu Pro
        115                 120                 125

Arg Glu Ala Asp Cys Val Phe
        130                 135

<210> SEQ ID NO 36
<211> LENGTH: 3715
<212> TYPE: DNA
<213> ORGANISM: Homo sapiens
<220> FEATURE:
<221> NAME/KEY: CDS
<222> LOCATION: (70)...(3381)

<400> SEQUENCE: 36
gcggccgcga attcggcacg agcagcagga caaagtgctc gggacaagga catagggctg      60 agagtagcc atg ggc tct gga gga gac agc ctc ctg ggg ggc agg ggt tcc     111
          Met Gly Ser Gly Gly Asp Ser Leu Leu Gly Gly Arg Gly Ser
              1               5                  10 ctg cct ctg ctg ctc ctg ctc atc atg gga ggc atg gct cag gac tcc       159
Leu Pro Leu Leu Leu Leu Leu Ile Met Gly Gly Met Ala Gln Asp Ser
 15                  20                  25                  30 ccg ccc cag atc cta gtc cac ccc cag gac cag ctg ttc cag ggc cct       207
Pro Pro Gln Ile Leu Val His Pro Gln Asp Gln Leu Phe Gln Gly Pro
                 35                  40                  45 ggc cct gcc agg atg agc tgc caa gcc tca ggc cag cca cct ccc acc       255
Gly Pro Ala Arg Met Ser Cys Gln Ala Ser Gly Gln Pro Pro Pro Thr
             50                  55                  60 atc cgc tgg ttg ctg aat ggg cag ccc ctg agc atg gtg ccc cca gac       303
Ile Arg Trp Leu Leu Asn Gly Gln Pro Leu Ser Met Val Pro Pro Asp
         65                  70                  75 cca cac cac ctc ctg cct gat ggg acc ctt ctg ctg cta cag ccc cct       351
Pro His His Leu Leu Pro Asp Gly Thr Leu Leu Leu Leu Gln Pro Pro
     80                  85                  90
```

```
gcc cgg gga cat gcc cac gat ggc cag gcc ctg tcc aca gac ctg ggt    399
Ala Arg Gly His Ala His Asp Gly Gln Ala Leu Ser Thr Asp Leu Gly
 95             100                 105                 110 gtc tac aca tgt gag gcc agc aac cgg ctt ggc acg gca gtc agc aga    447
Val Tyr Thr Cys Glu Ala Ser Asn Arg Leu Gly Thr Ala Val Ser Arg
                115                 120                 125 ggc gct cgg ctg tct gtg gct gtc ctc cgg gag gat ttc cag atc cag    495
Gly Ala Arg Leu Ser Val Ala Val Leu Arg Glu Asp Phe Gln Ile Gln
        130                 135                 140 cct cgg gac atg gtg gct gtg gtg ggt gag cag ttt act ctg gaa tgt    543
Pro Arg Asp Met Val Ala Val Val Gly Glu Gln Phe Thr Leu Glu Cys
145                 150                 155 ggg ccg ccc tgg ggc cac cca gag ccc aca gtc tca tgg tgg aaa gat    591
Gly Pro Pro Trp Gly His Pro Glu Pro Thr Val Ser Trp Trp Lys Asp
    160                 165                 170 ggg aaa ccc ctg gcc ctc cag ccc gga agg cac aca gtg tcc ggg ggg    639
Gly Lys Pro Leu Ala Leu Gln Pro Gly Arg His Thr Val Ser Gly Gly
175                 180                 185                 190 tcc ctg ctg atg gca aga gca gag aag agt gac gaa ggg acc tac atg    687
Ser Leu Leu Met Ala Arg Ala Glu Lys Ser Asp Glu Gly Thr Tyr Met
                195                 200                 205 tgt gtg gcc acc aac agc gca gga cat agg gag agc cgc gca gcc cgg    735
Cys Val Ala Thr Asn Ser Ala Gly His Arg Glu Ser Arg Ala Ala Arg
        210                 215                 220 gtt tcc atc cag gag ccc cag gac tac acg gag cct gtg gag ctt ctg    783
Val Ser Ile Gln Glu Pro Gln Asp Tyr Thr Glu Pro Val Glu Leu Leu
225                 230                 235 gct gtg cga att cag ctg gaa aat gtg aca ctg ctg aac ccg gat cct    831
Ala Val Arg Ile Gln Leu Glu Asn Val Thr Leu Leu Asn Pro Asp Pro
240                 245                 250 gca gag ggc ccc aag cct aga ccg gcg gtg tgg ctc agc tgg aag gtc    879
Ala Glu Gly Pro Lys Pro Arg Pro Ala Val Trp Leu Ser Trp Lys Val
255                 260                 265                 270 agt ggc cct gct gcg cct gcc caa tct tac acg gcc ttg ttc agg acc    927
Ser Gly Pro Ala Ala Pro Ala Gln Ser Tyr Thr Ala Leu Phe Arg Thr
                275                 280                 285 cag act gcc ccg gga ggc cag gga gct ccg tgg gca gag gag ctg ctg    975
Gln Thr Ala Pro Gly Gly Gln Gly Ala Pro Trp Ala Glu Glu Leu Leu
        290                 295                 300 gcc ggc tgg cag agc gca gag ctt gga ggc ctc cac tgg ggc caa gac   1023
Ala Gly Trp Gln Ser Ala Glu Leu Gly Gly Leu His Trp Gly Gln Asp
305                 310                 315 tac gag ttc aaa gtg aga cca tcc tct ggc cgg gct cga ggc cct gac   1071
Tyr Glu Phe Lys Val Arg Pro Ser Ser Gly Arg Ala Arg Gly Pro Asp
320                 325                 330 agc aac gtg ctc ctc ctg agg ctg ccg gaa aaa gtg ccc agt gcc cca   1119
Ser Asn Val Leu Leu Leu Arg Leu Pro Glu Lys Val Pro Ser Ala Pro
335                 340                 345                 350 cct cag gaa gtg act cta aag cct ggc aat ggc act gtc ttt gtg agc   1167
Pro Gln Glu Val Thr Leu Lys Pro Gly Asn Gly Thr Val Phe Val Ser
                355                 360                 365 tgg gtc cca cca cct gct gaa aac cac aat ggc atc atc cgt ggc tac   1215
Trp Val Pro Pro Pro Ala Glu Asn His Asn Gly Ile Ile Arg Gly Tyr
        370                 375                 380 cag gtc tgg agc ctg ggc aac aca tca ctg cca cca gcc aac tgg act   1263
Gln Val Trp Ser Leu Gly Asn Thr Ser Leu Pro Pro Ala Asn Trp Thr
                385                 390                 395 gta gtt ggt gag cag acc cag ctg gaa atc gcc acc cat atg cca ggc   1311
Val Val Gly Glu Gln Thr Gln Leu Glu Ile Ala Thr His Met Pro Gly
400                 405                 410
```

-continued

| | |
|---|---|
| tcc tac tgc gtg caa gtg gct gca gtc act ggt gct gga gct ggg gag<br>Ser Tyr Cys Val Gln Val Ala Ala Val Thr Gly Ala Gly Ala Gly Glu<br>415                     420                              425                            430 | 1359 |
| ccc agt aga cct gtc tgc ctc ctt tta gag cag gcc atg gag cga gcc<br>Pro Ser Arg Pro Val Cys Leu Leu Leu Glu Gln Ala Met Glu Arg Ala<br>                           435                              440                            445 | 1407 |
| acc caa gaa ccc agt gag cat ggt ccc tgg acc ctg gag cag ctg agg<br>Thr Gln Glu Pro Ser Glu His Gly Pro Trp Thr Leu Glu Gln Leu Arg<br>                   450                              455                            460 | 1455 |
| gct acc ttg aag cgg cct gag gtc att gcc acc tgc ggt gtt gca ctc<br>Ala Thr Leu Lys Arg Pro Glu Val Ile Ala Thr Cys Gly Val Ala Leu<br>         465                             470                            475 | 1503 |
| tgg ctg ctg ctt ctg ggc acc gcc gtg tgt atc cac cgc cgg cgc cga<br>Trp Leu Leu Leu Leu Gly Thr Ala Val Cys Ile His Arg Arg Arg Arg<br>480                              485                              490 | 1551 |
| gct agg gtg cac ctg ggc cca ggt ctg tac aga tat acc agt gag gat<br>Ala Arg Val His Leu Gly Pro Gly Leu Tyr Arg Tyr Thr Ser Glu Asp<br>495                     500                              505                            510 | 1599 |
| gcc atc cta aaa cac agg atg gat cac agt gac tcc cag tgg ttg gca<br>Ala Ile Leu Lys His Arg Met Asp His Ser Asp Ser Gln Trp Leu Ala<br>                   515                              520                            525 | 1647 |
| gac act tgg cgt tcc acc tct ggc tct cgg gac ctg agc agc agc agc<br>Asp Thr Trp Arg Ser Thr Ser Gly Ser Arg Asp Leu Ser Ser Ser Ser<br>                   530                              535                            540 | 1695 |
| agc ctc agc agt cgg ctg ggg gcg gat gcc cgg gac cca cta gac tgt<br>Ser Leu Ser Ser Arg Leu Gly Ala Asp Ala Arg Asp Pro Leu Asp Cys<br>         545                             550                            555 | 1743 |
| cgt cgc tcc ttg ctc tcc tgg gac tcc cga agc ccc ggc gtg ccc ctg<br>Arg Arg Ser Leu Leu Ser Trp Asp Ser Arg Ser Pro Gly Val Pro Leu<br>560                              565                              570 | 1791 |
| ctt cca gac acc agc act ttt tat ggc tcc ctc atc gct gag ctg ccc<br>Leu Pro Asp Thr Ser Thr Phe Tyr Gly Ser Leu Ile Ala Glu Leu Pro<br>575                     580                              585                            590 | 1839 |
| tcc agt acc cca gcc agg cca agt ccc cag gtc cca gct gtc agg cgc<br>Ser Ser Thr Pro Ala Arg Pro Ser Pro Gln Val Pro Ala Val Arg Arg<br>                   595                              600                            605 | 1887 |
| ctc cca ccc cag ctg gcc cag ctc tcc agc ccc tgt tcc agc tca gac<br>Leu Pro Pro Gln Leu Ala Gln Leu Ser Ser Pro Cys Ser Ser Ser Asp<br>                   610                              615                            620 | 1935 |
| agc ctc tgc agc cgc agg gga ctc tct tct ccc cgc ttg tct ctg gcc<br>Ser Leu Cys Ser Arg Arg Gly Leu Ser Ser Pro Arg Leu Ser Leu Ala<br>         625                             630                            635 | 1983 |
| cct gca gag gct tgg aag gcc aaa aag aag cag gag ctg cag cat gcc<br>Pro Ala Glu Ala Trp Lys Ala Lys Lys Lys Gln Glu Leu Gln His Ala<br>640                              645                              650 | 2031 |
| aac agt tcc cca ctg ctc cgg ggc agc cac tcc ttg gag ctc cgg gcc<br>Asn Ser Ser Pro Leu Leu Arg Gly Ser His Ser Leu Glu Leu Arg Ala<br>655                     660                              665                            670 | 2079 |
| tgt gag tta gga aat aga ggt tcc aag aac ctt tcc caa agc cca gga<br>Cys Glu Leu Gly Asn Arg Gly Ser Lys Asn Leu Ser Gln Ser Pro Gly<br>                   675                              680                            685 | 2127 |
| gct gtg ccc caa gct ctg gtt gcc tgg cgg gcc ctg gga ccg aaa ctc<br>Ala Val Pro Gln Ala Leu Val Ala Trp Arg Ala Leu Gly Pro Lys Leu<br>         690                             695                            700 | 2175 |
| ctc agc tcc tca aat gag ctg gtt act cgt cat ctc cct cca gca ccc<br>Leu Ser Ser Ser Asn Glu Leu Val Thr Arg His Leu Pro Pro Ala Pro<br>705                              710                              715 | 2223 |
| ctc ttt cct cat gaa act ccc cca act cag agt caa cag acc cag cct<br>Leu Phe Pro His Glu Thr Pro Pro Thr Gln Ser Gln Gln Thr Gln Pro | 2271 |

-continued

```
                720                 725                 730
ccg gtg gca cca cag gct ccc tcc tcc atc ctg ctg cca gca gcc ccc       2319
Pro Val Ala Pro Gln Ala Pro Ser Ser Ile Leu Leu Pro Ala Ala Pro
735                 740                 745                 750 atc ccc atc ctt agc ccc tgc agt ccc cct agc ccc cag gcc tct tcc       2367
Ile Pro Ile Leu Ser Pro Cys Ser Pro Pro Ser Pro Gln Ala Ser Ser
                755                 760                 765 ctc tct ggc ccc agc cca gct tcc agt cgc ctg tcc agc tcc tca ctg       2415
Leu Ser Gly Pro Ser Pro Ala Ser Ser Arg Leu Ser Ser Ser Ser Leu
            770                 775                 780 tca tcc ctg ggg gag gat caa gac agc gtg ctg acc cct gag gag gta       2463
Ser Ser Leu Gly Glu Asp Gln Asp Ser Val Leu Thr Pro Glu Glu Val
        785                 790                 795 gcc ctg tgc ttg gaa ctc agt gag ggt gag gag act ccc agg aac agc       2511
Ala Leu Cys Leu Glu Leu Ser Glu Gly Glu Glu Thr Pro Arg Asn Ser
    800                 805                 810 gtc tct ccc atg cca agg gct cct tca ccc ccc acc acc tat ggg tac       2559
Val Ser Pro Met Pro Arg Ala Pro Ser Pro Pro Thr Thr Tyr Gly Tyr
815                 820                 825                 830 atc agc gtc cca aca gcc tca gag ttc acg gac atg ggc agg act gga       2607
Ile Ser Val Pro Thr Ala Ser Glu Phe Thr Asp Met Gly Arg Thr Gly
                835                 840                 845 gga ggg gtg ggg ccc aag ggg gga gtc ttg ctg tgc cca cct cgg ccc       2655
Gly Gly Val Gly Pro Lys Gly Gly Val Leu Leu Cys Pro Pro Arg Pro
            850                 855                 860 tgc ctc acc ccc acc ccc agc gag ggc tcc tta gcc aat ggt tgg ggc       2703
Cys Leu Thr Pro Thr Pro Ser Glu Gly Ser Leu Ala Asn Gly Trp Gly
        865                 870                 875 tca gcc tct gag gac aat gcc gcc agc gcc aga gcc agc ctt gtc agc       2751
Ser Ala Ser Glu Asp Asn Ala Ala Ser Ala Arg Ala Ser Leu Val Ser
    880                 885                 890 tcc tcc gat ggc tcc ttc ctc gct gat gct cac ttt gcc cgg gcc ctg       2799
Ser Ser Asp Gly Ser Phe Leu Ala Asp Ala His Phe Ala Arg Ala Leu
895                 900                 905                 910 gca gtg gct gtg gat agc ttt ggt ttc ggt cta gag ccc agg gag gca       2847
Ala Val Ala Val Asp Ser Phe Gly Phe Gly Leu Glu Pro Arg Glu Ala
                915                 920                 925 gac tgc gtc ttc ata gat gcc tca tca cct ccc tcc cca cgg gat gag       2895
Asp Cys Val Phe Ile Asp Ala Ser Ser Pro Pro Ser Pro Arg Asp Glu
            930                 935                 940 atc ttc ctg acc ccc aac ctc tcc ctg ccc ctg tgg gag tgg agg cca       2943
Ile Phe Leu Thr Pro Asn Leu Ser Leu Pro Leu Trp Glu Trp Arg Pro
        945                 950                 955 gac tgg ttg gaa gac atg gag gtc agc cac acc cag cgg ctg gga agg       2991
Asp Trp Leu Glu Asp Met Glu Val Ser His Thr Gln Arg Leu Gly Arg
    960                 965                 970 ggg atg cct ccc tgg ccc cct gaa ctc tca gat ctc ttc cca gag aag       3039
Gly Met Pro Pro Trp Pro Pro Glu Leu Ser Asp Leu Phe Pro Glu Lys
975                 980                 985                 990 tca gct cca ctg tcg tat gcc caa ggc tgg tgc ttc tcc tgt aga tta       3087
Ser Ala Pro Leu Ser Tyr Ala Gln Gly Trp Cys Phe Ser Cys Arg Leu
                995                 1000                1005 ctc ctg aac cgt gtc cct gag act tcc cag acg gga atc aga acc act       3135
Leu Leu Asn Arg Val Pro Glu Thr Ser Gln Thr Gly Ile Arg Thr Thr
            1010                1015                1020 tct cct gtt cca ccc aca aga cct ggg ctg tgg tgt gtg ggt ctt ggc       3183
Ser Pro Val Pro Pro Thr Arg Pro Gly Leu Trp Cys Val Gly Leu Gly
        1025                1030                1035 ctg tgt ttc tct gca gct ggg gtc cac ctt ccc aag cct cca gag agt       3231
```

```
Leu Cys Phe Ser Ala Ala Gly Val His Leu Pro Lys Pro Pro Glu Ser
    1040                1045                1050 tct ccc tcc acg att gtg aaa aca aat gaa aac aaa att aga gca aag        3279
Ser Pro Ser Thr Ile Val Lys Thr Asn Glu Asn Lys Ile Arg Ala Lys
1055                1060                1065                1070 ctg acc tgg agc cct cag gga gca aaa cat cat ctc cac ctg act cct        3327
Leu Thr Trp Ser Pro Gln Gly Ala Lys His His Leu His Leu Thr Pro
                1075                1080                1085 agc cac tgc ttt ctc ctc tgt gcc atc cac tcc cac cac cag gtt gtt        3375
Ser His Cys Phe Leu Leu Cys Ala Ile His Ser His His Gln Val Val
            1090                1095                1100 ttg gcc tgaggagcag ccctgcctgc tgctcttccc ccaccatttg gatcacagga         3431
Leu Ala agtggaggag ccagaggtgc ctttgtggag gacagcagtg gctgctggga gagggctgtg      3491
gaggaaggag cttctcggag ccccctctca gccttacctg ggcccctcct ctagaagaa       3551 gctcaactct ctcccaacct caccatggaa agaaaataat tatgaatgcc actgaggcac      3611
tgaggcccta cctcatgcca aacaaagggt tcaaggctgg gtctagcgag gatgctgaag      3671
gaagggaggt atgagacccg taggtcaaaa gcaccatcct cgta                       3715

<210> SEQ ID NO 37
<211> LENGTH: 1104
<212> TYPE: PRT
<213> ORGANISM: Homo sapiens

<400> SEQUENCE: 37

Met Gly Ser Gly Gly Asp Ser Leu Leu Gly Arg Gly Ser Leu Pro
 1               5                  10                  15

Leu Leu Leu Leu Leu Ile Met Gly Gly Met Ala Gln Asp Ser Pro Pro
                20                  25                  30

Gln Ile Leu Val His Pro Gln Asp Gln Leu Phe Gln Gly Pro Gly Pro
                35                  40                  45

Ala Arg Met Ser Cys Gln Ala Ser Gly Gln Pro Pro Thr Ile Arg
 50                  55                  60

Trp Leu Leu Asn Gly Gln Pro Leu Ser Met Val Pro Pro Asp Pro His
 65                  70                  75                  80

His Leu Leu Pro Asp Gly Thr Leu Leu Leu Gln Pro Pro Ala Arg
                85                  90                  95

Gly His Ala His Asp Gly Gln Ala Leu Ser Thr Asp Leu Gly Val Tyr
                100                 105                 110

Thr Cys Glu Ala Ser Asn Arg Leu Gly Thr Ala Val Ser Arg Gly Ala
            115                 120                 125

Arg Leu Ser Val Ala Val Leu Arg Glu Asp Phe Gln Ile Gln Pro Arg
        130                 135                 140

Asp Met Val Ala Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
                180                 185                 190

Leu Met Ala Arg Ala Glu Lys Ser Asp Glu Gly Thr Tyr Met Cys Val
            195                 200                 205

Ala Thr Asn Ser Ala Gly His Arg Glu Ser Arg Ala Ala Arg Val Ser
        210                 215                 220

Ile Gln Glu Pro Gln Asp Tyr Thr Glu Pro Val Glu Leu Leu Ala Val
```

```
                225                 230                 235                 240
        Arg Ile Gln Leu Glu Asn Val Thr Leu Leu Asn Pro Asp Pro Ala Glu
                        245                 250                 255
        Gly Pro Lys Pro Arg Pro Ala Val Trp Leu Ser Trp Lys Val Ser Gly
                        260                 265                 270
        Pro Ala Ala Pro Ala Gln Ser Tyr Thr Ala Leu Phe Arg Thr Gln Thr
                        275                 280                 285
        Ala Pro Gly Gly Gln Gly Ala Pro Trp Ala Glu Glu Leu Leu Ala Gly
                        290                 295                 300
        Trp Gln Ser Ala Glu Leu Gly Gly Leu His Trp Gly Gln Asp Tyr Glu
        305                 310                 315                 320
        Phe Lys Val Arg Pro Ser Ser Gly Arg Ala Arg Gly Pro Asp Ser Asn
                        325                 330                 335
        Val Leu Leu Arg Leu Pro Glu Lys Val Pro Ser Ala Pro Pro Gln
                        340                 345                 350
        Glu Val Thr Leu Lys Pro Gly Asn Gly Thr Val Phe Val Ser Trp Val
                        355                 360                 365
        Pro Pro Pro Ala Glu Asn His Asn Gly Ile Ile Arg Gly Tyr Gln Val
                        370                 375                 380
        Trp Ser Leu Gly Asn Thr Ser Leu Pro Pro Ala Asn Trp Thr Val Val
        385                 390                 395                 400
        Gly Glu Gln Thr Gln Leu Glu Ile Ala Thr His Met Pro Gly Ser Tyr
                        405                 410                 415
        Cys Val Gln Val Ala Ala Val Thr Gly Ala Gly Ala Gly Glu Pro Ser
                        420                 425                 430
        Arg Pro Val Cys Leu Leu Leu Glu Gln Ala Met Glu Arg Ala Thr Gln
                        435                 440                 445
        Glu Pro Ser Glu His Gly Pro Trp Thr Leu Glu Gln Leu Arg Ala Thr
                        450                 455                 460
        Leu Lys Arg Pro Glu Val Ile Ala Thr Cys Gly Val Ala Leu Trp Leu
        465                 470                 475                 480
        Leu Leu Leu Gly Thr Ala Val Cys Ile His Arg Arg Arg Arg Ala Arg
                        485                 490                 495
        Val His Leu Gly Pro Gly Leu Tyr Arg Tyr Thr Ser Glu Asp Ala Ile
                        500                 505                 510
        Leu Lys His Arg Met Asp His Ser Asp Ser Gln Trp Leu Ala Asp Thr
                        515                 520                 525
        Trp Arg Ser Thr Ser Gly Ser Arg Asp Leu Ser Ser Ser Ser Ser Leu
                        530                 535                 540
        Ser Ser Arg Leu Gly Ala Asp Ala Arg Asp Pro Leu Asp Cys Arg Arg
        545                 550                 555                 560
        Ser Leu Leu Ser Trp Asp Ser Arg Ser Pro Gly Val Pro Leu Leu Pro
                        565                 570                 575
        Asp Thr Ser Thr Phe Tyr Gly Ser Leu Ile Ala Glu Leu Pro Ser Ser
                        580                 585                 590
        Thr Pro Ala Arg Pro Ser Pro Gln Val Pro Ala Val Arg Arg Leu Pro
                        595                 600                 605
        Pro Gln Leu Ala Gln Leu Ser Ser Pro Cys Ser Ser Ser Asp Ser Leu
                        610                 615                 620
        Cys Ser Arg Arg Gly Leu Ser Ser Pro Arg Leu Ser Leu Ala Pro Ala
        625                 630                 635                 640
        Glu Ala Trp Lys Ala Lys Lys Lys Gln Glu Leu Gln His Ala Asn Ser
                        645                 650                 655
```

-continued

```
Ser Pro Leu Leu Arg Gly Ser His Ser Leu Glu Leu Arg Ala Cys Glu
            660                 665                 670

Leu Gly Asn Arg Gly Ser Lys Asn Leu Ser Gln Ser Pro Gly Ala Val
            675                 680                 685

Pro Gln Ala Leu Val Ala Trp Arg Ala Leu Gly Pro Lys Leu Leu Ser
            690                 695                 700

Ser Ser Asn Glu Leu Val Thr Arg His Leu Pro Pro Ala Pro Leu Phe
705                 710                 715                 720

Pro His Glu Thr Pro Pro Thr Gln Ser Gln Gln Thr Gln Pro Pro Val
                725                 730                 735

Ala Pro Gln Ala Pro Ser Ser Ile Leu Leu Pro Ala Ala Pro Ile Pro
            740                 745                 750

Ile Leu Ser Pro Cys Ser Pro Pro Ser Pro Gln Ala Ser Ser Leu Ser
            755                 760                 765

Gly Pro Ser Pro Ala Ser Ser Arg Leu Ser Ser Ser Ser Leu Ser Ser
            770                 775                 780

Leu Gly Glu Asp Gln Asp Ser Val Leu Thr Pro Glu Glu Val Ala Leu
785                 790                 795                 800

Cys Leu Glu Leu Ser Glu Gly Glu Glu Thr Pro Arg Asn Ser Val Ser
                805                 810                 815

Pro Met Pro Arg Ala Pro Ser Pro Pro Thr Thr Tyr Gly Tyr Ile Ser
            820                 825                 830

Val Pro Thr Ala Ser Glu Phe Thr Asp Met Gly Arg Thr Gly Gly Gly
            835                 840                 845

Val Gly Pro Lys Gly Gly Val Leu Leu Cys Pro Pro Arg Pro Cys Leu
            850                 855                 860

Thr Pro Thr Pro Ser Glu Gly Ser Leu Ala Asn Gly Trp Gly Ser Ala
865                 870                 875                 880

Ser Glu Asp Asn Ala Ala Ser Ala Arg Ala Ser Leu Val Ser Ser Ser
                885                 890                 895

Asp Gly Ser Phe Leu Ala Asp Ala His Phe Ala Arg Ala Leu Ala Val
            900                 905                 910

Ala Val Asp Ser Phe Gly Phe Gly Leu Glu Pro Arg Glu Ala Asp Cys
            915                 920                 925

Val Phe Ile Asp Ala Ser Pro Pro Ser Pro Arg Asp Glu Ile Phe
            930                 935                 940

Leu Thr Pro Asn Leu Ser Leu Pro Leu Trp Glu Trp Arg Pro Asp Trp
945                 950                 955                 960

Leu Glu Asp Met Glu Val Ser His Thr Gln Arg Leu Gly Arg Gly Met
                965                 970                 975

Pro Pro Trp Pro Pro Glu Leu Ser Asp Leu Phe Pro Glu Lys Ser Ala
            980                 985                 990

Pro Leu Ser Tyr Ala Gln Gly Trp Cys Phe Ser Cys Arg Leu Leu Leu
            995                 1000                1005

Asn Arg Val Pro Glu Thr Ser Gln Thr Gly Ile Arg Thr Thr Ser Pro
    1010                1015                1020

Val Pro Pro Thr Arg Pro Gly Leu Trp Cys Val Gly Leu Gly Leu Cys
1025                1030                1035                1040

Phe Ser Ala Ala Gly Val His Leu Pro Lys Pro Glu Ser Ser Pro
                1045                1050                1055

Ser Thr Ile Val Lys Thr Asn Glu Asn Lys Ile Arg Ala Lys Leu Thr
    1060                1065                1070
```

```
                      Trp Ser Pro Gln Gly Ala Lys His His Leu His Leu Thr Pro Ser His
                              1075                1080                1085

Cys Phe Leu Leu Cys Ala Ile His Ser His His Gln Val Val Leu Ala
                              1090                1095                1100

<210> SEQ ID NO 38
<211> LENGTH: 3688
<212> TYPE: DNA
<213> ORGANISM: Mus musculus
<220> FEATURE:
<221> NAME/KEY: CDS
<222> LOCATION: (6)...(3050)
<220> FEATURE:
<221> NAME/KEY: CDS
<222> LOCATION: (3393)...(3509)
<220> FEATURE:
<221> NAME/KEY: CDS
<222> LOCATION: (3579)...(3680)

<400> SEQUENCE: 38 agtgt atg gga caa gga gag gag ccg aga gca gcc atg ggc tct gga gga        50
      Met Gly Gln Gly Glu Glu Pro Arg Ala Ala Met Gly Ser Gly Gly
        1               5                  10                  15 acg ggc ctc ctg ggg acg gag tgg cct ctg cct ctg ctg ctg ctt ttc         98
Thr Gly Leu Leu Gly Thr Glu Trp Pro Leu Pro Leu Leu Leu Leu Phe
             20                  25                  30 atc atg gga ggt gag gct ctg gat tct cca ccc cag atc cta gtt cac        146
Ile Met Gly Gly Glu Ala Leu Asp Ser Pro Pro Gln Ile Leu Val His
         35                  40                  45 ccc cag gac cag cta ctt cag ggc tct ggc cca gcc aag atg agg tgc        194
Pro Gln Asp Gln Leu Leu Gln Gly Ser Gly Pro Ala Lys Met Arg Cys
     50                  55                  60 aga tca tcc ggc caa cca cct ccc act atc cgc tgg ctg ctg aat ggg        242
Arg Ser Ser Gly Gln Pro Pro Pro Thr Ile Arg Trp Leu Leu Asn Gly
 65                  70                  75 cag ccc ctc agc atg gcc acc cca gac cta cat tac ctt ttg ccg gat        290
Gln Pro Leu Ser Met Ala Thr Pro Asp Leu His Tyr Leu Leu Pro Asp
 80                  85                  90                  95 ggg acc ctc ctg tta cat cgg ccc tct gtc cag gga cgg cca caa gat        338
Gly Thr Leu Leu Leu His Arg Pro Ser Val Gln Gly Arg Pro Gln Asp
                100                 105                 110 gac cag aac atc ctc tca gca atc ctg ggt gtc tac aca tgt gag gcc        386
Asp Gln Asn Ile Leu Ser Ala Ile Leu Gly Val Tyr Thr Cys Glu Ala
            115                 120                 125 agc aac cgg ctg ggc aca gca gtg agc cgg ggt gct agg ctg tct gtg        434
Ser Asn Arg Leu Gly Thr Ala Val Ser Arg Gly Ala Arg Leu Ser Val
        130                 135                 140 gct gtc ctc cag gag gac ttc cag atc caa cct cgg gac aca gtg gcc        482
Ala Val Leu Gln Glu Asp Phe Gln Ile Gln Pro Arg Asp Thr Val Ala
    145                 150                 155 gtg gtg gga gag agc ttg gtt ctt gag tgt ggt cct ccc tgg ggc tac        530
Val Val Gly Glu Ser Leu Val Leu Glu Cys Gly Pro Pro Trp Gly Tyr
160                 165                 170                 175 cca aaa ccc tcg gtc tca tgg tgg aaa gac ggg aaa ccc ctg tcc ctc        578
Pro Lys Pro Ser Val Ser Trp Trp Lys Asp Gly Lys Pro Leu Val Leu
                180                 185                 190 cag cca ggg agg cgc aca gta tct ggg gat tcc ctg atg gtg tca aga        626
Gln Pro Gly Arg Arg Thr Val Ser Gly Asp Ser Leu Met Val Ser Arg
            195                 200                 205 gca gag aag aat gac tcg ggg acc tat atg tgt atg gcc acc aac aat        674
Ala Glu Lys Asn Asp Ser Gly Thr Tyr Met Cys Met Ala Thr Asn Asn
        210                 215                 220
```

```
gct ggg caa cgg gag agc cga gca gcc agg gtg tct atc cag gaa tcc         722
Ala Gly Gln Arg Glu Ser Arg Ala Ala Arg Val Ser Ile Gln Glu Ser
225                 230                 235 cag gac cac aag gaa cat cta gag ctt ctg gct gtt cgc att cag ctg         770
Gln Asp His Lys Glu His Leu Glu Leu Leu Ala Val Arg Ile Gln Leu
240                 245                 250                 255 gaa aat gtg acc ctg cta aac ccc gaa cct gta aaa ggt ccc aag cct         818
Glu Asn Val Thr Leu Leu Asn Pro Glu Pro Val Lys Gly Pro Lys Pro
                260                 265                 270 ggg cca tcc gtg tgg ctc agc tgg aag gtg agc ggc cct gct gca cct         866
Gly Pro Ser Val Trp Leu Ser Trp Lys Val Ser Gly Pro Ala Ala Pro
            275                 280                 285 gct gag tca tac aca gct ctg ttc agg act cag agg tcc ccc agg gac         914
Ala Glu Ser Tyr Thr Ala Leu Phe Arg Thr Gln Arg Ser Pro Arg Asp
        290                 295                 300 caa gga tct cca tgg aca gag gtg ctg ctg cgt ggc ttg cag agt gca         962
Gln Gly Ser Pro Trp Thr Glu Val Leu Leu Arg Gly Leu Gln Ser Ala
    305                 310                 315 aag ctt ggg ggt ctc cac tgg ggc caa gac tat gaa ttc aaa gtg aga        1010
Lys Leu Gly Gly Leu His Trp Gly Gln Asp Tyr Glu Phe Lys Val Arg
320                 325                 330                 335 ccg tcc tcc ggc cgg gct cga ggc cct gac agc aat gtg ttg ctc ctg        1058
Pro Ser Ser Gly Arg Ala Arg Gly Pro Asp Ser Asn Val Leu Leu Leu
                340                 345                 350 agg ctg cct gaa cag gtg ccc agt gcc cca cct caa gga gtg acc tta        1106
Arg Leu Pro Glu Gln Val Pro Ser Ala Pro Pro Gln Gly Val Thr Leu
                355                 360                 365 aga tct ggc aac ggt agt gtc ttt gtg agt tgg gct cca cca cct gct        1154
Arg Ser Gly Asn Gly Ser Val Phe Val Ser Trp Ala Pro Pro Pro Ala
            370                 375                 380 gaa agc cat aat ggt gtc atc cgt ggt tac cag gtc tgg agc ctg ggc        1202
Glu Ser His Asn Gly Val Ile Arg Gly Tyr Gln Val Trp Ser Leu Gly
        385                 390                 395 aat gcc tca ttg cct gct gcc aac tgg acc gta gtg ggt gaa cag acc        1250
Asn Ala Ser Leu Pro Ala Ala Asn Trp Thr Val Val Gly Glu Gln Thr
400                 405                 410                 415 cag ctg gag atc gcc aca cga ctg cca ggc tcc tat tgt gtg caa gtg        1298
Gln Leu Glu Ile Ala Thr Arg Leu Pro Gly Ser Tyr Cys Val Gln Val
                420                 425                 430 gct gca gtc act gga gct ggt gct gga gaa ctc agt acc cct gtc tgc        1346
Ala Ala Val Thr Gly Ala Gly Ala Gly Glu Leu Ser Thr Pro Val Cys
                435                 440                 445 ctc ctt tta gag cag gcc atg gag caa tca gca cga gac ccc agg aaa        1394
Leu Leu Leu Glu Gln Ala Met Glu Gln Ser Ala Arg Asp Pro Arg Lys
            450                 455                 460 cat gtt ccc tgg acc ctg gaa cag ctg agg gcc acc ttg aga cga cca        1442
His Val Pro Trp Thr Leu Glu Gln Leu Arg Ala Thr Leu Arg Arg Pro
465                 470                 475 gaa gtc att gcc agt agt gct gtc cta ctc tgg ttg ctg cta cta ggc        1490
Glu Val Ile Ala Ser Ser Ala Val Leu Leu Trp Leu Leu Leu Leu Gly
480                 485                 490                 495 att act gtg tgt atc tac aga cga cgc aaa gct ggg gtg cac ctg ggc        1538
Ile Thr Val Cys Ile Tyr Arg Arg Arg Lys Ala Gly Val His Leu Gly
                500                 505                 510 cca ggt ctg tac aga tac acc agc gag gac gcc att cta aaa cac agg        1586
Pro Gly Leu Tyr Arg Tyr Thr Ser Glu Asp Ala Ile Leu Lys His Arg
            515                 520                 525 atg gac cac agt gac tcc cca tgg ctg gca gac acc tgg cgt tcc acc        1634
Met Asp His Ser Asp Ser Pro Trp Leu Ala Asp Thr Trp Arg Ser Thr
            530                 535                 540
```

```
tct ggc tct cga gac ctg agc agc agc agc ctt agt agt cgg ctg      1682
Ser Gly Ser Arg Asp Leu Ser Ser Ser Ser Leu Ser Ser Arg Leu
545                 550                 555 gga ttg gac cct cgg gac cca cta gag ggc agg cgc tcc ttg atc tcc  1730
Gly Leu Asp Pro Arg Asp Pro Leu Glu Gly Arg Arg Ser Leu Ile Ser
560                 565                 570                 575 tgg gac cct cgg agc ccc ggt gta ccc ctg ctt cca gac acg agc acg  1778
Trp Asp Pro Arg Ser Pro Gly Val Pro Leu Leu Pro Asp Thr Ser Thr
                    580                 585                 590 ttt tac ggc tcc ctc att gca gag cag cct tcc agc cct cca gtc cgg  1826
Phe Tyr Gly Ser Leu Ile Ala Glu Gln Pro Ser Ser Pro Pro Val Arg
                595                 600                 605 cca agc ccc aag aca cca gct gct agg cgc ttt cca tcc aag ttg gct  1874
Pro Ser Pro Lys Thr Pro Ala Ala Arg Arg Phe Pro Ser Lys Leu Ala
            610                 615                 620 gga acc tcc agc ccc tgg gct agc tca gat agt ctc tgc agc cgc agg  1922
Gly Thr Ser Ser Pro Trp Ala Ser Ser Asp Ser Leu Cys Ser Arg Arg
625                 630                 635 gga ctc tgt tcc cca cgc atg tct ctg acc cct aca gag gct tgg aag  1970
Gly Leu Cys Ser Pro Arg Met Ser Leu Thr Pro Thr Glu Ala Trp Lys
640                 645                 650                 655 gcc aaa aag aag cag gaa ttg cac caa gct aac agc tcc cca ctg ctc  2018
Ala Lys Lys Lys Gln Glu Leu His Gln Ala Asn Ser Ser Pro Leu Leu
                660                 665                 670 cgg ggc agc cac ccc atg gaa atc tgg gcc tgg gag ttg gga agc aga  2066
Arg Gly Ser His Pro Met Glu Ile Trp Ala Trp Glu Leu Gly Ser Arg
                675                 680                 685 gcc tcc aag aac ctt tct caa agc cca gga gaa gcg ccc cga gcc gtg  2114
Ala Ser Lys Asn Leu Ser Gln Ser Pro Gly Glu Ala Pro Arg Ala Val
            690                 695                 700 gta tcc tgg cgt gct gtg gga cca caa ctt cac cgc aac tcc agt gag  2162
Val Ser Trp Arg Ala Val Gly Pro Gln Leu His Arg Asn Ser Ser Glu
705                 710                 715 ctg gca tct cgt cca ctc cct cca aca ccc ctt tct ctt cgt gga gct  2210
Leu Ala Ser Arg Pro Leu Pro Pro Thr Pro Leu Ser Leu Arg Gly Ala
720                 725                 730                 735 tcc agt cat gac cca cag agc cag tgt gtg gag aag ctc caa gct ccc  2258
Ser Ser His Asp Pro Gln Ser Gln Cys Val Glu Lys Leu Gln Ala Pro
                740                 745                 750 tcc tct gac cca ctg cca gca gcc cct ctc tcc gtc ctc aac tct tcc  2306
Ser Ser Asp Pro Leu Pro Ala Ala Pro Leu Ser Val Leu Asn Ser Ser
                755                 760                 765 aga cct tcc agc ccc cag gcc tct ttc ctc tcc tgt cct agc cca tcc  2354
Arg Pro Ser Ser Pro Gln Ala Ser Phe Leu Ser Cys Pro Ser Pro Ser
            770                 775                 780 tcc agc aac ctg tcc agc tcc tcg ctg tca tcc tta gag gag gag gag  2402
Ser Ser Asn Leu Ser Ser Ser Ser Leu Ser Ser Leu Glu Glu Glu Glu
785                 790                 795 gat cag gac agc gtg ctc acc ccc gag gag gta gcc ctg tgt ctg gag  2450
Asp Gln Asp Ser Val Leu Thr Pro Glu Glu Val Ala Leu Cys Leu Glu
800                 805                 810                 815 ctc agt gat ggg gag gag aca ccc acg aac agt gta tct cct atg cca  2498
Leu Ser Asp Gly Glu Glu Thr Pro Thr Asn Ser Val Ser Pro Met Pro
                820                 825                 830 aga gct cct tcc ccg cca aca acc tat ggc tat atc agc ata cca acc  2546
Arg Ala Pro Ser Pro Pro Thr Thr Tyr Gly Tyr Ile Ser Ile Pro Thr
                835                 840                 845 tgc tca gga ctg gca gac atg ggc aga gct ggg ggg ggc gtg ggg tct  2594
Cys Ser Gly Leu Ala Asp Met Gly Arg Ala Gly Gly Gly Val Gly Ser
```

|     |     |
| --- | --- |
| ``` 850               855               860
gag gtt ggg aac tta ctg tat cca cct cgg ccc tgc ccc acc cct aca
Glu Val Gly Asn Leu Leu Tyr Pro Pro Arg Pro Cys Pro Thr Pro Thr
    865               870               875
``` | 2642 |
| ``` ccc agc gag ggc tcc ctg gcc aat ggt tgg ggc tca gct tct gag gac
Pro Ser Glu Gly Ser Leu Ala Asn Gly Trp Gly Ser Ala Ser Glu Asp
880               885               890               895
``` | 2690 |
| ``` aat gtc ccc agc gcc agg gcc agc ctg gtt agc tct tct gat ggc tcc
Asn Val Pro Ser Ala Arg Ala Ser Leu Val Ser Ser Ser Asp Gly Ser
                  900               905               910
``` | 2738 |
| ``` ttc ctc gct gat act cac ttt gct cgt gcc ctg gca gtg gct gtg gat
Phe Leu Ala Asp Thr His Phe Ala Arg Ala Leu Ala Val Ala Val Asp
                      915               920               925
``` | 2786 |
| ``` agc ttt ggc ctc agt ctg gat ccc agg gaa gct gac tgt gtc ttc act
Ser Phe Gly Leu Ser Leu Asp Pro Arg Glu Ala Asp Cys Val Phe Thr
              930               935               940
``` | 2834 |
| ``` gat gcc tca tca cct ccc tcc cct cgg ggt gat ctc tcc ctg acc cga
Asp Ala Ser Ser Pro Pro Ser Pro Arg Gly Asp Leu Ser Leu Thr Arg
    945               950               955
``` | 2882 |
| ``` agc ttc tct ctg cct ttg tgg gag tgg agg cca gac tgg ttg gaa gat
Ser Phe Ser Leu Pro Leu Trp Glu Trp Arg Pro Asp Trp Leu Glu Asp
960               965               970               975
``` | 2930 |
| ``` gct gag atc agc cac acc cag agg ctg ggg agg ggg ctg cct ccc tgg
Ala Glu Ile Ser His Thr Gln Arg Leu Gly Arg Gly Leu Pro Pro Trp
                  980               985               990
``` | 2978 |
| ``` cct cct gat tct agg gcc tct tcc cag cga agt tgg cta act ggt gct
Pro Pro Asp Ser Arg Ala Ser Ser Gln Arg Ser Trp Leu Thr Gly Ala
                      995              1000              1005
``` | 3026 |
| ``` gtg ccc aag gct ggt gat tcc tcc tgaattgtcc ctgagaaggc cagaagagca
Val Pro Lys Ala Gly Asp Ser Ser
              1010              1015
``` | 3080 |
| `cccagaccac tctcctgtct gtccctggc tttctcacat gtggaggtct tggcctatgc` | 3140 |
| `ttctctgtaa tagaagtcca ccgtcactag gcttctggag agctctgtca ttgggattgt` | 3200 |
| `taaaataaat gaaagcaaac caaaatatga tcacgggagt cttggattcc cactgagaac` | 3260 |
| `aagacagcat cttcaggaca gcagactctc cacaaccaga acctttggcc taagtaagcc` | 3320 |
| `tggctccgga gctcccacct aagtggatca tggaaagaag ggaagccaac caggtcttca` | 3380 |
| ``` ggaaggacag aa atg ttt ttt ggt gag ggc tat ggt gga gga cct gtg gaa
           Met Phe Phe Gly Glu Gly Tyr Gly Gly Gly Pro Val Glu
                      1020              1025
``` | 3431 |
| ``` gag ccc tct cat atc tac ttg gac tcc tcc ctt aga ggc cag ctc aac
Glu Pro Ser His Ile Tyr Leu Asp Ser Ser Leu Arg Gly Gln Leu Asn
    1030              1035              1040
``` | 3479 |
| ``` cct ttc ccc agt cac acc atg caa gga aac taaaggagaa aggtcgtgga
Pro Phe Pro Ser His Thr Met Gln Gly Asn
1045              1050
``` | 3529 |
| ``` tgcagtgggc cctatacagc gtcacagtca atgcttcaaa gtgagatca atg gag gag
                                                      Met Glu Glu
                                                              1055
``` | 3587 |
| ``` act gaa gga aag gac gca ggg aaa cag gga acc aat gcg cta ttc tca
Thr Glu Gly Lys Asp Ala Gly Lys Gln Gly Thr Asn Ala Leu Phe Ser
        1060              1065              1070
``` | 3635 |
| ``` ttc tac cgc cac tct gag ctt aag gaa ctt aat tct ata aaa ctg
Phe Tyr Arg His Ser Glu Leu Lys Glu Leu Asn Ser Ile Lys Leu
    1075              1080              1085
``` | 3680 |
| `taaagacg` | 3688 |

<210> SEQ ID NO 39
<211> LENGTH: 3688
<212> TYPE: DNA
<213> ORGANISM: Mus musculus

<400> SEQUENCE: 39

| | | | | | |
|---|---|---|---|---|---|
| tcacataccc | tgttcctctc | ctcggctctc | gtcggtaccc | gagacctcct | tgcccggagg | 60 |
| acccctgcct | caccggagac | ggagacgacg | acgaaaagta | gtaccctcca | ctccgagacc | 120 |
| taagaggtgg | ggtctaggat | caagtggggg | tcctggtcga | tgaagtcccg | agaccgggtc | 180 |
| ggttctactc | cacgtctagt | aggccggttg | gtggagggtg | ataggcgacc | gacgacttac | 240 |
| ccgtcgggga | gtcgtaccgg | tggggtctgg | atgtaatgga | aaacggccta | ccctgggagg | 300 |
| acaatgtagc | cggagacag | gtccctgccg | gtgttctact | ggtcttgtag | gagagtcgtt | 360 |
| aggacccaca | gatgtgtaca | ctccggtcgt | tggccgaccc | gtgtcgtcac | tcggcccac | 420 |
| gatccgacag | acaccgacag | gaggtcctcc | tgaaggtcta | ggttggagcc | ctgtgtcacc | 480 |
| ggcaccaccc | tctctcgaac | caagaactca | caccaggagg | daccccgatg | ggttttggga | 540 |
| gccagagtac | cacctttctg | cccttgggg | accaggaggt | cggtccctcc | gcgtgtcata | 600 |
| gaccctaag | ggactaccac | agttctcgtc | tcttcttact | gagcccctgg | atatacacat | 660 |
| accggtggtt | gttacgaccc | gttgccctct | cggctcgtcg | gtcccacaga | taggtcctta | 720 |
| gggtcctggt | gttccttgta | gatctcgaag | accgacaagc | gtaagtcgac | cttttacact | 780 |
| gggacgattt | ggggcttgga | cattttccag | ggttcggacc | cggtaggcac | accgagtcga | 840 |
| ccttccactc | gccgggacga | cgtggacgac | tcagtatgtg | tcgagacaag | tcctgagtct | 900 |
| ccagggggtc | cctggttcct | agaggtacct | gtctccacga | cgacgcaccg | aacgtctcac | 960 |
| gtttcgaacc | cccagaggtg | accccggttc | tgatacttaa | gtttcactct | ggcaggaggc | 1020 |
| cggcccgagc | tccgggactg | tcgttacaca | acgaggactc | cgacggactt | gtccacgggt | 1080 |
| cacggggtgg | agttcctcac | tggaattcta | gaccgttgcc | atcacagaaa | cactcaaccc | 1140 |
| gaggtggtgg | acgactttcg | gtattaccac | agtaggcacc | aatggtccag | acctcggacc | 1200 |
| cgttacgag | taacgacga | cggttgacct | ggcatcaccc | acttgtctgg | gtcgacctct | 1260 |
| agcggtgtgc | tgacggtccg | aggataacac | acgttcaccg | acgtcagtga | cctcgaccac | 1320 |
| gacctcttga | gtcatgggga | cagacggagg | aaaatctcgt | ccggtacctc | gttagtcgtg | 1380 |
| ctctggggtc | ctttgtacaa | gggacctggg | accttgtcga | ctcccggtgg | aactctgctg | 1440 |
| gtcttcagta | acgtcatca | cgacaggatg | agaccaacga | cgatgatccg | taatgacaca | 1500 |
| catagatgtc | tgctgcgttt | cgaccccacg | tggacccggg | tccagacatg | tctatgtggt | 1560 |
| cgctcctgcg | gtaagatttt | gtgtcctacc | tggtgtcact | gagggggtacc | gaccgtctgt | 1620 |
| ggaccgcaag | gtggagaccg | agagctctgg | actcgtcgtc | gtcgtcggaa | tcatcagccg | 1680 |
| accctaaccct | gggagccctg | ggtgatctcc | cgtccgcgag | gaactagagg | accctgggag | 1740 |
| cctcggggcc | acatggggac | gaaggtctgt | gctcgtgcaa | aatgccgagg | gagtaacgtc | 1800 |
| tcgtcggaag | gtcgggaggt | caggccggtt | cggggttctg | tggtcgacga | tccgcgaaag | 1860 |
| gtaggttcaa | ccgaccttgg | aggtcgggga | cccgatcgag | tctatcagag | acgtcggcgt | 1920 |
| cccctgagac | aagggggtgcg | tacagagact | ggggatgtct | ccgaaccttc | cggtttttct | 1980 |
| tcgtccttaa | cgtggttcga | ttgtcgaggg | gtgacgaggc | ccgtcggtg | gggtaccttt | 2040 |
| agacccggac | cctcaaccct | tcgtctcgga | ggttcttgga | aagagtttcg | ggtcctcttc | 2100 |
| gcggggctcg | gcaccatagg | accgcacgac | accctggtgt | tgaagtggcg | ttgaggtcac | 2160 |

```
tcgaccgtag agcaggtgag ggaggttgtg gggaaagaga agcacctcga aggtcagtac    2220
tgggtgtctc ggtcacacac ctcttcgagg ttcgagggag gagactgggt gacggtcgtc    2280
ggggagagag gcaggagttg agaaggtctg gaaggtcggg ggtccggaga aggagagga    2340
caggatcggg taggaggtcg ttggacaggt cgaggagcga cagtaggaat ctcctcctcc    2400
tcctagtcct gtcgcacgag tgggggctcc tccatcggga cacagacctc gagtcactac    2460
ccctcctctg tgggtgcttg tcacatagag gatacggttc tcgaggaagg ggcggttgtt    2520
ggataccgat atagtcgtat ggttggacga gtcctgaccg tctgtacccg tctcgaccgc    2580
ccccgcaccc cagactccaa cccttgaatg acataggtgg agcccgggacg gggtggggat    2640
gtgggtcgct cccgagggac cggttaccaa ccccgagtcg aagactcctg ttacaggggt    2700
cgcggtcccg gtcggaccaa tcgagaagac taccgaggaa ggagcgacta tgagtgaaac    2760
gagcacggga ccgtcaccga cacctatcga aacggagtc agacctaggg tcccttcgac     2820
tgacacagaa gtgactacgg agtagtggag ggaggggagc cccactagag agggactggg    2880
cttcgaagag agacggaaac accctcacct ccggtctgac caaccttcta cgactctagt    2940
cggtgtgggt ctccgacccc tccccgacg gagggaccgg aggactaaga tcccggagaa    3000
gggtcgcttc aaccgattga ccacgacacg ggttccgacc actaaggagg acttaacagg    3060
gactcttccg gtcttctcgt gggtctggtg agaggacaga caggggaccg aaagagtgta    3120
cacctccaga accggatacg aagagacatt atcttcaggt ggcagtgatc cgaagacctc    3180
tcgagacagt aaccctaaca attttattta ctttcgtttg gttttatact agtgccctca    3240
gaacctaagg gtgactcttg ttctgtcgta gaagtcctgt cgtctgagag gtgttggtct    3300
tggaaaccgg attcattcgg accgaggcct cgagggtgga ttcacctagt accttcttc    3360
ccttcggttg gtccagaagt ccttcctgtc tttacaaaaa accactcccg ataccacctc    3420
ctggacacct ctcgggaga gtatagatga acctgaggag ggaatctccg gtcgagttgg    3480
gaaagggggtc agtgtggtac gttcctttga tttcctcttt ccagcaccta cgtcacccgg    3540
gatatgtcgc agtgtcagtt acgaagtttc actctagtta cctcctctga cttccttttcc    3600
tgcgtcccctt tgtcccttgg ttacgcgata agagtaagat ggcggtgaga ctcgaattcc    3660
ttgaattaag atattttgac atttctgc                                       3688
```

<210> SEQ ID NO 40
<211> LENGTH: 1015
<212> TYPE: PRT
<213> ORGANISM: Mus musculus

<400> SEQUENCE: 40

Met Gly Gln Gly Glu Glu Pro Arg Ala Ala Met Gly Ser Gly Gly Thr
 1               5                  10                  15

Gly Leu Leu Gly Thr Glu Trp Pro Leu Pro Leu Leu Leu Phe Ile
            20                  25                  30

Met Gly Gly Glu Ala Leu Asp Ser Pro Pro Gln Ile Leu Val His Pro
        35                  40                  45

Gln Asp Gln Leu Leu Gln Gly Ser Gly Pro Ala Lys Met Arg Cys Arg
    50                  55                  60

Ser Ser Gly Gln Pro Pro Pro Thr Ile Arg Trp Leu Leu Asn Gly Gln
65                  70                  75                  80

Pro Leu Ser Met Ala Thr Pro Asp Leu His Tyr Leu Leu Pro Asp Gly
                85                  90                  95

Thr Leu Leu Leu His Arg Pro Ser Val Gln Gly Arg Pro Gln Asp Asp

```
                     100                 105                 110
Gln Asn Ile Leu Ser Ala Ile Leu Gly Val Tyr Thr Cys Glu Ala Ser
            115                 120                 125

Asn Arg Leu Gly Thr Ala Val Ser Arg Gly Ala Arg Leu Ser Val Ala
            130                 135                 140

Val Leu Gln Glu Asp Phe Gln Ile Gln Pro Arg Asp Thr Val Ala Val
145                 150                 155                 160

Val Gly Glu Ser Leu Val Leu Glu Cys Gly Pro Pro Trp Gly Tyr Pro
                165                 170                 175

Lys Pro Ser Val Ser Trp Trp Lys Asp Gly Lys Pro Leu Val Leu Gln
            180                 185                 190

Pro Gly Arg Arg Thr Val Ser Gly Asp Ser Leu Met Val Ser Arg Ala
            195                 200                 205

Glu Lys Asn Asp Ser Gly Thr Tyr Met Cys Met Ala Thr Asn Asn Ala
            210                 215                 220

Gly Gln Arg Glu Ser Arg Ala Ala Arg Val Ser Ile Gln Glu Ser Gln
225                 230                 235                 240

Asp His Lys Glu His Leu Glu Leu Leu Ala Val Arg Ile Gln Leu Glu
                245                 250                 255

Asn Val Thr Leu Leu Asn Pro Glu Pro Val Lys Gly Pro Lys Pro Gly
            260                 265                 270

Pro Ser Val Trp Leu Ser Trp Lys Val Ser Gly Pro Ala Ala Pro Ala
            275                 280                 285

Glu Ser Tyr Thr Ala Leu Phe Arg Thr Gln Arg Ser Pro Arg Asp Gln
            290                 295                 300

Gly Ser Pro Trp Thr Glu Val Leu Leu Arg Gly Leu Gln Ser Ala Lys
305                 310                 315                 320

Leu Gly Gly Leu His Trp Gly Gln Asp Tyr Glu Phe Lys Val Arg Pro
                325                 330                 335

Ser Ser Gly Arg Ala Arg Gly Pro Asp Ser Asn Val Leu Leu Leu Arg
            340                 345                 350

Leu Pro Glu Gln Val Pro Ser Ala Pro Pro Gln Gly Val Thr Leu Arg
            355                 360                 365

Ser Gly Asn Gly Ser Val Phe Val Ser Trp Ala Pro Pro Ala Glu
370                 375                 380

Ser His Asn Gly Val Ile Arg Gly Tyr Gln Val Trp Ser Leu Gly Asn
385                 390                 395                 400

Ala Ser Leu Pro Ala Ala Asn Trp Thr Val Val Gly Glu Gln Thr Gln
            405                 410                 415

Leu Glu Ile Ala Thr Arg Leu Pro Gly Ser Tyr Cys Val Gln Val Ala
            420                 425                 430

Ala Val Thr Gly Ala Gly Ala Gly Glu Leu Ser Thr Pro Val Cys Leu
            435                 440                 445

Leu Leu Glu Gln Ala Met Glu Gln Ser Ala Arg Asp Pro Arg Lys His
            450                 455                 460

Val Pro Trp Thr Leu Glu Gln Leu Arg Ala Thr Leu Arg Arg Pro Glu
465                 470                 475                 480

Val Ile Ala Ser Ser Ala Val Leu Leu Trp Leu Leu Leu Gly Ile
                485                 490                 495

Thr Val Cys Ile Tyr Arg Arg Arg Lys Ala Gly Val His Leu Gly Pro
            500                 505                 510

Gly Leu Tyr Arg Tyr Thr Ser Glu Asp Ala Ile Leu Lys His Arg Met
            515                 520                 525
```

```
Asp His Ser Asp Ser Pro Trp Leu Ala Asp Thr Trp Arg Ser Thr Ser
    530                 535                 540

Gly Ser Arg Asp Leu Ser Ser Ser Ser Leu Ser Ser Arg Leu Gly
545                 550                 555                 560

Leu Asp Pro Arg Asp Pro Leu Glu Gly Arg Arg Ser Leu Ile Ser Trp
                565                 570                 575

Asp Pro Arg Ser Pro Gly Val Pro Leu Leu Pro Asp Thr Ser Thr Phe
                580                 585                 590

Tyr Gly Ser Leu Ile Ala Glu Gln Pro Ser Ser Pro Val Arg Pro
                595                 600                 605

Ser Pro Lys Thr Pro Ala Ala Arg Arg Phe Pro Ser Lys Leu Ala Gly
    610                 615                 620

Thr Ser Ser Pro Trp Ala Ser Ser Asp Ser Leu Cys Ser Arg Arg Gly
625                 630                 635                 640

Leu Cys Ser Pro Arg Met Ser Leu Thr Pro Thr Glu Ala Trp Lys Ala
                645                 650                 655

Lys Lys Lys Gln Glu Leu His Gln Ala Asn Ser Ser Pro Leu Leu Arg
                660                 665                 670

Gly Ser His Pro Met Glu Ile Trp Ala Trp Glu Leu Gly Ser Arg Ala
                675                 680                 685

Ser Lys Asn Leu Ser Gln Ser Pro Gly Glu Ala Pro Arg Ala Val Val
    690                 695                 700

Ser Trp Arg Ala Val Gly Pro Gln Leu His Arg Asn Ser Ser Glu Leu
705                 710                 715                 720

Ala Ser Arg Pro Leu Pro Pro Thr Pro Leu Ser Leu Arg Gly Ala Ser
                725                 730                 735

Ser His Asp Pro Gln Ser Gln Cys Val Glu Lys Leu Gln Ala Pro Ser
                740                 745                 750

Ser Asp Pro Leu Pro Ala Ala Pro Leu Ser Val Leu Asn Ser Ser Arg
    755                 760                 765

Pro Ser Ser Pro Gln Ala Ser Phe Leu Ser Cys Pro Ser Pro Ser Ser
770                 775                 780

Ser Asn Leu Ser Ser Ser Ser Leu Ser Ser Leu Glu Glu Glu Asp
785                 790                 795                 800

Gln Asp Ser Val Leu Thr Pro Glu Glu Val Ala Leu Cys Leu Glu Leu
                805                 810                 815

Ser Asp Gly Glu Glu Thr Pro Thr Asn Ser Val Ser Pro Met Pro Arg
                820                 825                 830

Ala Pro Ser Pro Pro Thr Thr Tyr Gly Tyr Ile Ser Ile Pro Thr Cys
                835                 840                 845

Ser Gly Leu Ala Asp Met Gly Arg Ala Gly Gly Val Gly Ser Glu
    850                 855                 860

Val Gly Asn Leu Leu Tyr Pro Pro Arg Pro Cys Pro Thr Pro Thr Pro
865                 870                 875                 880

Ser Glu Gly Ser Leu Ala Asn Gly Trp Gly Ser Ala Ser Glu Asp Asn
                885                 890                 895

Val Pro Ser Ala Arg Ala Ser Leu Val Ser Ser Ser Asp Gly Ser Phe
                900                 905                 910

Leu Ala Asp Thr His Phe Ala Arg Ala Leu Ala Val Ala Val Asp Ser
                915                 920                 925

Phe Gly Leu Ser Leu Asp Pro Arg Glu Ala Asp Cys Val Phe Thr Asp
930                 935                 940
```

```
Ala Ser Ser Pro Pro Ser Pro Arg Gly Asp Leu Ser Leu Thr Arg Ser
945                 950                 955                 960

Phe Ser Leu Pro Leu Trp Glu Trp Arg Pro Asp Trp Leu Glu Asp Ala
            965                 970                 975

Glu Ile Ser His Thr Gln Arg Leu Gly Arg Gly Leu Pro Pro Trp Pro
        980                 985                 990

Pro Asp Ser Arg Ala Ser Ser Gln Arg Ser Trp Leu Thr Gly Ala Val
    995                 1000                1005

Pro Lys Ala Gly Asp Ser Ser
    1010                1015

<210> SEQ ID NO 41
<211> LENGTH: 39
<212> TYPE: PRT
<213> ORGANISM: Mus musculus

<400> SEQUENCE: 41

Met Phe Phe Gly Glu Gly Tyr Gly Gly Pro Val Glu Glu Pro Ser
1               5                   10                  15

His Ile Tyr Leu Asp Ser Ser Leu Arg Gly Gln Leu Asn Pro Phe Pro
            20                  25                  30

Ser His Thr Met Gln Gly Asn
        35

<210> SEQ ID NO 42
<211> LENGTH: 34
<212> TYPE: PRT
<213> ORGANISM: Mus musculus

<400> SEQUENCE: 42

Met Glu Glu Thr Glu Gly Lys Asp Ala Gly Lys Gln Gly Thr Asn Ala
1               5                   10                  15

Leu Phe Ser Phe Tyr Arg His Ser Glu Leu Lys Glu Leu Asn Ser Ile
            20                  25                  30

Lys Leu

<210> SEQ ID NO 43
<211> LENGTH: 1075
<212> TYPE: PRT
<213> ORGANISM: Homo sapiens

<400> SEQUENCE: 43

Met Gly Ser Gly Gly Asp Ser Leu Leu Gly Arg Gly Ser Leu Pro
1               5                   10                  15

Leu Leu Leu Leu Leu Ile Met Gly Gly Met Ala Gln Asp Ser Pro Pro
            20                  25                  30

Gln Ile Leu Val His Pro Gln Asp Gln Leu Phe Gln Gly Pro Gly Pro
        35                  40                  45

Ala Arg Met Ser Cys Gln Ala Ser Gly Gln Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Gln Pro Pro Ala Arg
            85                  90                  95

Gly His Ala His Asp Gly Gln Ala Leu Ser Thr Asp Leu Gly Val Tyr
            100                 105                 110

Thr Cys Glu Ala Ser Asn Arg Leu Gly Thr Ala Val Ser Arg Gly Ala
        115                 120                 125
```

-continued

```
Arg Leu Ser Val Ala Val Leu Arg Glu Asp Phe Gln Ile Gln Pro Arg
    130                 135                 140
Asp Met Val Ala Val Gly Glu Gln Phe Thr Leu Glu Cys Gly Pro
145                 150                 155                 160
Pro Trp Gly His Pro Glu Pro Thr Val Ser Trp Lys Asp Gly Lys
                165                 170                 175
Pro Leu Ala Leu Gln Pro Gly Arg His Thr Val Ser Gly Gly Ser Leu
                180                 185                 190
Leu Met Ala Arg Ala Glu Lys Ser Asp Glu Gly Thr Tyr Met Cys Val
            195                 200                 205
Ala Thr Asn Ser Ala Gly His Arg Glu Ser Arg Ala Ala Arg Val Ser
        210                 215                 220
Ile Gln Glu Pro Gln Asp Tyr Thr Glu Pro Val Glu Leu Leu Ala Val
225                 230                 235                 240
Arg Ile Gln Leu Glu Asn Val Thr Leu Leu Asn Pro Asp Pro Ala Glu
                245                 250                 255
Gly Pro Lys Pro Arg Pro Ala Val Trp Leu Ser Trp Lys Val Ser Gly
                260                 265                 270
Pro Ala Ala Pro Ala Gln Ser Tyr Thr Ala Leu Phe Arg Thr Gln Thr
            275                 280                 285
Ala Pro Gly Gly Gln Gly Ala Pro Trp Ala Glu Leu Leu Ala Gly
        290                 295                 300
Trp Gln Ser Ala Glu Leu Gly Gly Leu His Trp Gly Gln Asp Tyr Glu
305                 310                 315                 320
Phe Lys Val Arg Pro Ser Ser Gly Arg Ala Arg Gly Pro Asp Ser Asn
                325                 330                 335
Val Leu Leu Leu Arg Leu Pro Glu Lys Val Pro Ser Ala Pro Pro Gln
                340                 345                 350
Glu Val Thr Leu Lys Pro Gly Asn Gly Thr Val Phe Val Ser Trp Val
            355                 360                 365
Pro Pro Pro Ala Glu Asn His Asn Gly Ile Ile Arg Gly Tyr Gln Val
        370                 375                 380
Trp Ser Leu Gly Asn Thr Ser Leu Pro Pro Ala Asn Trp Thr Val Val
385                 390                 395                 400
Gly Glu Gln Thr Gln Leu Glu Ile Ala Thr His Met Pro Gly Ser Tyr
                405                 410                 415
Cys Val Gln Val Ala Ala Val Thr Gly Ala Gly Ala Gly Glu Pro Ser
                420                 425                 430
Arg Pro Val Cys Leu Leu Glu Gln Ala Met Glu Arg Ala Thr Gln
            435                 440                 445
Glu Pro Ser Glu His Gly Pro Trp Thr Leu Glu Gln Leu Arg Ala Thr
        450                 455                 460
Leu Lys Arg Pro Glu Val Ile Ala Thr Cys Gly Val Ala Leu Trp Leu
465                 470                 475                 480
Leu Leu Leu Gly Thr Ala Val Cys Ile His Arg Arg Arg Arg Ala Arg
                485                 490                 495
Val His Leu Gly Pro Gly Leu Tyr Arg Tyr Thr Ser Glu Asp Ala Ile
                500                 505                 510
Leu Lys His Arg Met Asp His Ser Asp Ser Gln Trp Leu Ala Asp Thr
            515                 520                 525
Trp Arg Ser Thr Ser Gly Ser Arg Asp Leu Ser Ser Ser Ser Ser Leu
530                 535                 540
```

```
Ser Ser Arg Leu Gly Ala Asp Ala Arg Asp Pro Leu Asp Cys Arg Arg
545                 550                 555                 560

Ser Leu Leu Ser Trp Asp Ser Arg Ser Pro Gly Val Pro Leu Leu Pro
                565                 570                 575

Asp Thr Ser Thr Phe Tyr Gly Ser Leu Ile Ala Glu Leu Pro Ser Ser
            580                 585                 590

Thr Pro Ala Arg Pro Ser Pro Gln Val Pro Ala Val Arg Arg Leu Pro
        595                 600                 605

Pro Gln Leu Ala Gln Leu Ser Ser Pro Cys Ser Ser Ser Asp Ser Leu
    610                 615                 620

Cys Ser Arg Arg Gly Leu Ser Ser Pro Arg Leu Ser Leu Ala Pro Ala
625                 630                 635                 640

Glu Ala Trp Lys Ala Lys Lys Gln Glu Leu Gln His Ala Asn Ser
                645                 650                 655

Ser Pro Leu Leu Arg Gly Ser His Ser Leu Glu Leu Arg Ala Cys Glu
                660                 665                 670

Leu Gly Asn Arg Gly Ser Lys Asn Leu Ser Gln Ser Pro Gly Ala Val
            675                 680                 685

Pro Gln Ala Leu Val Ala Trp Arg Ala Leu Gly Pro Lys Leu Leu Ser
    690                 695                 700

Ser Ser Asn Glu Leu Val Thr Arg His Leu Pro Pro Ala Pro Leu Phe
705                 710                 715                 720

Pro His Glu Thr Pro Pro Thr Gln Ser Gln Thr Gln Pro Pro Val
                725                 730                 735

Ala Pro Gln Ala Pro Ser Ser Ile Leu Leu Pro Ala Ala Pro Ile Pro
            740                 745                 750

Ile Leu Ser Pro Cys Ser Pro Ser Pro Gln Ala Ser Ser Leu Ser
        755                 760                 765

Gly Pro Ser Pro Ala Ser Ser Arg Leu Ser Ser Ser Ser Leu Ser Ser
770                 775                 780

Leu Gly Glu Asp Gln Asp Ser Val Leu Thr Pro Glu Glu Val Ala Leu
785                 790                 795                 800

Cys Leu Glu Leu Ser Glu Gly Glu Glu Thr Pro Arg Asn Ser Val Ser
                805                 810                 815

Pro Met Pro Arg Ala Pro Ser Pro Pro Thr Thr Tyr Gly Tyr Ile Ser
            820                 825                 830

Val Pro Thr Ala Ser Glu Phe Thr Asp Met Gly Arg Thr Gly Gly Gly
            835                 840                 845

Val Gly Pro Lys Gly Gly Val Leu Leu Cys Pro Pro Arg Pro Cys Leu
            850                 855                 860

Thr Pro Thr Pro Ser Glu Gly Ser Leu Ala Asn Gly Trp Gly Ser Ala
865                 870                 875                 880

Ser Glu Asp Asn Ala Ala Ser Ala Arg Ala Ser Leu Val Ser Ser Ser
                885                 890                 895

Asp Gly Ser Phe Leu Ala Asp Ala His Phe Ala Arg Ala Leu Ala Val
            900                 905                 910

Ala Val Asp Ser Phe Gly Phe Gly Leu Glu Pro Arg Glu Ala Asp Cys
            915                 920                 925

Val Phe Ile Asp Ala Ser Ser Pro Ser Pro Arg Asp Glu Ile Phe
            930                 935                 940

Leu Thr Pro Asn Leu Ser Leu Pro Leu Trp Glu Trp Arg Pro Asp Trp
945                 950                 955                 960

Leu Glu Asp Met Glu Val Ser His Thr Gln Arg Leu Gly Arg Gly Met
```

-continued

```
              965                 970                 975
Pro Pro Trp Pro Pro Glu Leu Ser Asp Leu Phe Pro Glu Lys Ser Ala
            980                 985                 990
Pro Leu Ser Tyr Ala Gln Gly Trp Cys Phe Ser Cys Arg Leu Leu Leu
            995                1000                1005
Asn Arg Val Pro Glu Thr Ser Gln Thr Gly Ile Arg Thr Thr Ser Pro
           1010                1015                1020
Val Pro Pro Thr Arg Pro Gly Leu Trp Cys Val Gly Leu Gly Leu Cys
1025                1030                1035                1040
Phe Ser Ala Ala Gly Val His Leu Pro Lys Pro Pro Glu Ser Ser Pro
           1045                1050                1055
Ser Thr Ile Val Lys Thr Asn Glu Asn Lys Ile Arg Ala Lys Leu Thr
           1060                1065                1070
Trp Ser Pro
       1075

<210> SEQ ID NO 44
<211> LENGTH: 38
<212> TYPE: PRT
<213> ORGANISM: Mus musculus

<400> SEQUENCE: 44

Ile Val Pro Glu Lys Ala Arg Arg Ala Pro Arg Pro Leu Ser Cys Leu
1               5                  10                  15
Ser Pro Gly Phe Leu Thr Cys Gly Gly Leu Gly Leu Cys Phe Ser Val
            20                  25                  30
Ile Glu Val His Arg His
        35

<210> SEQ ID NO 45
<211> LENGTH: 10
<212> TYPE: PRT
<213> ORGANISM: Mus musculus

<400> SEQUENCE: 45

Ala Ser Gly Glu Leu Cys His Trp Asp Cys
1               5                  10

<210> SEQ ID NO 46
<211> LENGTH: 5
<212> TYPE: PRT
<213> ORGANISM: Mus musculus

<400> SEQUENCE: 46

Lys Gln Thr Lys Ile
1               5

<210> SEQ ID NO 47
<211> LENGTH: 7
<212> TYPE: PRT
<213> ORGANISM: Mus musculus

<400> SEQUENCE: 47

Ser Arg Glu Ser Trp Ile Pro
1               5

<210> SEQ ID NO 48
<211> LENGTH: 1005
<212> TYPE: PRT
<213> ORGANISM: Mus musculus
```

<400> SEQUENCE: 48

```
Met Gly Ser Gly Gly Thr Gly Leu Leu Gly Thr Glu Trp Pro Leu Pro
  1               5                  10                  15
Leu Leu Leu Leu Phe Ile Met Gly Gly Glu Ala Leu Asp Ser Pro Pro
             20                  25                  30
Gln Ile Leu Val His Pro Gln Asp Gln Leu Leu Gln Gly Ser Gly Pro
         35                  40                  45
Ala Lys Met Arg Cys Arg Ser Ser Gly Gln Pro Pro Pro Thr Ile Arg
     50                  55                  60
Trp Leu Leu Asn Gly Gln Pro Leu Ser Met Ala Thr Pro Asp Leu His
 65                  70                  75                  80
Tyr Leu Leu Pro Asp Gly Thr Leu Leu Leu His Arg Pro Ser Val Gln
                 85                  90                  95
Gly Arg Pro Gln Asp Asp Gln Asn Ile Leu Ser Ala Ile Leu Gly Val
            100                 105                 110
Tyr Thr Cys Glu Ala Ser Asn Arg Leu Gly Thr Ala Val Ser Arg Gly
        115                 120                 125
Ala Arg Leu Ser Val Ala Val Leu Gln Glu Asp Phe Gln Ile Gln Pro
    130                 135                 140
Arg Asp Thr Val Ala Val Val Gly Glu Ser Leu Val Leu Glu Cys Gly
145                 150                 155                 160
Pro Pro Trp Gly Tyr Pro Lys Pro Ser Val Ser Trp Trp Lys Asp Gly
                165                 170                 175
Lys Pro Leu Val Leu Gln Pro Gly Arg Arg Thr Val Ser Gly Asp Ser
            180                 185                 190
Leu Met Val Ser Arg Ala Glu Lys Asn Asp Ser Gly Thr Tyr Met Cys
        195                 200                 205
Met Ala Thr Asn Asn Ala Gly Gln Arg Glu Ser Arg Ala Ala Arg Val
    210                 215                 220
Ser Ile Gln Glu Ser Gln Asp His Lys Glu His Leu Glu Leu Leu Ala
225                 230                 235                 240
Val Arg Ile Gln Leu Glu Asn Val Thr Leu Leu Asn Pro Glu Pro Val
                245                 250                 255
Lys Gly Pro Lys Pro Gly Pro Ser Val Trp Leu Ser Trp Lys Val Ser
            260                 265                 270
Gly Pro Ala Ala Pro Ala Glu Ser Tyr Thr Ala Leu Phe Arg Thr Gln
        275                 280                 285
Arg Ser Pro Arg Asp Gln Gly Ser Pro Trp Thr Glu Val Leu Leu Arg
    290                 295                 300
Gly Leu Gln Ser Ala Lys Leu Gly Gly Leu His Trp Gly Gln Asp Tyr
305                 310                 315                 320
Glu Phe Lys Val Arg Pro Ser Ser Gly Arg Ala Arg Gly Pro Asp Ser
                325                 330                 335
Asn Val Leu Leu Leu Arg Leu Pro Glu Gln Val Pro Ser Ala Pro Pro
            340                 345                 350
Gln Gly Val Thr Leu Arg Ser Gly Asn Gly Ser Val Phe Val Ser Trp
        355                 360                 365
Ala Pro Pro Pro Ala Glu Ser His Asn Gly Val Ile Arg Gly Tyr Gln
    370                 375                 380
Val Trp Ser Leu Gly Asn Ala Ser Leu Pro Ala Ala Asn Trp Thr Val
385                 390                 395                 400
Val Gly Glu Gln Thr Gln Leu Glu Ile Ala Thr Arg Leu Pro Gly Ser
                405                 410                 415
```

-continued

Tyr Cys Val Gln Val Ala Ala Val Thr Gly Ala Gly Ala Gly Glu Leu
            420                 425                 430

Ser Thr Pro Val Cys Leu Leu Leu Glu Gln Ala Met Glu Gln Ser Ala
        435                 440                 445

Arg Asp Pro Arg Lys His Val Pro Trp Thr Leu Glu Gln Leu Arg Ala
        450                 455                 460

Thr Leu Arg Arg Pro Glu Val Ile Ala Ser Ser Ala Val Leu Leu Trp
465                 470                 475                 480

Leu Leu Leu Leu Gly Ile Thr Val Cys Ile Tyr Arg Arg Arg Lys Ala
                485                 490                 495

Gly Val His Leu Gly Pro Gly Leu Tyr Arg Tyr Thr Ser Glu Asp Ala
                500                 505                 510

Ile Leu Lys His Arg Met Asp His Ser Asp Ser Pro Trp Leu Ala Asp
                515                 520                 525

Thr Trp Arg Ser Thr Ser Gly Ser Arg Asp Leu Ser Ser Ser Ser Ser
530                 535                 540

Leu Ser Ser Arg Leu Gly Leu Asp Pro Arg Asp Pro Leu Glu Gly Arg
545                 550                 555                 560

Arg Ser Leu Ile Ser Trp Asp Pro Arg Ser Pro Gly Val Pro Leu Leu
                565                 570                 575

Pro Asp Thr Ser Thr Phe Tyr Gly Ser Leu Ile Ala Glu Gln Pro Ser
                580                 585                 590

Ser Pro Pro Val Arg Pro Ser Pro Lys Thr Pro Ala Ala Arg Arg Phe
                595                 600                 605

Pro Ser Lys Leu Ala Gly Thr Ser Ser Pro Trp Ala Ser Ser Asp Ser
        610                 615                 620

Leu Cys Ser Arg Arg Gly Leu Cys Ser Pro Arg Met Ser Leu Thr Pro
625                 630                 635                 640

Thr Glu Ala Trp Lys Ala Lys Lys Gln Glu Leu His Gln Ala Asn
                645                 650                 655

Ser Ser Pro Leu Leu Arg Gly Ser His Pro Met Glu Ile Trp Ala Trp
            660                 665                 670

Glu Leu Gly Ser Arg Ala Ser Lys Asn Leu Ser Gln Ser Pro Gly Glu
            675                 680                 685

Ala Pro Arg Ala Val Val Ser Trp Arg Ala Val Gly Pro Gln Leu His
            690                 695                 700

Arg Asn Ser Ser Glu Leu Ala Ser Arg Pro Leu Pro Thr Pro Leu
705                 710                 715                 720

Ser Leu Arg Gly Ala Ser Ser His Asp Pro Gln Ser Gln Cys Val Glu
            725                 730                 735

Lys Leu Gln Ala Pro Ser Ser Asp Pro Leu Pro Ala Ala Pro Leu Ser
            740                 745                 750

Val Leu Asn Ser Ser Arg Pro Ser Pro Gln Ala Ser Phe Leu Ser
            755                 760                 765

Cys Pro Ser Pro Ser Ser Asn Leu Ser Ser Ser Ser Leu Ser Ser
        770                 775                 780

Leu Glu Glu Glu Glu Asp Gln Asp Ser Val Leu Thr Pro Glu Glu Val
785                 790                 795                 800

Ala Leu Cys Leu Glu Leu Ser Asp Gly Glu Glu Thr Thr Asn Ser
                805                 810                 815

Val Ser Pro Met Pro Arg Ala Pro Ser Pro Thr Thr Tyr Gly Tyr
            820                 825                 830

```
Ile Ser Ile Pro Thr Cys Ser Gly Leu Ala Asp Met Gly Arg Ala Gly
        835                 840                 845
Gly Gly Val Gly Ser Glu Val Gly Asn Leu Leu Tyr Pro Pro Arg Pro
    850                 855                 860
Cys Pro Thr Pro Thr Pro Ser Glu Gly Ser Leu Ala Asn Gly Trp Gly
865                 870                 875                 880
Ser Ala Ser Glu Asp Asn Val Pro Ser Ala Arg Ala Ser Leu Val Ser
                885                 890                 895
Ser Ser Asp Gly Ser Phe Leu Ala Asp Thr His Phe Ala Arg Ala Leu
            900                 905                 910
Ala Val Ala Val Asp Ser Phe Gly Leu Ser Leu Asp Pro Arg Glu Ala
        915                 920                 925
Asp Cys Val Phe Thr Asp Ala Ser Ser Pro Ser Pro Arg Gly Asp
    930                 935                 940
Leu Ser Leu Thr Arg Ser Phe Ser Leu Pro Leu Trp Glu Trp Arg Pro
945                 950                 955                 960
Asp Trp Leu Glu Asp Ala Glu Ile Ser His Thr Gln Arg Leu Gly Arg
                965                 970                 975
Gly Leu Pro Pro Trp Pro Pro Asp Ser Arg Ala Ser Ser Gln Arg Ser
            980                 985                 990
Trp Leu Thr Gly Ala Val Pro Lys Ala Gly Asp Ser Ser
        995                 1000                1005

<210> SEQ ID NO 49
<211> LENGTH: 3651
<212> TYPE: DNA
<213> ORGANISM: Homo sapiens

<400> SEQUENCE: 49
agtgctcggg acaaggacat agggctgaga gtagccatgg gctctggagg agacagcctc      60
ctgggggggca gggttccct gcctctgctg ctcctgctca tcatgggagg catggctcag     120
gactccccgc cccagatcct agtccacccc caggaccagc tgttccaggg ccctggccct     180
gccaggatga gctgccaagc ctcaggccag ccacctccca ccatccgctg gttgctgaat     240
gggcagcccc tgagcatggt gccccagac ccacaccacc tcctgcctga tgggacccct     300
ctgctgctac agcccctgc ccggggacat gcccacgatg ccaggccct gtccacagac     360
ctgggtgtct acacatgtga ggccagcaac cggcttggca cggcagtcag cagaggcgct     420
cggctgtctg tggctgtcct ccgggaggat ttccagatcc agcctcggga catggtggct     480
gtggtgggtg agcagtttac tctggaatgt gggccgccct ggggccaccc agagcccaca     540
gtctcatggt ggaaagatgg gaaacccctg gccctccagc ccggaaggca cacagtgtcc     600
gggggtccc tgctgatggc aagagcagag aagagtgacg aagggaccta catgtgtgtg     660
gccaccaaca gcgcaggaca tagggagagc cgcgcagccc gggtttccat ccaggagccc     720
caggactaca cggagcctgt ggagcttctg gctgtgcgaa ttcagctgga aaatgtgaca     780
ctgctgaacc cggatcctgc agagggcccc aagcctagac cggcggtgtg ctcagctgg     840
aaggtcagtg gccctgctgc gcctgcccaa tcttacacgg ccttgttcag gacccagact     900
gccccgggag gccagggagc tccgtgggca gaggagctgc tggccggctg gcagagcgca     960
gagcttggag gcctccactg gggccaagac tacgagttca agtgagacc atcctctggc    1020
cgggctcgag gccctgacag caacgtgctg ctcctgaggc tgccggaaaa agtgcccagt    1080
gccccacctc aggaagtgac tctaaagcct ggcaatggca ctgtctttgt gagctgggtc    1140
```

```
ccaccacctg ctgaaaacca caatggcatc atccgtggct accaggtctg gagcctgggc    1200
aacacatcac tgccaccagc caactggact gtagttggtg agcagaccca gctggaaatc    1260
gccacccata tgccaggctc ctactgcgtg caagtggctg cagtcactgg tgctggagct    1320
ggggagccca gtagacctgt ctgcctcctt ttagagcagg ccatggagcg agccacccaa    1380
gaacccagtg agcatggtcc ctggaccctg gagcagctga gggctacctt gaagcggcct    1440
gaggtcattg ccacctgcgg tgttgcactc tggctgctgc ttctgggcac cgccgtgtgt    1500
atccaccgcc ggcgccgagc tagggtgcac ctgggcccag tctgtacag atataccagt     1560 gaggatgcca tcctaaaaca caggatggat cacagtgact cccagtggtt ggcagacact    1620
tggcgttcca cctctggctc tcgggacctg agcagcagca gcagcctcag cagtcggctg    1680
ggggcggatg cccgggaccc actagactgt cgtcgctcct tgctctcctg ggactcccga    1740
agccccggcg tgcccctgct tccagacacc agcactttt atggctccct catcgctgag      1800
ctgccctcca gtaccccagc caggccaagt ccccaggtcc cagctgtcag gcgcctccca    1860
ccccagctgg cccagctctc cagcccctgt ccagctcag acagcctctg cagccgcagg     1920
ggactctctt ctccccgctt gtctctggcc ctgcagagg cttggaaggc caaaaagaag      1980
caggagctgc agcatgccaa cagttcccca ctgctccggg gcagccactc cttggagctc    2040
cgggcctgtg agttaggaaa tagaggttcc aagaaccttt cccaaagccc aggagctgtg    2100
ccccaagctc tggttgcctg gcgggccctg ggaccgaaac tcctcagctc tcaaatgag    2160 ctggttactc gtcatctccc tccagcaccc ctctttcctc atgaaactcc ccaactcag    2220 agtcaacaga cccagcctcc ggtggcacca caggctccct cctccatcct gctgccagca    2280
gcccccatcc ccatccttag cccctgcagt cccctagcc cccaggcctc ttccctctct    2340
ggccccagcc cagcttccag tcgcctgtcc agctcctcac tgtcatccct ggggaggat    2400 caagacagcg tgctgacccc tgaggaggta gccctgtgct tggaactcag tgagggtgag   2460
gagactccca ggaacagcgt ctctcccatg ccaagggctc cttcacccc caccacctat     2520 gggtacatca gcgtcccaac agcctcagag ttcacggaca tgggcaggac tggaggaggg    2580
gtggggccca agggggagt cttgctgtgc ccacctcggc cctgcctcac ccccacccccc    2640 agcgagggct ccttagccaa tggttggggc tcagcctctg aggacaatgc cgccagcgcc    2700
agagccagcc ttgtcagctc ctccgatggc tccttcctcg ctgatgctca ctttgcccgg    2760
gccctggcag tggctgtgga tagctttggt ttcggtctag agcccaggga ggcagactgc    2820
gtcttcatag atgcctcatc acctcctcc ccacgggatg agatcttcct gacccccaac     2880
ctctccctgc cctgtgggga gtggaggcca gactggttgg aagacatgga ggtcagccac    2940
acccagcggc tgggaagggg gatgcctccc tggcccctg aactctcaga tctcttccca    3000
gagaagtcag ctccactgtc gtatgcccaa ggctggtgct ctcctgtag attactcctg    3060 aaccgtgtcc ctgagacttc ccagacggga atcagaacca cttctcctgt tccacccaca    3120
agacctgggc tgtggtgtgt gggtcttggc ctgtgtttct ctgcagctgg ggtccacctt    3180
cccaagcctc cagagagttc tccctccacg attgtgaaaa caaatgaaaa caaaattaga    3240
gcaaagctga cctggagccc tcagggagca aaacatcatc tccacctgac tcctagccac    3300
tgctttctcc tctgtgccat ccactccac caccaggttc ttttggcctg aggagcagcc     3360
ctgcctgctg ctcttccccc accatttgga tcacaggaag tggaggagcc agaggtgcct    3420
ttgtggagga cagcagtggc tgctgggaga gggctgtgga ggaaggagct tctcggagcc    3480
ccctctcagc cttacctggg cccctcctct agagaagagc tcaactctct cccaacctca   3540
```

| | |
|---|---:|
| ccatggaaag aaaataatta tgaatgccac tgaggcactg aggccctacc tcatgccaaa | 3600 |
| caaagggttc aaggctgggt ctagcgagga tgctgaagga agggaggtat g | 3651 |

<210> SEQ ID NO 50
<211> LENGTH: 3607
<212> TYPE: DNA
<213> ORGANISM: Mus musculus

<400> SEQUENCE: 50

| | |
|---|---:|
| agtgtatggg acaaggagag gagccgagag cagccatggg ctctggagga acgggcctcc | 60 |
| tggggacgga gtggcctctg cctctgctgc tgcttttcat catgggaggt gaggctctgg | 120 |
| attctccacc ccagatccta gttcacccc aggaccagct acttcagggc tctggcccag | 180 |
| ccaagatgag gtgcagatca tccggccaac cacctcccac tatccgctgg ctgctgaatg | 240 |
| ggcagcccct cagcatggcc accccagacc tacattacct tttgccggat gggaccctcc | 300 |
| tgttacatcg gccctctgtc cagggacggc cacaagatga ccagaacatc ctctcagcaa | 360 |
| tcctgggtgt ctacacatgt gaggccagca accggctggg cacagcagtg agccggggtg | 420 |
| ctaggctgtc tgtggctgtc ctccaggagg acttccagat ccaacctcgg gacacagtgg | 480 |
| ccgtggtggg agagagcttg gttcttgagt gtggtcctcc ctgggctac ccaaaaccct | 540 |
| cggtctcatg gtggaaagac gggaaacccc tggtcctcca gccagggagg cgcacagtat | 600 |
| ctggggattc cctgatggtg tcaagagcag agaagaatga ctcggggacc tatatgtgta | 660 |
| tggccaccaa caatgctggg caacgggaga gccgagcagc cagggtgtct atccaggaat | 720 |
| cccaggacca caaggaacat ctagagcttc tggctgttcg cattcagctg gaaaatgtga | 780 |
| ccctgctaaa ccccgaacct gtaaaaggtc ccaagcctgg ccatccgtg tggctcagct | 840 |
| ggaaggtgag cggccctgct gcacctgctg agtcatacac agctctgttc aggactcaga | 900 |
| ggtcccccag ggaccaagga tctccatgga cagaggtgct gctgcgtggc ttgcagagtg | 960 |
| caaagcttgg gggtctccac tggggccaag actatgaatt caaagtgaga ccgtcctccg | 1020 |
| gccgggctcg aggccctgac agcaatgtgt tgctcctgag gctgcctgaa caggtgccca | 1080 |
| gtgccccacc tcaaggagtg accttaagat ctggcaacgg tagtgtcttt gtgagttggg | 1140 |
| ctccaccacc tgctgaaagc cataatggtg tcatccgtgg ttaccaggtc tggagcctgg | 1200 |
| gcaatgcctc attgcctgct gccaactgga ccgtagtggg tgaacagacc cagctggaga | 1260 |
| tcgccacacg actgccaggc tcctattgtg tgcaagtggc tgcagtcact ggagctggtg | 1320 |
| ctggagaact cagtaccct gtctgcctcc ttttagagca ggccatggag caatcagcac | 1380 |
| gagaccccag gaaacatgtt ccctggaccc tggaacagct gagggccacc ttgagacgac | 1440 |
| cagaagtcat tgccagtagt gctgtcctac tctggttgct gctactaggc attactgtgt | 1500 |
| gtatctacag acgacgcaaa gctggggtgc acctgggccc aggtctgtac agatacacca | 1560 |
| gcgaggacgc cattctaaaa cacaggatgg accacagtga ctccccatgg ctggcagaca | 1620 |
| cctggcgttc cacctctggc tctcgagacc tgagcagcag cagcagcctt agtagtcggc | 1680 |
| tgggattgga ccctcgggac ccactagagg gcaggcgctc cttgatctcc tgggaccctc | 1740 |
| ggagccccgg tgtaccctg cttccagaca cgagcacgtt ttacggctcc ctcattgcag | 1800 |
| agcagccttc cagccctcca gtccggccaa gcccaagac accagctgct aggcgctttc | 1860 |
| catccaagtt ggctggaacc tccagcccct gggctagcc agatagtctc tgcagccgca | 1920 |
| ggggactctg ttccccacgc atgtctctga cccctacaga ggcttggaag gccaaaaaga | 1980 |

```
agcaggaatt gcaccaagct aacagctccc cactgctccg gggcagccac cccatggaaa  2040
tctgggcctg ggagttggga agcagagcct ccaagaacct ttctcaaagc ccaggagaag  2100
cgccccgagc cgtggtatcc tggcgtgctg tgggaccaca acttcaccgc aactccagtg  2160
agctggcatc tcgtccactc cctccaacac ccctttctct tcgtggagct tccagtcatg  2220
acccacagag ccagtgtgtg gagaagctcc aagctccctc ctctgaccca ctgccagcag  2280
cccctctctc cgtcctcaac tcttccagac cttccagccc ccaggcctct ttcctctcct  2340
gtcctagccc atcctccagc aacctgtcca gctcctcgct gtcatcctta gaggaggagg  2400
aggatcagga cagcgtgctc accccgagg aggtagccct gtgtctggag ctcagtgatg   2460
gggaggagac acccacgaac agtgtatctc ctatgccaag agctccttcc ccgccaacaa  2520
cctatggcta tatcagcata ccaacctgct caggactggc agacatgggc agagctggcg  2580
ggggcgtggg gtctgaggtt gggaacttac tgtatccacc tcggccctgc cccaccccta  2640
cacccagcga gggctccctg gccaatggtt ggggctcagc ttctgaggac aatgtcccca  2700
gcgccagggc cagcctggtt agctcttctg atggctcctt cctcgctgat actcactttg  2760
ctcgtgccct ggcagtggct gtggatagct ttggcctcag tctggatccc agggaagctg  2820
actgtgtctt cactgatgcc tcatcacctc cctccctcg gggtgatctc tccctgaccc   2880
gaagcttctc tctgcctttg tgggagtgga ggccagactg gttggaagat gctgagatca  2940
gccacaccca gaggctgggg aggggctgc ctccctggcc tcctgattct agggcctctt   3000
cccagcgaag ttggctaact ggtgctgtgc ccaaggctgg tgattcctcc tgaattgtcc  3060
ctgagaaggc cagaagagca cccagaccac tctcctgtct gtccctggc tttctcacat   3120
gtggaggtct tggcctatgc ttctctgtaa tagaagtcca ccgtcactag gcttctggag  3180
agctctgtca ttgggattgt taaaataaat gaaagcaaac caaaatatga tcacgggagt  3240
cttggattcc cactgagaac aagacagcat cttcaggaca gcagactctc cacaaccaga  3300
accttggcc taagtaagcc tggctccgga gctcccacct aagtggatca tggaaagaag   3360
ggaagccaac caggtcttca ggaaggacag aaatgttttt tggtgagggc tatggtggag  3420
gacctgtgga agagccctct catatctact tggactcctc ccttagaggc cagctcaacc  3480
ctttccccag tcacaccatg caaggaaact aaaggagaaa ggtcgtggat gcagtgggcc  3540
ctatacagcg tcacagtcaa tgcttcaaag tgagatcaat ggaggagact gaaggaaagg  3600
acgcagg                                                            3607
```